(12) United States Patent
Castano Mansanet et al.

(10) Patent No.: US 7,642,361 B2
(45) Date of Patent: Jan. 5, 2010

(54) THIOPHENE AND FURAN COMPOUNDS

(75) Inventors: Ana Maria Castano Mansanet, Alcobendas (ES); Esteban Dominguez-Manzanares, Alcobendas (ES); Ana Maria Escribano, Alcobendas (ES); Maria Carmen Fernandez, Alcobendas (ES); William Joseph Hornback, Fishers, IN (US); Alma Maria Jimenez-Aguado, Alcobendas (ES); Eric George Tromiczak, Carmel, IN (US); Zhipei Wu, Noblesville, IN (US); Hamideh Zarrinmayeh, Carmel, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/596,419

(22) PCT Filed: Jan. 5, 2005

(86) PCT No.: PCT/US2005/000004

§ 371 (c)(1),
(2), (4) Date: Jun. 13, 2006

(87) PCT Pub. No.: WO2005/070916

PCT Pub. Date: Aug. 4, 2005

(65) Prior Publication Data

US 2007/0105852 A1    May 10, 2007

Related U.S. Application Data

(60) Provisional application No. 60/552,080, filed on Mar. 10, 2004.

(30) Foreign Application Priority Data

Jan. 9, 2004    (EP) .................................. 04380005

(51) Int. Cl.
C07D 333/38 (2006.01)
(52) U.S. Cl. ....................................................... 549/61
(58) Field of Classification Search .................... 549/61
See application file for complete search history.

(56) References Cited

U.S. PATENT DOCUMENTS 6,835,745 B2 * 12/2004 Coghlan et al. ............. 514/448

FOREIGN PATENT DOCUMENTS

| EP | 0273602 A | * | 2/1987 |
| EP | 0273602 | * | 12/1987 |
| EP | 0273602 A | | 7/1988 |
| WO | WO 0132604 | * | 5/2001 |

OTHER PUBLICATIONS

Augustin et al. Tetrahedron, 32(24), 3055-61, 1976).*
Reux et al. (Sulfur Letters, 13(5), 197-202, 1991).*
Reux, D. et al., Cyclization of 3-(alkylthio)-1,1,3-tricyano-1-propenes to thiophenes, Sulfur Letters, 1991, 197-202, 13(5).
Augustin, M. et al., Thiophenes trhough S-alkylation, Tetrahedron, 1976, 3055-61, 32(24).
Dehne and Krey, Pharmazie, 1978, 687 33(10).
Luteijn, J. M. et al., The Synthesis Of 2-(Alkylthio)- And 2-(Arylthio)-3cyanoththiophenes. The Nucleophilic Displacement Of The Alkylsulfinyl Group By Thiols, Tetrahedron, 1988, 5921, 44(18).
Ito, I. et al., Allosteric Potentiation Of Quisqualate Receptors By A Nootropic Drug Aniracetam, J. Physiology, 1990, 533-543, 424.
Ornstein, Paul L., Biarylpropylsulfonamides as Novel, Potent Potentiators of 2-Amino-3-(5-methyl-3-hydroxyisoxazol-4-yl)-propanoic Acid (AMPA) Receptors, J. Med. Chem, 2000, 4354,43.

* cited by examiner

*Primary Examiner*—D. Margaret Seaman
*Assistant Examiner*—Nizal S Chandrakumar
(74) *Attorney, Agent, or Firm*—Tonya L. Combs

(57) ABSTRACT

The present invention relates to thiophene and furan compounds and their pharmaceutically acceptable salts, and further relates to their use in treating schizophrenia, cognitive deficits associated with schizophrenia, Alzheimer's disease, dementia of the Alzheimer's type, mild cognitive impairment, or depression.

5 Claims, No Drawings

THIOPHENE AND FURAN COMPOUNDS

This is the national phase application, Under 35 USC 371, for PCT/US2005/000004, filed Jan. 5, 2005, which claims the benefit, under 35 USC 119(e), of EP provisional application number 04380005.1, filed Sep. 1, 2004, and U.S. provisional application Ser. No. 60/552,080, filed Mar. 10, 2004.

BACKGROUND OF THE INVENTION

Glutamate is the major excitatory neurotransmitter in the central nervous system. Three glutamate receptor ion channel subtypes have been identified based on their sensitivity to the selective activators (agonists) N-methyl-D-aspartate (NMDA), α-amino-3-hydroxy-5-methyl-4-isoxazole propionic acid (AMPA), and kainate.

AMPA receptors mediate cellular responses to glutamate by direct and indirect mechanisms. When activated by glutamate or AMPA, AMPA receptor ion channels allow sodium ions ($Na^+$) and calcium ions ($Ca^{2+}$) to pass directly through the channel pore. In addition, AMPA receptor ion channels can facilitate the activation of NMDA receptors by initiating cellular depolarization that relieves magnesium ion ($Mg^{2+}$)-dependent block of NMDA receptors.

Multiple AMPA receptor subtypes have been identified and cloned: GluR1, GluR2, GluR3, and GluR4 as disclosed by Hollmann and Heinemann, *Ann. Rev. Neurosci.,* 17, 31-108 (1994). Each subunit consists of a sequence of approximately 900 amino acids. Four subunits are thought to assemble to form a tetrameric ion channel complex with the functional properties of this ion channel most likely being determined by its subunit composition.

Ion channel currents activated by glutamate via AMPA receptors are transient. The time course of currents is modified by refractory states caused during glutamate binding which is referred to as desensitization and by the rate of glutamate removal from the ion channel binding site which results in deactivation. Ion influx through AMPA receptors may be enhanced by compounds that either prevent desensitization or by compounds that slow deactivation rates. Compounds that enhance glutamate-stimulated ion influx at AMPA receptors are known as positive AMPA receptor allosteric modulators or AMPA receptor potentiators. One such compound, which selectively potentiates AMPA receptor function, is cyclothiazide. Since AMPA receptors play a pivotal role in mediating fast excitatory transmission in the central nervous system, molecules that enhance AMPA receptor function have multiple therapeutic targets.

Compounds that allosterically potentiate AMPA receptors have been shown to enhance synaptic activity in vitro and in vivo as disclosed, for example, by I. Ito, et al., *J. Physiol.,* 424, 533-543 (1990) and A. Copani, et al., *Journal of Neurochemistry,* 58, 1199-1204 (1992). Such compounds have also been shown to enhance learning and memory in rats, monkeys, and humans, and are reviewed by Gouliaev and Senning, *Brain Research Reviews,* 19, 180-222 (1994).

International Patent Application Publication WO 98/33496 published Aug. 6, 1998 discloses certain sulfonamide derivatives which are useful, for example, for treating psychiatric and neurological disorders, for example cognitive disorders, Alzheimer's disease, age-related dementias, age-induced memory impairment, tardive dyskinesia, Huntington's chorea, myoclonus, Parkinson's disease, reversal of drug-induced states (such as cocaine, amphetamines, alcohol-induced states), depression, attention deficit disorder, attention deficit hyperactivity disorder, psychosis, cognitive deficits associated with psychosis, and drug-induced psychosis. P. L. Ornstein, et al. *J. Med. Chem.,* 43, 4354 (2000) further disclose biarylpropylsulfonamides which are potent potentiators of AMPA receptors. In addition, X. Li, et al., *Neuropharmacology,* 40, 1028 (2001) disclose antidepressant-like actions of an AMPA receptor potentiators. D. D. Schoepp, et al. and Tizzano, et al., *Society for Neuroscience Abstracts,* 26(1-2), 528.19 and 528.20, 30th Annual Meeting, New Orleans, (Nov. 4-9, 2000) disclose an orally active AMPA receptor potentiator that enhances spatial learning and memory performance in rats, and reverses both pharmacologically and age-associated learning and memory deficit in rats.

European Patent No. 0 273 602 discloses substituted 3-cyanothiophenes which are useful as herbicides. In addition, Luteijn and Wals, *Tetrahedron,* 44(18), 5921 (1988) disclose the synthesis of certain 3-cyanothiophenes, and Dehne and Krey, *Pharmazie,* 33(10), 687 (1978) disclose certain 4-phenyl-3-cyanothiophene derivatives.

SUMMARY OF THE INVENTION

The present invention provides compounds of Formula I:

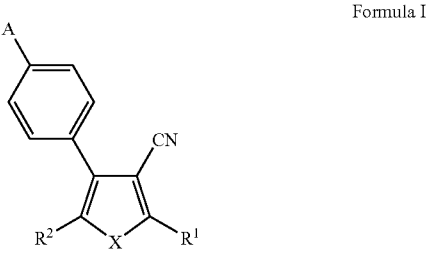

Formula I wherein

X represents S or O;

$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, —$SO_2$(1-4C)alkyl, —C(=O)(1-3C) alkyl, $NH_2$, —NH(1-4C)alkyl, —N[(1-4C)alkyl]$_2$, —NH (4-7C)cycloalkyl, or —N[(1-4C)alkyl]($CH_2$)$_r$N[(1-4C) alkyl]$_2$;

$R^2$ represents —CN, —$CO_2H$, —C(=O)NHR$^{13}$; —C(=O) NHOH, —C(=O)NHCN, —$SO_2OH$, —$SO_2$NH(1-4C) alkyl, —C(=O)NHSO$_2$(1-4C)alkyl, —PH(=O)(OH), —P(=O)(OH)$_2$, —P(=O)(OH)NH$_2$, —P(=O)(OH)CH [(1-4C)alkoxy]$_2$, —C(=O)NHSO$_2$CF$_3$, —C(=O) NHSO$_2$CH$_2$CF$_3$,

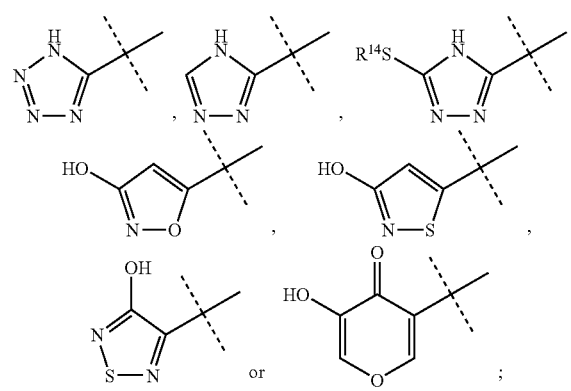

R⁴ represents hydrogen, OH, —CH₂OH, —CH₂O(1-4C) alkyl, F, Cl, CF₃, OCF₃, —CN, NO₂, NH₂, -(1-4C)alkyl, -(1-4C)alkoxy, —C(=O)NH(1-4C)alkyl, —C(=O)NH₂, —NHC(=O)(1-4C)alkyl, —(CH₂)$_m$NHSO₂R¹⁰, —(CH₂)$_n$ CN, —(CH₂)$_m$CO₂H, —(CH₂)$_m$CO₂(1-6C) alkyl, —C(=O)H, —C(=O)(1-4C)alkyl, —NH(1-4C) alkyl, —N[(1-4C)alkyl]₂, —SR¹⁰, —SOR¹⁰, —SO₂R¹⁰, SH, phenyl, or phenyl substituted with one or two substituents independently selected from the group consisting of F, Cl, Br, I, —CN, -(1-4C)alkyl, and -(1-4C)alkoxy;

R⁵ represents hydrogen; F, Cl, —CN, NO₂, NH₂, —(CH₂)$_m$NHSO₂R¹⁰, -(1-4C)alkyl, or -(1-4C)alkoxy;

R⁶ represents hydrogen, -(1-4C)alkyl, —SO₂R¹¹, or —C(=O)(1-4C)alkyl;

R⁷ represents hydrogen or -(1-4C)alkyl;

R⁸ represents hydrogen, F, Cl, Br, -(1-4C)alkyl, -(1-4C) alkoxy, NO₂, NH₂, —CN, —NHSO₂R¹¹, or —C(=O)(1-4C)alkyl;

R⁸ᵃ represents hydrogen, F, Cl, Br, -(1-4C)alkyl, NO₂, NH₂, NH(1-6C)alkyl, N[(1-6C)alkyl]₂, —C(=O)NH₂, —CN, —CO₂H, —S(1-4C)alkyl, —NHCO₂(1-4C)alkyl, or —C(=O)(1-4C)alkyl;

R¹⁰, R¹¹, and R¹² each independently represent -(1-4C)alkyl, —(CH₂)₃Cl, phenyl, —CH₂phenyl, or —(CH₂)₂phenyl, wherein phenyl, as used in substituent R¹⁰, R¹¹ or R¹², is unsubstituted or substituted with F, Cl, Br, CF₃, -(1-4C) alkyl, or -(1-4)alkoxy;

R¹³ represents hydrogen, -(1-4C)alkyl, —CH₂CF₃, triazole, or tetrazole;

R¹⁴ represents -(1-4C)alkyl;

R¹⁵ represents hydrogen or -(1-4C)alkyl;

m represents 0, 1, 2, or 3;

n represents 1, 2, 3, or 4;

p represents 1 or 2;

r represents 1 or 2; and

A is selected from the group consisting of —OH, Br, I, —(CH₂)$_m$CN, —C(CH₃)₂CN, NO₂, NH₂, —O(CH₂)$_n$NH₂, —O(CH₂)$_n$NHSO₂(1-4C)alkyl, —O(CH₂)$_n$SO₂(1-4C)alkyl, —C(=O)NH(CH₂)$_r$NHSO₂(1-4C)alkyl, —S(1-4C)alkyl, -(1-6C)alkyl, -(1-4C)alkoxy, -(2-4C)alkenyl, -(2-4C)alkenyloxy, —CO₂H, —CO₂(1-4C)alkyl, —CHO, —C(=O)(1-4C)alkyl, —C(=O)NH₂, —C(=O) NH(1-6C)alkyl, —C(=O)NR¹⁵(CH₂)$_m$phenyl wherein phenyl is unsubstituted or substituted with one or two substituents independently selected from the group consisting of OH, F, Cl, Br, I, NO₂, NH₂, —NHSO₂(1-4C) alkyl, —CN, -(1-4C)alkyl, and -(1-4C)alkoxy; —OSO₂CF₃, —O(CH₂)$_n$CN, —NHC(=O)(1-4C)alkyl, —NHC(=O)(CH₂)$_m$phenyl wherein phenyl is unsubstituted or substituted with one or two substituents independently selected from the group consisting of OH, F, Cl, Br, I, NO₂, NH₂, CN, -(1-4C)alkyl and -(1-4C)alkoxy; —(CH₂)$_m$NHSO₂R¹², —CH(CH₃)(CH₂)$_p$NHSO₂R¹², —(CH₂)$_p$CH(CH₃)NHSO₂R¹², —NH(CH₂)$_m$phenyl wherein phenyl is unsubstituted or substituted with one or two substituents independently selected from the group consisting of OH, F, Cl, Br, I, NO₂, NH₂, CN, -(1-4C)alkyl, and -(1-4C)alkoxy; —NH(1-4C)alkyl, —N[(1-4C)alkyl]₂, —C(=O)NH(3-6C)cycloalkyl, —C(=O)NH(CH₂)$_n$N[(1-4C)alkyl]₂, —C(=O)NH(CH₂)$_n$NH(1-4C)alkyl, —(CH₂)$_n$NH₂, —O(CH₂)$_n$SR¹⁴, —O(CH₂)$_n$OR¹⁴, —(CH₂)$_n$NHR¹², —(CH₂)$_n$NH(3-6C)cycloalkyl, —(CH₂)$_n$N[(1-4C)alkyl]₂, —NHC(=O)NHR¹², —NHC(=O)N[(1-4C)alkyl]₂,

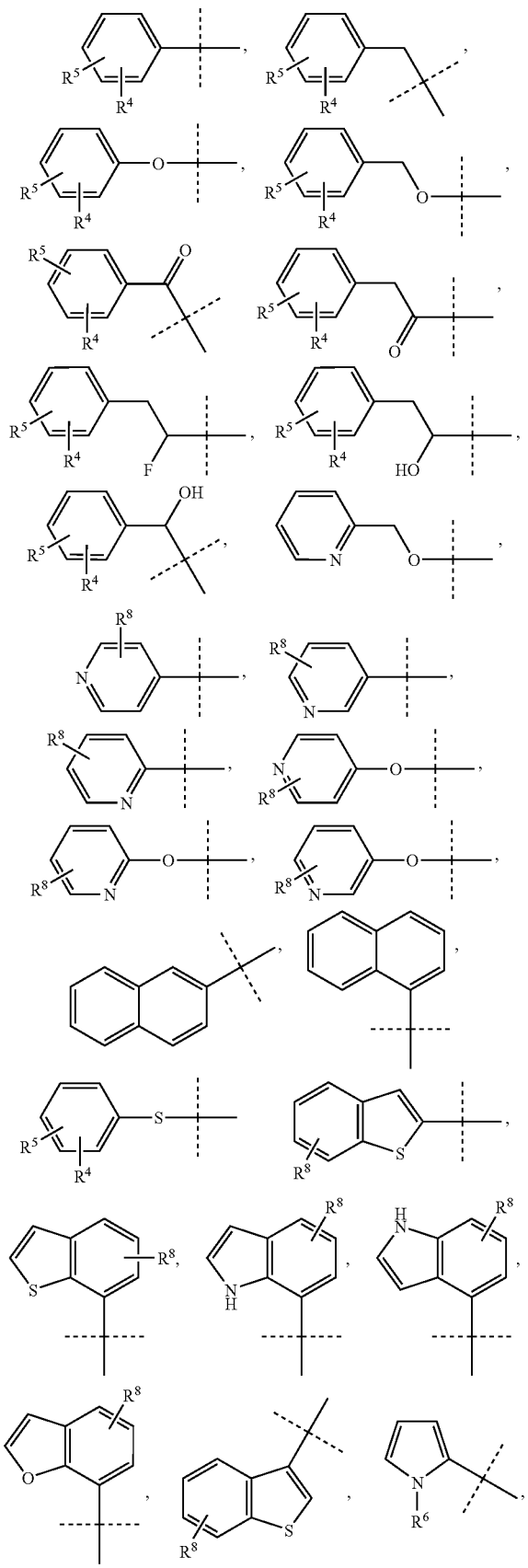

-continued

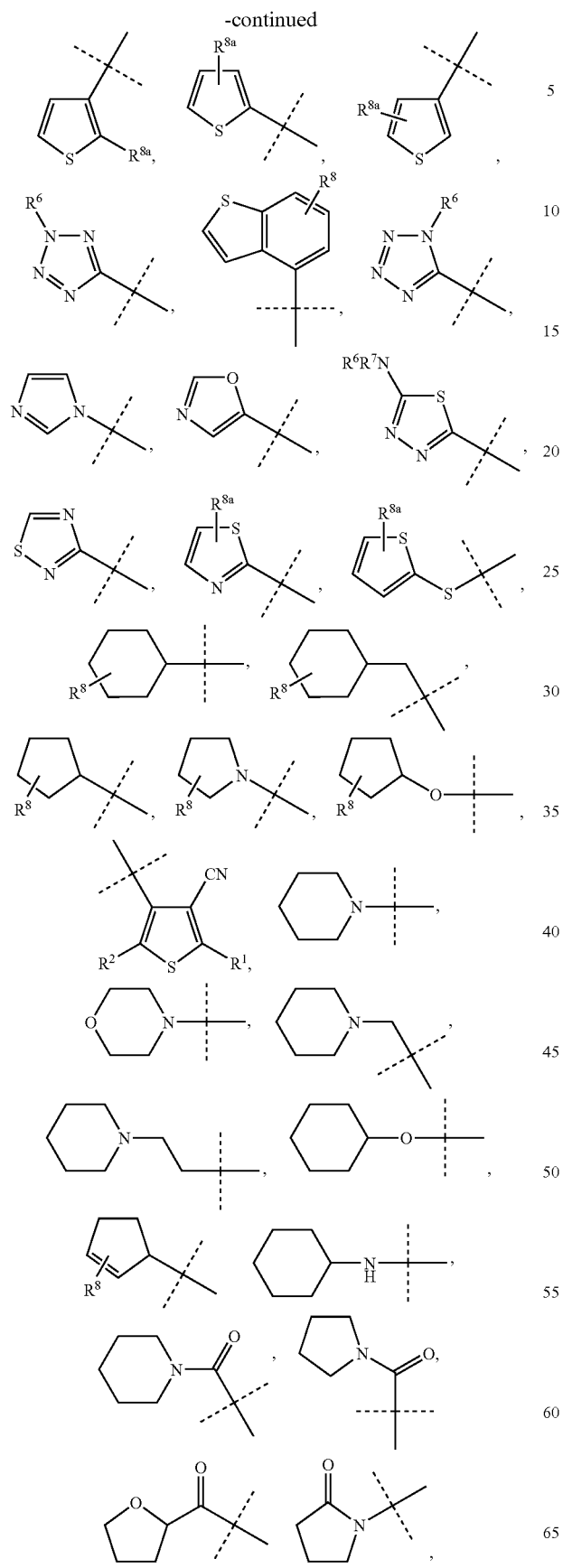

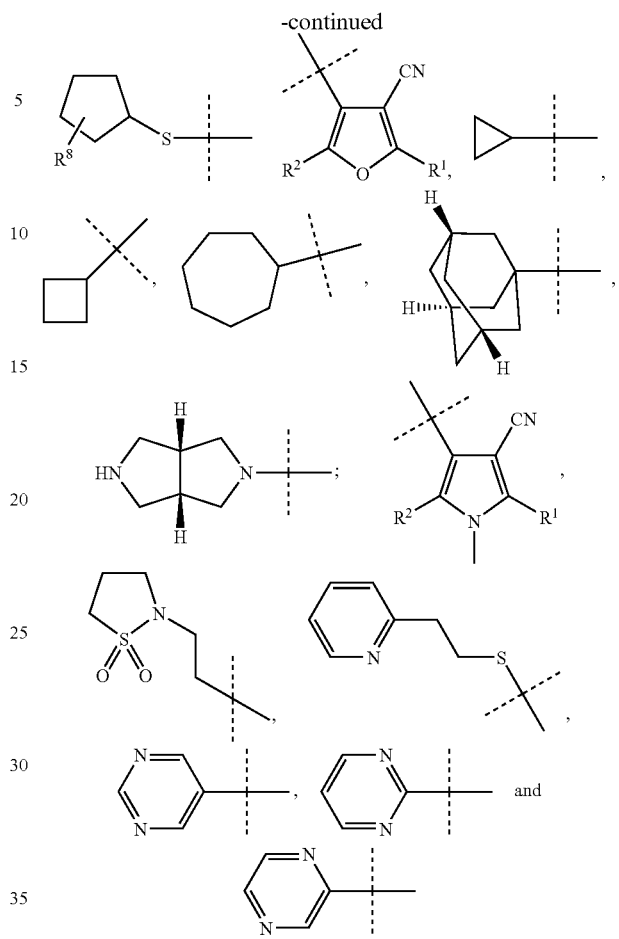

and the pharmaceutically acceptable salts thereof.

The present invention further provides compounds of Formula II:

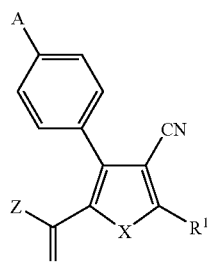

Formula II wherein

X represents S or O;

$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, —$SO_2$(1-4C)alkyl, —C(=O)(1-3C)alkyl, $NH_2$, —NH(1-4C)alkyl, —N[(1-4C)alkyl]$_2$, or —NH(4-7C)cycloalkyl;

Z represents —O-(1-6C)alkyl, —O-(2-4C)alkenyl, —O-(1-6C)alkylaryl, —O-(1-6C)alkyl(3-6C)cycloalkyl, —O-(1-6C)alkyl-N,N-(1-6C)dialkylamine, —O-(1-6C)alkyl-pyrrolidine, —O-(1-6C)alkyl-piperidine, —O-(1-6C)alkyl-morpholine, or NH(1-6C)alkyl;

$R^4$ represents hydrogen, OH, —CH$_2$OH, —CH$_2$O(1-4C)alkyl, F, Cl, CF$_3$, OCF$_3$, —CN, NO$_2$, NH$_2$, -(1-4C)alkyl, -(1-4C)alkoxy, —C(=O)NH(1-4C)alkyl, —NHC(=O)(1-4C)alkyl, —(CH$_2$)$_m$NHSO$_2$R$^{10}$, —(CH$_2$)$_n$CN, —(CH$_2$)$_m$CO$_2$H, —(CH$_2$)$_m$CO$_2$(1-6C)alkyl, —C(=O)H, —C(=O)(1-4C)alkyl, —NH(1-4C)alkyl, —N[(1-4C)alkyl]$_2$, —SR$^{10}$, —SOR$^{10}$, —SO$_2$R$^{10}$, SH, phenyl, or phenyl substituted with one or two substituents independently selected from the group consisting of F, Cl, Br, I, —CN, -(1-4C)alkyl, and -(1-4C)alkoxy;

$R^5$ represents hydrogen; F, Cl, —CN, NO$_2$, NH$_2$, —(CH$_2$)$_m$NHSO$_2$R$^{10}$, -(1-4C)alkyl, or (1-4C)alkoxy;

$R^6$ represents hydrogen, -(1-4C)alkyl, —SO$_2$R$^{11}$, or C(=O)(1-4C)alkyl;

$R^7$ represents hydrogen or -(1-4C)alkyl;

$R^8$ represents hydrogen, F, Cl, Br, -(1-4C)alkyl, NO$_2$, NH$_2$, —CN, —NHSO$_2$R$^{11}$, or —C(=O)(1-4C)alkyl;

$R^{8a}$ represents hydrogen, F, Cl, Br, -(1-4C)alkyl, NO$_2$, NH$_2$, —CN, —S(1-4C)alkyl, or —C(=O)(1-4C)alkyl;

$R^{10}$, $R^{11}$, and $R^{12}$ each independently represent -(1-4C)alkyl, phenyl, —CH$_2$phenyl, or —(CH$_2$)$_2$phenyl, wherein phenyl, as used in substituent $R^9$, $R^{10}$, $R^{11}$ or $R^{12}$, is unsubstituted or substituted with F, Cl, Br, CF$_3$, -(1-4C)alkyl, or -(1-4)alkoxy;

$R^{15}$ represents hydrogen or -(1-4C)alkyl;

m represents 0, 1, 2, or 3;

n represents 1, 2, 3, or 4;

p represents 1 or 2; and

A is selected from the group consisting of I, —(CH$_2$)$_m$CN, NO$_2$, NH$_2$, -(1-6C)alkyl, -(1-4C)alkoxy, -(2-4C)alkenyl, -(2-4C)alkenyloxy, —CO$_2$H, —CO$_2$(1-4C)alkyl, —CHO, —C(=O)(1-4C)alkyl, —C(=O)NH$_2$, —C(=O)NH(1-6C)alkyl, —C(=O)NR$^{15}$(CH$_2$)$_m$phenyl wherein phenyl is unsubstituted or substituted with one or two substituents independently selected from the group consisting of OH, F, Cl, Br, I, NO$_2$, NH$_2$, —NHSO$_2$(1-4C)alkyl, —CN, -(1-4C)alkyl and -(1-4C)alkoxy; —OSO$_2$CF$_3$, —O(CH$_2$)$_n$CN, —NHC(=O)(1-4C)alkyl, —NHC(=O)(CH$_2$)$_m$phenyl wherein phenyl is unsubstituted or substituted with one or two substituents independently selected from the group consisting of OH, F, Cl, Br, I, NO$_2$, NH$_2$, —CN, -(1-4C)alkyl and -(1-4C)alkoxy; —(CH$_2$)$_m$NHSO$_2$R$^{12}$, —CH(CH$_3$)(CH$_2$)$_p$NHSO$_2$R$^{12}$, —(CH$_2$)$_p$CH(CH$_3$)NHSO$_2$R$^{12}$, —NH(CH$_2$)$_m$phenyl wherein phenyl is unsubstituted or substituted with one or two substituents independently selected from the group consisting of OH, F, Cl, Br, I, NO$_2$, NH$_2$, —CN, -(1-4C)alkyl, and -(1-4C)alkoxy; —NH(1-4C)alkyl, —N[(1-4C)alkyl]$_2$, —C(=O)NH(3-6C)cycloalkyl, —C(=O)NH(CH$_2$)$_n$N[(1-4C)alkyl]$_2$, —C(=O)NH(CH$_2$)$_n$NH(1-4C)alkyl, —(CH$_2$)$_n$NH$_2$, —O(CH$_2$)$_n$SR$^{14}$, —O(CH$_2$)$_n$OR$^{14}$, —(CH$_2$)$_n$NHR$^{12}$, —(CH$_2$)$_n$NH(3-6C)cycloalkyl, —(CH$_2$)$_n$N[(1-4C)alkyl]$_2$, —NHC(=O)NHR$^{12}$, —NHC(=O)N[(1-4C)alkyl]$_2$,

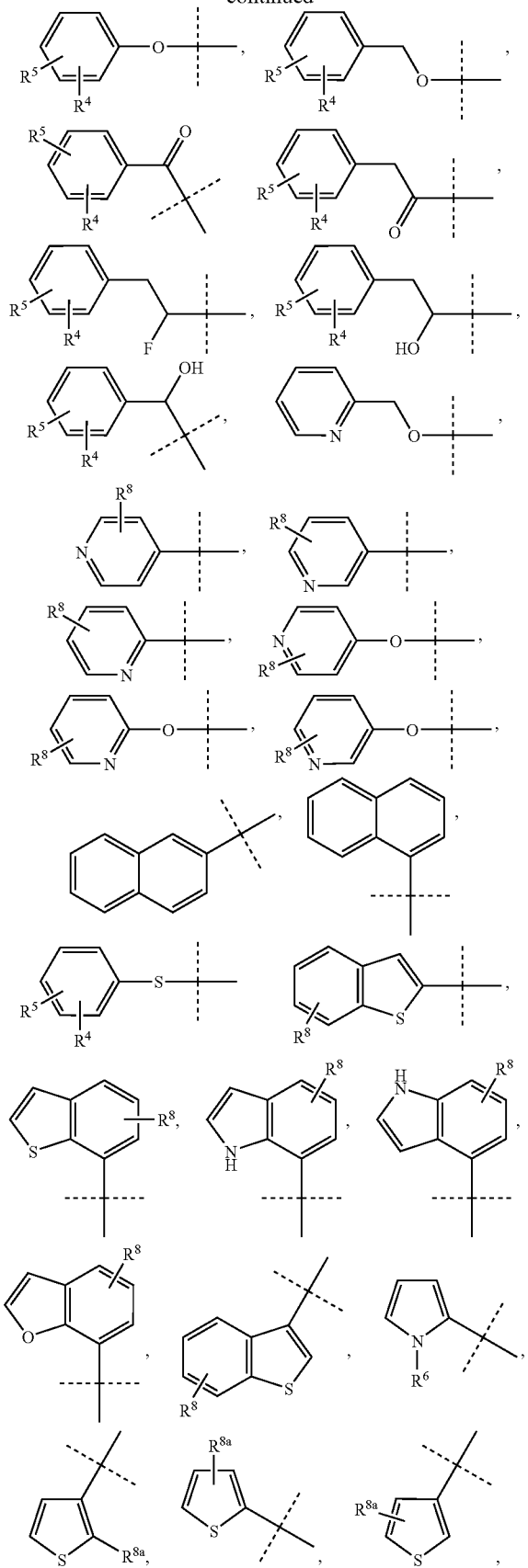

-continued

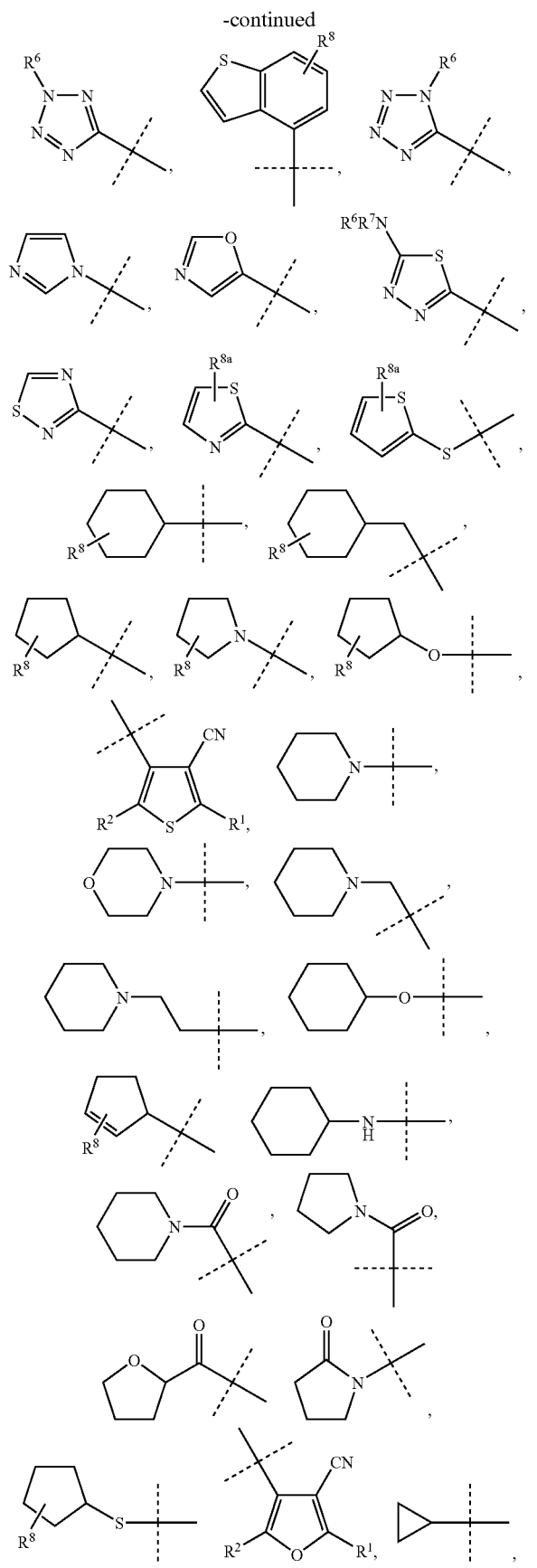

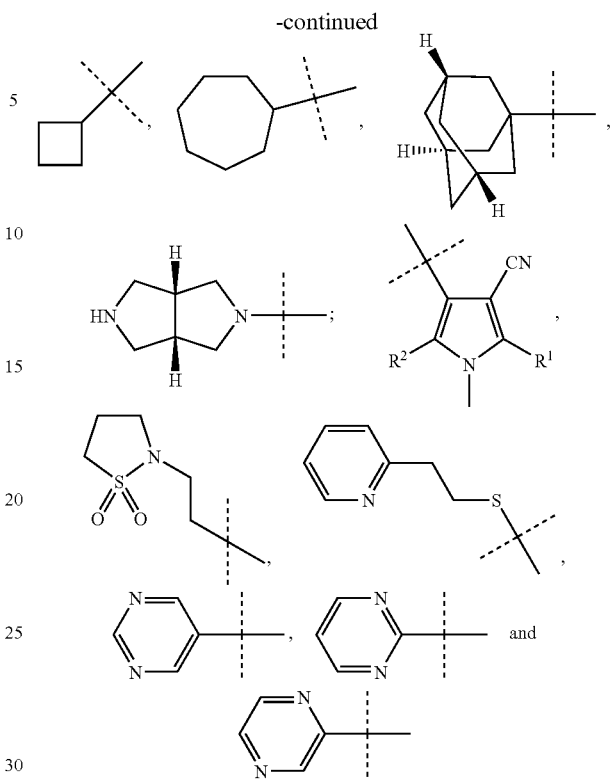

and the pharmaceutically acceptable salts thereof.

It is appreciated by one of ordinary skill in the art that compounds of Formula II encompass both useful intermediates for the preparation of compounds of Formula I and also prodrugs of Formula I.

The present invention further provides a method of potentiating glutamate receptor function in a patient, which comprises administering to said patient an effective amount of a compound of Formula I.

In addition, the present invention further provides a method of treating schizophrenia, cognitive deficits associated with schizophrenia, Alzheimer's disease, dementia of the Alzheimer's type, mild cognitive impairment, Parkinson's disease, or depression, in a patient, which comprises administering to said patient an effective amount of a compound of Formula I or Formula II.

According to another aspect, the present invention provides the use of a compound of Formula I or Formula II, or a pharmaceutically acceptable salt thereof, for the manufacture of a medicament for treating schizophrenia, cognitive deficits associated with schizophrenia, Alzheimer's disease, dementia of the Alzheimer's type, mild cognitive impairment, Parkinson's disease, or depression.

In addition, the present invention provides the use of a compound of Formula I or Formula II, or a pharmaceutically acceptable salt thereof, for treating schizophrenia, cognitive deficits associated with schizophrenia, Alzheimer's disease, dementia of the Alzheimer's type, mild cognitive impairment, Parkinson's disease, or depression.

The invention further provides pharmaceutical compositions comprising, a compound of Formula I, or a pharmaceutically acceptable salt thereof, and a pharmaceutically acceptable carrier, diluent, or excipient.

The invention further provides pharmaceutical compositions comprising, a compound of Formula II, or a pharmaceutically acceptable salt thereof, and a pharmaceutically acceptable diluent or carrier.

This invention also encompasses novel intermediates used in the preparation of compounds of Formula I and Formula II, prodrugs of the compounds of Formula I, and processes for the synthesis of the compounds of Formula I and Formula II.

In addition, the present invention provides a pharmaceutical composition which comprises a first component which is a compound of Formula I or Formula II, or a pharmaceutically acceptable salt thereof, and a second component which is an antipsychotic.

The present invention provides a pharmaceutical composition which comprises a first component which is a compound of Formula I or Formula II, or a pharmaceutically acceptable salt thereof, and a second component which is an antidepressant.

In addition, the present invention provides a pharmaceutical composition which comprises a first component which is a compound of Formula I or Formula II, or a pharmaceutically acceptable salt thereof, and a second component which is a drug useful in treating a cognitive disorder.

The invention further provides a method for treating a patient suffering from or susceptible to schizophrenia or cognitive deficits associated with schizophrenia comprising administering to said patient an effective amount of a first component which is a compound of Formula I or Formula II, or a pharmaceutically acceptable salt thereof, in combination with an effective amount of a second component which is an antipsychotic.

The invention further provides a method for treating a patient suffering from or susceptible to depression, comprising administering to said patient an effective amount of a first component which is a compound of Formula I or Formula II, or a pharmaceutically acceptable salt thereof, in combination with an effective amount of a second component which is an antidepressant.

The invention further provides a method for treating a patient suffering from or susceptible to a cognitive disorder, comprising administering to said patient an effective amount of a first component which is a compound of Formula I or Formula II, or a pharmaceutically acceptable salt thereof, in combination with an effective amount of a second component which is a drug useful in treating a cognitive disorder.

DETAILED DESCRIPTION OF THE INVENTION

As used herein the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by compounds of Formula I or Formula II, and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; dementia of the Alzheimer's type, age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, Parkinson's disease; reversal of drug-induced states (such as cocaine, amphetamines, alcohol-induced states); depression; attention deficit disorder; attention deficit hyperactivity disorder; psychosis such as schizophrenia; cognitive deficits associated with psychosis such as schizophrenia, drug-induced psychosis, stroke, and sexual dysfunction. Compounds of Formula I or Formula II may also be useful for improving memory (both short term and long term) and learning ability. The present invention provides the use of compounds of Formula I and Formula II for the treatment of each of these conditions.

It is understood by one of ordinary skill in the art that cognition includes various "domains". These domains include short-term memory, long term memory, working memory, executive function, and attention. As used herein the term "cognitive disorder" is meant to encompass any disorder characterized by a deficit in one or more of the cognitive domains, including but not limited to short term memory, long term memory, working memory, executive function, and attention. It is further understood that the term "cognitive disorder" includes, but is not limited to the following specific disorders: age-related cognitive decline, mild cognitive impairment, Alzheimer's disease, dementia, dementia of the Alzheimer's type, Parkinson's dementia, Lewy Body dementia, substance-induced persisting dementia, alcohol-induced persisting dementia, alcohol-induced cognitive impairment, AIDS-induced dementia, learning disorders, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, cognitive deficits associated with amylotrophic lateral sclerosis, and cognitive deficits associated with multiple sclerosis.

The fourth edition of the Diagnostic and Statistical Manual of Mental Disorders (DSM-IV) (1994, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV and that terminology and classification systems evolve with medical scientific progress.

As used herein the term "a drug useful in treating a cognitive disorder" includes, but is not limited to acetylcholinesterase inhibitors, NMDA receptor antagonists, 5-$HT_6$ antagonists, M1 agonists, serotonin reuptake inhibitors, norepinephrine reuptake inhibitors, selective norepinephrine reuptake inhibitors, combined serotonin-norepinephrine reuptake inhibitors, monoamine oxidase inhibitors, phosphodiesterase-4 inhibitors, tricyclic antidepressants, and AMPA receptor potentiators. More specifically, the term "a drug useful in treating a cognitive disorder" includes, but is not limited to the following compounds which are well known and readily available to one of ordinary skill in the art: donepezil, rivastigmine, galantamine, memantine, tacrine, phenserine, physostigmine, xanomeline, CX516, milameline, aniracetam, piracetam, oxiracetam, suritozole, fluoxetine, sertraline, citalopram, duloxetine, atomoxetine, venlafaxine, milnacipran, fluvoxamine, paroxetine, buproprion, reboxetine, imipramine, and rolipram.

As used herein the term "antidepressant" includes serotonin reuptake inhibitors, norepinephrine-serotonin reuptake inhibitors, selective norepinephrine reuptake inhibitors, and the like. For example, "antidepressant" includes fluoxetine, venlafaxine, citalopram, fluvoxamine, paroxetine, sertraline, milnacipran and duloxetine. Fluoxetine and duloxetine are preferred antidepressants.

As used herein the term "antipsychotic" includes typical and atypical antipsychotics. Thus, the term "antipsychotic" includes, for example, haloperidol, chlorpromazine, clozapine, risperidone, olanzapine, aripiprazole, ziprasidone, sertindole, amisulpride, zotepine, sulpiride, and quitiapine. Olanzapine is the preferred antipsychotic.

As used herein "fluoxetine" will be used to mean any acid addition salt or the free base, and to include either the racemic mixture or either of the R and S enantiomers. Fluoxetine hydrochloride is a preferred salt.

The following specific combinations are preferred:
Formula I/fluoxetine
Formula I/duloxetine
Formula I/paroxetine
Formula I/olanzapine
Formula I/risperidone
Formula I/aripiprazole
Formula I/sertindole
Formula I/quetiapine
Formula I/ziprasidone
Formula I/zotepine
Formula I/memantine
Formula I/donepezil
Formula I/rivastigmine
Formula I/galantamine,
Formula I/tacrine
Formula I/CX516
Formula I/atomoxetine
Formula II/fluoxetine
Formula II/duloxetine
Formula II/paroxetine
Formula II/olanzapine
Formula II/risperidone
Formula II/aripiprazole
Formula II/sertindole
Formula II/quetiapine
Formula II/ziprasidone
Forumla II/zotepine
Formula II/memantine
Formula II/donepezil
Formula II/rivastigmine
Formula II/galantamine,
Formula II/tacrine
Formula II/CX516
Formula II/atomoxetine The present invention includes the pharmaceutically acceptable salts of the compounds defined by Formula I and Formula II. A compound of this invention can possess a sufficiently acidic group, a sufficiently basic group, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above Formulas which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science,* 66, 2-19 (1977), which are known to the skilled artisan. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-napththalenesulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid. The HCl salt is most preferred.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein the term "prodrug" refers to compounds that are drug precursors, which following administration, release the drug in vivo via a chemical or physiological process. For example, a prodrug, on being brought to the physiological pH or through enzyme action, is converted to the desired drug form in vivo by enzymatic and/or chemical hydrolytic cleavage of an ester to provide the corresponding carboxylic acid drug.

Various forms of prodrugs are known to one of ordinary skill in the art. For examples of such prodrug derivatives, see *Design of Prodrugs,* edited by H. Bundgaard, (Elsevier, 1985); D. Fleisher, et al., *Advanced Drug Delivery Reviews,* 19, 115, (1996); H. Bundgaard, *Advanced Drug Delivery Reviews,* 8, 1-38 (1992); H. Bundgaard, et al., *Journal of Pharmaceutical Sciences,* 77, 285 (1988); and N. Kakeya, et al., *Chem Pharm Bull,* 32, 692 (1984).

Examples of prodrugs of Formula I are those that form in vivo cleavable esters or amides. An in vivo cleavable ester or amide is, for example, an ester or amide which is cleaved in the human or animal body to produce the parent acid of Formula Ia. The amide and ester moieties may incorporate other functional groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, *Advanced Drug Delivery Reviews* (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Medicinal Chemistry* (1996) 39, 10.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I and Formula II can be prepared by one of ordinary skill in the art utilizing well known techniques and processes, such as those disclosed by J. Jacques, et al., *"Enantiomers, Racemates, and Resolutions"*, John Wiley and Sons, Inc., 1981, and E. L. Eliel and S. H. Wilen," *Stereochemistry of Organic Compounds"*, (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120

As used herein the term "(1-6C)alkyl" refers to a straight or branched, monovalent, saturated aliphatic chain of 1 to 6 carbon atoms and includes, but is not limited to, methyl, ethyl, propyl, isopropyl, butyl, isobutyl, t-butyl, pentyl, isopentyl, and hexyl. The term "(1-6C)alkyl" includes within its definition the term "(1-4C)alkyl".

As used herein, the terms "Me", "Et", "Pr", "iPr", "Bu" and "t-Bu" refer to methyl, ethyl, propyl, isopropyl, butyl and tert-butyl respectively.

As used herein, the terms "Halo", "Halide" or "Hal" refers to a chlorine, bromine, iodine or fluorine atom, unless otherwise specified herein.

As used herein, the term "Ph" refers to a phenyl group.

As used herein the term "(2-4C)alkenyl" refers to a straight or branched, monovalent, unsaturated aliphatic chain having from two to four carbon atoms. Typical (2-4C)alkenyl groups include ethenyl (also known as vinyl), 1-methylethenyl, 1-methyl-1-propenyl, 1-butenyl, 2-methyl-2-propenyl, 1-propenyl, 2-propenyl, 2-butenyl, and the like.

As used herein the term "-(1-6C)alkoxy" refers to a straight or branched alkyl chain having from one to six carbon atoms attached to an oxygen atom. Typical -(1-6C)alkoxy groups include methoxy, ethoxy, propoxy, isopropoxy, butoxy, t-butoxy, pentoxy and the like. The term "-(1-6C)alkoxy" includes within its definition the term "-(1-4C)alkoxy".

As used herein the term "(2-4C)alkenyloxy" refers to a straight or branched unsaturated aliphatic chain having from two to four carbon atoms which is attached to an oxygen atom.

As used herein the term "(3-8C)cycloalkyl" refers to a saturated hydrocarbon ring structure containing from three to eight carbon atoms. Typical $C_3$-$C_8$ cycloalkyl groups include cyclopropyl, cyclobutyl, cyclopentyl, cyclohexyl, cycloheptyl, cyclooctyl, and the like. The term "(3-8C)cycloalkyl" includes within its definition the term "(4-7C)cycloalkyl" and "(3-6C)cycloalkyl".

As used herein the term "(1-20C)alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein the term "(2-6C)alkenyl" refers to a straight or branched, monovalent, unsaturated aliphatic chain having from two to six carbon atoms. Typical (2-6C)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the terms "aryl" or "Ar" refer to a carbocyclic or heterocyclic group which may contain one or more fused or non-fused phenyl rings and includes, for example, phenyl, biphenyl, 1- or 2-naphthyl, 1,2-dihydronaphthyl, 1,2,3,4-tetrahydronaphthyl, and the like. In addition, the aryl group may be substituted or unsubstituted as set forth herein. The terms "aryl" or "Ar" include, but are not limited to the following:

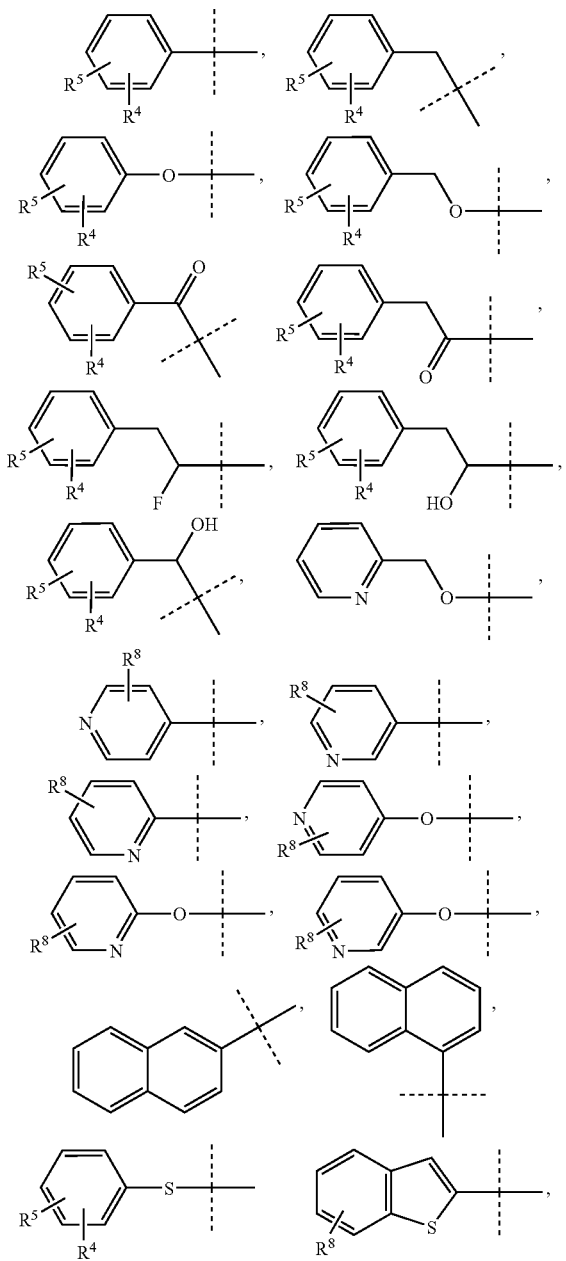

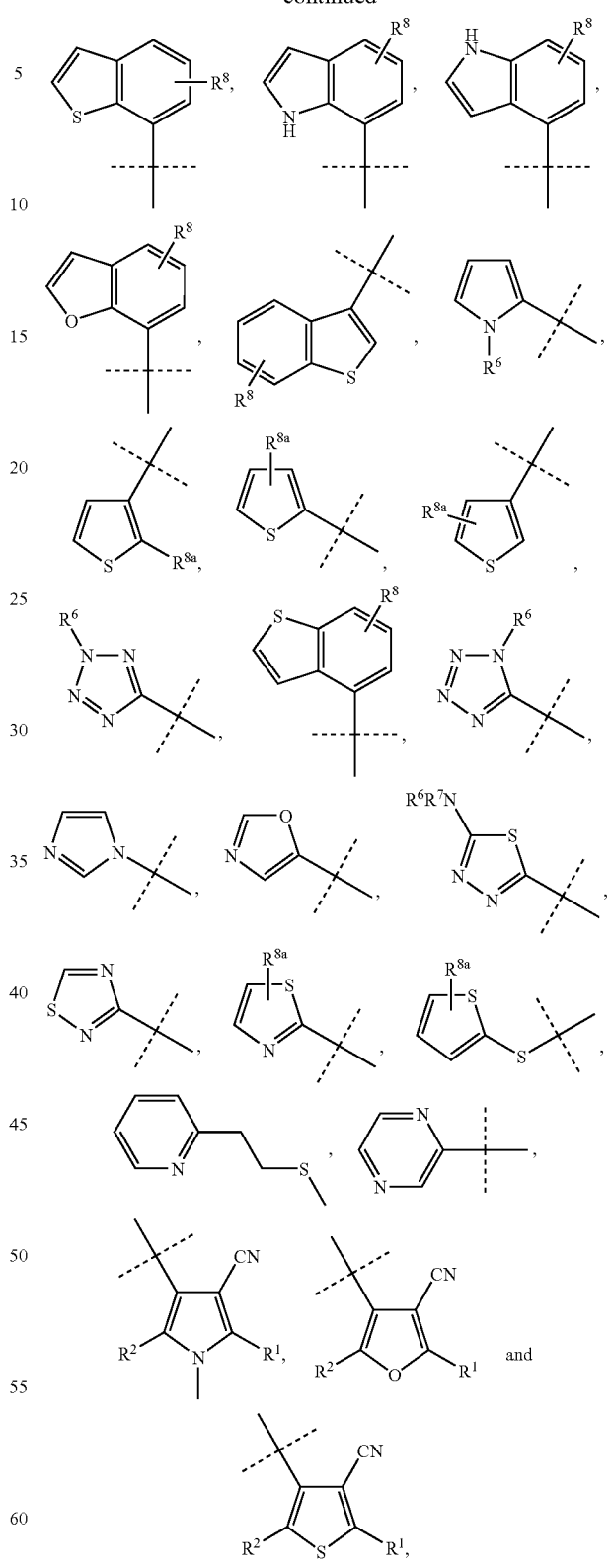

wherein the substitutents are as defined herein.

As used herein, the term "phenethyloxy" refers to the following structure:

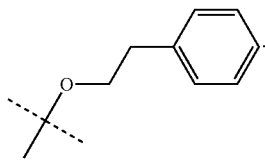

As used herein, the term "(1-6C)alkylaryl" includes the following:

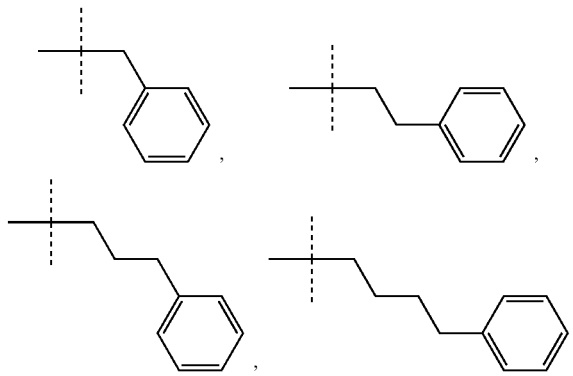

and the like.

As used herein, the term "-(1-6C)alkyl(3-8C)cycloalkyl" refers to a straight or branched, monovalent, saturated aliphatic chain of 1 to 6 carbon atoms which has a (3-8C) cycloalkyl attached to the aliphatic chain. Included within the term "-(1-6C)alkyl(3-8C)cycloalkyl" are the following:

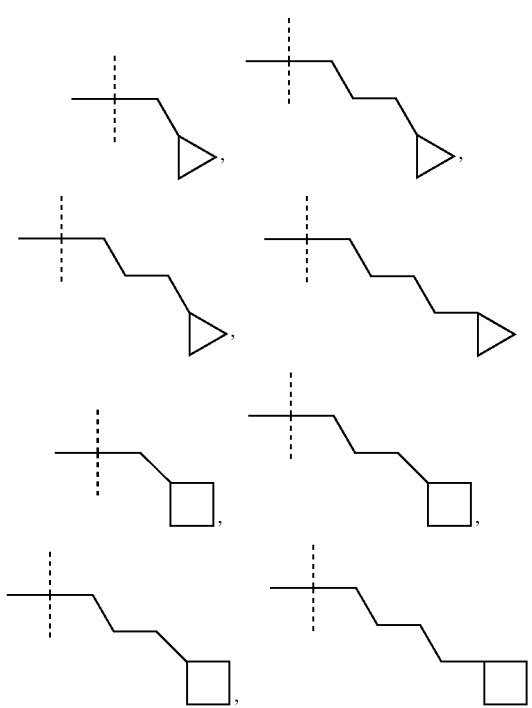

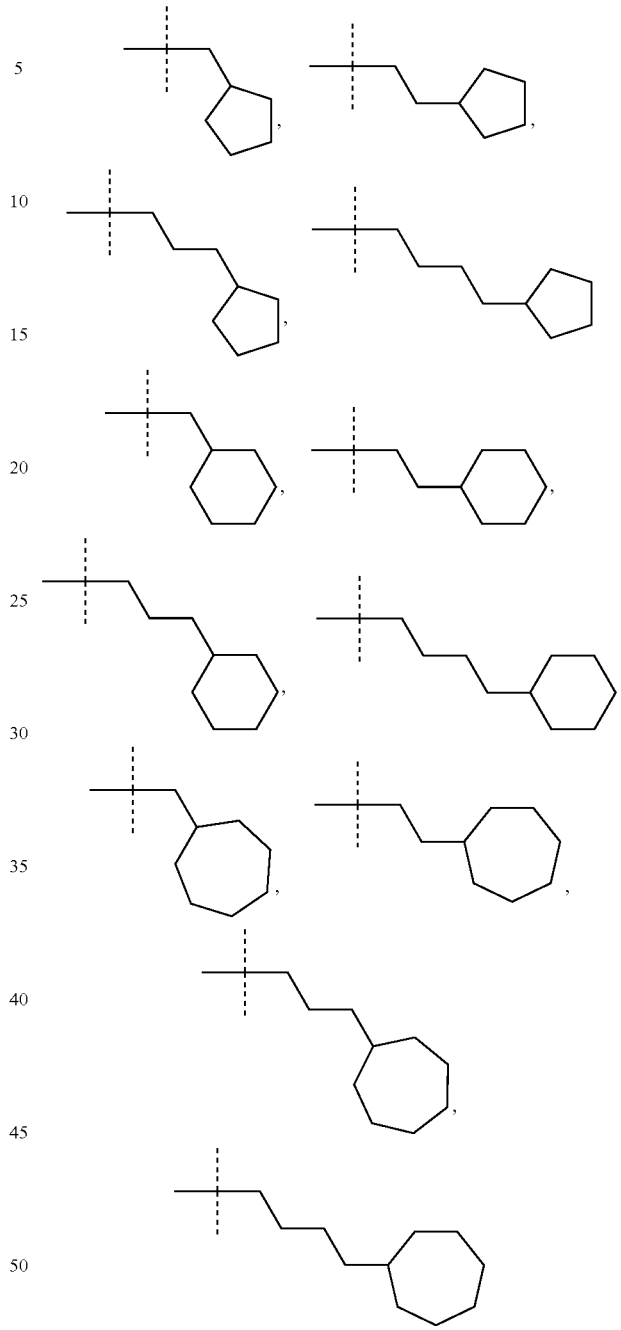

As used herein the term "N,N-(1-6C)dialkylamine" refers to a nitrogen atom substituted with two straight or branched, monovalent, saturated aliphatic chains of 1 to 6 carbon atoms. Included within the term "N,N-(1-6C)dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "-(1-6C)alkyl-N,N-(1-6C)dialkylamine" refers to straight or branched, monovalent, saturated aliphatic chain of 1 to 6 carbon atoms which has an N,N-(1-6C)dialkylamine attached to the aliphatic chain. Included within the term "-(1-6C)alkyl-N,N-(1-6C)dialkylamine" are the following:

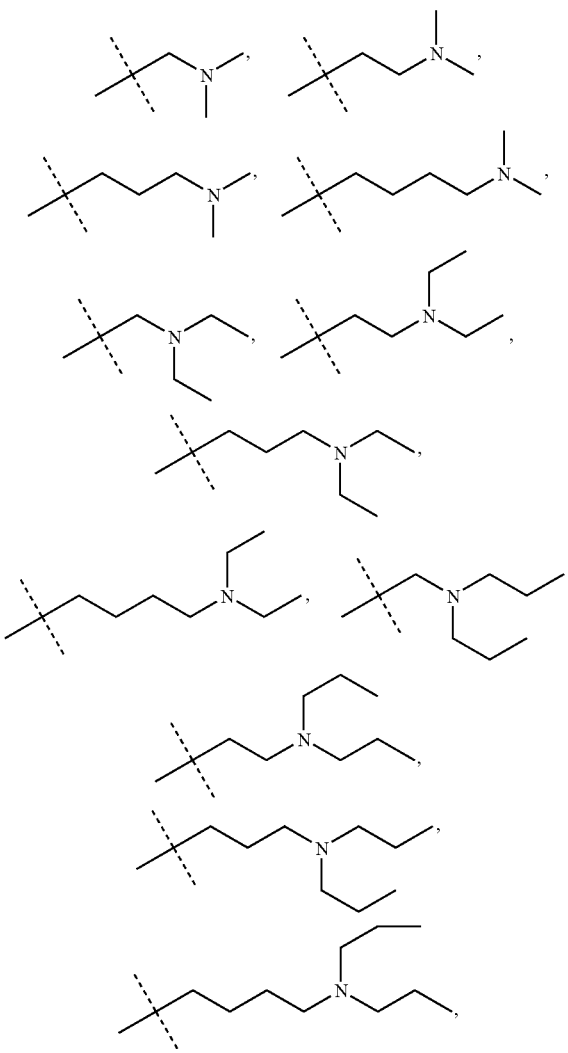

and the like.

As used herein the term "-(1-6C)alkyl-pyrrolidine" refers to a straight or branched, monovalent, saturated aliphatic chain of 1 to 6 carbon atoms which has a pyrrolidine attached to the aliphatic chain. Included within the scope of the term "-(1-6C)alkyl-pyrrolidine" are the following:

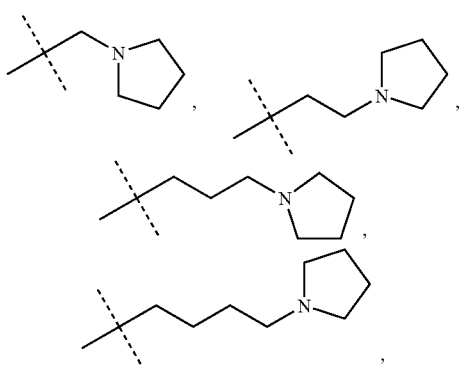

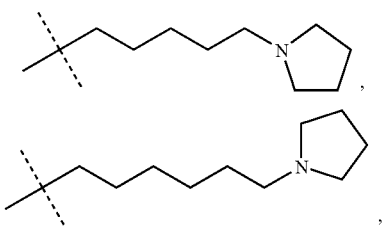

and the like.

As used herein the term "-(1-6C)alkyl-piperidine" refers to a straight or branched, monovalent, saturated aliphatic chain of 1 to 6 carbon atoms which has a piperidine attached to the aliphatic chain. Included within the scope of the term "-(1-6C)alkyl-piperidine" are the following:

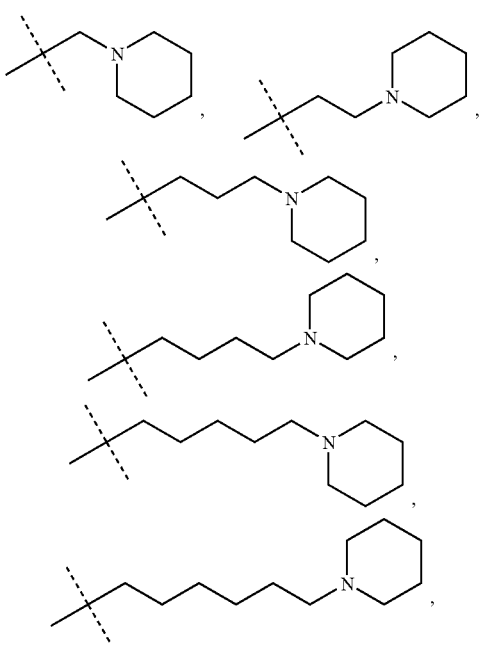

and the like.

As used herein the term "-(1-6C)alkyl-morpholine" refers to a straight or branched, monovalent, saturated aliphatic chain of 1 to 6 carbon atoms which has a morpholine attached to the aliphatic chain. Included within the scope of the term "-(1-6C)alkyl-morpholine" are the following:

-continued

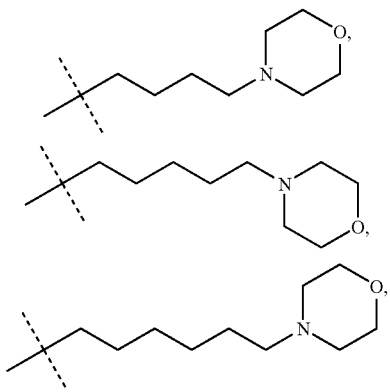

and the like.

As used herein the term "bis(pinacolato)diboron" refers to the following structure:

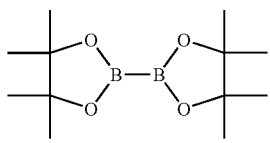

As used herein, the term "Hartwig's Ligand" refers to the following compound:

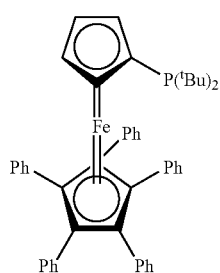

As used herein, "BINAP" refers to the following compound:

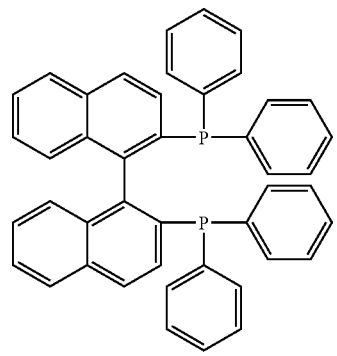

The compounds of Formula I and Formula II can be prepared by one of ordinary skill in the art following art recognized techniques and procedures. More specifically, compounds of Formula I and Formula II can be prepared as set forth in the schemes, methods, and examples set forth below. The reagents and starting materials are readily available to one of ordinary skill in the art. All substituents, unless otherwise specified, are as previously defined.

Scheme I

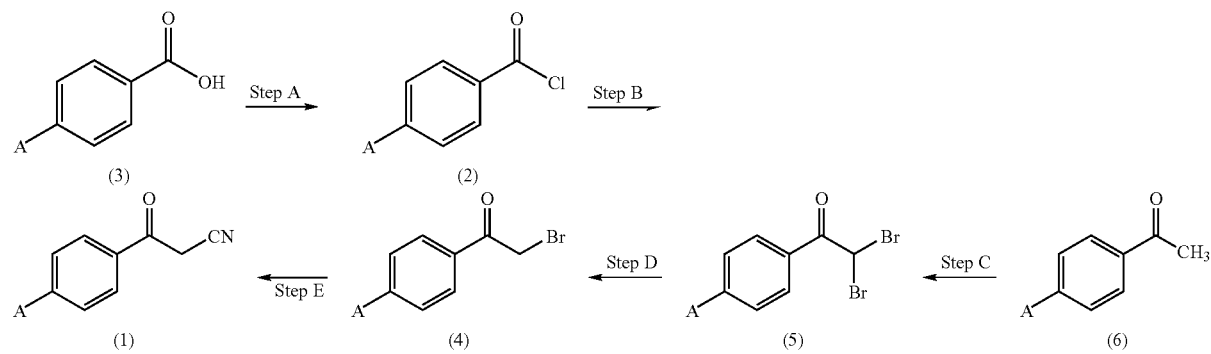

In Scheme I, step A, the suitable benzoic acid of structure (3) is combined with an acid chloride under conditions well known in the art to provide the benzoyl chloride of structure (2).

In Scheme I, step B, the benzoyl chloride of structure (2), is combined with cyanoacetic acid under conditions well known in the art to provide the propionitrile of structure (1) where A is as defined within. More specifically, butyllithium (4 molar excess) is added to a stirring solution of benzoyl chloride of structure (2) (2 molar excess) in a suitable solvent such as THF at about −78° C. The temperature is raised to about 0° C. and then cooled to about −78° C. The benzoyl chloride of structure (2) in a solution of THF is added dropwise. The reaction is allowed to rise to room temperature over a period of one hour. Hydrochloric acid is added and the propionitrile of structure (1) is isolated using techniques well known in the art. Commerically available benzoyl chlorides of structure (2) include but are not limited to methoxybenzoyl chloride, nitrobenzoyl chloride, iodobenzoyl chloride Alternatively, the propionitrile of structure (1) can be prepared by starting with the acetophenone of structure (6). In Scheme I, step C. The suitable acetophenone of structure (6) is dissolved in concentrated sulfuric acid and cooled to about 0° C. Bromine is then added and the reaction is allowed to warm to room temperature and stir for approximately 6 hours. The reaction is quenched and the resulting dibromo of structure (5) precipitates and is isolated using techniques well known in the art, for example, collection of the resulting solids by filtration, rinsing the solids with water, and drying to provide the dibromo ethanone of structure (5).

In Scheme I, step D, the bromo ethanone of structure (4) is prepared from the dibromo ethanone of structure (5) by conditions well known in the literature. More specifically, the dibromo ethanone of structure (5) is dissolved in a suitable organic solvent such as THF and cooled to about 0° C. The solution is treated with diethylphosphite and triethylamine and allowed to come to room temperature. After quenching after 6 hours with water, the resulting bromo of structure (4) precipitates and is isolated using techniques well known in the art, for example, collection of the resulting solids by filtration, rinsing the solids with water, and drying to provide the bromo of structure (4).

In Scheme I, step E, the propionitrile of structure (1) is formed by the nucleophilic displacement of the bromide of structure (4) with sodium cyanide in an appropriate solvent such as acetonitrile. The propionitrile of structure (1) is isolated using techniques well known in the art, such as adding ethyl acetate to the reaction mixture. The organic layer is washed with saturated NaCl solution, dried over anhydrous magnesium sulfate, filtered, and concentrated to provide the propionitrile of structure (1).

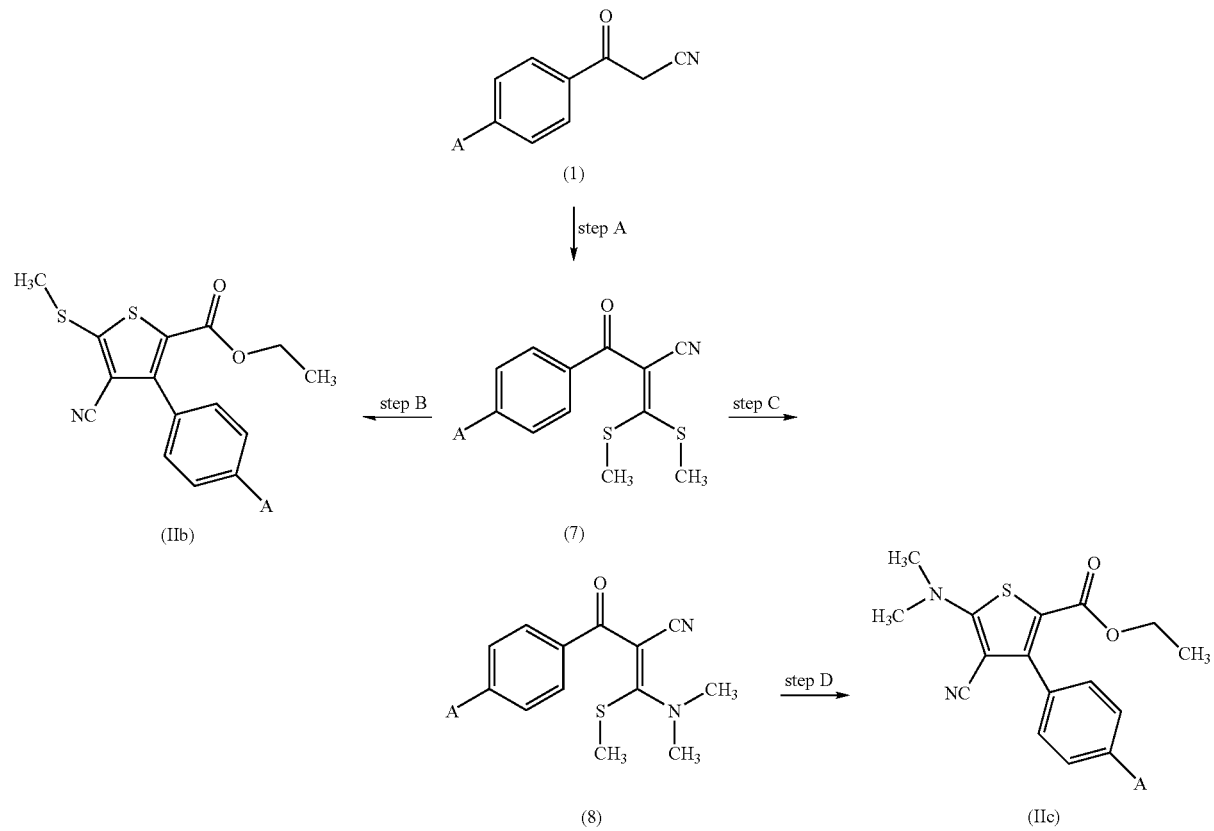

In Scheme II, step A, the compound of structure (7) is prepared from propionitrile of structure (1) under conditions well known in the art. More specifically, the compound of structure (1) is stirred with about 1 equivalent of carbon disulfide in an appropriate solvent such as DMSO. The reaction mixture is cooled to about −15° C. and about 2 to 2.4 equivalents of sodium hydride is added and the reaction mixture is warmed to room temperature for about 2.5 hours. The reaction mixture is then cooled to about −15° C. and iodomethane is added dropwise and the reaction is stirred for about 2 hours to about 24 hours and then quench with water. The compound of structure (7) is then isolated and purified using techniques well known in the art, such as extraction with a suitable organic solvent, such as ethyl acetate. The organic extracts are combined, washed with sat. NaCl, dried over anhydrous magnesium sulfate, filtered, and concentrated under vacuum to provide the crude compound of structure (7). The crude compound of structure (7) can be purified by techniques well known in the art, such as silica gel chromatography.

In Scheme II, step C, the compound of structure (8) is prepared from the compound of structure (7) under conditions well known in the art. More specifically, the compound of structure (7) is stirred in an appropriate solvent such as acetonitrile at room temperature. An amine such as dimethylamine is added to the solution and the reaction mixture is allowed to stir for approximately 12 hours. The compound of structure (8) is isolated by removing the solvent in vacuo.

In Scheme II, steps B and D, the compounds of formula (IIb) and (IIc) are prepared from compounds of structure (7) and (8), respectively. The compound of structure (7) or (8) are combined with about 1.1 equivalents of ethylthioglycolate in suitable solvent such as ethanol. An appropriate base such as triethylamine or potassium acetate (approximately 1.1 to 3 equivalents) is added. The reaction mixture is heated to reflux for about 0.5 to 2 hours and immediately removed from the heat when the reflux is reached. The reaction is then cooled and the compounds of formula (IIb) or (IIc) are isolated using techniques well known in the art, for example, collection of the resulting solids from the partial evaporation of the solvent and rinsing the solids with cold ethanol to provide the compounds of formula (IIb) or (IIc).

Scheme III

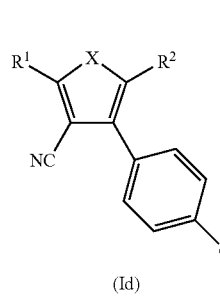

(Id)

step A

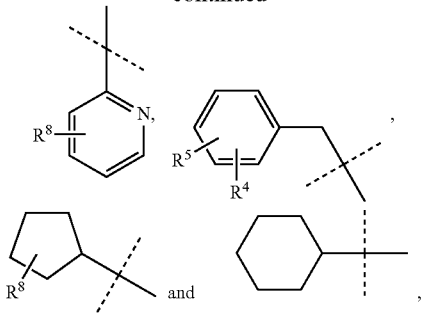

under deprotection conditions. See for example Theodora Greene, "Protective Groups in Organic Synthesis," John Wiley & Sons, Inc, pages 143-169 (1991). More specifically, for example, the compound of formula (Id) is dissolved in methylene chloride and cooled to about −78° C. and boron tribromide is added. The reaction mixture is allowed to stir at about −20° C. for about 16 hours. The product is then isolated and purified using techniques well known to one of ordinary skill in the art, such as extraction techniques, and chromatography. For example, the above reaction is diluted with water, dried over anhydrous sodium sulfate, filtered and concentrated under vacuum to provide the compound of formula (Ie). A phenyl sulfonate ester, for example, formed by reaction of a phenol with a sulfonyl chloride in pyridine or aqueous sodium hydroxide, is cleaved by warming in aqueous sodium hydroxide to provide the compound of formula (Ie). A benzyl ether is deprotected for example, by catalytic hydrogenation in a suitable solvent such as methanol, ethyl acetate, acetic anhydride-benzene to provide the compound of formul (Ie).

Scheme IV (Ie)

(If)

step A

In Scheme III, step A, when the A substituent of the compound of formula (I) is a phenyl ether such as the compound of formula (Id), the phenyl ether is readily converted to the compound of formula (Ie), wherein $R^{16}$ represents -(1-4C)alkyl, -(2-4C)alkenyl, —$(CH_2)_n$CN, $SO_2CF_3$, (Ig)

In Scheme IV, step A when the A substituent of the compound of formula (I) or compound of formula (II) is a nitro group such as the compound of formula (If), the nitro group is readily converted to the compound of formula (Ig) under reducing conditions well know in the art. For example, the nitro compound is dissolved in a suitable solvent such as ethanol and a reducing agent such as tin chloride is added. The reaction can be heated to about 75° C. for about 30 minutes and then allowed to proceed overnight at room temperature. One can also monitor the progress of the reaction by methods known in the art, for example thin layer chromatography. The product is then isolated and purified using techniques well known to one of ordinary skill in the art, such as extraction techniques and chromatography. For example, the above reaction mixture is diluted with a saturated solution of sodium bicarbonate. The product is extracted with a suitable organic solvent, such as ethyl acetate, dried over anhydrous sodium sulfate, filtered, and concentrated under vacuum to provide the compound of formula (Ig).

The amino group of the compound of formula (Ig) can be further transformed by methods well known in the art. For example, the amino group of the compound of formula (Ig) can be transformed into an amide by reacting the amino group with a suitable acyl chloride or anhydride in the presence of a base such as triethylamine. The amino function of the compound of formula (Ig) can be further transformed into a sulfonamide by reacting the amino group with a suitable sulfonyl chloride in the presence of pyridine or aqueous base such as triethylamine. The amino function of the compound of formula (Ig) can be alkylated to form a primary amine by reductive amination by forming the imine with a suitable aldehyde in an appropriate solvent such a methanol or ethanol. The reduction of the imine is carried out in a appropriate solvent such as methanol or ethanol and a suitable reducing agent such as sodium cyanoborohydride. A secondary amine can be formed by reacting the amine with the appropriate halide such as methyl iodide in the presence of a base such as potassium carbonate.

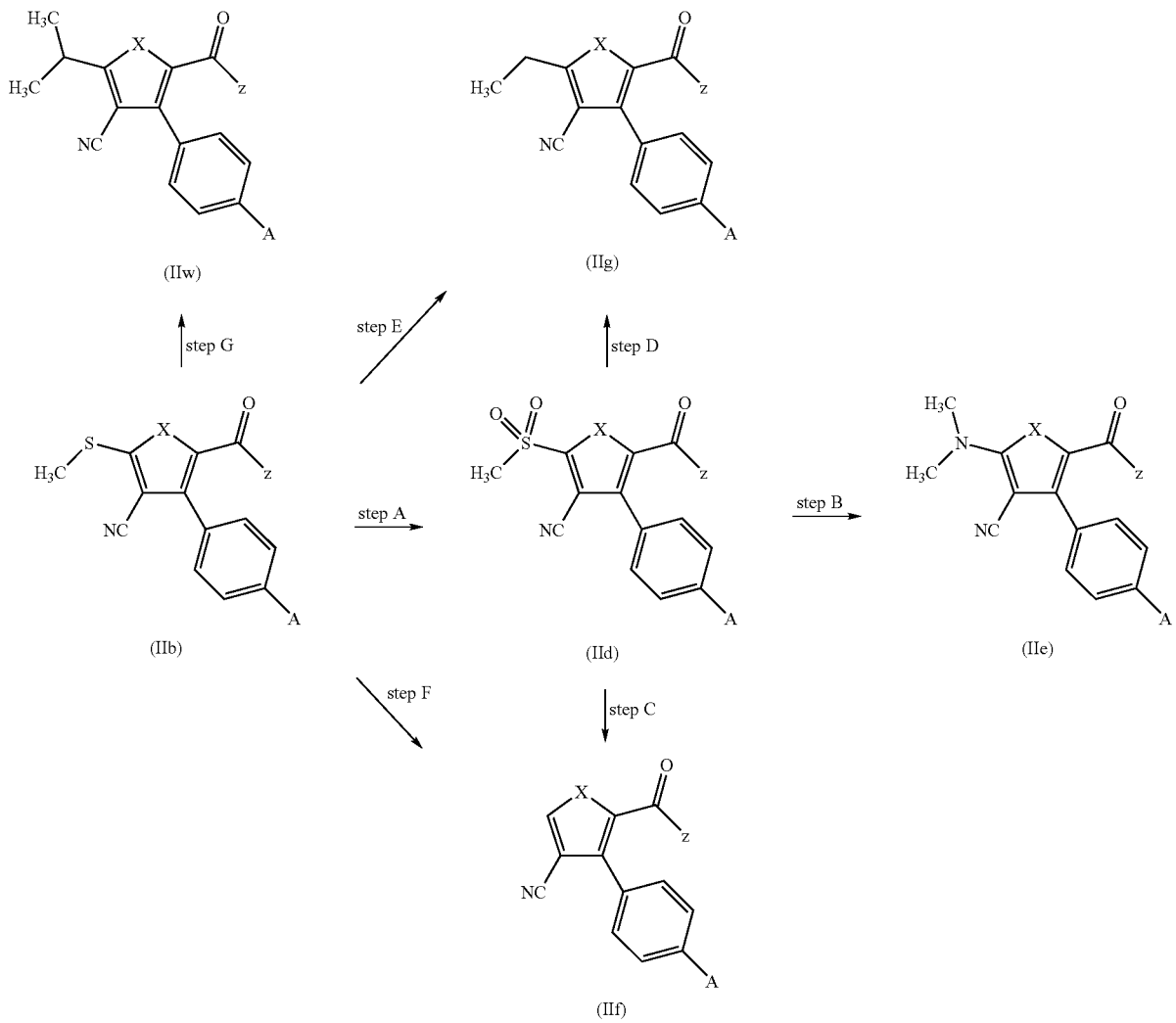

In Scheme V, step A, the compound of formula (IId) can be synthesized from the compound of formula (IIb) by oxidization methods known in the art. More specifically, for example the compound of formula (IIb) are dissolved in a suitable solvent such as methylene chloride and cooled to about 0° C. An oxidizing agent for example, three equivalents of m-chloroperbenzoic acid is added, and the reaction mixture is allowed to stir at room temperature for about three days or until the reaction is complete. The product is then isolated and purified using techniques well known to one of ordinary skill in the art, such as extraction techniques and chromatography. For example, the above reaction is diluted with a suitable organic solvent, such as methylene chloride, washed with saturated sodium bicarbonate, brine, dried over anhydrous magnesium sulfate, filtered and concentrated under vacuum to provide the compound of formula (IId).

In Scheme V, the compound of formula (IId) can be subjected to nucleophilic and reduction conditions to form the compound of formula (IIe, IIg, IIf). In Scheme V, step B, the compound of formula (IIe) can be prepared by dissolving the sulfonyl compound of formula (IId) in a suitable solvent such as tetrahydrofuran then adding the base, dimethyl amine, and stirring for about 2 hours. The reaction can be concentrated under vacuum and purified if necessary to provide the compound of formula (IIe).

In Scheme V, steps C, D, E, F and G, the compound of formula (IIg) and the compound of formula (IIf) and the compound of formula (IIw) can be prepared by reacting the compound of formula (IIb) and the compound of formula (IId) under reducing conditions, for example a suitable reducing agent would be sodium borohydride or diethylzinc or isopropyl zinc with an optional catalyst such as 1,3-bis-(diphenylphosphino)propane nickel (II) chloride and an appropriate solvent would be ethanol or methylene chloride. Alternative examples for conditions can be found in Larock "Comprehensive Organic Transformations $2^{nd}$ edition" pages 53-60, 1999.

(II) complex and a borane such as bis(pinacolato)borane are added. Under a nitrogen atmosphere, the reaction is heated to reflux for about 5 to 20 hours. The product is then isolated using techniques well known to one of ordinary skill in the art, such as extraction techniques. For example, the above reaction is cooled, diluted with a suitable organic solvent, such as ethyl acetate, washed with water, brine, dried over anhydrous sodium sulfate, filtered through Celite®, and concentrated under vacuum to provide the crude compound of formula (IXa). An additional acid wash such as a dilute acid wash might be necessary. The crude compound of formula (IXa) can be purified by techniques well known in the art, such as silica gel chromatography using a solvent mixture, such as ethyl acetate:hexanes.

In Scheme VI, step B, the compound of formula (IXb) can be prepared from the compound of formula (II) by methods known in the art. For example, the iodo compound is dissolved in dimethylformamide and a catalyst such as dichlorobis(triphenylphosphine)-palladium(II) and the tin compound such as hexamethylditin are added. Under a nitrogen atmosphere, the reaction is heated to about 80° C. for about two hours. The product is then isolated and purified using techniques well known to one of ordinary skill in the art, such as extraction techniques and chromatography. For example, the above reaction mixture is diluted with water. The product Scheme VI

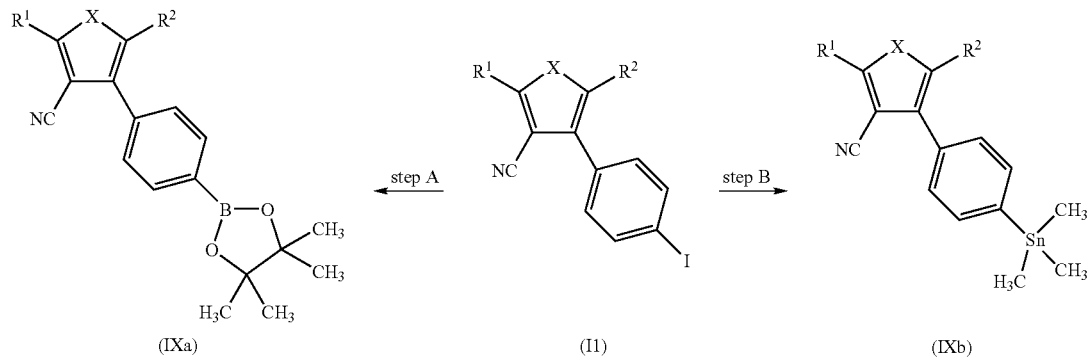

(IXa)  (II)  (IXb)

In Scheme VI, step A, the compound of formula (IXa) can be prepared from the compound of formula (II) by methods known in the art. For example, the iodo or bromo compound of formula (II) is dissolved in an appropriate solvent such as acetonitrile or dimethylsulfoxide and a base such as triethylamine or potassium acetate is added. A catalyst such as [1,1'-bis(disphenylphosphino)-ferrocene]dichloropalladium is extracted with a suitable organic solvent, such as ethyl acetate, dried over anhydrous sodium sulfate, filtered, and concentrated under vacuum to provide the crude compound of formula (IXb). The crude compound of Formula (IXb) can be purified by techniques well known in the art, such as silica gel chromatography using a eluent, such as ethyl acetate:hexanes.

Scheme VII

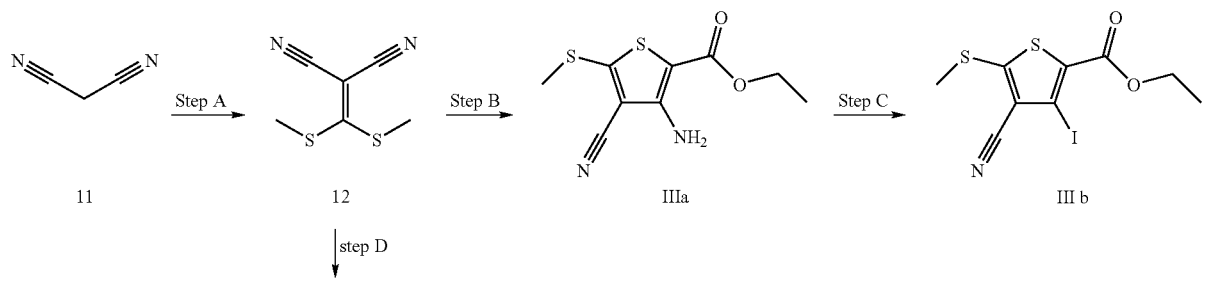

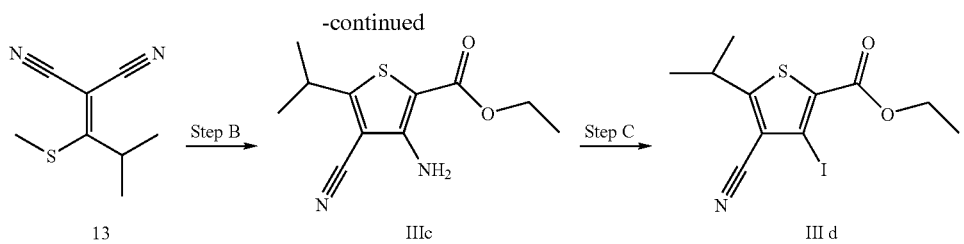

In Scheme VII, step A, the compound of structure (12) is prepared from malononitrile under conditions well known in the art. More specifically, the anion of malononitrile is formed by adding about 2.1 equivalents of sodium hydride under a nitrogen atmosphere at about −15° C. After anion formation, about 1 equivalent of carbon disulfide is added and the reaction mixture is warmed to room temperature. After about 2.5 hours additional sodium hydride is added and the temperature is maintained at room temperature. Cool the reaction to about −15° C. and add about 2 equivalents of iodomethane dropwise and stir the reaction for about 2 hours to about 24 hours and then quench with water. The desired intermediate of structure (12) precipitates and is collected by filtration and washed with water, partially air-dry, and washed with hexanes. The crude product can be recrystallized from a suitable solvent such as 2-propanol, washed with cold 2-propanol and hexanes and isolated.

In Scheme VII, step B, the compounds of structure (IIIa) and (IIIc) are synthesized by combining compounds of structure (12) and (13) respectfully, with ethylthioglycolate inn a appropriate solvent such as ethanol. An appropriate base such as triethylamine or potassium acetate is added. The reaction mixture is refluxed for about 30 minutes to 2 hours. Cool the reaction mixture to about 35° C. over about 45 minutes then cool to 3° C. over 20 minutes and maintain about 3° C. for about 20 minutes. The precipate that forms is isolated, washed with a solvent such as ethanol and ether and dried.

In Scheme VII, step C, the compounds of structure (IIIa) and (IIIc) are dissolved in an appropriate solvent such as acetonitrile and placed in a nitrogen atmosphere. An excess of methylene iodine is added and the reaction mixture is warmed to about 35° C. to 45° C. i-Amylnitrite is slowly added via an addition funnel. A vigorous reaction might occur so care should be taken upon addition of the i-amylnitrite. After about half of the i-amylnitrite is added, the temperature is warmed to about 55° C. to initiate the reaction. Add the remaining i-amylnitrite maintaining the reaction mixture at about 60° C. After addition, stir for about 45 minutes at about room temperature to 45° C. The reaction mixture is cooled to about 5° C. and hexanes are added. The resulting precipitate is collected by filtration and washed with acetone/hexanes, diethyl ether/hexanes, and hexanes and dried to give the compounds of formula (IIIb) and (IIId).

In Scheme VII, step D, the compound of structure (13) is prepared from the compound of structure (12) by reacting the compound of structure (12) with a magnesium chloride such as ispropylmagnesium chloride in an appropriate solvent such as tetrahydrofuran and a temperature of about −40° C. for about 18 to 24 hours. The reaction is quenched with ammonium chloride, extracted with a solvent such as ethyl acetate, dried over magnesium sulfate, remove solvents under vacuum and purified by chromatography using an eluent such as hexane and ethyl acetate to provide compound of formula (13).

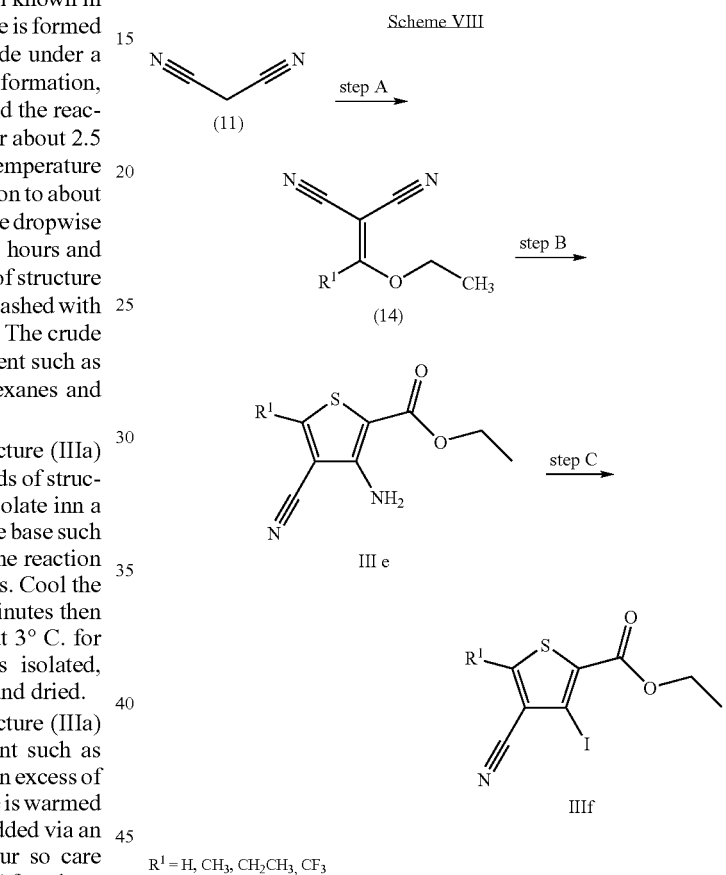

$R^1$ = H, $CH_3$, $CH_2CH_3$, $CF_3$

In Scheme VIII, step A, the compound of structure (14) is synthesized by methods known in the art. For example, malononitrile is mixed with the appropriate starting materials such as triethylorthopropionate, triethylorthoethylate, or diethoxymethoxyethane in an appropriate solvent such as anhydrous dimethylsulfoxide. The reaction is refluxed under nitrogen for about 1.5 hours. The product is isolated by vacuum distillation at 10-15 torr at 135-142° C. The literature reference, Middleton, *J. Fluorine Chem.*, 20, 1982, p 397-418, can be followed for the synthesis of the compound of structure (14) $R^1$=$CF_3$.

In Scheme VIII, step B, the compound of structure (IIIe) is synthesized by combining the compound of structure (14) with ethylthioglycolate in an appropriate solvent such as ethanol. An appropriate base such as potassium acetate or triethylamine is added. The reaction mixture is refluxed for about 30 minutes to 2 hours. The product can be isolated by adding water to the reaction mixture and cooling to 5° C. for about 1 hour. The precipate that forms is isolated, washed with a solvent such as water/ethanol, and dried.

In Scheme VIII, step C, the compound of structure (IIIe) is dissolved in an appropriate solvent such as acetonitrile and placed in a nitrogen atmosphere. An excess of diiodo methane is added and the reaction mixture is warmed to about 35 to 45° C. i-Amylnitrite is slowly added via an addition funnel. A vigorous reaction might occur so care should be taken upon addition of the i-amylnitrite. After about half of the i-amylnitrite is added, the temperature is warmed to about 55° C. to initiate the reaction. Add the remaining i-amylnitrite maintaining the reaction mixture at about 60° C. to about 80° C. After addition, stir for about 45 minutes at about room temperature to 45° C. The reaction mixture is concentrated under vacuum, passed through a plug of silica gel eluting with methylene chloride, and concentrated under vacuum. The oil can be mixed with 2-propanol and hexanes and cooled to about 5° C. The resulting crude precipitate is collected by filtration, rinsed with 2-propanol/hexane or hexane and dried at room temperature. The compound of structure (IIIf) is purified by silica gel chromatography using methylene chloride/hexane solvent system. The product can also be recrystallized from a suitable solvent, such as from hexanes.

Scheme IX

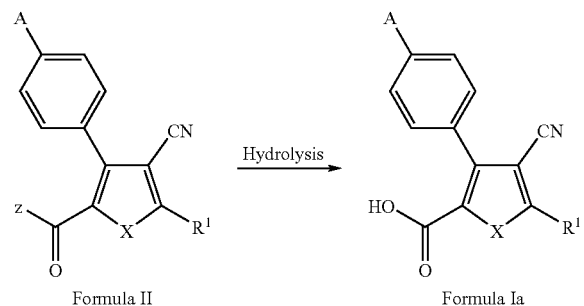

Formula II    Formula Ia

In Scheme IX, the compound of Formula II is converted to the carboxylic acid of Formula Ia under conditions well known in the art by treatment with a suitable hydrolysis agent, such as a suitable base or enzyme. For example, the compound of Formula (II) is dissolved in a suitable organic solvent or solvent mixture, such as THF, methanol, ethanol, and the like. The mixture is treated with water and a slight excess of a suitable base, such as lithium hydroxide, sodium hydroxide, potassium hydroxide, and the like, and stirred for about 1 to 18 hours at a temperature of about 25° C. to about 60° C. The compound of Formula (Ia) is then isolated and purified by techniques well known in the art, such as extraction techniques and recrystallization. For example, the reaction mixture is acidified with a suitable acid, such as 1N HCl and the compound of Formula (Ia) is then extracted from the mixture with a suitable organic solvent, such as methylene chloride. The organic extracts are then combined, dried over anhydrous magnesium sulfate, filered, and concentrated under vacuum. The residue can then be purified by recrystallization from a suitable organic solvent such as ethyl acetate to provide purified the compound of Formula (Ia). If a precipitate forms when the acid is added the solid is collected by filtration to provide purified the compound of Formula (Ia).

Scheme X

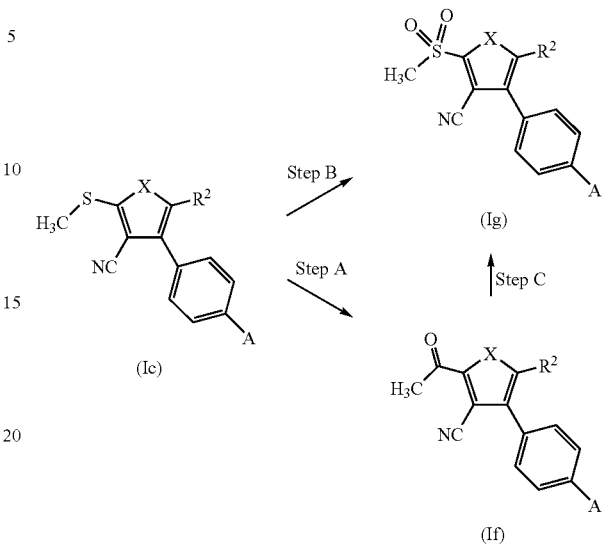

In Scheme X, step A, the compound of formula (If) can be synthesized from the compound of formula (Ic) by oxidization methods known in the art. More specifically, for example the compound of formula (Ic) is dissolved in a suitable solvent such as methylene chloride and cooled to about 0° C. An oxidizing agent for example, m-chloroperbenzoic acid of about 1.0 equivalent is added, and the reaction mixture is allowed to stir at room temperature for about three days or until the reaction is complete. The product is then isolated and purified using techniques well known to one of ordinary skill in the art, such as extraction techniques and chromatography. For example, the above reaction is diluted with a suitable organic solvent, such as methylene chloride, washed with saturated sodium bicarbonate, brine, dried over anhydrous magnesium sulfate, filtered and concentrated under vacuum to provide the compound of formula (If).

In Scheme X, step B, the compound of formula (Ig) can be synthesized from the compound of formula (Ic) by methods described for step A of SchemeX except that about 3.0 equivalents of the oxidizing agent such as m-chloroperbenzoic acid is used.

In Scheme X, step C the compound of formula (Ig) can be synthesized from the compound of formula (If) by methods described for step A of SchemeX except that about 1.5 equivalents of the oxidizing agent such as m-chloroperbenzoic acid is used.

Scheme XI

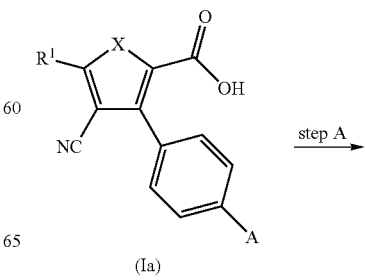

(Ia)

step A

-continued

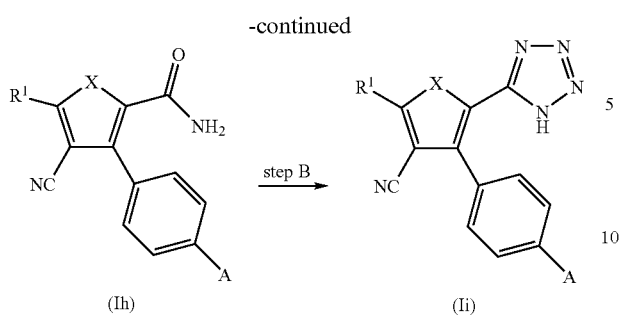

(Ih)  →  (Ii)   step B

In Scheme XI, step A, the carboxylic acid of the compound of formula (Ia) is converted to the primary amide of the compound of formula (Ih) under conditions well known in the art. For example, the compound of formula (Ia) is dissolved in a suitable organic solvent, such as methylene chloride or THF and treated with about 1.1 to 1.3 equivalents of oxalyl chloride at temperature of about 0° C. to 25° C. followed by addition of a catalytic amount of DMF with stirring. The reaction mixture is allowed to stir for about 1 to 8 hours and then it is concentrated under reduced vacuum. The residue is then dissolved in a suitable organic solvent, such as methylene chloride or THF and treated with a slight excess of an ammonia hydroxide or ammonia/methanol solution at room temperature with stirring. A precipitate might form. The reaction mixture is allowed to stir for about 1 to 4 hours and then it is concentrated under vacuum and purified by techniques well known in the art, such as chromatography on silica gel with a suitable eluent, such as methanol/dichloromethane to provide the purified primary amide of the compound of formula (Ih).

In Scheme XI, step B, the primary amide of the compound of formula (Ih) is the converted to the tetrazole the compound of formula (Ii) under standard conditions. For example, about 1 to 2 equivalents silicon tetrachloride and about 3 to 12 equivalents of sodium azide are combined in a suitable organic solvent, such as acetonitrile and stirred at room temperature for about 20 minutes. About 1 equivalent of the primary amide of the compound of formula (Ih) is added to the stirring mixture and the reaction mixture is heated at about 100° C. for about 8 to 24 hours. The reaction is concentrated under vacuum and purified such as chromatography on silica gel with a suitable eluent, such as methanol/acetic acid/dichloromethane to provide the purified compound of formula (Ii).

Scheme XII

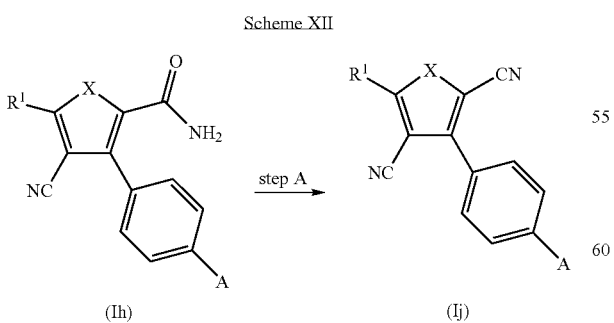

(Ih) → (Ij)  step A

In Scheme XIII, step A, the primary amide of the compound of formula (Ih) is converted to the dicyano compound of formula (Ij) under standard conditions. For example, the amide is dissolved in a suitable solvent such as acetonitrile and paraformaldeyde and formic acid are added. The reaction mixture is heated for about 6 hours. The reaction is concentrated under vaccum and purified such as chromatography on silica gel with a suitable eluent, such as ethyl acetate/hexane to provide the purified dicyano compound of formula (Ij).

Scheme XIII

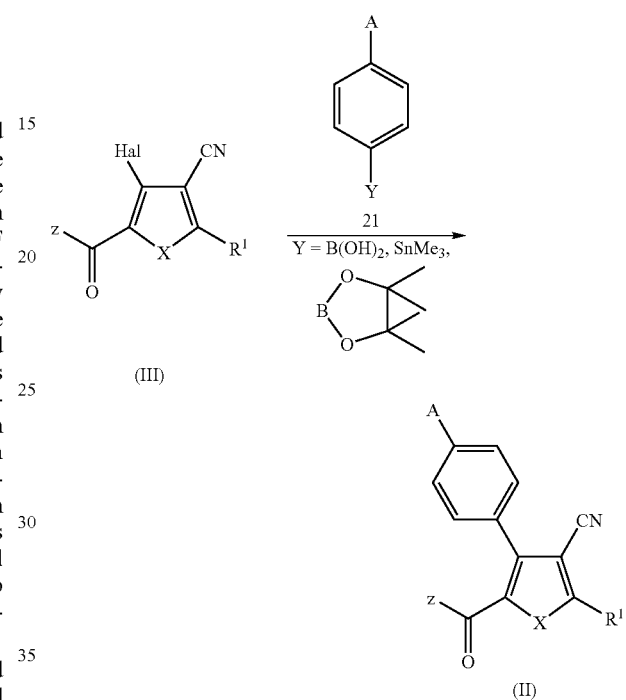

In Scheme XIII, the compound of structure (III), wherein Hal is iodo or bromo, is coupled to a suitable phenyl boronic acid of structure (21) or suitable phenyl boronic ester of structure (21) or suitable phenyl trimethylstannyl of structure (21), under Suzuki-Type or Stille-Type coupling reaction conditions well known to one of ordinary skill in the art to provide the compound of formula (II). See Suzuki, A., *Journal of Organometallic Chemistry*, 576, 147-168 (1999), and Miyaura and Suzuki, *Chemical Reviews*, 95, 2457-2483 (1995) for examples of general cross-coupling techniques and for methods for preparing suitable starting materials and reagents. It is understood by one of ordinary skill in the art, that in general, a phenyl boronic ester can be used in place of the phenyl boronic acid of structure (21) in the palladium catalyzed cross-coupling reactions described herein. Examples of phenyl boronic acids of structure (21) and phenyl boronic ester of structure (21) include the following:

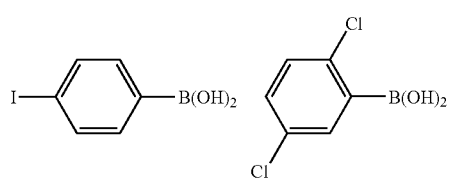

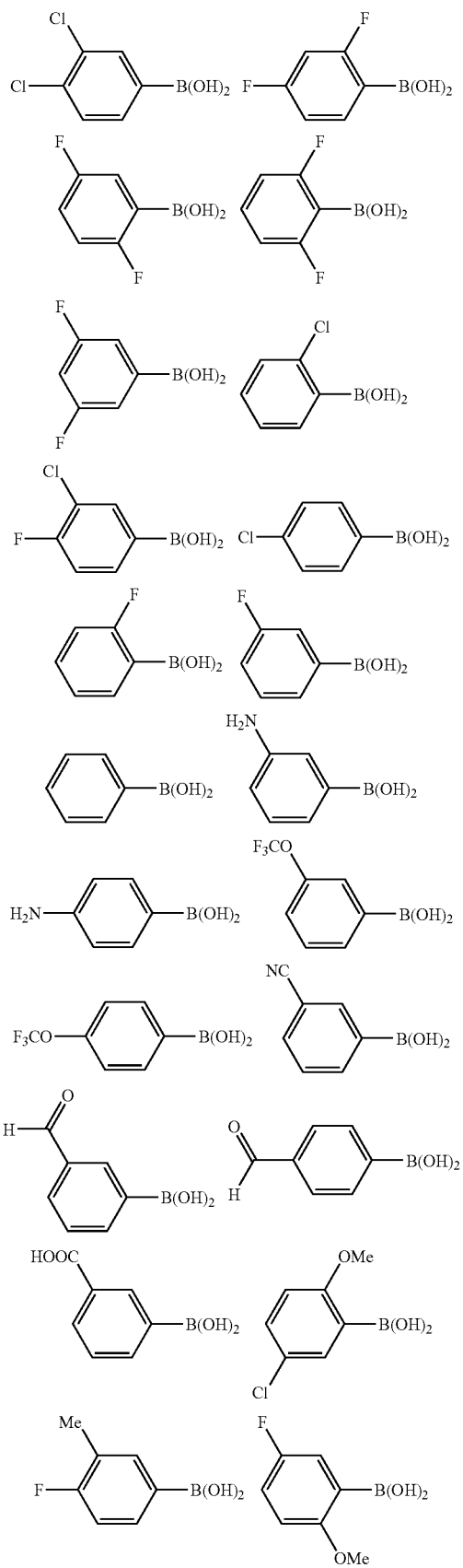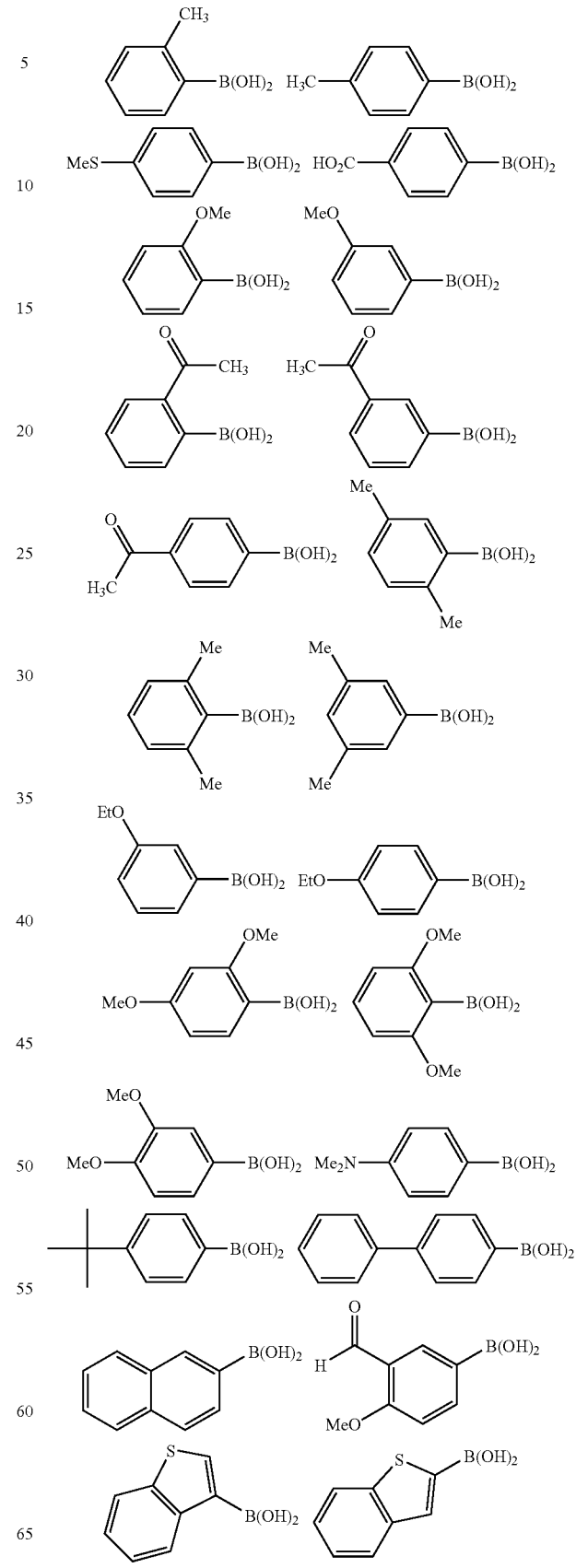

-continued
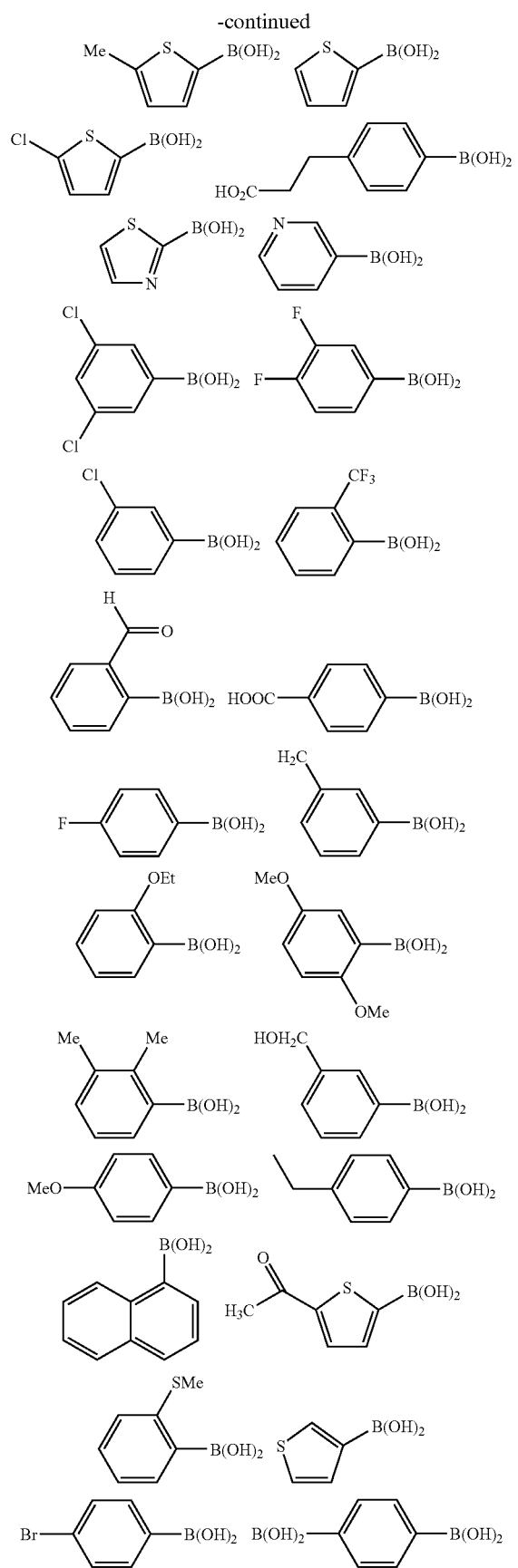
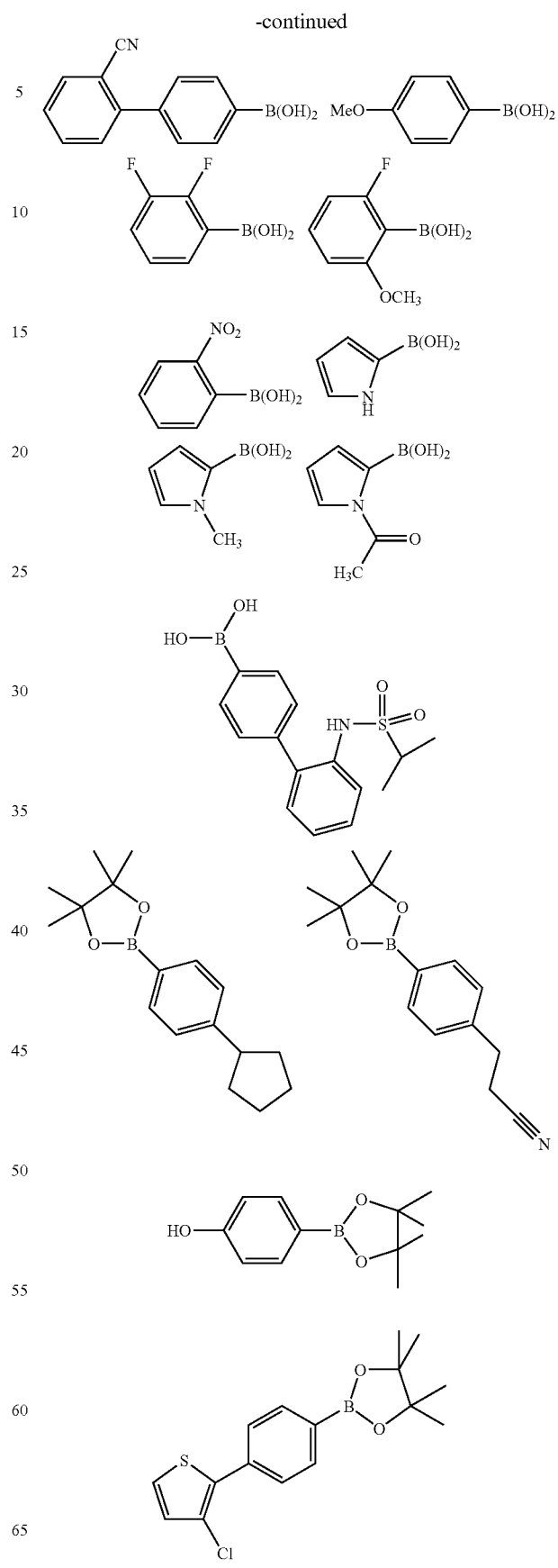

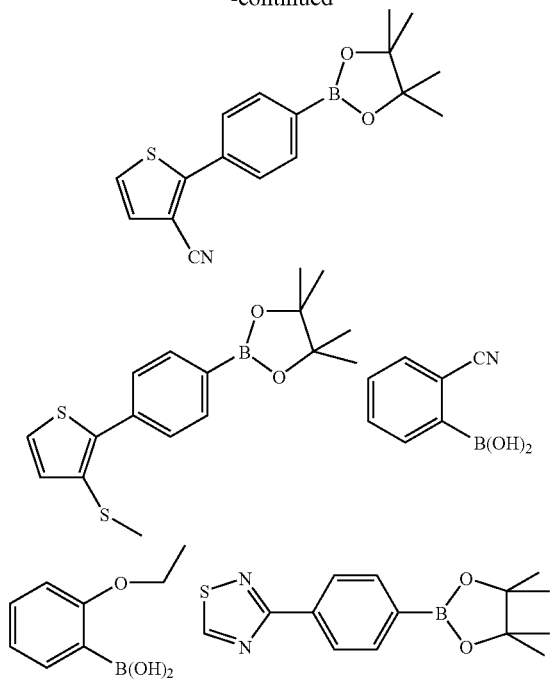

and the like. More specifically, the compound of structure (III) is combined with about 1.1 to 1.5 equivalents of the suitable phenyl boronic acid of structure (21) or the suitable phenyl boronic ester of structure (21) in a suitable organic solvent. Examples of suitable organic solvents include 1,4-dioxane, dimethoxyethane, benzene, toluene, acetone, ethanol, and the like. About 0.01 to 0.10 equivalents of a suitable catalyst, such as tetrakis(triphenylphosphine)palladium or [1,1-bis(diphenylphospino)ferrocene]dichloro-palladium(II) or palladium black and about 1.7 to 5 equivalents of a suitable base are added to the reaction mixture with stirring. Examples of suitable bases include 2M $Na_2CO_3$, $NaHCO_3$, $Cs_2CO_3$, $Tl_2CO_3$, $K_3PO_4$, CsF, triethylamine, $K_2CO_3$, and the like. The reaction is heated to about 60° C. to 100° C. for about 1 to 18 hours, then cooled to room temperature, optionally quenching with water. If solids form a filtering through Celite® might be necessary. The phases are separated. The product is then isolated and purified by techniques well known in the art, such as extraction and chromatography. For example, the aqueous phase is extracted with a suitable organic solvent, such as dichloromethane or ethyl acetate, the organic extracts are combined, washed with optional acid, water, brine, dried over anhydrous magnesium sulfate or sodium sulfate, filtered, and concentrated under vacuum to provide the crude compound of Formula (II). This crude material, compound of Formula (II), can then be purified by flash chromatography on silica gel with a suitable eluent, such as ethyl acetate:hexane. Optionally, the organic extracts can be first concentrated under vacuum then the crude oil extracted with a suitable solvent such as heptane. The supernatant is decanted and the recovered oil is mixed with silica gel for about 3 minutes. The mixture is filtered and concentrated the filtrate under vacuum to obtain a solid. The solid can be triturated with a suitable solvent such as pentane and the solids are collected by filtration to provide the crude compound of Formula (II). The crude compound of Formula (II) can be purified by dissolving the solid in a mixture of pentane and cyclohexane and heating to about 44° C. and adding silica gel and stirring for about 3 minutes. Filter the solution and concentrate the filtrate under vacuum to about ⅓ the volume to form a suspension. Collect the particles and wash the particles with a suitable solvent such as pentane and dry to provide the compound of Formula (II). Another option for the isolation of the product is to dilute the crude product with water and heat the solution to about 70° C. for about 15 minutes. Decant the aqueous and redilute with water and heat the solution to about 70° C. for about 15 minutes and filter. Isolate the solids and dissolve in a suitable solvent such as ethanol/water and heat to about 80° C. Cool this solution slowly over 12 hours to 0° C. with slow stirring. Filter the preciptate through a filter such as a sintered glass and dry under vacuum and/or air-dry to afford the compound of Formula (II).

Scheme XIV

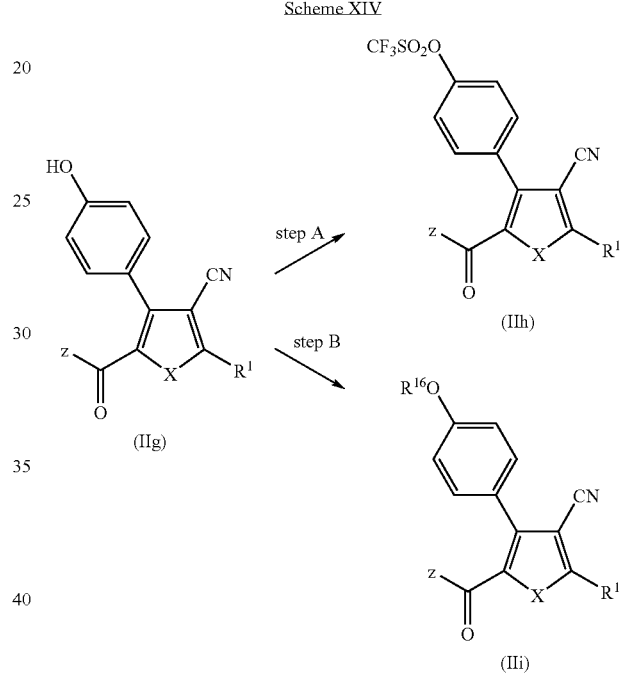

In scheme XIV, step A, the compound of formula (IIg) are dissolved in a suitable solvent such as dichloromethane under a nitrogen atmosphere and a suitable base such as pyridine or sodium hydride is added and the reaction mixture is cooled to about −4° C. to −70° C. Trifluoromethanesulfonic anhydride is added over about a 6 minute period. The reaction mixture is allowed to stir for about 1 hour. Additional base and anhydride might be needed in order to complete the reaction. Ethanol is added. After about 2 to 3 hours, the reaction is quenched with water. The product is then isolated and purified by techniques well known in the art, such as extraction and chromatography. For example, the aqueous phase is extracted with a suitable organic solvent, such as dichloromethane, the organic extracts are combined, washed with water, dried over anhydrous magnesium sulfate, filtered, and concentrated under vacuum to provide the crude compound of formula (IIh). The powder is triturated with a suitable solvent such as ethyl acetate and hexane, filtered and dried to give the compound of formula (IIh).

In scheme XIV, step B, the compound of formula (IIi) can be prepared by using methods well known in the art. For example, Larock "Comprehensive Organic Transformations $2^{nd}$ edition" pp. 896-897, 1999 specifically discuss the formation of phenyl ethers from phenols of the compound of formula (IIg). More specifically, the phenol is dissolved in a suitable solvent such as acetonitrile, dimethylformamide, dimethylsulfoxide, or methylene chloride. About 1.1 to 1.5 equiv. of a suitable base such as potassium carbonate, potassium hydroxide, sodium hydroxide or sodium hydride is added. The reaction mixture is then stirred at room temperature for about 15 minutes to 1 hour and then treated with about 1.5 equivalents of the suitable alkylating agent, such as $R^{16}$-Hal ($R^{16}$ defined within and Hal=Br, Cl, I) and the reaction is heated to about reflux or stirred at room temperature for about 1 to 24 hours. Examples of suitable alkylating agents are methyl iodide, ethyl iodide, propyl iodide, isopropyl iodide, ethyl bromide, propyl bromide, butyl bromide, butyl chloride, tert-butyl bromide, cyclopropyl bromide, cylcohexyl bromide, bromoacetonitrile, 3-bromopropionitrile, 4-bromobutyronitrile, 2-cyanobenzyl bromide, 3-cyanobenzyl bromide, 4-cyanobenzyl bromide, 2-fluorobenzyl bromide, 3-fluorobenzyl bromide, 4-fluorobenzyl bromide, and the like. The product is then isolated and purified by techniques well known in the art, such as quenching the reaction mixture with water and extracting with a suitable solvent such as ethyl acetate. The organic layer is washed with water, saturated sodium chloride, dried over anhydrous magnesium sulfate, filtered, concentrated under vacuum to give the compounds of formula (IIi).

Alternatively, the phenol is dissolved in a suitable solvent such as toluene and cooled to about 0° C. The appropriate alcohol, $R^{16}$—OH, is added along with the triphenylphosphine and approximately 1.5 to 2 equivalents of DIAD (Diisopropyl azodicarboxylate). The product is then isolated and purified by techniques well known in the art, such as letting the reaction warm slowly to room temperature, removing the solvent under vacuum and puified by chromatography to give the compound of formula (IIi).

Alternatively, the phenol is dissolved in an appropriate solvent such as acetonitrile and treated with about 5 equivalents of potassium fluoride on alumina, a catalytic amount of a crown ether, such as 18-crown-6, and a suitable fluorosubstitued aryl derivative, such as 2-fluorobenzonitrile, 3-fluorobenzonitrile, 4-fluorobenzonitrile, 1-fluoro-2-nitrobenzene, 1-fluoro-3-nitrobenzene, 1-fluoro-4-nitrobenzene, and the like. The reaction mixture is heated to reflux for about 12 to 24 hours. The product is then isolated and purified by techniques well known in the art, such as letting the reaction cool to room temperature, partition the reaction mixture between a suitable solvent such as ethyl acete or ether and water, and separating the aqueous layer and the alumina sediments. The organic phase is washed with saturated sodium chloride, dried over sodium sulfate, filtered, and concentrated under vacuum to give the crude compound of formula (IIi). The crude material is purified by chromatography to give the compound of formula (IIi).

Alternatively, the phenol is dissolved in a suitable solvent such as methylene chloride and molecular sieves are optionally added along with a suitable aryl boronic acid, such as those disclosed herein, an example is 4-fluorophenylboronic acid and about 2 equivalents of copper(II) acetate. The reaction mixture is stirred of about 18 to about 24 hours. The product is then isolated and purified by techniques well known in the art, such as the reaction mixture is filtered through diatomaceous earth for example, concentrated under vacuum, and purifed by chromatography to give the compound of formula (IIi).

The ester group can be transformed into the carboxylic acid group as described previously in Scheme IX.

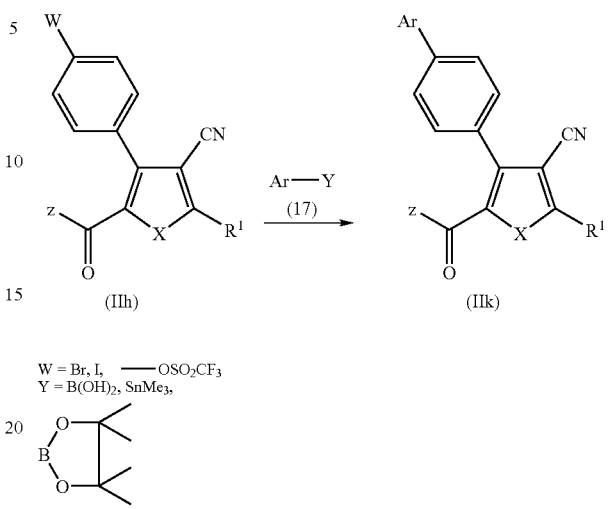

In Scheme XV, the compound of Formula (IIh) is coupled to a suitable aryl boronic acid of structure (17) or suitable aryl borate ester of structure (17), or suitable trimethyl stannyl of structure (17) wherein Ar represents a suitable aryl group, in a manner analogous to the procedure set forth in Scheme XIII to provide the compound of Formula (IIk).

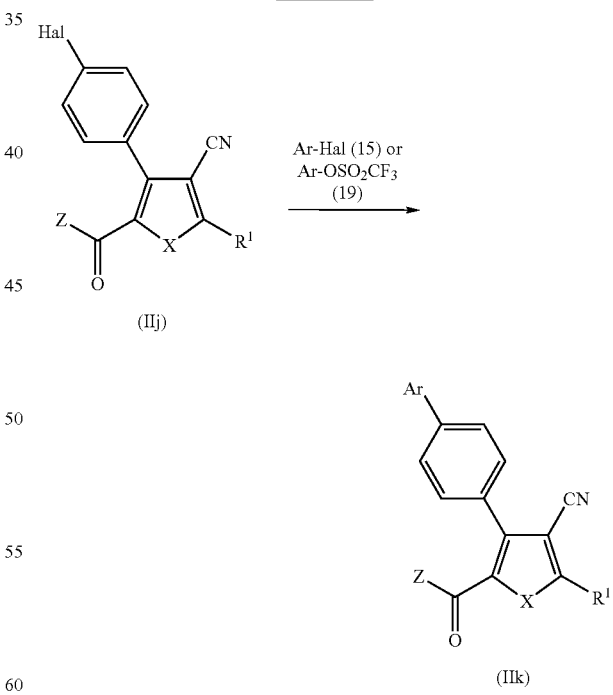

In Scheme XVI, the compound of Formula (IIj) is coupled to an aryl halide or triflate of structure (19), wherein Ar represents a suitable aryl group, under Suzuki-Type coupling reaction conditions well known to one of ordinary skill in the art to provide the compound of Formula (IIk). These Suzuki- Type coupling reaction conditions are well known to one of ordinary skill in the art. For example, see Suzuki, A., *Journal of Organometallic Chemistry*, 576, 147-168 (1999), Miyaura and Suzuki, *Chemical Reviews*, 95, 2457-2483 (1995), Ishiyama, T, et al., *J. Org. Chem.*, 60, 7508 (1995), and Ishiyama, T, et al., *Tetrahedron Lett.*, 38, 3447 (1997). More specifically, about 1.1 equivalents of the suitable aryl halide (15) or suitable aryl triflate (19) is combined with about 1.2 equivalents of bis(pinacolato)diboron, about 0.03 equivalents of a suitable catalyst, such as PdCl$_2$(dppf) in suitable organic solvent, such as DMF, dioxane, or DMSO, and the reaction mixture is heated to about 80° C. for about 1 to 4 hours with stirring. The reaction is then cooled to room temperature and about one equivalent of the compound of Formula (IIj) is added with an additional 0.3 equivalents of PdCl$_2$(dppf) and about 5 equivalents of a suitable base, such as 2M sodium carbonate, potassium acetate, or K$_3$PO$_4$. The reaction mixture is then heated to about 80° C. for about 1 to 18 hours, cooled to room temperature, and quenched with water. The compound of Formula (IIk) is then isolated and purified by techniques well known in the art such as those set forth in Scheme XIII above.

Scheme XVIII

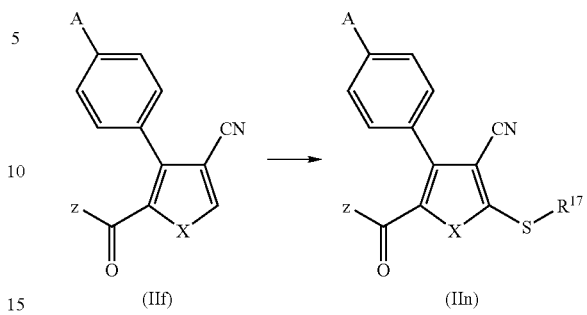

R$^{17}$ represents -(1-4C)alkyl

In Scheme XVIII, the compound of Formula (IIf) is converted to the compound of Formula (IIn) under standard conditions. For example, the compound of Formula (IIf) is dissolved in a suitable organic solvent, such as THF and cooled to about −78° C. About 1.1 equivalents of lithium bis(trimethylsilyl)amide is added and the solution is allowed to stir for about 0.5 to 1 hour. Then about 1.2 equivalents of a suitable (1-4C)alkyl disulfide is added to the reaction mixture which is allowed to warm to room temperature and stir for about 2 to 6 hours before quenching with water. The compound of formula (IIn) is then isolated and purified by techniques well known in the art, such as extraction and chromatography.

Scheme XVII

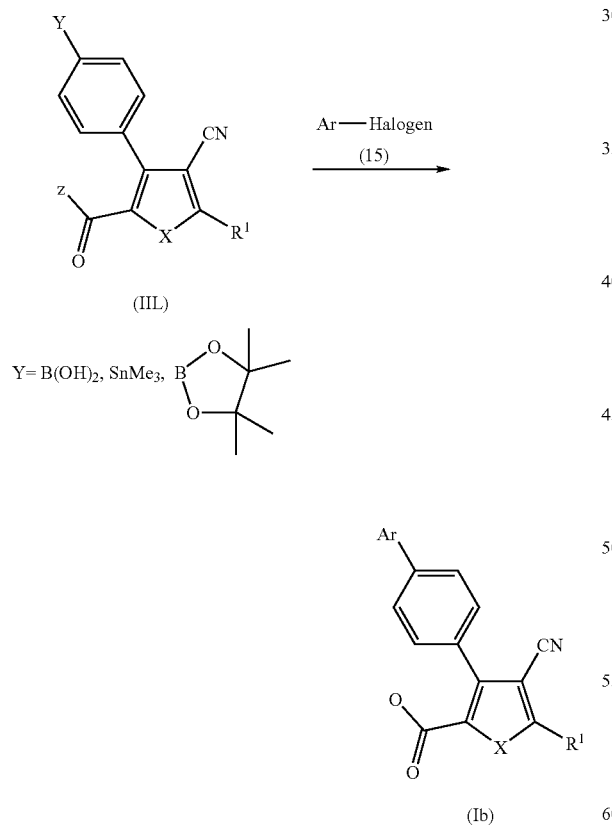

Scheme XIX

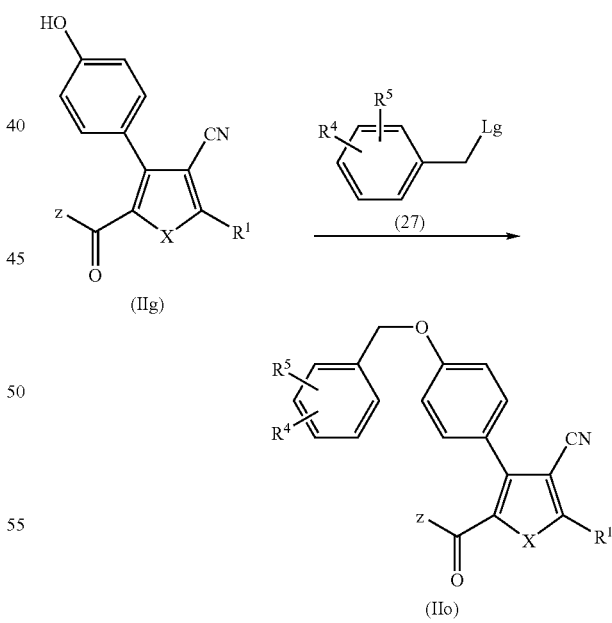

Lg represents a suitable leaving group

In Scheme XVII, the compound of Formula (IIL) is coupled to a suitable aryl halide of structure (15) wherein Ar represents a suitable aryl group, in a manner analogous to the procedure set forth in Scheme (XIII) to provide the compound of Formula (Ib).

In Scheme XIX, the compound of Formula (IIg) is converted to the compound of Formula (IIo) under conditions well known in the art. For example, the compound of Formula (IIg) is dissolved in a suitable organic solvent, such as acetone and treated with about 1.2 equivalents of a compound of structure (27) wherein Lg represents a suitable leaving group, such as Br and about 1.5 equivalents of a suitable base, such as potassium carbonate. The reaction mixture is allowed to stir at room temperature for about 8 to 24 hours. The product is then isolated and purified by techniques well known in the art. For example, the reaction mixture is concentrated under vacuum and the residue is purified by flash chromatography on silica gel with a suitable eluent to provide the purified compound of formula (IIo).

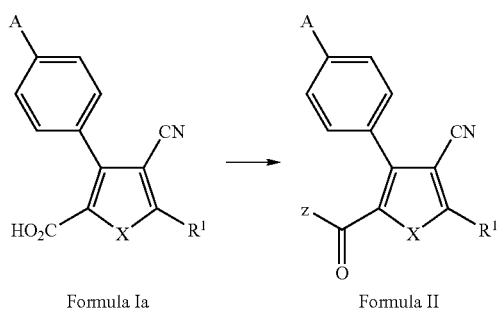

Scheme XX

Formula Ia        Formula II

In Scheme XX, the compound of Formula (Ia) is readily converted to the compound of Formula (II) under esterification or amidation conditions well known in the art. See for example Theodora Greene, "Protective Groups in Organic Synthesis," John Wiley & Sons, Inc, pages 154-184 and pages 249-265, (1981). More specifically, for example, the compound of Formula (Ia) is dissolved in a suitable organic solvent and treated with a suitable acid, such as hydrochloric acid. Examples of suitable organic solvents include, methyl alcohol, ethyl alcohol, propyl alcohol, isopropyl alcohol, n-butyl alcohol, isobutyl alcohol, t-butyl alcohol, pentyl alcohol, isopentyl alcohol, hexyl alcohol, 3-methylpentyl alcohol, 2-ethylbutyl alcohol, and the like. The reaction is heated at about 30° C. to about 60° C. for about 1 hour to about 16 hours. The product is then isolated and purified using techniques well known to one of ordinary skill in the art, such as extraction techniques and chromatography. For example, the above reaction is cooled, diluted with a suitable organic solvent, such as ethyl acetate, washed with saturated sodium bicarbonate, brine, dried over anhydrous magnesium sulfate, filtered and concentrated under vacuum to provide the compound of Formula (II). This material may be further purified by flash chromatography on silica gel with a suitable eluent such as ethyl acetate/hexane.

Alternatively, the compound of Formula (Ia) is dissolved in a suitable organic solvent and treated with an excess of thionyl chloride. Examples of suitable organic solvents are anhydrous methyl alcohol, ethyl alcohol, propyl alcohol, isopropyl alcohol, butyl alcohol, isobutyl alcohol, t-butyl alcohol, pentyl alcohol, isopentyl alcohol, hexyl alcohol, 3-methylpentyl alcohol, 2-ethylbutyl alcohol, and the like. The solution is stirred at reflux for about 1 to 3 hours, and at room temperature for about 8 to 16 hours. The mixture is then concentrated under vacuum, and the residue is purified in a manner analogous to the procedures described above to provide the compound of Formula (II).

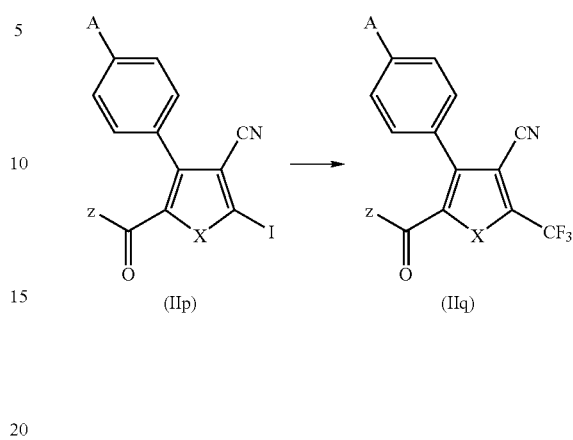

Scheme XXI (IIp)        (IIq)

In Scheme XXI, the compound of Formula (IIp) is converted to the compound of Formula (IIq) under standard conditions wherein a trifluoromethyl group replaces the iodo functionality. For example, see Chen and Wu, *J. Chem. Soc., Chem. Comm.*, 1989, page 705 for general synthetic techniques. More specifically, the compound of Formula (IIp) is combined with a catalytic amount of copper iodide or copper bromide, such as about 0.2 equivalents of copper bromide, and about 2 equivalents of methyl 2,2-difluoro-2-(fluorosulfonyl)acetate in a suitable organic solvent, such as DMF or DMSO. The reaction mixture is heated at reflux for about 30 minutes to about 6 hours and the resulting compound of Formula (IIq) is isolated and purified by techniques well known in the art. For example, the reaction mixture is diluted with water and extracted with a suitable organic solvent, such as ethyl acetate. The organic extracts are combined, dried over anhydrous sodium sulfate, filtered, and concentrated under vacuum to provide the crude material. This material can then be purified by radial chromatography on silica gel with a suitable eluent, such as ethyl acetate:hexanes to provide the purified compound of Formula (IIq).

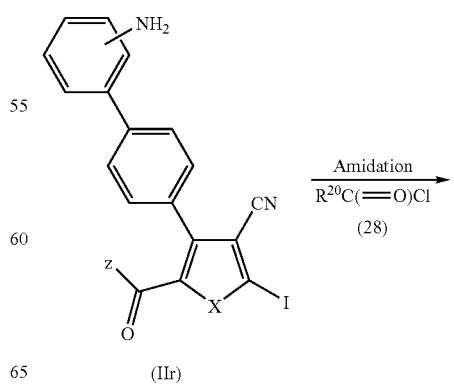

Scheme XXII (IIr)

-continued

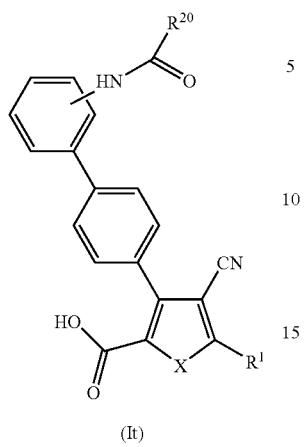

(It)

$R^{20}$ = (1-4C)alkyl

In Scheme XXII, the compound of Formula (IIr) is amidated under conditions well known in the art to provide the compound of Formula It. For example, the compound of Formula (IIr) is dissolved in a suitable organic solvent, such as THF and treated with about 3 equivalents of a suitable base, such as triethylamine, and about 1.1 to 1.4 equivalents of the acid chloride of structure (28), such as acetyl chloride, propionyl chloride, butyryl chloride, isobutyryl chloride, and the like. The reaction mixture is stirred at room temperature for about 2 to 8 hours. The resulting compound of Formula (It) is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the compound of Formula (It).

-continued

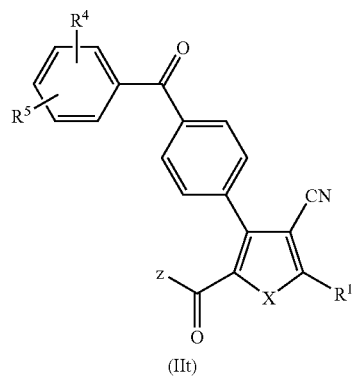

(IIt)

In Scheme XXIII the carboxylic acid of the compound of formula (IIs) is converted to the ketone of the compound of formula (IIt) under conditions well known in the art. For example, the carboxylic acid of the compound of formula (IIs) is dissolved in a suitable organic solvent, such as THF and treated with about 1.1 to 1.3 equivalents of oxalyl chloride. To this solution is added a catalytic amount of DMF and the reaction is stirred at room temperature for about 2 hours. The reaction mixture is then concentrated under vacuum to provide the corresponding acid chloride. This acid chloride is then dissolved in THF and added to a stirring mixture of about 1.2 equivalents of the suitable boronic acid (17a), a catalytic amount of a suitable palladium catalyst, such as tetrakis (triphenylphosphine)-palladium(0), and a suitable base, such as cesium carbonate in a suitable organic solvent, such as toluene. The reaction mixture is then heated at reflux for about 12 to 24 hours, cooled, and poured into water.

The resulting ketone of the compound of formula (IIt) is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the compound of formula (IIt).

Scheme XXIII

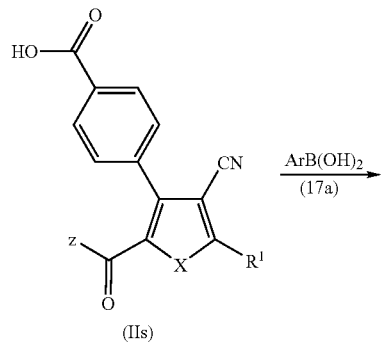

(IIs)

Scheme XXIV

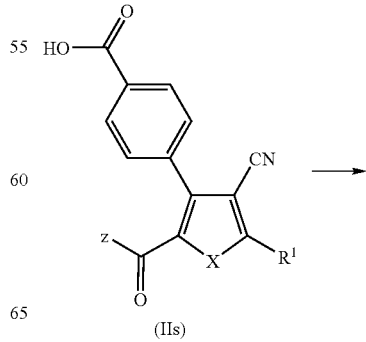

(IIs)

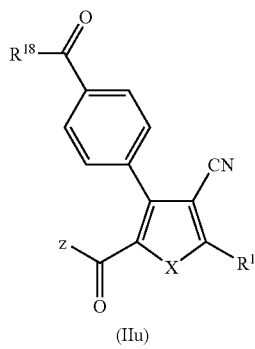

(IIu)

R[18] represents (1-4C)alkyl

In Scheme XXIV the compound of formula (IIs) is converted to the ketone of the compound of formula (IIu) under conditions well known in the art. For example, the compound of formula (IIs) is dissolved in a suitable organic solvent, such as THF and treated with about 1.1 to 1.3 equivalents of oxalyl chloride. To this solution is added a catalytic amount of DMF and the reaction is stirred at room temperature for about 2 hours. The reaction mixture is then concentrated under vacuum to provide the corresponding acid chloride. This acid chloride is then dissolved in a suitable organic solvent, such as THF and added to about 0.14 equivalents of copper cyanide, about 0.14 equivalents lithium bromide, and about 1.4 equivalents of a zinc reagent of formula R[18]ZnBr in THF at about -30° C. with stirring. The reaction mixture is allowed to warm to room temperature and stir for about 4 hours, and poured into water.

The resulting ketone of the compound of formula (IIu) is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the amide of the compound of formula (IIu).

Scheme XXV

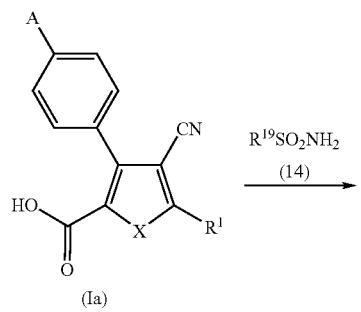

(Ia)

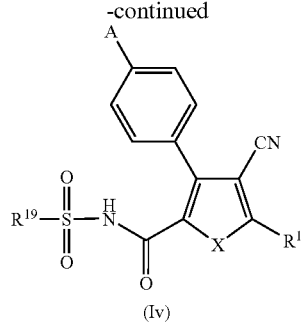

(Iv)

R[19] represents (1-4C)alkyl.

In Scheme XXV, the compound of formula (Ia) is converted to the sulfonamide of the compound of formula (Iv) under conditions well known in the art. For example, the compound of formula (Ia) is dissolved in a suitable organic solvent, such as dichloromethane followed by addition of about 1.1 equivalents of a suitable base, such as N,N-dimethylaminopyridine and about 1.2 equivalents of EDCI. To this stirring mixture at room temperature is added about 1.1 equivalents of the sulfonamide of structure (14), R[19]SO$_2$NH$_2$, and the reaction mixture is allowed to stir for about 3 to 18 hours. The resulting sulfonamide of the compound of formula (Iv) is then isolated and purified by one of ordinary skill in the art using extraction techniques and chromatography. For example, the reaction mixture is poured into 1N HCl and extracted with a suitable organic solvent, such as dichloromethane. The organic extracts are combined, washed with water and brine, dried over anhydrous magnesium sulfate, filtered, and concentrated under vacuum. The crude residue is then purifed by flash chromatography on silica gel with a suitable eluent, such as dichloromethane:methanol to provide the purified sulfonamide of the compound of formula (Iv).

Scheme XXVI

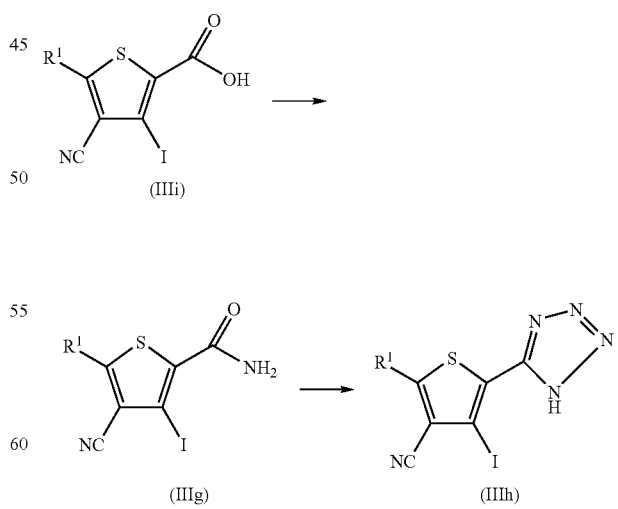

In Scheme XXVI, the compounds of formula (IIIh) can be prepared by methods previously described in Scheme XI.

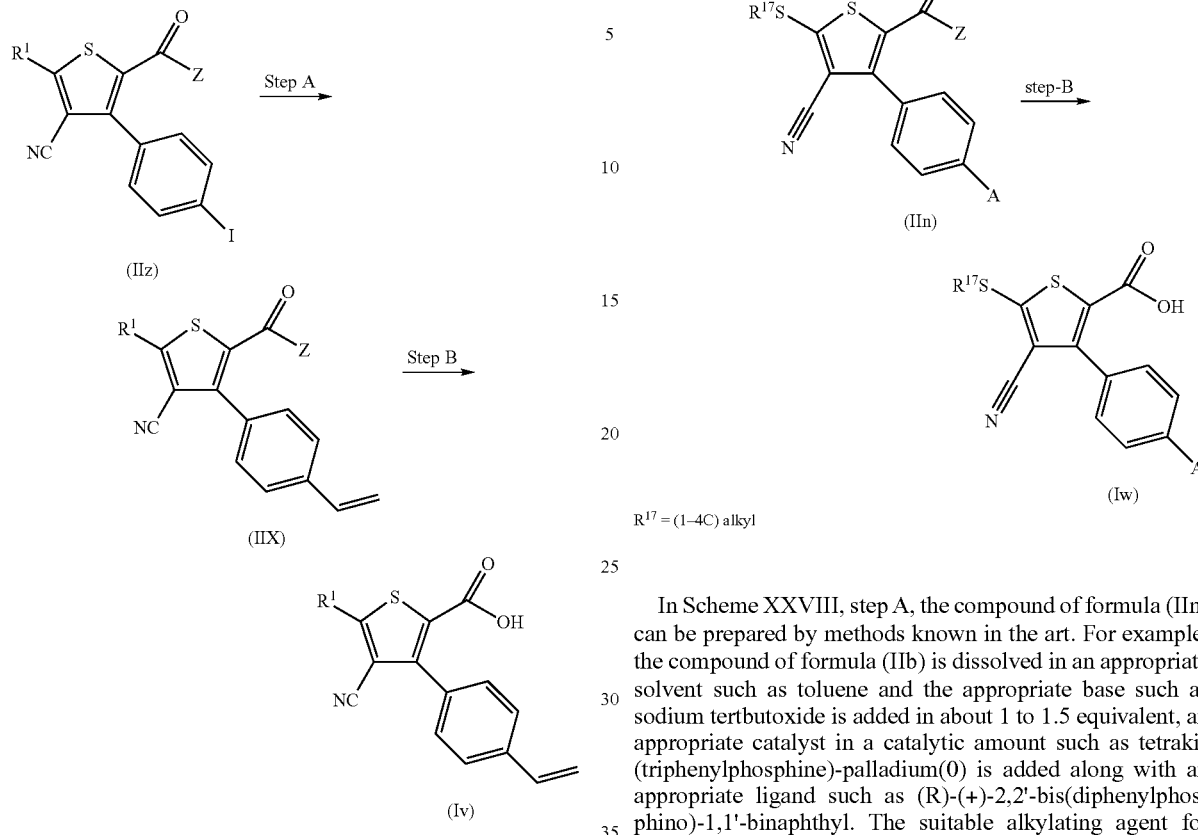

In Scheme XXVII, step A, the compound of formula (IIx) can be prepared by methods known in the art. For example, the compound of formula (IIz) is dissolved in an appropriate solvent such as tetrahydrofuran and the appropriate catalyst is added in about a 1% ratio to the starting material. Approximate one equivalent of the appropriate coupling reagent such as tributyl vinyl stannane is added along with an appropriate base such as lithium chloride. The reaction is allowed to react overnight and is then isolated and purified by one of ordinary skill in the art using extraction techniques and chromatography. For example, the reaction mixture is concentrated to dryness, washed with hexane to remove excess of stannane, added water and filtered the precipitate to provide the compound of formula (IIx). The ester of compound of formula (IIx) is hydrolyzed by methods in Scheme IX to give the compound of formula (Iv).

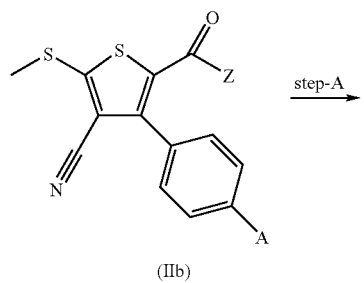

In Scheme XXVIII, step A, the compound of formula (IIn) can be prepared by methods known in the art. For example, the compound of formula (IIb) is dissolved in an appropriate solvent such as toluene and the appropriate base such as sodium tertbutoxide is added in about 1 to 1.5 equivalent, an appropriate catalyst in a catalytic amount such as tetrakis (triphenylphosphine)-palladium(0) is added along with an appropriate ligand such as (R)-(+)-2,2'-bis(diphenylphosphino)-1,1'-binaphthyl. The suitable alkylating agent for example, ethanethiol, propanethiol, isopropylthio is added in about 2 equivalents. The reaction mixture is heated to about 90° C. under nitrogen, filtered over celite, and the solvent is removed by vaccum. This material can be purified by methods known in the art such as silica gel chromatography using a solvent system such as hexane and ethyl acetate to give the final compound of formula (IIn). The ester of compound of formula (IIn) is hydrolyzed by methods in Scheme IX to give the compound of formula (Iw).

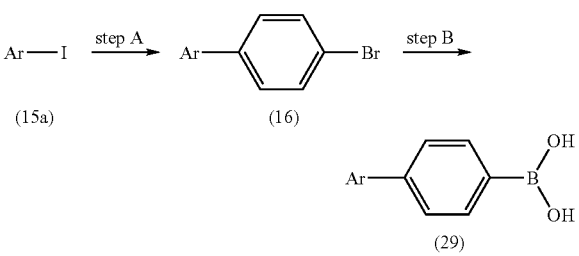

In Scheme XXIX, step A, the compound of structure (16) can be prepared by methods described previously in Scheme (XIII). In Scheme XXIX, step B, the compound of structure (16) is dissolved in an appropriate solvent such as anhydrous tetrahydrofuran and cooled to about −110° C. A solution of about 1.6 M n-butyllithium is added via a cannula while maintaining the temperature to about −95° C. A suitable trialkylborate is added, such as trimethyl borate is added to the anion and the temperature of reaction is returned to room temperature over a period of about two hours. The borate ester is hydrolyzed with an acid such as hydrochloride acid. The product is then isolated and purified by techniques well known in the art, such as extraction and chromatography. For example, the aqueous phase is extracted with a suitable organic solvent, such as dichloromethane, the organic extracts are combined, washed with brine, dried over anhydrous magnesium sulfate, filtered, and concentrated under vacuum to provide the crude compound of structure (29). The crude boronic acid is dissolved in an appropriate base such as aqueous sodium hydroxide and washed with ethyl ether. The aqueous solution is cooled to about 0° C. and acidified with an acid such as hydrochloric acid. The crude product of formula (29) is extracted with a suitable organic solvent, such as dichloromethane, the organic extracts are combined, dried over anhydrous magnesium sulfate, filtered, and concentrated under vacuum to provide the compound of structure (29). For example, 2'-carbonitrile-biphenyl-boronic acid can be synthesized by using the starting materials 2-iodobenzonitrile and 4-bromophenylboronic acid.

Scheme XXX

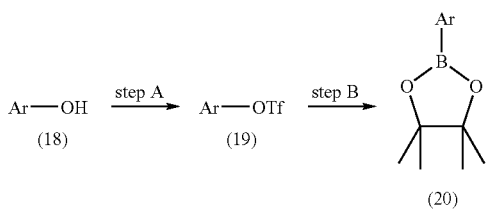

In Scheme XXX step A, the phenol of structure (18) is dissolved in a suitable solvent such as methylene chloride or tetrahydrofuran and cooled to about −20° C. to about −70° C. A base such as pyridine or sodium hydride is added and the anion is allowed to formed for about an hour. The triflate group is added by the reagent trifluoromethanesulfonic anhydride or depending on other subsituents of the compound of structure (18), N-phenyltrifluoromethanesulphonimide might be considered. The reaction is allowed to proceed at room temperature for about 90 minutes to overnight. The reaction can be quenched with 1N hydrochloric acid or evaporated to dryness. The crude material is isolated by extracting the aqueous layer with a suitable solvent such as methylene chloride or diethylether. The organic phase is washed with water, saturated sodium bicarbonate, optional saturated sodium chloride, drying over sodium sulfate or magnesium sulfate. The crude material can be used further without purification or can be purified by silica gel chromatography using an eluent such as ethyl acetate/hexane to give the compound of structure (19).

In Scheme XXX, Step B, compounds of structure (20) are prepared essentially the same as in Scheme XXIX using the trifluoro-methanesulfonic acid 4-cyclopentylphenyl ester instead of the iodo compound and extracting with methylene chloride.

An alternative method might be used if substituents of the aromatic ring would not be appropriate to conditions described in Scheme (XXX) step (A) would include the use of the palladium catalyst PdCl$_2$ (dppf) and the base potassium acetate, and the solvent dimethylformamide.

For example, 2-(4-cyclopentyl-phenyl)-4,4,5,5-tetramethyl-[1,3,2]dioxaborlane can be synthesized by this method using the starting materials 4-cyclopentyl phenol and trifluoromethanesulfonic anhydride and the base pyridine. Also, 3-[4,4,5,5-tetramethyl-[1,3,2]dioxaborlane-2-yl)-phenyl-propionitrile can be prepared from 3-(4-hydroxy-phenyl)-propionitrile.

Scheme XXXI

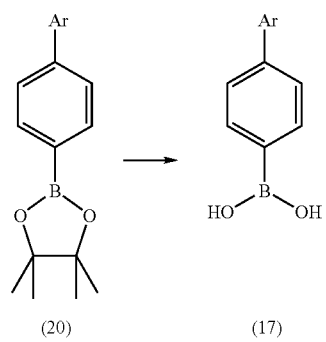

In Scheme XXXI, the compound of structure (20) is oxidized by using methods well known in the art. For example, the compound of structure (20) is dissolved in an appropriate solvent such as acetone and an oxidizing agent such as sodium periodate. A ammonium acetate solution is also added. The reaction is also stirred at room temperature for about twenty hours. The product is then isolated and purified by techniques well known in the art, such as the reaction mixture is filtered, concentrated under vacuum, aqueous layer extracted with a suitable solvent such as methylene chloride, organic layers combined, dried over sodium sulfate, and concentrated under vacuum to give the crude compound of structure (17). To the crude compound of structure (17), hexanes and tert-butylmethyl ether can be added to the crude product until a solid is formed. The solid can be isolated by filtration to give pure compounds of structure (17).

The examples set forth herein represent typical syntheses of the compounds of the present invention. The following examples have been labeled as follows for ease of reference: "Example E-1" refers for example to compounds wherein $R^2$ represents an ester group; "Example A-1" refers for example to compounds wherein $R^2$ is a carboxylic acid group; "Example AM-1" refers for example to compounds wherein $R^2$ is an amide group; "Example CN-1" refers for example to compounds wherein $R^2$ is a cyano group; "Example S-1" refers for example to compounds wherein $R^2$ is a sulfonamide group; and "Example T-1" refers for example to compounds wherein $R^2$ is a triazole or tetrazole group. The reagents and starting materials are readily available to one of ordinary skill in the art.

As used herein, the terms listed in the following table have the corresponding meanings as indicated:

| Term | Meaning |
|---|---|
| Ex. | Example |
| MS(FIA) | Flow injection analysis mass spectrometry |
| MS(FD) | Field distortion mass spectrometry |
| MS(IS) | Ion spray mass spectrometry |
| MS(FAB) | Fast atom bombardment mass spectrometry |
| MS(ES) | Electron spray mass spectrometry |
| HRMS | High resolution mass spectrometry |
| $^1$H NMR | Proton nuclear magnetic resonance spectrometry |
| eq. | equivalents |
| g | grams |
| mg | milligrams |

-continued

| Term | Meaning |
| --- | --- |
| L | liters |
| mL | milliliters |
| μL | microliters |
| mol | moles |
| mmol | millimoles |
| psi | pounds per square inch |
| m.p. | melting point |
| DSC | differential scanning calorimetry |
| J/g | joules per gram |
| min | minutes |
| h or hr | hours |
| °C. | degrees celsius |
| TLC | thin layer chromatography |
| HPLC | high performance liquid chromatography |
| $R_f$ | retention factor |
| $R_t$ | retention time |
| δ | parts per million down-field from tetramethylsilane |
| aq. | aqueous |
| Celite ® | diatomaceous earth filtering agent |
| HMPA | hexamethylphosphoramide |
| RT | room temperature |
| DMF | N,N-dimethylformamide |
| DMSO | methyl sulfoxide |
| LDA | lithium diisopropylamide |
| EtOAc | ethyl acetate |
| THF | tetrahydrofuran |
| iPrOAc | isopropyl acetate |
| HOBt | 1-hydroxybenzotriazole |
| methyl DAST | dimethylaminosulfur trifluoride |
| DMAP | dimethylaminopyridine |
| DAST | diethylaminosulfur triflouride |
| TFA | trifluoroacetic acid |
| MTBE | tert-butyl methyl ether |
| DBU | 1,8-diazabicyclo[5.4.0]undec-7-ene |
| TEA | triethylamine |
| TBDMS | tert-butyldimethylsilyl |
| NBS | N-bromosuccinimide |
| $Et_3N$ | triethylamine |
| $(Boc)_2O$ | di-tert-butyl dicarbonate |
| DME | 1,2-dimethoxyethane |
| EtOH | ethanol |
| MeOH | methanol |
| Triflate | —$SO_3CF_3$ functional group |
| (dppf) | 1,1'-bis(diphenylphosphino)ferrocene |
| S.M. | starting material |
| DCC | dicyclohexylcarbodiimide |
| $Pd_2(dba)_3$ | tris(dibenzylideneacetone)-dipalladium(0) |
| EDCI | 1-ethyl-3-[3-(dimethylamino)propyl]-carbodiimide HCl |
| SELECTFLUOR ® | 1-chloromethyl-4-fluoro-1,4-diazoniabicyclo[2.2.2]octane bis-(tetrafluoroborate) |
| DIAD | Diisopropyl azodicarboxylate |

Preparation 1

4'-Bromo-biphenyl-2-carbonitrile

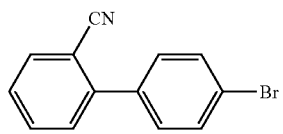

Combine 2-iodobenzonitrile (9.0 g, 38.5 mmol), 4-bromophenylboronic acid (10.4 g, 51.8 mmol), 2M aqueous sodium carbonate (20 mL) and tetrakis(triphenylphosphine)-palladium(0) (4.5 g, 3.9 mmol) in 300 mL of dioxane and heat to 80° C. under nitrogen with stirring. After 3 hours cool to room temperature and dilute with 900 mL of ethyl acetate. Wash with water (2×50 mL), brine (1×50 mL) and dry over sodium sulfate. Filter and evaporate to a yellow solid. Chromatograph on silica gel two times, eluting with a gradient of 100% toluene to 1/9 ethyl acetate/toluene to give the title compound as a tan solid, 5.42 g (55%). MS (FAB)=257 ($M^+$); HPLC analysis is 95%.

Preparation 2

2'-Carbonitrile-biphenyl-boronic acid

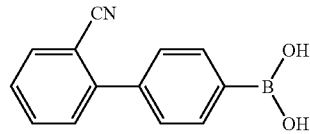

Dissolve 4'-bromo-biphenyl-2-carbonitrile (2.0 g, 7.8 mmol) in 40 mL of ethyl acetate and dry over magnesium sulfate. Filter off drying agent and evaporate; dissolve the dried starting material in 100 mL of anhydrous tetrahydrofuran and cool to −100° C. Next add dropwise via cannula a solution of 1.6M n-butyllithium in hexanes (5.9 mL, 9.4 mmol), keeping the internal temperature less than −95° C. After 5 minutes, add anhydrous trimethyl borate (1.6 mL, 14.0 mmol) in one portion to the yellow-orange solution of the anion and allow the resulting mixture to come to room temperature over two hours. Next adding 40 mL of 5N hydrochloric acid hydrolyzes the borate ester and extract the boronic acid with methylene chloride (3×100 mL). Wash the combined organic layers with brine (1×50 mL), dry over magnesium sulfate, filter and evaporate. Dissolve the crude boronic acid in 100 mL of 1N aqueous sodium hydroxide and wash with ethyl ether (2×50 mL) to remove the non-acidic impurities. Cool the washed aqueous layer to 0° C. and acidify with 100 mL of 5N aqueous hydrochloric acid. Extract the product with methylene chloride (3×100 mL), dry organic layer over magnesium sulfate, filter, and evaporate to give the title compound, 1.22 g (71%) as a white solid: MS: (ES−, m/e)=222 ($M^+$−1); HPLC=75%.

Preparation 3

Trifluoro-methanesulfonic acid 4-cyclopentyl-phenyl ester

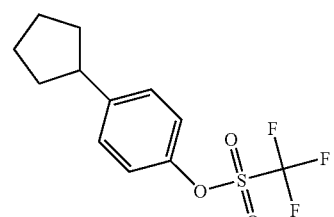

Add dry pyridine (1.4 mL, 17.3 mmol) to a solution of 4-cyclopentyl-phenol (1.0 g, 5.86 mmol) in 35 mL of $CH_2Cl_2$ and cool to −70° C. under nitrogen. Add trifluoro-methanesulfonic anhydride (1.2 mL, 7.13 mmol) dropwise and remove the cooling bath and allow the reaction to warm to room temperature. Ninety minutes later pour the mixture into 50 mL cold 1N HCl. Shake and separate the layers; wash with organics with ice-water (1×20 mL) and saturated aqueous NaHCO$_3$ (1×20 mL) and dry over Na$_2$SO$_4$. Filter and evaporate to a brown oil, 1.8 g, which is used without further purification.

Preparation 4

2-(4-Cyclopentyl-phenyl)-4,4,5,5-tetramethyl-[1,3,2]dioxaborlane

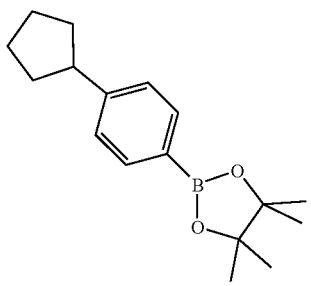

Prepare the title compound in a manner analogous to the procedure set forth in 4-cyano-5-ethyl-3-[4-[4,4,5,5-tetramethyl-[1,3,2]dioxaborolan-2-yl)-phenyl]-thiophene-2-carboxylic acid ethyl ester using the crude trifluoro-methanesulfonic acid 4-cyclopentyl-phenyl ester (5.86 mmol), refluxing for 4 hours and extracting with CH$_2$Cl$_2$ instead of EtOAc. Yield=1.8 g dark red oil which is used without further purification.

Preparation 5

Trifluoro-methanesulfonic acid 4-(2-cyano-ethyl)-phenyl ester

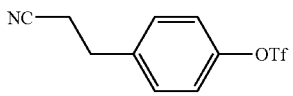

Add NaH 95% (90 mg, 3.74 mmol) to a −20° C. solution of 3-(4-hydroxy-phenyl)-propionitrile or 4-cyclopentylphenol (commercially availables) (3.4 mmol) in dry THF (25 ml) under nitrogen atmosphere and stir at this temperature for 1 hour. Add N-phenyltrifluorometheanesulphonimide (commercially available) (3.74 mmol, 1.1 eq) in one portion and stir overnight at room temperature. Evaporate solvents to dryness and partition the crude between diethyl ether and water. Wash the organic phase with sodium carbonate 10% solution and NaCl sat. solution, dry over MgSO$_4$ and remove the solvent in vacuo. Purification by flash chromatography (hexane:ethyl acetate, 4:1) to provide the title compound.

Preparation 6

3-[4-(4,4,5,5-Tetramethyl-[1,3,2]dioxaborolan-2-yl)-phenyl-propionitrile

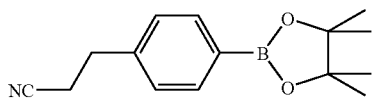

Heat at 80° C. a mixture trifluoro-acetic acid 4-(2-cyano-ethyl)-phenyl ester (2.63 mmol), PdCl$_2$(dppf) (0.5 mmol, 0.2 eq), bis(pinacolato)diboron (commercially available) (3.156 mmol, 1.2 eq) and potasium acetate (774 mg, 7.89 mmol, 3 eq) in DMF (16 ml) under nitrogen atmosphere overnight. Partition the reaction mixture between ethyl acetate and ice-water. Wash the organic phase with HCl 10% solution and water, dry over MgSO$_4$ and filter over Celite® and remove the solvent in vacuo. Purification by flash chromatography (hexane:ethyl acetate 4:1) provides the title compound.

Preparation 7

4'-Bromo-biphenyl-2-ylamine

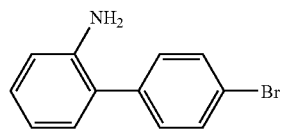

Add 4-bromophenyl boronic acid (5.0 g, 24.82 mmol), tetrakis(triphenylphosphine)palladium (0) (0.717 g, 0.620 mmol) and 2 M Na$_2$CO$_3$ (10 mL) to a solution of 2-iodoaniline (4.5 g, 20.69 mmol) in toluene (2 mL):ethanol (20 mL), degas and heat at 80° C. under nitrogen. After 4 h, add water and extract with ethyl acetate. Combine the organic layers, dry over sodium sulfate, filter and concentrate under reduced pressure to give a residue. Purify the residue by flash chromatography (silica gel) eluting with ethyl acetate:hexane 1:12 to provide the title compound (3.53 g, 69%): Mass spectrum (m/e): 248 (M+1); 249 (M+2). $^1$HNMR (CDCl$_3$), δ3.62 (s, 2H); 6.75-6.89 (m, 2 H); 7.08-7.18 (m, 2H); 7.21-7.40 (m, 2H); 7.55-7.63 (m, 2H):

Preparation 8

Propane-2-sulfonic acid (4'-Bromo-biphenyl-2-yl)-amide

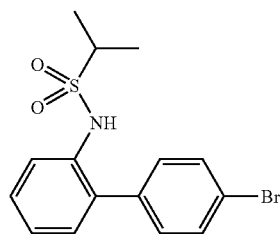

Add dropwise 1,8-diazabicyclo[5.4.0]undec-7-ene (DBU) drop wise (8.76 mL, 56.92 mmol) to a solution of 4'-bromo-biphenyl-2-ylamine (3.53 g, 14.23 mmol) in dichloromethane (50 ml) at 0° C., followed by drop wise addition of isopropylsulfonyl chloride (3.29 mL, 28.46 mmol) and stir the reaction at room temperature for 24 h. Remove solvent under reduce pressure and purify the residue by silica and eluting with ethyl acetate:hexane 1:4 to ethyl acetate to provide the title compound (4.93 g, 98%): Mass spectrum (m/e): 355 (M+1); 353 (M−1); $^1$HNMR (CDCl$_3$) δ 1.24 (d, 6H, J=6.7 Hz); 3.28 (sep, 1H, J=6.9 Hz); 6.22 (s, 1H); 7.12-7.41 (m, 5H); 7.55-7.68 (m, 3H).

Preparation 9

Propane-2-sulfonic acid (4'-(4,4,5,5-tetramethyl-[1,3,2]dioxaborolan-2-yl)-biphenyl-2-yl)-amide

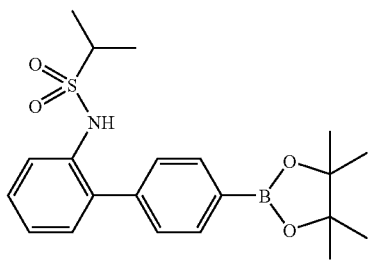

Heat at 80° C. a mixture of propane-2-sulfonic acid (4'-bromo-biphenyl-2-yl)-amide (4.0 g, 11.22 mmol), bis(pinacolato)diboron (3.22 g, 12.34 mmol), [1,1'-bis(diphenylphosphino)ferrocene]-dichloropalladium(II) complex with dichloromethane (1:1) (0.276 g, 0.337 mmol) and potassium acetate (3.32 g, 33.87 mmol) in dry dimethyl sulfoxide (25 mL). After 16 h add water and extract with ethyl acetate. Combine organic layers, dry over sodium sulfate and evaporate under reduce pressure. Dissolve the residue in dichloromethane and wash with a solution of 0.1N HCl. Combine the organic layers, dry over sodium sulfate, filter and concentrate under reduced pressure. Purify the residue by flash chromatography (silica gel) eluting with ethyl acetate:hexane 1:3 to provide the title compound (4.07 g, 90%): Mass spectrum (m/e): 424 (M+23); 400 (M−1); $^1$HNMR (CDCl$_3$) δ 1.19 (d, 6H, J=6.7 Hz); 1.37 (s, 12H); 3.19 (sep, 1H, J=6.9 Hz); 6.38 (s, 1 H); 7.16-7.39 (m, 6H); 7.61-7.72 (m, 1H); 7.64-7.94 (m, 1H).

Preparation 10

Propane-2-sulfonic acid (4'-(boronic acid)-biphenyl-2-yl)-amide

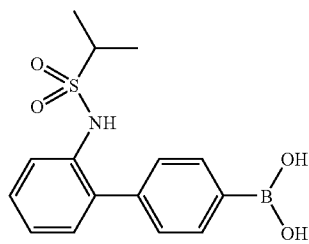

Add sodium periodate (1.12 g, 5.25 mmol) followed by a solution of 1 N ammonium acetate (8 mL) to a suspension of propane-2-sulfonic acid [4'-(4,4,5,5-tetramethyl-[1,3,2]dioxaborolan-2-yl)-biphenyl-2-yl)-amide (0.7 g, 1.75 mmol) in acetone (16 mL)/water (0.8 mL). Stir the mixture at room temperature under nitrogen for 20 h. Filter the precipitate and evaporate organic layer. Extract aqueous layer with dichloromethane. Combine organic layers, dry over sodium sulfate and evaporate the solvent under reduced pressure. Add hexanes and tert-butylmethyl ether to the residue until a solid is formed and filter the solid to provide the title compound (0.37 g, 67%). Mass spectrum (m/e): 337 (M+18); 318 (M−1); $^1$HNMR (CDCl$_3$) δ 1.22 (d, 6H, J=6.7 Hz); 3.24 (sep, 1H, J=6.9 Hz); 6.46 (s, 1H); 7.18-7.89 (m, 6H); 8.38-8.42 (m, 1H).

Preparation 12

3-Methylsulfanyl-thiophene

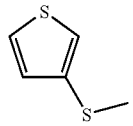

Add dropwise a solution of n-BuLi (63.2 ml, 1.6 M) to a solution of 3-bromothiophene (15 g, 92 mmol) in hexane (135 ml) at −40° C. Add THF (45 ml) to the flask and the 3-lithiothiophene precipitates as a white solid. Add more hexane (45 ml) and warm the reaction mixture to room temperature. Add dropwise methyl disulfide (9.1 ml, 101.2 mmol) to the resulting solution and stir the reaction mixture for 12 hours at room temperature. Add water (approx. 100 mL) to the flask, separate the organic layer, dry with magnesium sulphate and evaporate the solvent yielding 13 g (95%) of the title compound as a colorless oil.

Preparation 13

2-Iodo-3-methylsulfanyl-thiophene

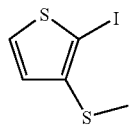

Add dropwise a solution of bis(pyridine)iodonium (I) tetrafluoroborate (46 g, 123 mmol, see J. Org. Chem., 55, 3104, (1990) in dichloromethane (500 ml) to a solution of 3-methylsulfanyl-thiophene (16 g, 123 mmol) in dichloromethane (300 ml) at room temperature. After 10 minutes add water, separate the organic layer, dry with magnesium sulphate and evaporate the solvent. Dissolve the crude product in ethyl acetate (200 ml) and wash with a solution of NaHSO$_3$ 10% (3×100 ml). Separate the organic layer, dry with magnesium sulphate and evaporate the solvent yielding 23 g (74%) of the title compound as a slightly colored oil.

Preparation 14

3-Methylsulfanyl-2-phenyl-thiophene

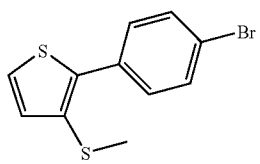

Degas a solution of 2-iodo-3-methylsulfanyl-thiophene (18 g, 70.3 mmol), 4-bromobenzeneboronic acid (14.1 g, 70.3 mmol), potassium carbonate (21.4 g, 155 mmol), tetrakis(triphenylphosphine)-palladium (0) (8.1 g, 7.02 mmol) in a mixture of anhydrous dimethoxyethane (300 ml) and absolute ethanol (150 ml) with Ar or N₂ for 15 min and stir for 12 hours at 80° C. Cool the reaction mixture to room temperature, add water (100 ml) and extract the crude product with dichloromethane (3×150 ml). Purify the title compound by column chromatography using hexane as eluent solvent yielding the title compound 12 g (60%) as a white solid.

NOTE: This product is also light sensitive and it is highly recommended to be used immediately. We have observed decomposition of aprox 5% of the material after 12 hours.

Preparation 15

4,4,5,5-Tetramethyl-2-[4-(3-methylsulfanyl-thiophen-2-yl)-phenyl]-[1,3,2]dioxaborolane

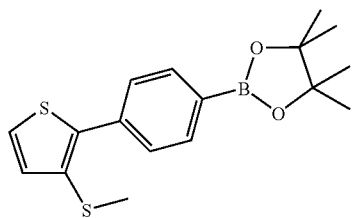

Combine 3-methylsulfanyl-2-phenyl-thiophene (12 g, 42 mmol), bis(pinacolato)diboron (11.8 g, 46.2 mmol), potassium acetate (13.6 g, 138.9 mmol), PdCl₂(dppf) (3.42 g, 4.2 mmol) in anhydrous DMSO (150 ml) and stir at 80° C. for 12 hours. Cool the reaction mixture to room temperature, dilute with ethyl acetate (200 ml), and wash with water (3×100 ml). Separate the organic layer and dry with magnesium sulphate. To this solution, add 10 g of silica and evaporate the solvent. Place the resulting mixture in a sintered glass funnel and elute with a 10:1 mixture of Hexane/EtOAc. The catalyst remains in the silica. Evaporate the solvent and obtain the solid which was disgregated with hexane (to eliminate most of the bis(pinacolato)diboron which is the major impurity) yielding 6 g (50%) of the title compound.

Preparation 16

Thiophen-3-yl-carbamic acid tert-butyl ester

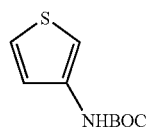

Using the method of Barker (Barker, J. M.; Huddleston, P. R.; Wood, M. L. *Synthetic Communications* 1995, 25(23), 3729-3734) reflux methyl-3-aminothiophene-2-carboxylate (42.8 g, 0.27 mol) at 120° C. with 2M sodium hydroxide aqueous solution (270 mL) for 30 min. Cool the reaction mixture to 0° C. and acidify to pH 5.0 (Congo red) with concentrated hydrochloric acid. Filter the thick precipitate and dry the solid. Dissolve the solid in acetone (300 mL) and dry (MgSO₄) the resulting solution, filter, and evaporate at 20° C. Perform as soon as possible because the acid decomposes quite rapidly (≈1 hour the solid turns black). Treat the resulting thick oil with oxalic acid dihydrate (26.7 g) in 2-propanol (100 mL) at 38° C. for 45 min. Allow the mixture to reach room temperature, dilute with ether (40 mL), filter the solid, and wash with ether. Exposure to light and air, the resulting white solid (33.1 g) became pale lilac. Dissolve the resulting salt (33.1 g) in water (400 mL) and basify with concentrated NH₃. Upon exposure to light and air, the salt is more stable than the acid and it is possible to keep it in a brown bottle under argon or nitrogen atmosphere for approx. 2 days. Extract the mixture with dichloromethane (3×200 mL) and combine the extracts, dry over MgSO₄, and evaporate to give a brown oil (15 g, 56%).

Dissolve 3-aminothiophene (15 g, 0.15 mol) in dichloromethane (300 mL) and add Et₃N (42.2 mL, 0.3 mol) at 0° C. Add a solution of (Boc)₂O (39.3 g, 0.18 mol) in methylene chloride (100 mL) dropwise at 0° C. and stir the mixture overnight at r.t. T.L.C. (Hexane/Ethyl acetate 9:1) shows complete disappearance of starting material. Quench the reaction by addition of water (200 mL). Extract the mixture with dichloromethane (2×200 mL), combine the extracts, dry over MgSO₄ and evaporate. Purification by flash chromatography (Silica gel-Hexane/ethyl acetate 9:1) gives 20.1 g (67%) of title compound as a white solid.

Preparation 17

(2-Iodo-thiophen-3-yl)-carbamic acid tert-butyl ester

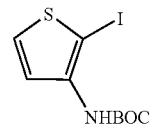

Using the method of Monroe et. al. (Campaigne, E.; Monroe, P. A. *J.A.C.S.* 1954, 76, 2447-2450) add to a boiling solution of thiophen-3-yl-carbamic acid tert-butyl ester (21.0 g, 0.1 mol) in dichloromethane (400 mL) NIS (23.7 g, 0.1 mol) in small portions. Heat the reaction with the heating bath at 65° C. for 20 min. Checking by T.L.C. (Hexane/ethyl acetate 9:1) shows complete consumption of starting material. Take the reaction to room temperature, evaporate the solvent and purification by flash chromatography (Silica gel-Hexane/ethyl acetate 9:1) of the crude to obtain 30.0 g (88%) of title compound as a white solid.

Preparation 18

[2-(4-Bromo-phenyl)-thiophen-3-yl]-carbamic acid tert-butyl ester

Heat (2-iodo-thiophen-3-yl)-carbamic acid tert-butyl ester (16.88 g, 0.52 mol), 4-bromophenylboronic acid (15.65 g, 0.78 mol), Na₂CO₃ (1.01 g, 1.04 mol) and Pd(PPh₃)₄ (5.79 g, 0.052 mol) in 375 ml of an anhydrous and deoxygenated 2:1 DME/EtOH mixture to 80° C. under nitrogen atmosphere for 24 h. Anaylsis by T.L.C. (Hexane/Ethyl acetate 9:1) shows complete disapperence of starting material. Evaporate the organic solvents, prior to the addition of water (200 mL). Extract the mixture with dichloromethane (3×150 mL) and dry the combined organic phases (MgSO$_4$) and concentrate to furnish a crude mixture as a yellowish solid. Purification by flash chromatography (Silica gel-Hexane/Ethyl acetate 49:1) yielded 10.8 g (60%) of title compound as a pale yellow solid.

Preparation 19

2-(4-Bromo-phenyl)-thiophen-3-yl amine

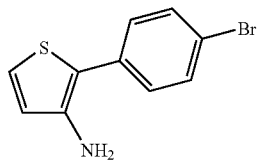

Treat a solution of [2-(4-bromo-phenyl)-thiophen-3-yl]-carbamic acid tert-butyl ester (10.8 g, 0.3 mol) in Ethyl acetate (75 mL) at 0° C., dropwise with 244 mL (8 mL/mmol) of freshly prepared 1N HCl in Ethyl acetate and stir the mixture at r.t. overnight. Dissolve the white precipitate with H$_2$O (100 mL) and neutralize with a NaHCO$_3$ saturated solution. Extract the mixture with Ethyl acetate (3×100 mL) and dry the combined organics and concentrate to give a slightly colored solid. Purification by flash chromatography (Silica gel-Hexane/Ethyl acetate 49:1 then 9:1) furnishes 5.7 g (74%, at 1.0 g scale, the reaction was quantitative) of title compound as a pale yellow solid.

Preparation 22

2-(4-Bromo-phenyl)-3-chloro-thiophene

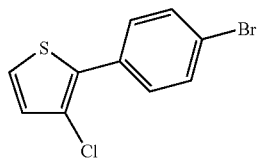

Add dropwise a solution of 2-(4-bromo-phenyl)-thiophen-3-yl amine (1.0 g, 3.94 mmol) in dry acetonitrile (7 mL) to a mixture of t-BuONO (1.87 mL, 15.76 mmol) and CuCl$_2$ (1.06 g, 7.87 mmol) in dry acetonitrile (15 mL) at 0° C. Stir the reaction for 2 h. Analysis by T.L.C. (Hexane) shows complete consumption of starting material. Add water (20 mL) and extract the mixture with Ethyl acetate (2×20 mL). Combine the organic layers and dry and concentrate to give a crude solid. Purification by flash chromatography (Silica gel-Hexane) gives 0.75 g (70%) of the title compound as a pale yellow oil.

Preparation 23

2-[4-(3-Chloro-thiophen-2-yl)-phenyl]-4,4,5,5-tetramethyl-[1,3,2]dioxabrolane

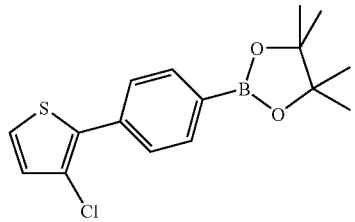

Deoxygenate by purging with nitrogen a mixture of 2-(4-bromo-phenyl)-3-chloro-thiophene (1.0 g, 3.66 mmol), bis(pinacolato)diboron (1.39 g, 5.48 mmol), KOAc (1.18 g, 12.08 mmol) and Pd(dppf)$_2$Cl$_2$ catalyst (0.3 g, 0.37 mmol) in dry DMF (20 mL) and heat at 80° C. overnight. Anaylsis by T.L.C. (Hexane/Ethyl acetate 4:1) shows complete consumption of starting material. Add water (20 mL) and extract with ether (3×20 mL). Wash the combined organic with water and dry and concentrate to give a crude solid. Purification by flash chromatography (Silica gel-Hexane/Ethyl acetate 99:1) gives pure 1.05 g (89%) of the title compound as a pale yellow solid.

Preparation 24

2-Iodo-thiophene-3-carbonitrile

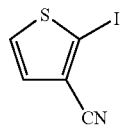

Add dropwise to a solution of diisopropylamine (32.1 mL, 229 mmol) in THF (1 L) at −40° C. n-BuLi (143 mL, 229 mmol) and stir for 30 minutes. Cool the reaction mixture to −78° C. and add 3-cyanothiophene (25 g, 229 mmol). After stirring for 15 minutes, add a solution of N-iodosuccinimide (52 g, 229 mmol) in THF (250 mL) and warm the reaction mixture to room temperature. Add water (aprox. 200 mL) to the flask, separate the organic layer, dry with magnesium sulphate and evaporate the solvent. Purification by column chromatography (hexane-methyltertbutyl ether 100/1) yields 20 g (40%) as a white solid: $^1$H NMR (CDCl$_3$): δ 7.10 (d, J=5.6 Hz, 1H), 7.47 (d, J=5.6 Hz, 1H. $^{13}$C NMR (CDCl$_3$): δ 87.1, 115.8, 120.8, 130.6, 133.

Preparation 25

2-(4-Bromo-phenyl)-thiophene-3-carbonitrile

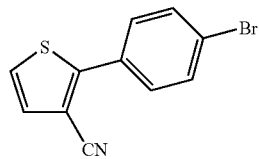

Degass a solution of 2-iodo-thiophene-3-carbonitrile (20 g, 85 mmol), 4-bromobenzeneboronic acid (18.8 g, 94 mmol), potassium carbonate (26 g, 187 mmol) and tetrakis(triphenylphosphine)-palladium (0) (10 g, 8.5 mmol) in a mixture of anhydrous dimethoxyethane (300 mL) and absolute ethanol (150 mL) with Ar or N₂ for 15 min and stir for 12 hours at 80° C. Cool the reaction mixture to room temperature, add water (100 ml) and extract the crude product dichloromethane (3×150 mL). Purification by chromatography (hexane-ethyl acetate 10/1) yields 16.3 g (72%) as a white solid: ¹H NMR (CDCl₃): δ 7.32 (m, 2H), 7.62 (m, 4H).

Preparation 26

2-[4-(4,4,5,5-Tetramethyl-[1,3,2]dioxaborolan-2-yl)-phenyl]-thiophene-3-carbonitrile

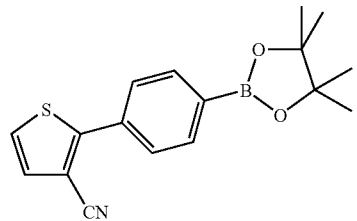

Stir a solution of 2-(4-bromo-phenyl)-thiophene-3-carbonitrile (16.3 g, 62 mmol), bis(pinacolato)diboron (17.2 g, 68 mmol), potassium acetate (20 g, 204 mmol), PdCl₂(dppf) (5 g, 6.1 mmol) in anhydrous DMSO (200 mL) at 80° C. for 12 hours. Cool the reaction mixture to room temperature, dilute with ethyl acetate (250 mL), and wash with water (3×100 mL). Separate the organic layer and dry with magnesium sulphate and evaporate the solvent. Purify the crude product by column chromatography using a mixture of hexane ethyl acetate (8/1) of eluent solvent to provide the title compound: ¹H NMR (CDCl₃): δ 1.37 (s, 12H), 7.32 (m, 2H), 7.76 (d, J=8.3 Hz, 2H). 7.91 (d, J=8.3 Hz, 2H); ¹³C NMR (CDCl₃): δ 25.2, 84.5, 106.8, 116.1, 126.2, 127.3, 131.0, 134.1, 135.9, 154.0.

General Preparation 27

4-A-Benzoyl chloride

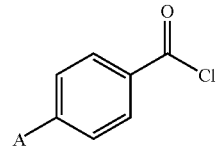

Dissolve 4-A-benzoic acid (wherein A is defined wherein) (7.0 mmol) in thionyl chloride (1.0 ml) and heat at 50° C. After 1 hour, remove solvent in vacuo to give 1.63 g (quantitative) of title compound which is used without further purification in next steps.

General Preparation 28

3-Oxo-3-(4-A-phenyl)-propionitrile

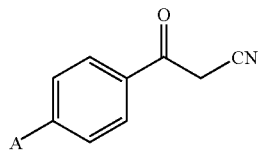

Add butyllithium (1.6 M in hexane) (28 mmol) to a stirring solution of cyanoacetic acid (14 mmol) (dry previously with MgSO₄ in Ethyl acetate) in THF (80 ml) and cool at −78° C. under a nitrogen atmosphere. Allow the reaction temperature to slowly rise to 0° C. Recool the slurry to −78° C. and add dropwise a solution of 4-A-benzoyl chloride, prepared in general preparation 27, (7.0 mmol) in 10 ml of THF and stir at −78° C. After 1 hour, allow the reaction mixture to gradually come to room temperature over a period of 1 hour. Add HCl (1N solution) and extract with ethyl acetate. Wash organic phase with NaHCO₃, sat. NaCl, dry over MgSO₄ and remove solvent in vacuo. Purification by chromatography (hexane:ethyl acetate mixture) provides the title compound General Preparation 29

2-(4-A-benzoyl)-3,3-bis-methylsulfanyl-acrylonitrile

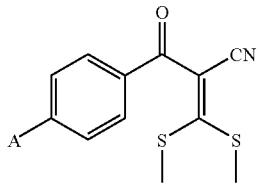

Add in two portions NaH 95% (7.63 mmol) to a stirring solution of 3-oxo-3-(4-A-phenyl)-propionitrile, prepared in general preparation 28, (3.47 mmol) and CS₂ (3.47 mmol) in 10 ml of DMSO at 15° C. under nitrogen atmosphere. Gradually, warm to room temperature. After 2 hours, add iodomethane (6.94 mmol) (dropwise) and stir for 1 h. Add the crude reaction over ice-water mixture and extract with ethyl acetate. Wash organic phase with sat. NaCl, dry over MgSO₄, and remove solvent in vacuo. Purification by chromatography (hexane:ethyl acetate mixture) provides the title compound.

General Preparation 30

2,2-Dibromo-1-(4-A-phenyl)-ethanone

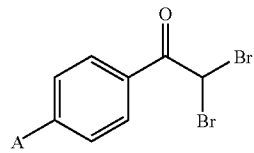

Dissolve 4-A-acetophenone, wherein A is defined herein, (4.9 mmol) in concentrated sulfuric acid (1 ml) and cool the resulting solution to 0° C. Add, dropwise, bromine (4.9 mmol), warm to room temperature, and stir for 6 hours. Pour the reaction mixture into ice-water and a solid precipitates. Collect the solid by filtration, wash with water, and air-dry to afford the title compound.

General Preparation 31

2-Bromo-1-(4-A-phenyl)-ethanone

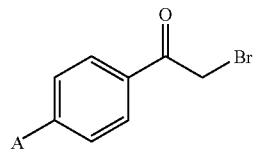

Add diethylphosphite (4.87 mmol), triethylamine (4.87 mmol) to a solution of 2,2-dibromo-1-(4-A-phenyl)-ethanone, prepared in general preparation 30, (4.63 mmol) in THF (7 m) at 0° C. Warn to room temperature and stir. After 6 hours, pour the reaction mixture into ice-water and a solid crash out. Collect the solid by filtration, wash with water, and air-dry to afford the title compound.

General Preparation 32

3-(4-A-phenyl)-3-oxo-propionitrile

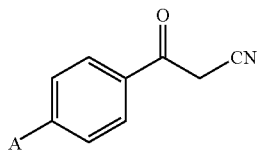

Stir 2-bromo-1-(4-A-phenyl)-ethanone, prepared in preparation 31, (1.99 mmol), sodium cyanide (2.19 mmo, 1.1 eq) in acetonitrile (6 ml) at room temperature for 2 days. Dissolve the reaction in ethyl acetate, wash with NaCl sat. solution, water, dry over $MgSO_4$ and filter. Remove the solvent in vacuo to give 430 mg (95% yield) of title compound.

General Preparation 33

2-(4-A-Benzoyl)-3-dimethylamino-3-methylsulfanyl-acrylonitrile

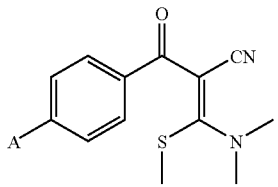

Add dimethylamine 40% aq. solution (0.49 mmol) to a mixture of 2-(4-A-benzoyl)-3,3-dimethylsulfanyl-acrylonitrile, prepared in general preparation 29, (0.49 mmol) in acetonitrile (1 ml) and stir at room temperature. After 12 hours, remove the solvents in vacuo to give title compound.

Preparation 34

Bis(methylthio)methylenepropanedinitrile

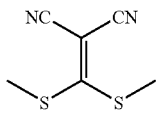

Add malononitrile (50.0 g, 757 mmol) to dry DMSO (600 mL), mechanically stir, cool to 15° C., and place under nitrogen. Add NaH (60%, 40 g, 1.00 mol) in small portions over 25 min keeping the internal temperature <25° C. and stir mixture. After 10 min, slowly add carbon disulfide (45.5 mL, 757 mmol) over 20 min at the same temperature. Stir at room temperature for 2.5 h then add additional NaH (60%, 29.6 g, 0.74 mol) while keeping the temperature constant with exter- nal cooling. Stir for 1.5 h at rt then cool to 15° C. Add iodomethane (103.7 mL, 1.67 mol) over 15 min. Stir resulting mixture overnight then pour into water (2.8 L). Stir the resulting dark orange precipitate for 15 min then collect by filtration, wash with water, partially air-dry, and wash with hexanes. Air-dry the tan powder to a constant weight (103 g) then recrystallize from 2-propanol. Filter solid, wash with cold 2-propanol and hexanes, then dry to afford the title compound: $^1$H NMR (DMSO-$d_6$): δ 2.78 (s, 6H); $^{13}$C NMR (DMSO-$d_6$): δ 186.0, 113.3, 74.2, 18.9.

Preparation 35

3-Amino-4-cyano-5-methylsulfanyl-thiophene-2-carboxylic acid ethyl ester

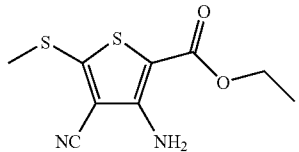

Stir a slurry of bis(methylthio)methylenepropanedinitrile, prepared in preparation 34, (69.29 g, 407 mmol) in ethanol (1.1 L) under nitrogen at rt then add ethyl thioglycolate (44.9 mL, 407 mmol) followed by triethylamine (56.7 mL, 407 mmol). Heat the resulting mixture at 65° C. for 30 min. Cool slowly to 35° C. over 45 min, then cool to 3° C. over 20 min and maintain at that temperature for 20 min. Collect precipitate by filtration, wash with cold ethanol and ether to afford the title compound: $^1$H NMR (CDCl$_3$) δ 5.77 (bs, 2H), 4.28 (q, J=7.1, 2H), 2.64 (s, 3H), 1.33 (t, J=7.1, 3H); TLC (25% hexanes/ethyl acetate) R$_f$=0.25).

Preparation 36

4-Cyano-3-iodo-5-methylsulfanyl-thiophene-2-carboxylic acid ethyl ester

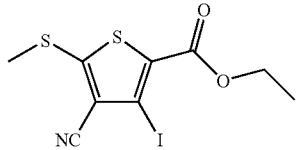

CAUTION! Care should be taken to insure that the reaction has initiated prior to addition of all of the i-amyl nitrite as a vigorous reaction ensues with nitrogen evolution and an exotherm! Stir a slurry of ethyl 3-amino-4-cyano-5-methylthio-thiophene-2-carboxylate, prepared in preparation 35, (5.00 g, 20.6 mmol) in acetonitrile (25 mL) under nitrogen then add CH$_2$I$_2$ (582 mL, 72.2 mmol). Warm to 35° C. resulting in a dark homogenous solution, then add i-amyl nitrite (6.93 mL, 51.6 mmol) slowly. After addition of the nitrite, let reaction slowly cool to ambient temperature over 45 min. Cool further the resulting slurry to 5° C. and add hexanes (15 mL). Collect the resulting solid by filtration washing with acetone/hexanes (1:10), diethyl ether/hexanes (1:3), then hexanes to afford the title compound: $^1$H NMR (CDCl$_3$) δ 4.38 (q, J=7.0, 2H), 2.70 (s, 3H), 1.40 (t, J=7.0, 3H); TLC (CH$_2$Cl$_2$) R$_f$=0.5).

Preparation 37

2-(2-Methyl-1-methylsulfanyl-2-propylidene)-malononitrile

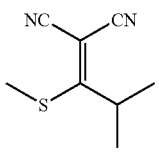

Add isopropylmagnesium chloride 2M in THF (3 ml, 6.0 mmol) to a solution of bis(methylthio)methylenepropanedinitrile, prepared in preparation 34, (1 g, 5.88 mmol) in THF (58 ml) at −40° C. Stir the mixture from −40° C. to room temperature overnight. Then, add NH$_4$Cl sat. sol. To the mixture and extract with Ethyl acetate. Dry organic layer over MgSO$_4$ and remove the solvents under vacuum. Purify the compound by flash chromatography (Hex:Ethyl acetate, 3:1) to give 389 mg (40% yield) of title compound: $^1$H NMR (CDCl$_3$, 300 MHz): 3.32 (sep, J=6.8 Hz, 1H); 2.83 (s, 3H); 1.28 (d, J=6.9 Hz, 6H).

Preparation 37a

3-Amino-4-cyano-5-isopropyl-thiophene-2-carboxylic acid ethyl ester

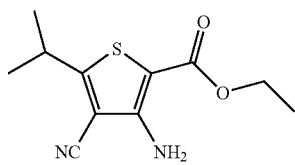

Following the procedure set forth in preparation 35, using 2-(2-methyl-1-methylsulfanyl-propylidene)-malononitrile, prepared in preparation 37, obtains the title compound. MS (ES+, m/e): 239 (M+1).

Preparation 37b

4-Cyano-3-iodo-5-isopropyl-thiophene-2-carboxylic acid ethyl ester

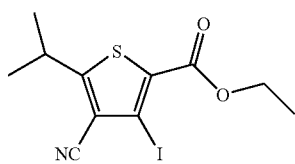

Following the procedure set forth in preparation 36, using 3-amino-4-cyano-5-isopropyl-thiophene-2-carboxylic acid ethyl ester, prepared in preparation 37a obtains the title compound. MS (ES+, m/e): 350 (M+1).

Preparation 38a 2-(1-Ethoxy-propylidene)-malononitrile

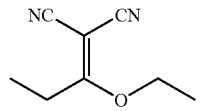

Heat a mixture of triethyl orthopropionate (446 g, 2.53 mol) and malononitrile (163.9 g, 2.48 mol) at reflux under nitrogen for 1.5 h. Cool the mixture and stir overnight. Distill the dark mixture under vacuum (10-15 torr, 135-142° C.) to afford the title compound as a pale yellow oil: $^1$H NMR (CDCl$_3$) δ 4.40 (q, J=7.0, 2H), 2.63, (q, J=7.7, 2H), 1.41 (t, J=7, 3H), 1.23 (t, J=7.7, 3H); $^{13}$C NMR (CDCl$_3$) 189.7, 113.3, 111.8, 68.3, 64.1, 25.5, 14.6, 11.3.

Preparation 38b

Additional preparation of 2-(1-Ethoxy-propylidene)-malononitrile

Maolononitrile (1.888 kg, 28.3 moles, 1.01 eq), and triethylorthopropionate (5.008 kg, 28.0 moles, 1.0 eq), are charged to a 12 L 4-neck reaction flask equipped with an overhead stirrer, heating mantle, nitrogen inlet, and condenser. The reaction mixture is heated (vigorous reflux) for 3 hours at 84° C. The mixture is allowed to cool to room temperature and held overnight. The mixture is warmed and ethanol is removed under reduced pressure while slowly increasing the pot temperature to 65° C. Once distillation of ethanol is complete, the pot temperature is increased to 151-160° C. and the distillation is continued at 14 mm Hg, which affords 4.090 kg (97.3% yield) of title compound as a clear yellow distillate.

Preparation 39a

3-Amino-4-cyano-5-ethyl-thiophene-2-carboxylic acid ethyl ester

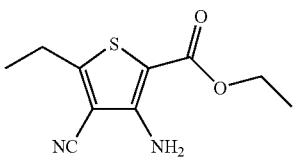

Add 2-(1-ethoxy-propylidene)-malononitrile, prepared in preparation 38, (230.0 g, 1531 mmol) in ethanol (1.3 L) stir with overhead stirring under nitrogen at rt and add ethyl thioglycolate (168.8 mL, 1531 mmol) and potassium acetate (225.4 g, 2297 mmol). Heat the resulting red mixture at 60° C. for 2 h. Add water (300 mL) and cool the mixture to 5° C. for 1 h. Collect the precipitate that forms by filtration, wash with 20-25% water/ethanol, and dry at rt for 3 d affording the title compound as light orange needles: $^1$H NMR (DMSO-d$_6$) δ 6.76 (bs, 2H), 4.18 (q, J=7.1, 2H), 2.86 (q, J=7.5, 2H), 1.223

(t, J=7.1, 3H), 1.220 (t, J=7.5, 3H); $^{13}$C NMR (DMSO-d$_6$) 163.8, 163.7, 153.7, 112.9, 100.0, 96.3, 60.0, 23.2, 14.3, 14.2.

Preparation 39b

Additional preparation of 3-Amino-4-cyano-5-ethyl-thiophene-2-carboxylic acid ethyl ester Ethanol, (11.0 L), 2-(1-ethoxy-propylidene)-malononitrile, (2.003 kg, 13.34 moles, 1.0 eq), ethyl-2-mercaptoacetate (1.652 kg, 13.34 moles, 1.0 eq.), and potassium acetate (1.983 kg, 20.0 moles, 1.5 eq.) are charged to a 22L 3-neck reaction flask equipped with an addition funnel, thermocouple, overhead stirrer, and condenser. The reaction mixture becomes dark red and exotherms to 72° C. The mixture is stirred for 1.25 hours while cooling to 60° C. Deionized water (2.6 L), is added to the reaction mixture over 30 minutes while cooling to 53° C. The reaction mixture is then cooled to 10° C. over 3.5 hours. The resulting suspension is filtered to recover the precipitate, and the filter cake is rinsed with a chilled mixture of 1.1 L ethanol and 3.9 L water. The filter cake is vacuum dried at room temperature, affording the title compound (2.552 kg) in 85.3% yield.

Preparation 40a

4-Cyano-5-ethyl-3-iodo-thiophene-2-carboxylic acid ethyl ester

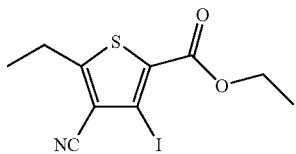

CAUTION! Care should be taken to insure that the reaction has initiated prior to addition of all of the i-amyl nitrite as a vigorous reaction ensues with nitrogen evolution and an exotherm. Stir a slurry of 3-amino-4-cyano-5-ethyl-thiophene-2-carboxylic acid ethyl ester, prepared in preparation 39, (150.0 g, 668.8 mmol) in acetonitrile (900 mL) under nitrogen then add CH$_2$O$_2$ (188.6 mL, 2341 mmol). Warm to 45° C. resulting in a dark homogenous solution, slowly add via an addition funnel i-amyl nitrite (188.7 mL, 1404 mmol). After addition of about 40-50 mL of i-amyl nitrite, warm the reaction to 55° C. to initiate reaction. Exchange the heating mantel immediately for an ice bath to keep temperature at 60° C. and add the remaining nitrite at a rate maintaining the temperature constant. Stir for 45 min while slowly cooling to 45° C. Concentrate the mixture in vacuo (ca. 15 torr, 50° C.). Take the resulting dark sludge and pass it through a plug of silica gel (1 kg; eluting with CH$_2$Cl$_2$). Remove the CH$_2$Cl$_2$ in vacuo, mix the dark oil with 2-propanol (1 L) then hexanes (300 mL), and cool to 5° C. Collect the resulting solid by filtration, wash with cold 2-propanol/hexanes (3:1), and dry at ambient temperature. Purify the solid by chromatography on silica gel (2.5 kg, eluting with 50-70% CH$_2$Cl$_2$/hexanes) to provide the title compound: mass spectrum (EI+): m/z 335 (M$^+$); $^1$H NMR (DMSO-d$_6$) δ 4.29 (q, J=7.1, 2H), 3.04 (q, J=7.5, 2H), 1.29 (t, J=7.1, 3H), 1.27 (t, J=7.5, 3H); $^{13}$C NMR (DMSO-d$_6$) δ 165.3, 159.3, 128.8, 118.1, 114.4, 92.4, 61.7, 23.2, 14.6, 14.0.

Preparation 40b

Additional preparation of 4-Cyano-5-ethyl-3-iodo-thiophene-2-carboxylic acid ethyl ester 3-Amino-4-cyano-5-ethyl-thiophene-2-carboxylic acid ethyl ester (44.9 g, 0.2 moles, 1.0 eq), acetonitrile (0.9L), and diiodomethane (216.4 g, 0.8 moles, 4.0 eq, filtered to remove Cu stabilizer) are charged to a 3L 3-neck reaction flask equipped with an addition funnel, thermocouple, overhead stirrer, and Friedrich condenser. A bump tank and secondary condenser are attached to the outlet of the Friedrich condenser. Isoamyl nitrite (48.8 g, 0.4 moles, 2.0 eq) diluted with heptane (45 ml) is charged to the addition funnel. The reaction mixture is inerted using a nitrogen sweep of the headspace for about 2 minutes. The reactor is closed and the nitrogen is set for by-pass through a bubbler. The reaction mixture is warmed to 70° C. A 20 ml portion of the isoamyl nitrite-heptane solution is added rapidly. After 2-3 minutes the reaction initiates as evidenced by an abrupt exotherm to 77° C. and a vigorous release of nitrogen. After stirring for another 2-3 minutes, cautious addition of the remainder of the isoamyl nitrite-heptane solution is resumed and is complete after 0.5 hrs. Nitrogen evolution is controlled and is complete at the end of the addition. The mixture is cooled to 23° C., transferred to a rotary evaporator, and is concentrated under reduced pressure to 210 g of non-volatile residue.

SiO$_2$ (380 g) is charged to a 95 cm diameter column (bed depth 110 cm). The silica gel is wetted with heptane. The non-volatile residue from above is dissolved in 105 ml of heptane and 105 ml of methylene chloride. The solution is poured onto the silica gel, and is eluted with 3.5 L heptane to remove the diiodomethane. This is discarded, and the silica gel is further eluted with 1:1 heptane:methylene chloride. The first 4.2 L is discarded, and the following 2.6 L is collected, combined and is stripped, affording 56 g (84%) of crude product. The crude product is slurried in 250 ml heptane for 2 hrs, then is collected by filtration and vacuum dried. This affords the title compound (51.3 g) in 76.5% yield.

Preparation 41

3-Amino-4-cyano-5-methyl-thiophene-2-carboxylic acid ethyl ester

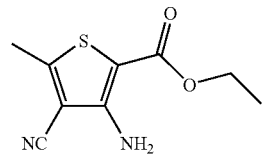

Follow the procedure set forth in preparation 39, using 2-(1-ethoxy-ethylidene)-malononitrile to prepare the title compound: $^1$H NMR (CDCl$_3$, 300 MHz) δ 5.7 (br s, 2H), 4.28 (q, J=7.2, 2H), 2.57 (s, 3H), 1.34 (t, J=7.2, 3H).

Preparation 42

4-Cyano-5-methyl-3-iodo-thiophene-2-carboxylic acid ethyl ester

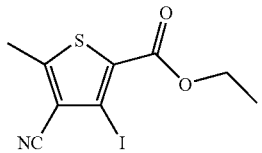

Follow the procedure set forth in preparation 40, using 3-amino-4-cyano-5-methyl-thiophene-2-carboxylic acid ethyl ester, prepared in preparation 41, to prepare the title compound: (EI+): m/z 322 (M$^+$+1); MS (ES+, m/e):322 (M+1); $^1$H NMR (CDCl$_3$, 300 MHz) δ 4.38 (q, J=7.05, 2H), 2.74 (s, 3H), 1.39 (t, J=7.2, 3H).

Preparation 43

3-Amino-4-cyanothiophene-2-carboxylic acid ethyl ester

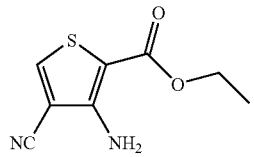

Follow the procedure set forth in preparation 39, using 2-ethoxymethylene-malononitrile to prepare the title compound: MS (ES+, m/e): 197 (M+1).

Preparation 44

4-Cyano-3-iodo-thiophene-2-carboxylic acid ethyl ester

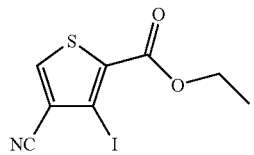

Follow the procedure set forth in preparation 40, using 3-amino-4-cyanothiophene-2-carboxylic acid ethyl ester, prepared in preparation 43, to prepare the title compound: MS (ES+, m/e): 308 (M+1).

Preparation 45

3-Amino-4-cyano-5-trifluoromethyl-thiophene-2-carboxylic acid ethyl ester

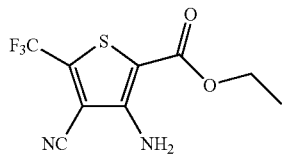

Combine 1,1-dicyano-2-chloro-2-(trifluoromethyl)ethylene (0.554 mmol) (prepared by the method of Middleton, J. Fluorine Chem., 20, 1982, p 397-418) and ethanol in a 50 ml flask. Add ethyl 2-mercaptoacetate (0.554 mmol) and potassium acetate (0.831 mmol) and heat to 60-70° C. for 30-40 minutes. Cool the reaction and add water. Product crystallizes as yellowish needles. Filter crystals and wash with 1:1 ethanol/water. Dry solid under reduced pressure to give the title compound as light yellow crystals: $^1$H NMR (400 MHz, CDCl$_3$) δ 5.88 (s, 2H), 4.36 (q, 2H, J=7.2 Hz), 1.38 (t, 3H, J=7.0 Hz), MS found (M−1) 262.9.

Preparation 47

4-Cyano-3-iodo-5-trifluoromethyl-thiophene-2-carboxylic acid ethyl ester

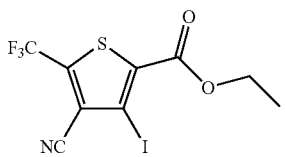

Combine 3-amino-4-cyano-5-trifluoromethyl-thiophene-2-carboxylic acid ethyl ester, prepared in preparation 45, (1.12 mmol), diiodomenthane (3.92 mmol), and isoamyl nitrite (2.8 mmol) in CH$_3$CN and heat to 80° C. After 45 minutes, cool to room temperature and concentrate in vacuo. Purify the dark residue by flash chromatography eluting with methylene chloride. Concentration of desired fractions and recrystallization from hexanes provides the title compound: $^1$H NMR (400 MHz, CDCl$_3$) δ 4.45 (q, 2H, J=7.2 Hz) and 1.44 (t, 3H, J=7.3 Hz), $^{19}$F NMR (CDCl$_3$) δ—57.6 ppm (s).

Preparation 48

4-Cyano-3-iodo-5-methanesulfonyl-thiophene-2-carboxylic acid ethyl ester

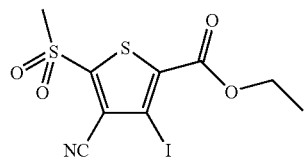

Prepare the title compound in a manner analogous to the procedure set forth in example E-6, 3-(4-iodophenyl)-4-cyano-5-methanesulfonyl-thiophene-2-carboxylic acid ethyl ester, using 4-cyano-3-iodo-5-methylsulfanyl-thiophene-2-carboxylic acid ethyl ester, prepared in preparation 36, as the starting material: MS (ES+, m/e): 386 (M+1).

Preparation 49

4-Cyano-3-iodo-5-ethyl-thiophene-2-carboxylic acid ethyl ester

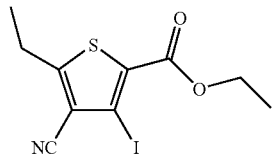

Prepare the title compound in a manner analogous to the procedure set forth in example E-9, 3-(4-iodophenyl)-4-cyano-5-ethyl-thiophene-2-carboxylic acid ethyl ester, using 4-cyano-3-iodo-5-methanesulfonyl-thiophene-2-carboxylic acid ethyl ester, prepared in preparation 48, as the starting material: MS (ES+, m/e): 336 (M+1).

Preparation 50

4-Cyano-3-iodo-5-dimethylamino-thiophene-2-carboxylic acid ethyl ester

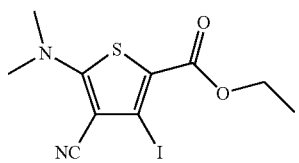

Prepare the title compound in a manner analogous to the procedure set forth in example E-7, 3-(4-iodophenyl)-4-cyano-5-dimethylamino-thiophene-2-carboxylic acid ethyl ester, using 4-cyano-3-iodo-5-methanesulfonyl-thiophene-2-carboxylic acid ethyl ester, from preparation 48, as starting material: MS (ES+, m/e): 351 (M+1).

Preparation 51

4-Cyano-3-iodo-5-ethyl-thiophene-2-carboxylic acid

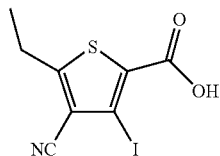

Prepare the title compound in a manner analogous to the procedure set forth in example A-2, 3-(4-tert-Butyl-phenyl)-4-cyano-5-methylsulfanyl-thiophene-2-carboxylic acid, using 4-Cyano-3-iodo-5-ethyl-thiophene-2-carboxylic acid ethyl ester, preparation 40 or preparation 49: MS (ES+, m/e): 262 (M-COOH).

Preparation 52

4-Cyano-3-iodo-5-ethyl-thiophene-2-carboxylic acid amide

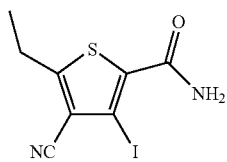

Prepare the title compound in a manner analogous to the procedure set forth in example AM-2, 3-(4-tert-butyl-phenyl)-4-cyano-5-methylsulfanyl-thiophene-2-carboxylic acid amide, using 4-cyano-3-iodo-5-ethyl-thiophene-2-carboxylic acid, preparation 51: MS (ES+, m/e): 329 (M+23).

Preparation 53

4-Iodo-2-ethyl-5-(1H-tetrazol-5-yl)-thiophene-3-carbonitrile

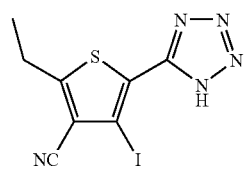

Prepare the title compound in a manner analogous to the procedure set forth in example T-2, 4-(4-tert-butyl-phenyl)-2-methylsulfanyl-5-(1H-tetrazol-5-yl)-thiophene-3-carbonitrile using 4-cyano-3-iodo-5-ethyl-thiophene-2-carboxylic acid amide, prepared in preparation 52: MS (ES+, m/e): 330 (M−1).

Preparation 54

4-Cyano-3-iodo-5-methyl-thiophene-2-carboxylic acid

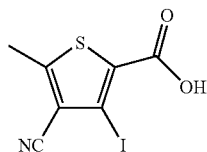

Prepare the title compound in a manner analogous to the procedure set forth in preparation 51, 4-cyano-3-iodo-5-ethyl-thiophene-2-carboxylic acid, using 4-cyano-3-iodo-5-ethyl-thiophene-2-carboxylic acid ethyl ester, prepared in preparation 40 or preparation 49: MS (ES+, m/e): 294 (M+1).

Preparation 55

4-Cyano-3-iodo-5-methyl-thiophene-2-carboxylic acid amide

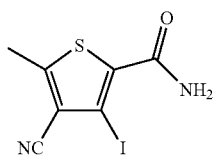

Prepare the title compound in a manner analogous to the procedure set forth in preparation 52, 4-cyano-3-iodo-5-ethyl-thiophene-2-carboxylic acid amide using 4-cyano-3- iodo-5-methyl-thiophene-2-carboxylic acid, prepared in preparation 54: MS (ES+, m/e): 293 (M+1).

Preparation 56

4-Iodo-2-methyl-5-(1H-tetrazol-5-yl)-thiophene-3-carbonitrile

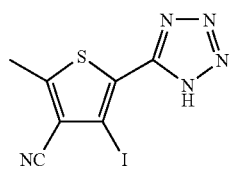

Prepare the title compound in a manner analogous to the procedure set forth in preparation 53, 4-iodo-2-ethyl-5-(1H-tetrazol-5-yl)-thiophene-3-carbonitrile, using 4-cyano-3-iodo-5-methyl-thiophene-2-carboxylic acid amide, prepared in preparation 55: MS (ES+, m/e): 316 (M−1).

Preparation 57

Propane-2-sulfonic acid (2-chloro-pyridin-3-yl)-amide

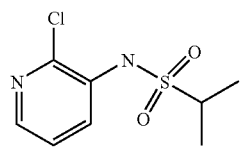

Prepare the title compound in a manner analogous to the procedure set forth in general example A-8 (step 1) using as starting material 2-chloro-3-aminopyridine, to provide the title compound in a 89% yield: Mass spectrum (m/e): 235 (M+1).

Preparation 58

Propane-2-sulfonic acid (6-bromo-pyridin-2-yl)-amide

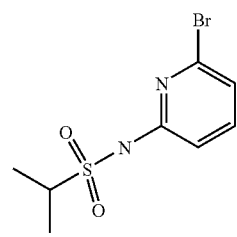

Prepare the following compound in a manner analogous to the procedure set forth in general example A-8 (step 1) using as starting material 6-bromo-2-aminopyridine, to provide the title compound as white solid: Mass spectrum (m/e): 280 (M+1).

Preparation 60

3-[4-(4,4,5,5,-Tetramethyl-[1,3,2]dioxaborolan-2-yl)-phenyl]-[1,2,4]thiadiazole

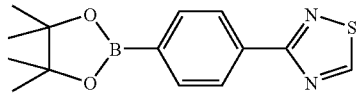

Add DMF (5 mL) to a mixture of 3-(4-bromophenyl)-[1,2,4]thiadiazole (0.241 g, 1.0 mmol,), bis(pinacole)borane (0.305 g, 1.2 mmol), 1,1'-bis(diphenylphosphino)ferrocene palladium(II) dichloride (1:1) dichloromethane complex (0.089 g, 0.11 mmol) and potassium acetate (0.305 g, 3.11 mmol). Bubble with nitrogen and stir at 80° C. for 2 h. Cool down and add ice-water and ethyl acetate. Separate layers and wash the organic layer with water (×3) and back-extract the combined aqueous layers with ethyl acetate (×2). Wash the combined organic layers with brine, dry over anhydrous sodium sulfate and concentrate under reduced pressure over Celite®. Purify by flash chromatography (silica gel) eluting with hexanes-ethyl acetate 10:1 first, then 5:1 to give a white solid in quantitative yield. $^1$H NMR: δ 9.89 (s, 1H); 8.34 (m, 2H); 7.94 (m, 2H); 1.37 (s, 12H).

Preparation 61

3-(tert-Butyl-phenyl-3-oxo-propionitrile

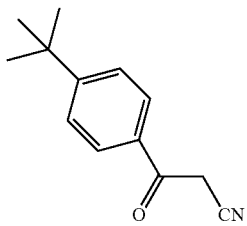

Add to a −70° C. solution of cyanoacetic acid (2.55 g, 30 mmol) in THF (100 ml), n-butyl lithium (1.6 M, 37.5 ml, 60 mmol) dropwise and allow the mixture to warm up to 0° C. for 1 h before it cools down again to −70° C. Add acid chloride (2.93, 15 mmol) to the mixture slowly and stir the mixture at −70° C. for 1 h. Stir the reaction mixture at RT for another extra 1 h and pour into water (50 ml) and HCl (1M, 50 ml). Extract the organic with EtOAc (3×75 ml). Wash the combined organics with water (3×100 ml), brine (50 ml), dry over magnesium sulfate, filter and concentrate under reduced pressure. Purification by flash chromatography (silica gel) of the yellow residue eluting with ethyl acetate:hexanes (2:8) provides the desired title compound (1.8 g, 58% yield): Mass spectrum (M−1)=200.

Preparation 62

2-(4-tert-Butyl-benzoyl)-3,3-bis-methylsulfanyl-acrylonitrile

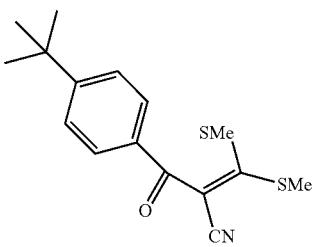

Add to a 15° C. solution of 3-(tert-Butyl-phenyl-3-oxo-propionitrile (1.8 g, 8.94 mmol), in DMSO (30 ml) carbon disulfide (0.53 ml, 8.94 mmol) and sodium hydride (0.75 mg, 18.778 mmol) and stir at RT for 2 h. Cool the reaction mixture down to 10° C. before treating with methyl iodide (1.34 ml, 21.46 mmol). Stir the mixture at RT for 1 h and pour into water (100 ml). Extract the organic with EtOAc (3×100 ml). Combine organics, wash with water (3×100 ml), brine (50 ml), dry over magnesium sulfate, filter and concentrate under reduced pressure. Purify by flash chromatography (silica gel) the yellow crude product residue eluting with ethyl acetate: hexanes (2:8) to provide the title compound (2.25 g, 86% yield): Mass spectrum (M−1)=292.

Preparation 63

3-Chloropropane-1-sulfonic acid {2-[4-(4,4,5,5-tetramethyl-[1,3,2]dioxaborolan-2-yl)-phenyl]-ethyl}-amide

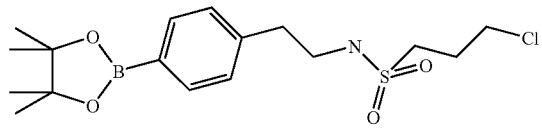

Add 3-chloropropanesulfonyl chloride (0.285 g, 1.6 mmol) to a suspension of 2-[4-(4,4,5,5-tetramethyl-[1,3,2]dioxaborolan-2-yl)-phenyl]-ethylamine (0.383 g, 1.3 mmol) in dichloromethane (10 mL) at 0° C. Then slowly add DBU (0.457 g, 3.0 mmol) and allow the mixture to warm up to 23° C. Stir 2 h at 23° C. and add more dichloromethane and 1M HCl. Separate layers and wash organic phase with more HCl (×2). Back-extract aqueous phase with dichloromethane (×2). Combine organic phases and wash them with brine, dry over sodium sulfate, concentrate over Celite® and purify by flash chromatography (silica gel), eluting with hexanes-ethylacetate 3:1 to give 0.333 g of the desired compound as a thick oil. Mass spectrum ESI positive (m/z): 388 (M+1), 410 (M+23).

Preparation 64

3-Thiophenyl-carbamic acid tert-butyl ester

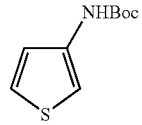

Prepare 3-aminothiophene as described in Barker, J. M.; Huddleston, P. R.; Wood, M. L. *Synthetic Communications* 1995, 25(23), 3729-3734, starting from methyl-3-aminothiophene-2-carboxylate (42.8 g, 0.27 mol). Treat immediately the resulting thick oil with oxalic acid dihydrate (26.7 g) in 2-propanol (100 mL) at 38° C. for 45 min. Cool down to room temperature and dilute with diethyl ether (40 mL). Filter the resulting solid and wash it with diethyl ether. Disolve the resulting salt (33.1 g) in water (400 mL) and basify with concentrated aqueous ammonia. Extract the mixture with dichloromethane (3×200 mL), dry the combined extracts (magnesium sulfate) and evaporate to give a brown oil (15 g, 56%). Disolve the oil in dichloromethane (300 mL) and add triethylamine (42.2 mL, 0.3 mol) at 0° C. Then add a solution of di tert-butyl pirocarbonate (39.3 g, 0.18 mol) in dichloromethane (100 mL) dropwise at 0° C. and stir the mixture overnight at 23° C. Add water (200 mL) and extract with dichloromethane (2×200 mL). Dry the combined organic extracts (magnesium sulfate) and concentrate in vacuo. Purify by flash chromatography (silica gel) eluting with hexanes/ethyl acetate 9:1 to obtain 20.1 g (67%) of the title compound as a white solid. 1H NMR (CDCl3) δ: 7.49 (m, 3H), 6.50 (br s, 1H), 1.53 (s, 9H).

Preparation 65

2-Bromothiophen-3-yl-carbamic acid tert-butyl ester

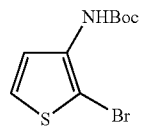

Add NBS (8.9 g, 0.05 mol) to a boiling solution of 3-thiophenyl-carbamic acid tert-butyl ester (10.0 g, 0.05 mol) in dichloromethane (500 mL) in small portions and stir the mixture at 65° C. for 20 min. Cool down, remove solvent in vacuo and purify the crude material by flash chromatography (silica gel) eluting with hexanes/diethyl ether 19:1 to obtain 11.1 g (80%) as a white solid: $^1$H NMR (CDCl$_3$) δ: 7.55 (br s, 1H), 7.24 (d, J=4.0 Hz, 1H), 6.56 (br s, 1H), 1.52 (s, 9H).

Preparation 66

(2-tri-n-butylstannyl-thiophen-3-yl)-carbamic acid tert-butyl ester

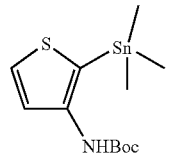

Add n-buthyl lithium (19.8 ml, 1.6 M/hexane) dropwise to a solution 2-Bromothiophen-3-yl-carbamic acid tert-butyl ester (4 g, 14.4 mmol) in anhydrous THF (35 ml) at −78° C. Stir the mixture for 45 minutes and add trimethyltin chloride (3.16 g, 15.8 mmol). Allow the reaction mixture to reach room temperature. Add brine (aprox. 50 mL) and extract with ethyl acetate (2×50 mL). Dry the combined organic layers over magnesium sulfate and concentrate under vacuum yielding 4.9 g of the title compound as colorless oil: $^1$H NMR (CDCl$_3$, 300 MHZ) δ: 7.49 (d, J=4.8 Hz, 1H), 7.13 (d, J=4.4 Hz, 1H), 1.49 (s, 9H), 0.36 (s, 9H).

GENERAL EXAMPLE E-1

4-Cyano-3-(4-A-phenyl)-5-methylsulfanyl-thiophene-2-carboxylic acid ethyl ester

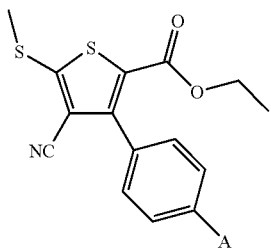

Add ethylthioglycolate (3.8 mmol) to a stirring suspension of 3,3-bis-methylsulfanyl-2-(4-A-benzoyl)-acrylonitrile, prepared in preparation 29, (3.46 mmol) in 15 ml of EtOH, followed by Et$_3$N (3.8 mmol). Heat the mixture to reflux temperature and remove the heat as soon as reflux is reached. Cool the mixture and evaporate a little amount of solvent under vacuum. A solid precipitates. Filter to collect the solid and wash with cold ethanol to provide the title compound.

GENERAL EXAMPLE E-2

4-Cyano-5-dimethylamino-3-(4-A-phenyl)-thiophene-2-carboxylic acid ethyl ester

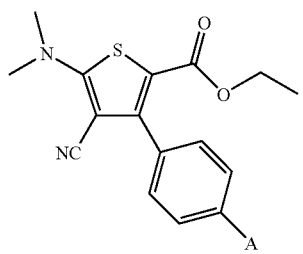

Add ethylthioglycolate (3.8 mmol) to a stirring suspension of 2-(4-A-benzoyl)-3-dimethylamino-3-methylsulfanyl-acrylonitrile, prepared in preparation 33, (3.46 mmol) in 15 ml of EtOH. Add Et$_3$N (3.8 mmol) and heat the mixture to reflux temperature and turn off the heat as soon as reaching reflux. Cool the mixture and evaporate a little amount of solvent under vacuum. A solid precipitates. Filter the solid and wash with cold ethanol to provide the title compound.

EXAMPLE E-3

3-(4-Iodophenyl)-4-cyano-5-methylsulfanyl-thiophene-2-carboxylic acid ethyl ester

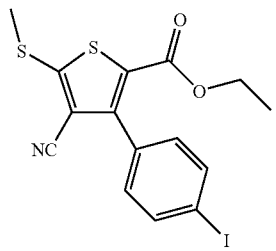

By using a similar procedure as described in general preparation 28, 29 and general example E-1 the title compound is prepared using 4-iodobenzoyl chloride: $^1$H NMR (500 MHz, DMSO): δ 7.82(d, 2H), 7.23(d, 2H), 4.12(q, 2H), 2.81(s, 3H),1.11 (t, 3H).

EXAMPLE E-4

3-(4-Hydroxyphenyl)-4-Cyano-5-methylsulfanyl-thiophene-2-carboxylic acid ethyl ester

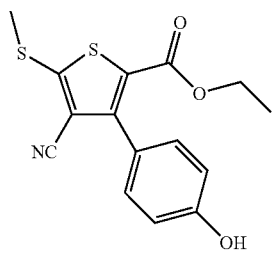

Step 1

Follow the procedure set forth in general preparations 28, 29, and general example E-1, using 4-methoxybenzoyl chloride to form 3-(4-methoxyphenyl)-4-cyano-5-methylsulfanyl-thiophene-2-carboxylic acid ethyl ester.

Step 2

Add 0.45 mmol of BBr$_3$ (1.0M solution in CH$_2$Cl$_2$) to a solution of the previously prepared methoxy analog (0.3 mmol) in CH$_2$Cl$_2$ (7.0 mL) cooled at −78° C. Stir at −20° C. for 16 h. Add water and extract with ethyl acetate (2×10 mL). Dry over Na$_2$SO$_4$, filter and evaporate to dryness to provide the title compound which is used without further purification. MS (ES+, m/e): 320 (M+1).

EXAMPLE E-5

3-(4-Aminophenyl)-4-cyano-5-methylsulfanyl-thiophene-2-carboxylic acid ethyl ester

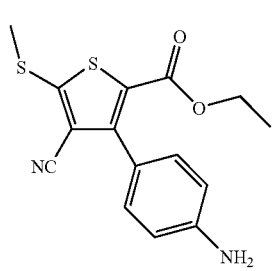

Step 1

Follow the procedure set forth in general preparations 28, 29, and general example E-1, using 4-nitrobenzoyl chloride to form 3-(4-nitrophenyl)-4-cyano-5-methylsulfanyl-thiophene-2-carboxylic acid ethyl ester.

Step 2

Add anhydrous $SnCl_2$ (7.0 equivalents) to a solution of the previously prepared nitro analog (4.6 mmol) in EtOH (40 mL). Heat the reaction at 75° C. for 30 min and then at room temperature overnight. Add a saturated solution of $NaHCO_3$ (pH=11-12) and extract with ethyl acetate (2×50 mL). Dry over $Na_2SO_4$, filter and evaporate to dryness to provide the title compound which is used without further purification. Yield 70%; MS (ES+, m/e): 319 (M+1).

EXAMPLE E-6

3-(4-Iodophenyl)-4-cyano-5-methanesulfonyl-thiophene-2-carboxylic acid ethyl ester

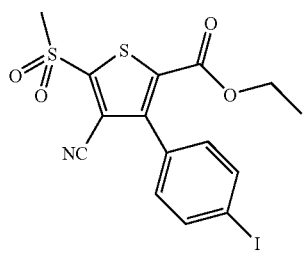

Add slowly m-chloroperbenzoic acid 70% (MCPBA) (8.4 mmol) to a solution of 3-(4-iodophenyl)-4-cyano-5-methylsulfanyl-thiophene-2-carboxylic acid ethyl ester, prepared in Example E-3, (2.8 mmol) in $CH_2Cl_2$ (5 mL) and cool to 0° C. Remove the ice-bath and stir the reaction. After 3 days, dilute with 10 mL of $CH_2Cl_2$ and wash with 10% aqueous $NaHSO_3$ (1×10 mL), water (1×10 mL), saturated $NaHCO_3$ (1×10 mL) and brine (1×10 mL). Dry over $Na_2SO_4$, filter and evaporate to dryness to provide the title compound which is used without further purification. Yield 90%. MS (ES+, m/e)=($M^+$+1).

EXAMPLE E-7

3-(4-Iodophenyl)-4-Cyano-5-dimethylamino-thiophene-2-carboxylic acid ethyl ester

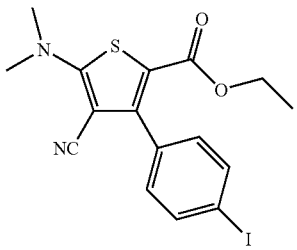

Add 3 mL of 2N dimethylamine in THF to 3-(4-iodophenyl)-4-cyano-5-methanesulfonyl-thiophene-2-carboxylic acid ethyl ester (0.23 mmol) and stir under nitrogen at room temperature for 2 h. Evaporate to dryness to provide the title compound which is used without further purification. Yield 95%. MS (ES+, m/e)=427 ($M^+$+1).

EXAMPLE E-8

3-(4-Iodophenyl)-4-cyano-thiophene-2-carboxylic acid ethyl ester

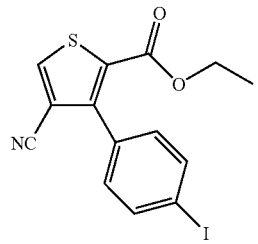

Add $NaBH_4$ (0.26 mmol) to a solution of 3-(4-iodophenyl)-4-cyano-5-methylsulfanyl-thiophene-2-carboxylic acid ethyl ester, prepared in example E-3, in 2 mL of EtOH at 0° C. Remove the ice-bath and stir at room temperature. After 30 min, add additional $NaBH_4$ (0.26 mmol) and stir and additional 30 minutes. Remove the solvent in vacuo and extract the residue with 50 mL of 1/9 $MeOH/CH_2Cl_2$. Evaporate and chromatograph (hexane:ethyl acetate 3:1) over silica gel to provide the title compound: MS (ES+, m/e): 384 (M+1).

EXAMPLE E-9

3-(4-Iodophenyl)-4-cyano-5-ethyl-thiophene-2-carboxylic acid ethyl ester

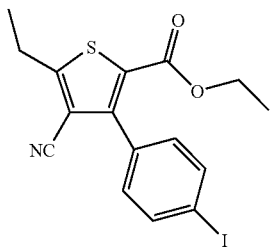

Add dropwise diethylzinc (1.0M in hexanes, 16 mmol) to a solution of 3-(4-iodophenyl)-4-cyano-5-methanesulfonylthiophene-2-carboxylic acid ethyl ester (2.78 mmol) in 15 mL of anhydrous CH$_2$Cl$_2$ and stir under nitrogen at room temperature for 5 days. Cool to 0° C. and carefully quench with ice followed by 10 mL of saturated NH$_4$Cl. Filter the mixture through Celite and rinse the filter pad with 100 mL of CH$_2$Cl$_2$. Wash the combined organic layers with brine (1×20 mL), dry over Na$_2$SO$_4$, filter, and evaporate. Chromatograph (hexane:ethyl acetate 3:1) over silca gel to provide the title compound: MS (ES+, m/e): 412 (M+1).

EXAMPLE E-10

4-Cyano-5-ethyl-3-(4-iodo-phenyl)-thiophene-2-carboxylic acid ethyl ester

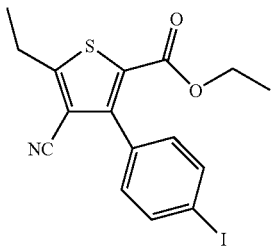

Add dropwise diethylzinc (1.0M in hexanes, 7 ml, 6.99 mmol, 3 eq) to a mechanically stirring suspension of 4-cyano-3-(4-iodo-phenyl)-5-methylsulfanyl-thiophene-2-carboxylic acid ethyl ester (1 gr, 2.33 mmol) and 1,3-bis-(diphenylphosphino)propane nickel (II) chloride (24 mg, 0.0466 mmol, 0.02 eq) in dry THF (12 ml) and heat the resulting mixture 60° C. for 30 min. Cool the reaction to room temperature and remove solvents in vacuo. Purify the solid by chromatography on silica gel (eluting with 10-80% Ethyl acetate/hexane) to provide the title compound in 60% yield: Mass spectrum (EI+): m/z 412 (M$^+$+1); $^1$H NMR (CDCl$_3$, 200 MHz): δ 7.72 (d, 2H, J=8.5); 7.05 (d, 2H, J=8.5); 4.14 (q, 2H, J=7.2); 3.01 (q, 2H, J=7.2); 1.36 (t, 3H, J=7.5); 1.17 (t, 3H, J=7.2).

EXAMPLE E-11

4-Cyano-5-ethyl-3-[4-(4,4,5,5-tetramethyl-[1,3,2]dioxaborolan-2-yl)-phenyl]-thiophene-2-carboxylic acid ethyl ester

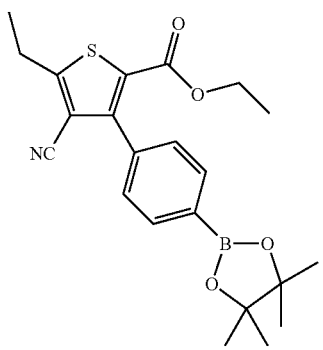

Dissolve 4-cyano-5-ethyl-3-(4-iodo-phenyl)-thiophene-2-carboxylic acid ethyl ester in 3 mL dry CH$_3$CN and add Et$_3$N (0.15 mL, 1.08 mmol), [1,1'-bis(disphenylphosphino)-ferrocene]dichloropalladium(II) complex with dichloromethane (25 mg. 0.03 mmol), and pinacolborane (51 μL, 0.34 mmol). Heat the mixture to reflux under nitrogen for 5.5 hours. Cool and dilute with 50 mL of EtOAc and wash with water (2×20 mL) and brine (1×20 mL). Dry over Na$_2$SO$_4$, filter through Celite® and evaporate to 122 mg. The crude boronate is used without further purification.

EXAMPLE E-12

4-Cyano-5-ethyl-3-(4-trimethylstannyl-phenyl)-thiophene-2-carboxylic acid ethyl ester

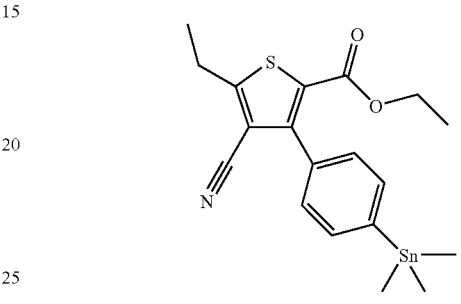

Add bis-trimethyltin (0.878 g, 2.67 mmol) and dichlorobis(triphenylphosphine)-palladium(II) (0.085 g, 0.121 mmol) to a solution of 4-cyano-5-ethyl-3-(4-iodo-phenyl)-thiophene-2-carboxylic acid ethyl ester (1.0 g, 2.43 mmol) in dry dimethylformamide (5 mL), heat at 80° C. under nitrogen. After 2 h, add water and extract with ethyl acetate. Combine the organic layers, dry over sodium sulfate, filter and concentrate under reduced pressure to give a residue. Purify the residue by flash chromatography (silica gel) eluting with ethyl acetate:hexane 1:10 to provide the title compound (0.89 g, 82%): $^1$H-NMR (CDCl$_3$) δ 0.31 (s, 9H, J$^{118}{}_{Sn}$=5.3 Hz, J$^{119}{}_{Sn}$=1.1 Hz); 1.21 (t, 3H, J=7.1 Hz); 1.43 (t, 3H, J=7.1 Hz); 3.08 (c, 2H, J=7.3 Hz); 4.21 (c, 2H, J=7.0 Hz); 7.38-7.70 (m, 4H).

EXAMPLE E-13

4-Cyano-5-ethyl-3-(4-hydroxy-phenyl)-thiophene-2-carboxylic acid ethyl ester

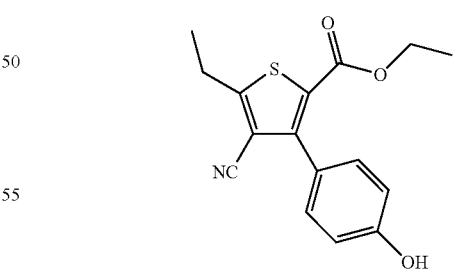

Add 4-cyano-5-ethyl-3-iodo-thiophene-2-carboxylic acid ethyl ester (50.0 g, 0.149 mol) and 4-(4,4,5,5-tetramethyl-[1,3,2]dioxaborolan-2-yl)-phenol (Aldrich#52,257-0 or 36.1 g, 0.164 mol) to a 2000 mL, 3-neck round-bottom flask equipped with magnetic stir bar, internal temperature probe and glycol-cooled condenser fitted with a nitrogen inlet. Add absolute ethanol (250 mL) to the reaction flask. Add a solution of potassium carbonate (61.9 g, 0.448 mol) in water (250 mL) to the flask, followed by palladium black (794 mg, 0.00746 mol). Stir and heat the mixture under nitrogen at 70° C. for 3 hours. Filter the reaction mixture through Celite® that was pre-saturated with ethyl acetate. Wash the collected solids with ethyl acetate (500 mL). Neutralize the filtrate with 1N HCl (450 mL) and extract the aqueous phase with ethyl acetate (2×200 mL). Combine the organic extracts and concentrate the solution under reduced pressure to afford a brown, semi-solid product (59.9 g) contaminated with pinacol. Dilute the crude material with water (100 mL) and heat to 70° C. for 15 minutes. Decant the dark colored aqueous supernatent, replace with fresh water (100 mL) and reheat to 70° C. Decant the aqueous supernatent and add water (100 mL) to the flask again to afford granular tan-brown solids. Filter the solids to give 60.7 g of a wet cake that is now free from pinacol. Dissolve the solids in an 80° C. solution of ethanol (200 mL) and water (200 mL), and cool slowly for approximately 12 hours with slow stirring. Cool the resulting suspension to 0° C. and filter the precipitate through a sintered glass funnel under vacuum. Air-dry the solids for 2 hours to afford the title compound (38.3 g, 85.3%) as a tan powder: $^1$H NMR (CDCl$_3$, 300 MHz): δ 7.30 (d, 2H, J=8.7); 6.85 (d, 2H, J=8.4); 4.23 (q, 2H, J=7.2); 3.08 (q, 2H, J=7.2); 1.43 (t, 3H, J=7.5); 1.24 (t, 3H, J=7.2).

EXAMPLE E-14

4-Cyano-5-ethyl-3-(4-trifluoromethanesulfonyloxy-phenyl)-thiophene-2-carboxylic acid ethyl ester

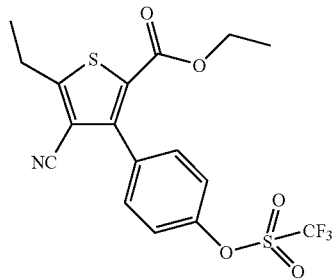

Add 4-cyano-5-ethyl-3-(4-hydroxy-phenyl)-thiophene-2-carboxylic acid ethyl ester (30.0 g, 0.0996 mol) and dichloromethane (550 mL) to a 1000 mL, 3-neck round-bottom flask equipped with magnetic stir bar, internal temperature probe and nitrogen inlet. Add pyridine (12 mL, 0.15 mol) to the dark brown solution and cool the resulting light brown solution to −4° C. Attach a pressure-equalizing addition funnel containing trifluoromethanesulfonic anhydride (20 mL, 33.7 g, 0.119 mol) and add the funnel contents to the reaction mixture over 6 min. After 60 min, add pyridine (5 mL) and trifluoromethanesulfonic anhydride (10.0 mL) if the reaction is not complete (by HPLC). Add absolute ethanol (250 mL) to the reaction flask. After 135 minutes, pour the reaction mixture into water (1000 mL) and extract with dichloromethane (300 mL). Wash the dichloromethane extract with water (2×200 mL) and dry (MgSO$_4$). Filter the MgSO$_4$ and concentrate the filtrate under reduced pressure to afford a light brown powder (40.5 g). Triturate the powder with 5:95 ethyl acetate/hexanes (500 mL) at room temperature, filter under vacuum and air-dry to obtain the title compound (37.9 g, 87.9%) as a tan powder: $^1$H NMR (CDCl$_3$, 300 MHz): δ 7.51 (d, 2H, J=9.3); 7.37 (d, 2H, J=9.0); 4.19 (q, 2H, J=6.9); 3.10 (q, 2H, J=7.5); 1.44 (t, 3H, J=7.5); 1.17 (t, 3H, J=7.2).

EXAMPLE E-15

3-(4-Bromo-phenyl)-4-cyano-5-ethyl-thiophene-2-carboxylic acid ethyl ester

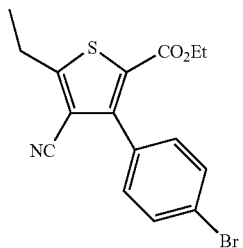

Add a solution of 4-cyano-5-ethyl-3-iodo-thiophene-2-carboxylic acid ethyl ester (43.0 g, 0.128 mol) in dioxane (113 mL) to a suspension of dichlorobis(tri-o-tolylphosphine)palladium (II) (4.53 g, 0.00576 mole) in propionitrile (213 mL) within a 1000 mL, 3-neck round-bottom flask equipped with magnetic stir bar, internal temperature probe, and a glycol-cooled condenser fitted with a nitrogen inlet. Add a turbid solution of 4-bromophenyl boronic acid (28.7 g, 0.141 mol), sodium carbonate (14.5 g, 0.137 mol) in water (100 mL) and dioxane (100 mL) to the reaction vessel. Add an additional portion of sodium carbonate (14.0 g, 0.132 mol) and stir the reactor contents at room temperature while sparging (subsurface) with nitrogen for 5 min. Heat the reaction mixture to 75° C. and observe that the reaction mixture gradually darkens to deep red over 1 hour. Observe that HPLC analysis indicates substantial consumption of 4-bromophenyl boronic acid and 4-cyano-5-ethyl-3-iodo-thiophene-2-carboxylic acid ethyl ester (flow rate: 1.5 mL/min; detection: 210 nm; mobile phase: isocratic 65/35 (v/v) acetonitrile/0.1% trifluoroacetic acid in water; column: Zorbax® SB-Phenyl; 4.6 mm×25 cm; 5 microns at 35 C). Cool the mixture to 30° C. and separate the phases. Extract the aqueous phase with dichloromethane (100 mL). Combine the organic phases and concentrate under reduced pressure to afford an oil (62 g). Extract the oil twice with heptane (250 mL and 100 mL) at 85° C. and decant the supernatent to leave a dark insoluble oil (6.0 g). Combine the heptane extracts and stir with silica gel (5.0 g) for 3 minutes. Filter the mixture and concentrate the filtrate under reduced pressure to afford a solid. Triturate the solids with pentane (150 mL) and recover the solids by filtration followed by air-drying to afford the crude title compound (37.5 g). Dissolve the crude title compound in a mixture of pentane (600 mL) and cyclohexane (150 mL) at 44° C. and stir the resulting solution with silica gel (2.5 g) for 3 min. Filter the mixture and concentrate the filtrate under reduced pressure to a volume of 200 mL. Filter the resulting suspension and wash the filter cake with pentane (3×30 mL) and dry in a vacuum oven (40° C.) to afford the title compound (28.5 g, 61.1%): $^1$H NMR (CDCl$_3$, 300 MHz): δ 7.58 (d, 2H, J=8.4); 7.29 (d, 2H, J=8.7); 4.21 (q, 2H, J=7.2); 3.09 (q, 2H, J=7.5); 1.43 (t, 3H, J=7.5); 1.22 (t, 3H, J=7.2).

EXAMPLE E-16

3-(4-Boronic acid-phenyl)-4-cyano-5-ethyl-thiophene-2-carboxylic acid ethyl ester

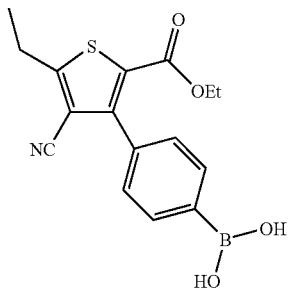

Stir and heat the mixture of 4-cyano-5-ethyl-3-iodo-thiophene-2-carboxylic acid ethyl ester (500 mg, 1.49 mmol), bis-phenylboronic acid (500 mg, 3 mmol, 2 eq), 1,1'-bis(diphenylphosphino)ferrocenedichloropalladium(II) (130 mg, 0.149 mmol, 0.1 eq) in sodium carbonate 2M solution (3 ml, 5.96 mmol, 4 eq) and DME (12.5 ml) at 90° C. for 30 min. Pour the reaction mixture into water and extract with dichloromethane. Wash the dichloromethane extract with HCl 10% and dry (MgSO$_4$). Filter the MgSO$_4$ and concentrate the filtrate under reduced pressure to afford a light brown powder. Purification by extraction cartridge (waters Oasis® HLB 20 cc, 1 gr LP Extraction cartridges) to provide the title compound in 50% yield: Mass spectrum (EI+): m/z 330 (M$^+$+1); $^1$H NMR (CDCl$_3$, 200 MHz): δ8.0 (s abr. 2H); 7.78 (d, 2H, J=8.06); 7.4 (d, 2H, J=8.06); 4.18 (q, 2H, J=7.2); 3.08 (q, 2H, J=7.2); 1.43 (t, 3H, J=7.5); 1.17 (t, 3H, J=7.2) plus biscoupled product 4-Cyano-5-ethyl-3-{4-(4-cyano-5-ethyl)thiophen-3-yl-phenyl}-thiophene-2-carboxylic acid ethyl ester in 7% yield Mass spectrum (EI+): m/z 493. (M$^+$+1).

GENERAL EXAMPLE E-17

3-(4-OR$^{16}$-phenyl)-4-cyano-5-R$^1$-thiophene-2-carboxylic acid ethyl ester

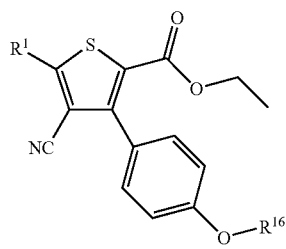

GENERAL EXAMPLE E-17-A

Stir and heat at 85° C. a suspension of 4-cyano-3-(4-hydroxy-phenyl)-5-R$^1$-thiophene-2-carboxylic acid ethyl ester (0.157 mmol), R$^{16}$—X (0.235 mmol, 1.5 eq) and base (0.47 mmol, 3 eq) in 2 ml of acetonitrile for 24 hours. Check for no starting material by t.l.c. (hexane:ethyl acetate, 8:1). Pour the reaction mixture into water and extract with ethyl acetate. Wash the ethyl acetate, extract with NaCl sat, and dry (MgSO$_4$). Filter the MgSO$_4$ and concentrate the filtrate under reduced pressure to afford the title compound.

GENERAL EXAMPLE E-17-B

Combine and stir a mixture of 4-cyano-3-(4-hydroxy-phenyl)-5-R$^1$-thiophene-2-carboxylic acid ethyl ester (0.31 mmol), R$^{16}$—OH (0.47 mmol, 1.5 eq) and triphenylphosphine (0.47 mmol, 1.5 eq) in toluene (5 ml) at 0° C. under nitrogen atmosphere, add DIAD (93 ul, 0.47 mmol, 1.5 eq) dropwise. After this, let reaction slowly cool to room temperature over 12 hours. Remove solvent in vacuo and purify the title compound by flash chromatography (hexane:ethyl acetate 4:1).

GENERAL EXAMPLE E-17-C

Heat at 90° C. for 12 h a stirring mixture of 4-cyano-3-(4-hydroxy-phenyl)-5-methylsulfanyl-thiophene-2-carboxylic acid ethyl ester (100 mg, 0.31 mmol), 2-fluorobenzonitrile (34 ul, 0.31 mmol), 18-crown-6 (9 mg, 0.013 mmol, 0.1 eq), and 40% w/w KF-Al$_2$O$_3$ (250 mg) in CH$_3$CN (2 mL). Cool the reaction mixture to rt, partition between equal amounts of ether and water, and shake vigorously. Draw the aqueous layer and alumina sediments from the funnel, and wash the resulting organic phase once with saturated NaCl (aq), dry (Na$_2$SO$_4$), filter the Na$_2$SO$_4$, and concentrate in vacuo. Purification by flash chromatography (hexane:ethyl acetate 4:1) affords the title compound.

GENERAL EXAMPLE E-17-D

Stir at room temperature a mixture of 4-cyano-3-(4-hydroxy-phenyl)-5-methyl sulfanyl-thiophene-2-carboxylic acid ethyl ester (100 mg, 0.31 mmol), 4-fluorophenylboronic acid (88 mg, 0.63 mmol), copper acetate (56 mg, 0.31 mmol, 1 eq), 4 A molecular sieves and triethylamine (215 ul, 1.55 mmol) in CH$_2$Cl$_2$ (3 mL) for 24 hours. Filter, concentrate in vacuo and purify by flash chromatography (hexane:ethyl acetate 4:1) to give the title compound.

EXAMPLE E-18

3-[4-(2-tert-Butoxycarbonylamino-ethoxy)-phenyl]-4-cyano-5-methylsulfanyl-thiophene-2-carboxylic acid ethyl ester

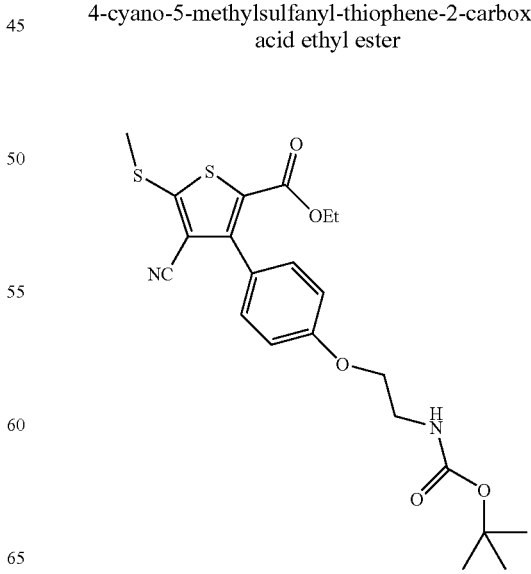

Prepare the title compound in a manner analogous to the procedure set forth in General Example 3-(4-OR[16]-phenyl)-4-cyano-5-R[1]-thiophene-2-carboxylic acid ethyl ester using NHBoc-aminoethanol and eluting with (hexane:ethyl acetate, 4:1). Obtain title compound quantitative. Rf (hexane: ethyl acetate, 4:1)=0.2. Mass spectrum (EI+): m/z 463 (M$^+$+1).

EXAMPLE E-19

3-[4-(2-Amino-ethoxy)-phenyl]-4-cyano-5-methyl-sulfanyl-thiophene-2-carboxylic acid ethyl ester trifluoroacetate salt

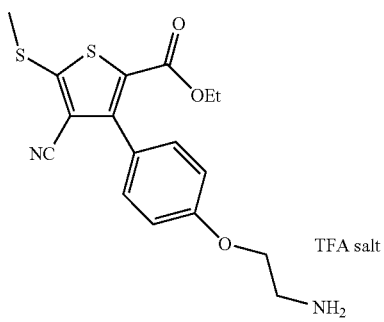

Combine 4-cyano-3-{4-[2-(2,2-dimethyl-propionylamino)-ethoxy]-phenyl}-5-methylsulfanyl-thiophene-2-carboxylic acid ethyl ester (211 mg, 0.45 mmol) and CH$_2$Cl$_2$ (1 ml), add trifluoroacetic acid 99% (1 ml) and stir at room temperature for 2 days. Remove the solvents in vacuo to give 222 mg (quantitative yield) of title compound: Rf (hexane:ethyl acetate, 4:1)=0.1. Mass spectrum (EI+): m/z 363 (M$^+$+1 free base).

EXAMPLE E-20

4-Cyano-5-methylsulfanyl-3-{4-[2-(propane-2-sulfonylamino)-ethoxy]-phenyl}-thiophene-2-carboxylic acid ethyl ester

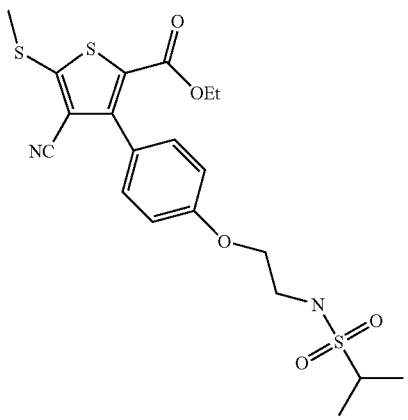

Combine 3-[4-(2-amino-ethoxy)-phenyl]-4-cyano-5-methyl sulfanyl-thiophene-2-carboxylic acid ethyl ester (222 mg, 0.46 mmol) and CH$_2$Cl$_2$ (5 ml) and stir. Add triethylamine (128 ul, 0.92 mmol, 2 eq) and isopropylsulphonyl chloride (103 ul, 0.92 mmol, 2 eq) at room temperature. Stir the mixture overnight. Remove the solvents in vacuo. Purification by flash chromatography (Hexane:ethyl acetate, 2:1) gives title compound as white solid (59 mg, 30%): Rf (hexane:ethyl acetate, 1:1)=0.4; mass spectrum (EI+): m/z 469 (M$^+$+1).

EXAMPLE E-21

3-(4-tert-Butyl-phenyl)-4-cyano-5-trifluoromethyl-thiophene-2-carboxylic acid ethyl ester

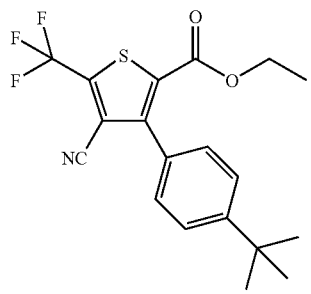

Combine 4-cyano-3-iodo-5-trifluoromethyl-thiophene-2-carboxylic acid ethyl ester (0.136 mmol) with 4-t-butyl-phenyl boronic acid (0.163 mmol), palladium acetate (0.027 mmol), 1,1'-Bis(di-i-propylphosphino)ferrocene (0.027 mmol), and potassium fluoride in DME at room temperature. Stirred at room temperature for 17 hours. Concentrated reaction in vacuo and purified by radial chromatography eluting with hexanes/methylene chloride to provide the title compound. $^1$H NMR (400 MHz, CDCl$_3$) δ 7.41 (q, 4H, J=21.7 Hz), 4.26 (q, 2H, J=7.0 Hz), 1.37 (s, 9H) and 1.21 (t, 3H, J=7.3 Hz), $^{19}$F NMR (CDCl$_3$) δ—57.2 ppm (s).

EXAMPLE E-22

3-(4-tert-Butyl-phenyl)-4-cyano-5-methanesulfanyl-thiophene-2-carboxylic acid methyl ester

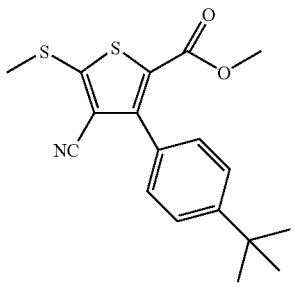

By using a method similar to general preparation 28, general preparation 29, general example E-1 obtains the title compound.

EXAMPLE E-23

3-(4-tert-Butyl-phenyl)-4-cyano-5-methanesulfonyl-thiophene-2-carboxylic acid methyl ester

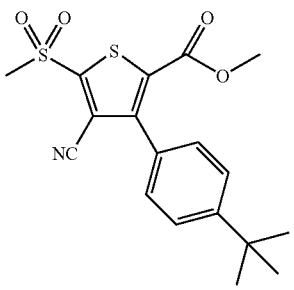

Combine 3-(4-tert-Butyl-phenyl)-4-cyano-5-methanesulfanyl-thiophene-2-carboxylic acid methyl ester (0.29 mmol) and methylene chloride and add m-chloroperoxybenzoic acid (1.02 mmol of 80-85% tech.) and reflux for 30 minutes. Dilute the reaction with methylene chloride and wash with sodium bicarbonate solution. Separate the organic layer and dry over sodium sulfate, filter, and concentrate under reduced pressure to provide the title compound as a white solid.

EXAMPLE E-24

5-Azido-3-(tert-butyl-phenyl)-4-cyano-thiophene-2-carboxylic acid methyl ester

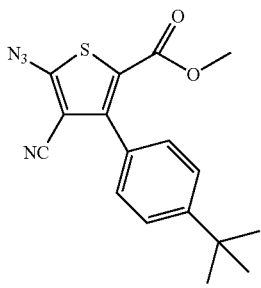

Add sodium azide (1.4 mmol) to a solution of 3-(4-tert-butyl-phenyl)-4-cyano-5-methanesulfonyl-thiophene-2-carboxylic acid methyl ester (0.28 mmol) in DMF and stir the mixture at room temperature for 2.5 hours. Dilute the reaction with diethyl ether and water. Separate the organic layer, dry over sodium sulfate, and concentrate under reduced pressure to provide the title compound as an oil. $^1$H NMR (400 MHz, CDCl$_3$) δ 7.48-7.33 (m, 4H), 3.77 (s, 3H), 1.36 (s, 9H).

EXAMPLE E-25

5-Amino-3-(4-tert-butyl-phenyl)-4-cyano-thiophene-2-carboxylic acid methyl ester

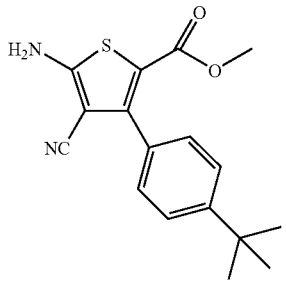

Combine 5-azido-3-(tert-butyl-phenyl)-4-cyano-thiophene-2-carboxylic acid methyl ester (0.309 mmol) and THF at room temperature and add a fresh THF solution of 0.1M SmI (0.93 mmol). Stir the reaction for 15 minutes and quench with 2M sodium carbonate solution until pH was greater than 9.0. Dilute the reaction with ethyl acetate and wash successively with 2M sodium carbonate, water, and brine. Separate the organics, dry over sodium sulfate, filter, and concentrate to give the title compound as a dark solid: $^1$H NMR (400 MHz, CDCl$_3$) δ 7.46-7.36 (m, 4H), 5.23 (s, 2H), 3.71 (s, 3H), 1.36 (s, 9H), MS found (M+1) 315.1.

EXAMPLE E-26

3-(4-tert-butyl-phenyl-4-cyano-5-iodo-thiophene-2-carboxylic acid methyl ester

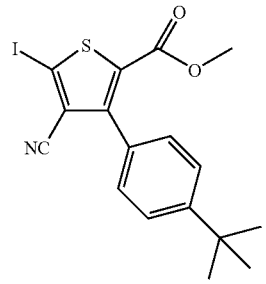

Combine 5-amino-3-(4-tert-butyl-phenyl)-4-cyano-thiophene-2-carboxylic acid methyl ester (0.29 mmol) in acetonitrile and add diiodomethane (1.02 mmol) and iso-amyl nitrite (0.73 mmol) and heat to 100° C. After 15 minutes, cool the reaction slowly to room temperature and stir an additional 1 hour. Concentrate the reaction to a dark oil which is purified by radial chromatography on a 2000 micron silica plate eluting with 50/50 methylene chloride/hexane and then 100% methylene chloride. Concentrate desired fractions were to give the title compound. $^1$H NMR (400 MHz, CDCl$_3$) δ 7.41 (m, 4H), 3.78 (s, 3H), 1.37 (s, 9H).

EXAMPLE E-27

3-(4-tert-Butyl-phenyl)-4-cyano-5-trifluoromethyl-thiophene-2-carboxylic acid methyl ester

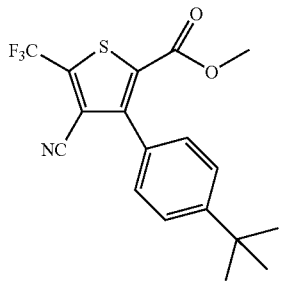

Combine 3-(4-tert-butyl-phenyl)-4-cyano-5-iodo-thiophene-2-carboxylic acid methyl ester (0.08 mmol) and DMF and add methyl 2,2-difluoro-2-(fluoro-sulfonyl)acetate (0.164 mmol), cuprous bromide (0.016 mmol) and heat to 90° C. After 10 minutes, cool the reaction, dilute with diethyl ether, and wash with water and brine. Separate the organics, dry over sodium sulfate, filter, and concentrate in vacuo to a yellow oil. Purify the oil by radial chromatography on a 1000 micron silica plate eluting with methylene chloride/hexane, 3:1. Concentrate the desired fractions to provide the title compound: $^1$H NMR (400 MHz, CDCl$_3$) δ 7.43 (m, 4H), 3.83 (s, 3H), 1.38 (s, 9H), $^{19}$F NMR (CDCl$_3$) δ—57.06 ppm (s).

EXAMPLE E-28

5-Azido-4-cyano-3-(4-iodo-phenyl)-thiophene-2-carboxylic acid ethyl ester

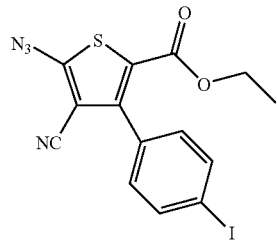

Using a method substantially in accordance with the method of example 5-azido-3-(tert-butyl-phenyl)-4-cyano-thiophene-2-carboxylic acid methyl ester starting with the compound 3-(4-iodophenyl)-4-cyano-5-methanesulfonyl-thiophene-2-carboxylic acid ethyl ester gives the title compound.

EXAMPLE E-29

5-Amino-4-cyano-3-(4-iodo-phenyl)-thiophene-2-carboxylic acid ethyl ester

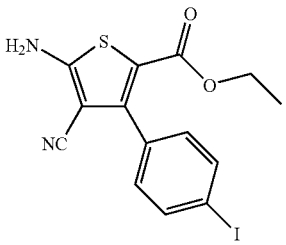

Using a method substantially in accordance with the method of example 5-amino-3-(4-tert-butyl-phenyl)-4-cyano-thiophene-2-carboxylic acid methyl ester starting with the compound 5-azido-4-cyano-3-(4-iodo-phenyl)-thiophene-2-carboxylic acid ethyl ester gives the title compound.

EXAMPLE E-30

5-Amino-4-cyano-3-(2'methylsulfanyl-biphenyl-4-yl)-thiophene-2-carboxylic acid ethyl ester

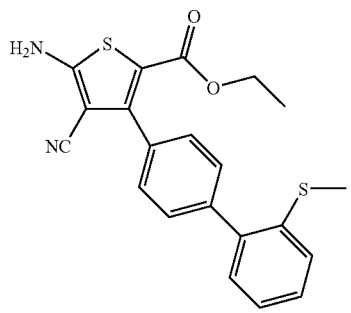

Combine 5-amino-4-cyano-3-(4-iodo-phenyl)-thiophene-2-carboxylic acid ethyl ester (0.829 mmol) in dioxane and add 2-(methylthio)phenylboronic acid, tetrakis(triphenylphosphine)palladium (0), and 1.4 ml of 2M sodium carbonate solution and heat to reflux. After 3 hours, purification by radial chromatography (6000 micron Si plate) eluting with 10-20% ethylacetate/methylene chloride provides the title compound: $^1$H NMR (400 MHz, CDCl$_3$) δ 7.49-7.19 (m, 8H), 5.26 (s, 2H), 4.17 (q, 2H, J=7.2 Hz), 2.38 (s, 3H), 1.18 (t, 3H, J=7.0 Hz), MS found (M+1) 395.1.

EXAMPLE E-31

4-Cyano-5-iodo-3-(2'-methylsulfanyl-biphenyl-4-yl)-thiophene-2-carboxylic acid ethyl ester

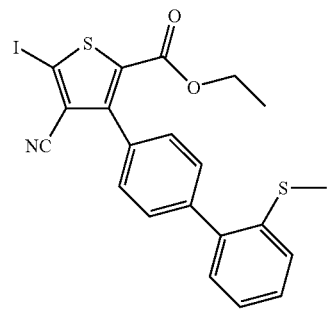

Using a method substantially in accordance with the method of 3-(4-tert-butyl-phenyl-4-cyano-5-iodo-thiophene-2-carboxylic acid methyl ester starting with the compound 5-amino-4-cyano-3-(2'methylsulfanyl-biphenyl-4-yl)-thiophene-2-carboxylic acid ethyl ester gives the title compound: $^1$H NMR (400 MHz, CDCl$_3$) δ 7.53-7.20 (m, 8H), 4.23 (q, 2H, J=7.2 Hz), 2.38 (s, 3H), 1.22 (t, 3H, J=7.0 Hz).

EXAMPLE E-33

4-Cyano-3-(2'-methylsulfanyl-biphenyl-4-yl)-5-trifluoromethyl-thiophene-2-carboxylic acid ethyl ester

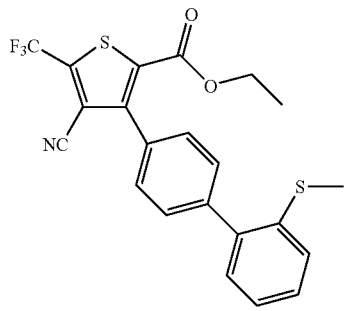

Using a method substantially in accordance with the method of 3-(4-tert-butyl-phenyl)-4-cyano-5-trifluoromethyl-thiophene-2-carboxylic acid methyl ester starting with the compound, 4-cyano-5-iodo-3-(2'-methylsulfanyl-biphenyl-4-yl)-thiophene-2-carboxylic acid ethyl ester gives the title compound: $^1$H NMR (400 MHz, CDCl$_3$) δ 7.82-7.47 (m, 8H), 4.27 (q, 2H, J=7.2 Hz), 2.38 (s, 3H), 1.22 (t, 3H, J=7.3 Hz).

EXAMPLE E-34

5-Amino-4-cyano-3-(2'-cyano-biphenyl-4-yl)-thiophene-2-carboxylic acid ethyl ester

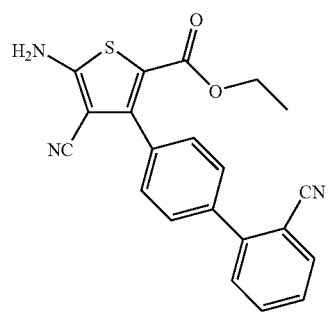

Using a method substantially in accordance with the method of 5-amino-4-cyano-3-(2'methylsulfanyl-biphenyl-4-yl)-thiophene-2-carboxylic acid ethyl ester starting with the compound 5-amino-4-cyano-3(4-iodo-phenyl)-thiophene-2-carboxylic acid ethyl ester and 2-(cyano)phenyl-boronic acid gives the title compound: $^1$H NMR (400 MHz, CDCl$_3$) δ 7.81-7.44 (m, 8H), 5.29 (s, 2H), 4.16 (q, 2H, J=7.2 Hz), 1.17 (t, 3H, J=7.3 Hz), MS found (M−1) 372.0 and (M+1)+NH$_3$ 391.0.

EXAMPLE E-35

4-Cyano-3-(2'-cyano-biphenyl-4-yl)-5-iodo-thiophene-2-carboxylic acid ethyl ester

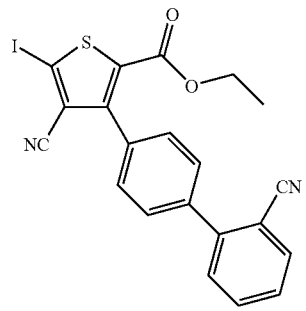

Using a method substantially in accordance with the method of 3-(4-tert-butyl-phenyl-4-cyano-5-iodo-thiophene-2-carboxylic acid methyl ester starting with the compound, 5-amino-4-cyano-3-(2'-cyano-biphenyl-4-yl)-thiophene-2-carboxylic acid ethyl ester gives the title compound: $^1$H NMR (400 MHz, CDCl$_3$) δ 7.81-7.46 (m, 8H), 4.22 (q, 2H, J=7.2 Hz), 1.20 (t, 3H, J=7.0 Hz), MS found (M+1)+NH$_3$ 502.

EXAMPLE E-36

4-Cyano-3-(2'-cyano-biphenyl-4-yl)-5-trifluoromethyl-thiophene-2-carboxylic acid ethyl ester

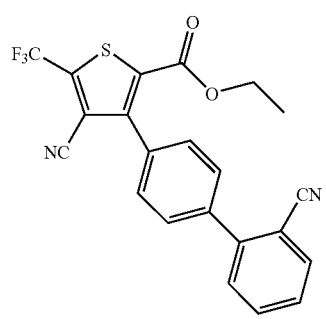

Using a method substantially in accordance with the method of 3-(4-tert-butyl-phenyl)-4-cyano-5-trifluoromethyl-thiophene-2-carboxylic acid methyl ester starting with the compound from example E-35, 4-cyano-3-(2'-cyano-biphenyl-4-yl)-5-iodo-thiophene-2-carboxylic acid ethyl ester, gives the title compound: $^1$H NMR (400 MHz, CDCl$_3$) δ 7.82-7.47 (m, 8H), 4.27 (q, 2H, J=7.2 Hz), 1.22 (t, 3H, J=7.3 Hz), $^{19}$F NMR (CDCl$_3$) δ—57.06 ppm (s), MS found (M+1)+NH$_3$ 444.0.

EXAMPLE E-37

4-Cyano-3-(2'-cyano-biphenyl-4-yl)-5-methylsulfanyl-thiophene-2-carboxylic acid ethyl ester

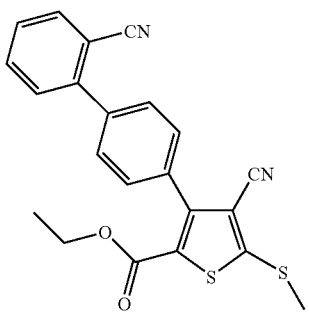

Combine 4-cyano-3-iodo-5-methylsulfanyl-thiophene-2-carboxylic acid ethyl ester (400 mg, 1.13 mmol), 2'-carbonitrile-biphenyl-boronic acid (907 mg, 4.1 mmol), cesium carbonate (2.2 g, 6.75 mmol) and tetrakis(triphenylphosphine)-palladium(0) (130 mg, 0.11 mmol) in 5 mL of tetrahydrofuran/water (4/1) and heat to 80° C. under nitrogen with stirring. After 24 hours the reaction is cooled, diluted with 100 mL of ethyl acetate and washed with water (2×25 mL) and brine (1×25 mL) and dried over sodium sulfate. The dried solution is filtered, evaporated and chromatographed over silica gel, eluting with a gradient of toluene/ethyl acetate (100/0 to 98/2), to give the title compound in 20% yield (91 mg). HPLC analysis is 96%.

EXAMPLE E-38

4-Cyano-3-(2'-cyano-biphenyl-4-yl)-5-methanesulfonyl-thiophene-2-carboxylic acid ethyl ester

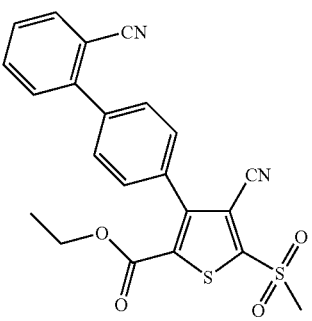

Prepare a solution of 4-cyano-3-(2'-cyano-biphenyl-4-yl)-5-methylsulfanyl-thiophene-2-carboxylic acid ethyl ester (200 mg, 0.49 mmol) in 5 mL of $CH_2Cl_2$, cool to 0° C. and add MCPBA (345 mg, 2.0 mmol). Remove the ice-bath and stir the reaction overnight. Dilute with 50 mL of $CH_2Cl_2$ and wash with 10% aqueous $NaHSO_3$ (1×10 mL), water (1×10 mL), saturated $NaHCO_3$ (1×10 mL) and brine (1×10 mL). Dry over $Na_2SO_4$, filter and evaporate to a white solid which is used without further purification. Yield=95 mg (90%). MS (ES+, m/e)=437 ($M^+$+1).

EXAMPLE E-39

4-Cyano-3-(2'-cyano-biphenyl-4-yl)-5-dimethylamino-thiophene-2-carboxylic acid ethyl ester

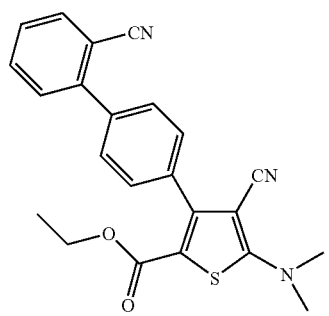

Add 4-cyano-3-(2'-cyano-biphenyl-4-yl)-5-methanesulfonyl-thiophene-2-carboxylic acid ethyl ester (100 mg, 0.23 mmol) to 3 mL of 2N dimethylamine in THF and stir under nitrogen at room temperature for 90 minutes. Evaporate to a tan solid which is used without further purification. MS(ES+, m/e)=402 ($M^+$+1); HPLC=89%.

EXAMPLE E-40

3-(4-tert-Butyl-phenyl)-4-cyano-5-methanesulfonyl-thiophene-2-carboxylic acid ethyl ester

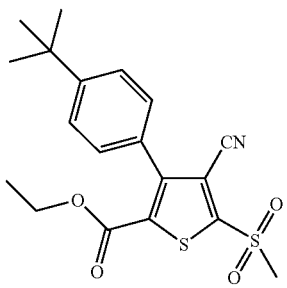

Prepare the title compound in a manner analogous to the procedure set forth in Example E-38 using 3-(4-tert-butyl-phenyl)-4-cyano-5-methylsulfanyl-thiophene-2-carboxylic acid ethyl ester.

EXAMPLE E-41

3-(4-tert-Butyl-phenyl)-4-cyano-5-ethyl-thiophene-2-carboxylic acid ethyl ester

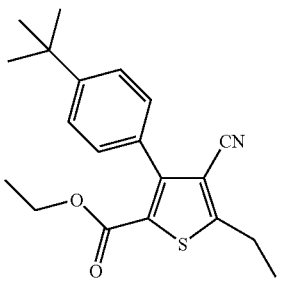

Add diethylzinc (1.0M in hexanes, 16 mL, 16 mmol) to a solution of 3-(4-tert-butyl-phenyl)-4-cyano-5-methanesulfonyl-thiophene-2-carboxylic acid ethyl ester (2.78 mmol) in 15 mL of anhydrous $CH_2Cl_2$ and stir under nitrogen at room temperature for 5 days. Cool to 0° C. and carefully quench with ice followed by 10 mL of saturated $NH_4Cl$. Filter the mixture through Celite® and rinse the filter pad with 100 mL of $CH_2Cl_2$. Wash the combined organic layers with brine (1×20 mL), dry over $Na_2SO_4$, filter and evaporate. Chromatograph over silica gel with 100% toluene to give the title compound as a clear oil, 625 mg (66%). MS (FAB)=341 ($M^+$); HPLC=98%.

EXAMPLE E-42

4-Cyano-3-(2'-cyano-biphenyl-4-yl)-5-ethyl-thiophene-2-carboxylic acid ethyl ester

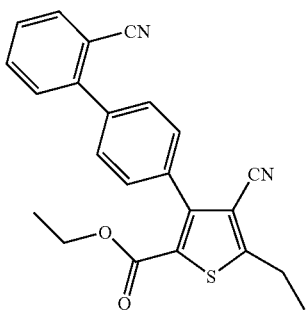

Prepare a solution of 4-cyano-5-ethyl-3-[4-(4,4,5,5-tetramethyl-[1,3,2]dioxaborolan-2-yl)-phenyl]-thiophene-2-carboxylic acid ethyl ester (0.26 mmol), 2-iodobenzonitrile (41 mg, 0.18 mmol), 2M aqueous $Na_2CO_3$ (0.6 mL, 1.2 mmol) and tetrakis(triphenylphosphine)-palladium(0) (20 mg, 0.02 mmol) in 3 mL of dioxane and heat to 80° C. under nitrogen. After 3 hours cool to room temperature, dilute with 50 mL of EtOAc and wash with water (2×10 mL) and brine (1×10 mL). Dry the organics over $Na_2SO_4$, filter and evaporate. Chromatograph on silica gel (100/0 to 3/1 toluene/EtOAc) to give the title compound as a yellow foam. Yield=61 mg (91%). HPLC=80%.

EXAMPLE E-43

4-Cyano-3-(4-cyclopentyl-phenyl)-5-ethyl-thiophene-2-carboxylic acid ethyl ester

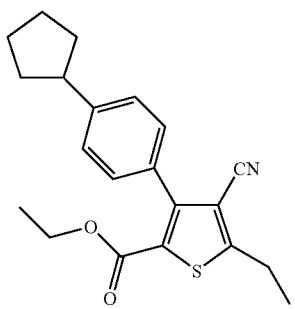

Prepare the title compound in a manner analogous to the procedure set forth in Example E-42 using 4-cyano-5-ethyl-3-iodo-thiophene-2-carboxylic acid ethyl ester (393 mg, 1.28 mmol) and the crude 2-(4-cyclopentyl-phenyl)-4,4,5,5-tetramethyl-[1,3,2]dioxaborolane by refluxing for 3.5 hours. Yield=185 mg (41%). HPLC=91%.

EXAMPLE E-44

4-Cyano-5-ethyl-3-(2'-methylsulfanyl-biphenyl-4-yl)-thiophene-2-carboxylic acid ethyl ester

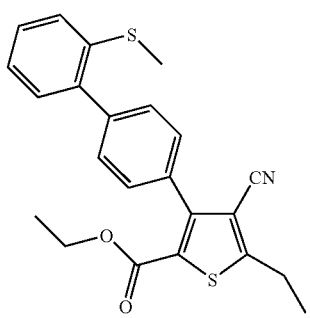

Prepare the title compound in a manner analogous to the procedure set forth in Example E-37 using 4-cyano-5-ethyl-3-(4-iodo-phenyl)-thiophene-2-carboxylic acid ethyl ester (315 mg, 0.77 mmol) and 2-thiomethylphenylboronic acid (220 mg, 1.3 mmol). Yield=244 mg (78%). HPLC=99%.

EXAMPLE E-45

4-Cyano-5-ethyl-3-(2'-methoxy-biphenyl-4-yl)-thiophene-2-carboxylic acid ethyl ester

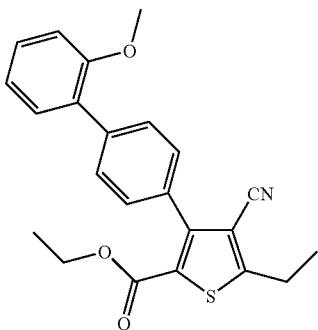

Prepare the title compound in a manner analogous to the procedure set forth in Example E-37 using 4-cyano-5-ethyl-3-(4-iodo-phenyl)-thiophene-2-carboxylic acid ethyl ester (410 mg, 1.0 mmol) and 2-methoxyphenylboronic acid (280 mg, 1.75 mmol). Yield=333 mg (85%). HPLC=99%.

EXAMPLE E-46

4-Cyano-3-(2'-ethoxy-biphenyl-4-yl)-5-ethyl-thiophene-2-carboxylic acid ethyl ester

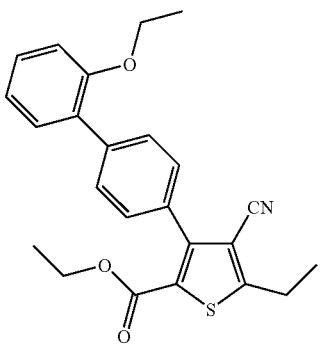

Prepare the title compound in a manner analogous to the procedure set forth in Example E-37 using 4-cyano-5-ethyl-3-(4-iodo-phenyl)-thiophene-2-carboxylic acid ethyl ester (410 mg, 1.0 mmol) and 2-ethoxyphenylboronic acid (300 mg, 1.81 mmol). Yield=314 mg (77%). HPLC=99%.

EXAMPLE E-47

4-Cyano-5-ethyl-3-(2'-propoxy-biphenyl-4-yl)-thiophene-2-carboxylic acid ethyl ester

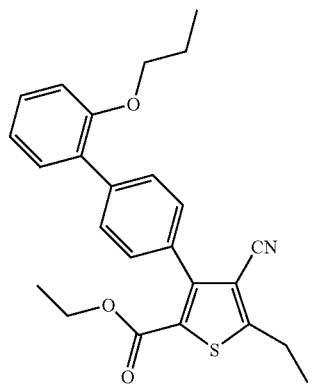

Add $K_2CO_3$ (220 mg, 1.6 mmol) to a solution of 4-cyano-5-ethyl-3-(2'-hydroxy-biphenyl-4-yl)-thiophene-2-carboxylic acid ethyl ester (200 mg, 0.53 mmol) in 2 mL of dry DMF at 0° C. and stir at this temperature for 1 hour. Treat with n-propyl iodide (0.2 mL, 2 mmol) and allow to warm to room temperature. After 3 hours pour into 25 mL cold 0.2N HCl. Extract with EtOAc (2×50 mL) and wash the combined EtOAc layers with water (2×20 mL) and brine (1×20 mL). Dry over $Na_2SO_4$, filter and evaporate to an oil. Chromatograph on silica gel (1/9-1/3 EtOAc/hexanes) to give the title compound as a tan solid, 158 mg (71%). HPLC=99%.

EXAMPLE E-48

4-Cyano-5-ethyl-3-(2'-propoxy-biphenyl-4-yl)-thiophene-2-carboxylic acid ethyl ester

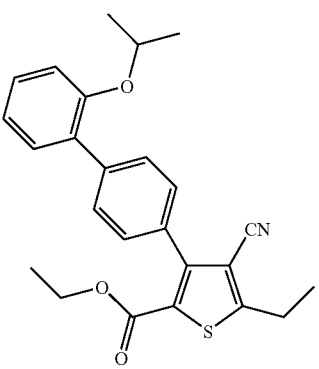

Prepare the title compound in a manner analogous to the procedure set forth in Example E-47 using 4-cyano-5-ethyl-3-(2'-hydroxy-biphenyl-4-yl)-thiophene-2-carboxylic acid ethyl ester (200 mg, 0.53 mmol) and isopropyl iodide. Yield=169 mg (76%). HPLC=99%.

EXAMPLE E49

3-(4-tert-Butyl-phenyl)-4-cyano-5-ethyl-thiophene-2-carboxylic acid dimethylaminomethyleneamide

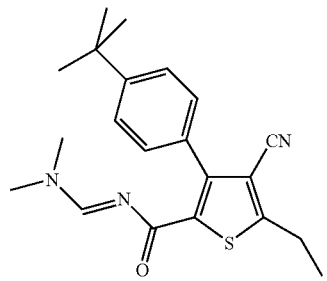

Prepare a solution of 3-(4-tert-butyl-phenyl)-4-cyano-5-ethyl-thiophene-2-carboxylic acid amide (270 mg, 0.86 mmol) in 4 mL of dry dimethoxymethyl-dimethyl-amine and heat to reflux under nitrogen. After 1 hour allow 1 mL of solvent to distill out of the reaction, then cool the mixture to room temperature. Dilute the slurry with 10 mL of hexanes, filter off the resulting yellow product and wash with 5 mL hexanes. Vacuum-dry the solid overnight to give 261 mg (82%) of the title compound. MS(ES+, m/e)=368 ($M^+$+1).

EXAMPLE E-50

4-Cyano-3-(2'-cyano-biphenyl-4-yl)-thiophene-2-carboxylic acid ethyl ester

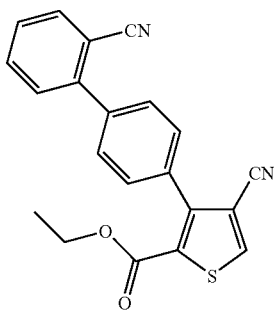

Add $NaBH_4$ (10 mg, 0.26 mmol) to a solution of 4-cyano-3-(2'-cyano-biphenyl-4-yl)-5-methanesulfonyl-thiophene-2-carboxylic acid ethyl ester (95 mg, 0.22 mmol) in 2 mL of EtOH at 0° C. Remove the ice-bath and stir at room temperature. After 30 minutes add another 10 mg of $NaBH_4$ and stir an additional 30 minutes. Remove the solvents in vacuo and extract the residue with 50 mL of 1/9 MeOHJ $CH_2Cl_2$. Evaporate and chromatograph over silica gel (100/0 to 90/10 toluene/EtOAc) to give 44 mg (56%) of the title compound as a white solid. HPLC=94%.

EXAMPLE E-51

4-Cyano-5-isopropyl-3-(4-iodo-phenyl)-thiophene-2-carboxylic acid ethyl ester

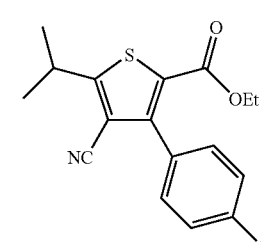

Add dropwise isopropylzinc solution ($ZnCl_2$ 1M in $Et_2O$ (10.5 ml) and isopropylzinc 2M in THF (10.5 ml) previously mixed at 10° C. under $N_2$ atmosphere) to a mechanically stirring suspension of 4-cyano-3-(4-iodo-phenyl)-5-methyl-sulfanyl-thiophene-2-carboxylic acid ethyl ester (1.5 gr, 3.5 mmol) and 1,3-bis-(diphenylphosphino)propane nickel (II) chloride (380 mg, 0.71 mmol) in dry THF (35 ml) and heat the resulting mixture 60° C. for 1 hour. Cool the reaction to room temperature and remove solvents in vacuo. Purify the solid by chromatography on silica gel (eluting with 10-80% Ethyl acetate/hexane) to provide the title compound in 25% yield: Mass spectrum (EI+): m/z 426 ($M^+$+1).

EXAMPLE E-52

3-(4-tert-Butyl-phenyl)-4-cyano-5-ethylsulfanyl-thiophene-2-carboxylic acid ethyl ester

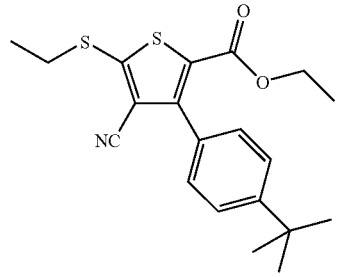

Combine 3-(4-tert-Butyl-phenyl)-4-cyano-5-ethylsulfanyl-thiophene-2-carboxylic acid ethyl ester (0.14 mmol), ethanethiol (0.28 mmol), sodium tertbutoxide (0.21 mmol) and (R)-(+)-2,2'-Bis(diphenylphosphino)-1,1'-binaphthyl (0.015 mmol) and tetrakis(triphenylphosphine)-palladium(0) (0.007 mmol) in 2 mL of toluene and heat to 90° C. under nitrogen with stirring overnight. Filter the reaction mixture over celite and evaporate the solvents under vacuum. Chromatograph on silica gel, eluting with a gradient of 1/3 ethyl acetate/hexane to give the title compound as a yellow solid (quantitative yield). Mass spectrum (m/e): 374 (M+1).

EXAMPLE E-53

3-(4-tert-Butyl-phenyl)-4-cyano-5-propylsulfanyl-thiophene-2-carboxylic acid ethyl ester

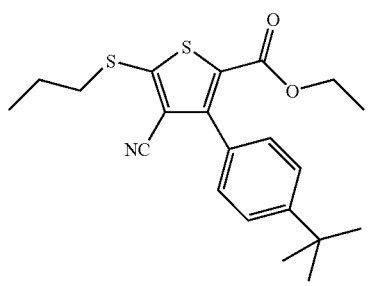

Prepare the title compound in a manner analogous to the procedure set forth in example E-52, 3-(4-tert-Butyl-phenyl)-4-cyano-5-ethylsulfanyl-thiophene-2-carboxylic acid ethyl ester to provide the title compound. Mass spectrum (m/e): 388 (M+1).

EXAMPLE E-54

3-(4-tert-Butyl-phenyl)-4-cyano-5-isopropylsulfanyl-thiophene-2-carboxylic acid ethyl ester

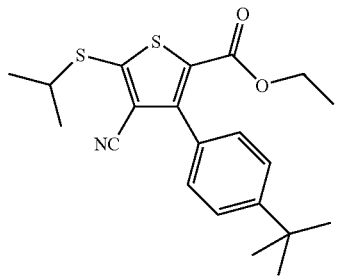

Prepare the title compound in a manner analogous to the procedure set forth in example E-52, 3-(4-tert-Butyl-phenyl)-4-cyano-5-ethylsulfanyl-thiophene-2-carboxylic acid ethyl ester to provide the title compound. Mass spectrum (m/e): 388 (M+1).

EXAMPLE E-55

4-cyano-5-ethyl-3-(4-[1,2,4]-thiadiazol-2-yl-phenyl)-thiophene-2-carboxylic acid ethyl ester

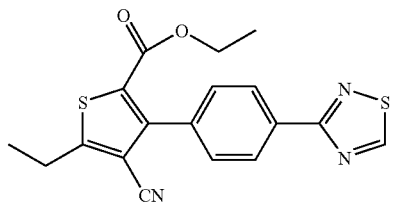

Add DME (3 mL) to a mixture of 3-[4-(4,4,5,5,-tetramethyl-[1,3,2]dioxaborolan-2-yl)-phenyl]-[1,2,4]thiadiazole (0.066 g, 0.23 mmol), 4-Cyano-3-iodo-5-ethyl-thiophene-2-carboxylic acid ethyl ester (0.071 g, 0.20 mmol), 1,1'-bis(diphenylphosphino)ferrocene palladium(II) dichloride (1:1) dichloromethane complex (0.009 g, 0.01 mmol) and cesium fluoride (0.103 g, 0.68 mmol) under nitrogen and stir at 80° C. for 3 h. Cool down and add ice-water and ethyl acetate. Separate layers and wash the organic layer with water (3×) and back-extract the combined aqueous layers with ethyl acetate (2×). Wash the combined organic layers with brine, dry over anhydrous sodium sulfate and concentrate under reduced pressure over Celite®. Purify by flash chromatography (silica gel) eluting with hexanes-ethyl acetate 10:1 first, then 5:1 to give 0.06 g of the title compound as a white solid. Mass spectrum ESI positive (m/z): 370 (M+1).

EXAMPLE E-56

4-Cyano-5-ethyl-3-(4-thiazol-2-yl-phenyl)-thiophene-2-carboxylic acid ethyl ester

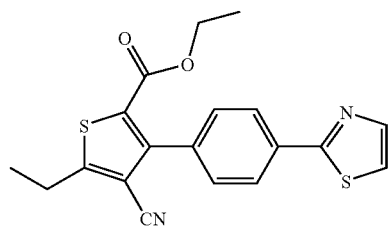

Add a solution of 2-(tributylstannyl)thiazole (0.565 g, 1.51 mmol) in dry toluene (2 mL) to a mixture of 4-cyano-5-ethyl-3-(4-bromo-phenyl)-thiophene-2-carboxylic acid ethyl ester (0.5 g, 1.37 mmol) and tetrakis(triphenyl-phosphine)palladium(0) (0.158 g, 0.14 mmol) in dry toluene (3 mL) under nitrogen atmosphere and stir at 110° C. for 3 h. Concentrate under reduced pressure over Celite® and purify by flash chromatography (silica gel) eluting with hexanes-ethyl acetate 9:1 first, then with 5:1. Wash the product thus obtained with diethyl ether-hexanes 1:2 to give 0.303 g of pure title product. Mass spectrum ESI positive (m/z): 369 (M+1).

EXAMPLE E-57

(R.S) 4-Cyano-3-[4-(2-cyano-cyclopent-2-enyl)-phenyl]-5-ethyl-thiophene-2-carboxylic acid ethyl ester

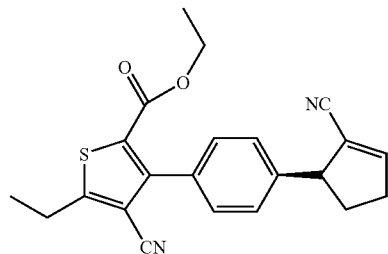

Add dry DMF (4 mL) to a mixture of 4-cyano-5-ethyl-3-(4-trifluoromethanesulfonyloxy-phenyl)-thiophene-2-carboxylic acid ethyl ester (1.0 g, 2.3 mmol), dichloro (bistriphenyl phosphine)palladium(II) (0.160 g, 0.22 mmol), 1,3-bis (diphenylphosphino)propane (0.105 g, 0.25 mmol), lithium bromide (0.380 g, 4.38 mmol) and solid sodium bicarbonate (0.385 g, 4.58 mmol) under nitrogen followed by addition of 1-cyanocyclopentene (0.4 mL). Heat the mixture to 150° C. and stir overnight. Cool down, add ethyl acetate and 1.2 M HCl and separate phases. Wash organic layer with more 1.2 M HCl (3×) and back-extract the combined aqueous layers with ethyl acetate once. Wash organic layer with brine, dry over sodium sulfate and concentrate in vacuo over Celite®. Purify by flash chromatography (silica gel) eluting with hexanes-ethyl acetate 4:1; 1:1, and ethyl acetate pure to give 0.160 g of the title compound as a mixture of isomers contaminated with the decarboxylated product. Mass spectrum ESI positive (m/z) 377 (M+1), 394 (M+18).

EXAMPLE E-58

4-Cyano-3-[4-(5-cyano-thiophen-2-yl-phenyl)-5-ethyl thiorphene-2-carboxylic acid ethyl ester

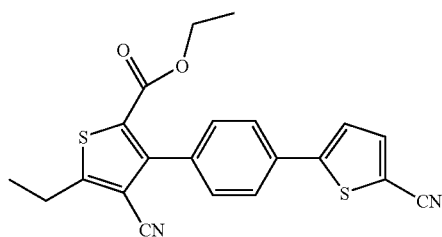

Mix 4-cyano-5-ethyl-3-(4-bromo-phenyl)-thiophene-2-carboxylic acid ethyl ester(1 Equiv.), 5-cyano-2-thiophene boronic acid (1.8 equiv) and tetrakis(triphenylphosphine) palladium(0) (0.09 equiv). Add DME (3 mL), ethanol (1.5 mL), 2M aqueous solution of sodium carbonate (0.55 mL) and stir at 90° C. under nitrogen for 24 h. Concentrate in vacuo and purify by preparative TLC (2 mm of silica gel plates) eluting with hexanes-ethyl acetate gradient (4:1) to give 0.052 g of the title compound as a white solid. Mass spectrum ESI positive (m/z): 393 (M+1), 410 (M+18).

EXAMPLE E-59

3-[4-5-acetyl-thiophen-2-yl)-phenyl]-4-cyano-5-ethyl-thiophene-2-carboxylic acid, ethyl ester

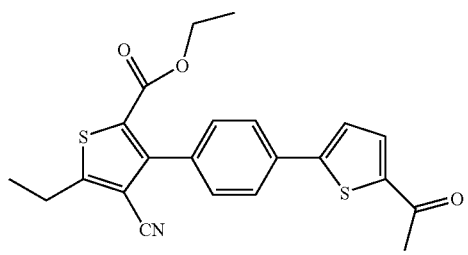

Prepare the title compound in a manner analogous to the procedure set forth in Example E-58 using 5-acetyl-2-thiophene boronic acid and stirring for 24 h. Concentrate and purify by preparative TLC (2 mm of silica gel plates) eluting with hexanes-ethyl acetate (3:1; 2:1) to give 0.042 g of the title compound as a white solid. Mass spectrum ESI positive (m/z): 410 (M+1).

EXAMPLE E-61

3-(4-Acetylaminophenyl)-4-cyano-5-methylsulfanyl-thiophene-2-carboxylic acid ethyl ester

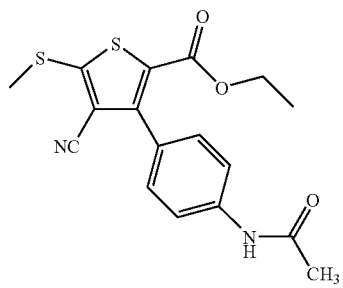

Combine 3-(4-aminophenyl)-4-cyano-5-methylsulfanyl-thiophene-2-carboxylic acid ethyl ester (0.1 g, 1.0 eq) in CH$_2$Cl$_2$ (5 mL) and stir. Add triethylamine (1.5 eq) and acetyl chloride (1.0 eq) at room temperature. Stir the mixture overnight. Add a saturated solution of NH$_4$Cl and extract with CH$_2$Cl$_2$ (2×50 mL). Dry over NaSO$_4$, filter and evaporate to dryness. Purification by chromatography (hexane: ethyl acetate 4:1) provides the title compound (0.125 g, yield 90%). MS (ES+, m/e): 361 (M+1).

EXAMPLE E-62

4-Cyano-3-(4-methanesulfonylamino-phenyl)-5-methylsulfanyl-thiophene-2-carboxylic acid ethyl ester

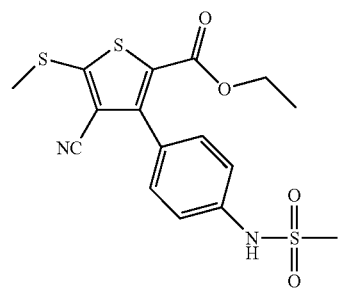

Combine 3-(4-Aminophenyl)-4-cyano-5-methylsulfanyl-thiophene-2-carboxylic acid ethyl ester (0.1 g, 1.0 eq) in CH$_2$Cl$_2$ (5 mL) and stir. Add triethylamine (1.5 eq) and methanesulfonyl chloride (1.0 eq) at room temperature. Stir the mixture overnight. Add a saturated solution of NH$_4$Cl and extract with CH$_2$Cl$_2$ (2×50 mL). Dry over NaSO$_4$, filter and evaporate to dryness. Purification by chromatography (hexane:ethyl acetate 4:1) provides the title compound (0.028 g, Yield 25%). MS (ES+, m/e): 397 (M+1).

EXAMPLE E-63

3-(4-Benzylamino-phenyl)-4-cyano-5-methylsulfanyl-thiophene-2-carboxylic acid ethyl ester

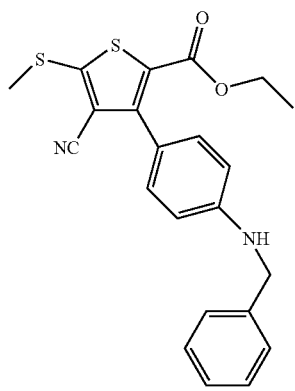

Step 1

Combine 3-(4-aminophenyl)-4-cyano-5-methylsulfanyl-thiophene-2-carboxylic acid ethyl ester (0.1 g, 1.0 eq) in MeOH (5 mL) and stir under nitrogen atmosphere. Add molecular sieves 4A (0.04 g) and benzaldehyde (2.0 eq) at room temperature. Stir the mixture overnight. Filter through celite and evaporate to dryness.

Step 2

Combine the above crude in a mixture of MeOH (3.0 mL) and acetic acid (6.0 mL) and stir at room temperature. Add NaCNBH$_3$ (1.1 eq). Stir the mixture overnight. Add a saturated solution of NaHCO$_3$ and extract with CH$_2$Cl$_2$ (2×50 mL). Dry over NaSO$_4$, filter and evaporate to dryness. Purification by chromatography (hexane:ethyl acetate 4:1) provides the title compound (0.030 g, Yield 25%). Purification by chromatography (hexane:ethyl acetate 4:1) provides the title compound (0.03 g, Yield 22%). MS (ES+, m/e): 409 (M+1).

EXAMPLE E-64

4-Cyano-3-(4-methylamino-phenyl)-5-methylsulfanyl-thiothene-2-carboxylic acid ethyl ester

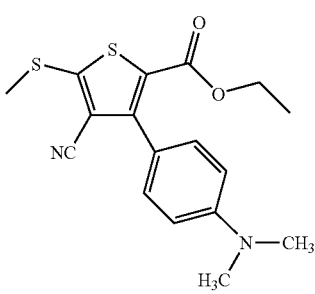

Combine 3-(4-aminophenyl)-4-cyano-5-methylsulfanyl-thiophene-2-carboxylic acid ethyl ester (0.1 g, 1.0 eq) in CH$_3$CN (8.0 mL) and stir. Add potassium carbonate (4.0 eq) and methyl iodide dropwise (1.5 eq) at 0° C. Stir the mixture for 3 days at room temperature. Add water and extract with ethyl acetate (2×50 mL). Dry over NaSO$_4$, filter and evaporate to dryness. Purification by chromatography (hexane: ethyl acetate 2:1) provides the title compound (0.007 g, Yield 7%). MS (ES+, m/e): 333 (M+1).

EXAMPLE E-65

4-Cyano-5-methylsulfanyl-3-(4-vinyl-phenyl)-thiophene-2-carboxylic acid ethyl ester

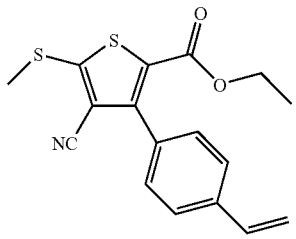

Combine 4-cyano-3-(4-iodo-phenyl)-5-methylsulfanyl-thiophene-2-carboxylic acid ethyl ester (0.1 g, 1.0 eq) in THF (5.0 mL) and stir. Add Pd(PPh$_3$)$_4$ (1%), tributyl-vinyl-stannane (0.9 eq) and LiCl. Reflux the mixture overnight. Concentrate to dryness. Wash with hexane to remove excess of stannane. Add water and filter the precipitate to provide the title compound (0.04 g, Yield 38%). MS (ES+, m/e): 330 (M+1).

EXAMPLE E-66

3-(4-tert-butyl-phenyl)4-cyano-5-methylsulfanyl-furan-2-carboxylic acid ethyl ester

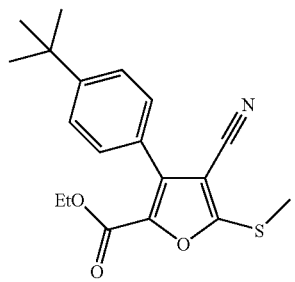

Add a solution of the bromoethyl acetate (2.13 ml, 19.17 mmol) in THF (10 ml) dropwise to a −78° C. solution of the lithium hexamethylsillylamide (1M, 21 ml, 20.7 mmol) in THF. Stir the mixture at −78° C. for 10 minutes and treat with a dropwise solution of 2-(4-tert-butyl-benzoyl)-3,3-bis-methylsulfanyl-acrylonitrile (2.25 g, 7.67 mmol) in THF (20 ml). Stir the mixture at −78° C. for 30 minutes and at RT for 6 h. Pour into a saturated solution of ammonium chloride (100 ml). Extract organic with EtOAc (3×100 ml). Combine the organics wash with water (3×100 ml), brine (100 ml), dry over magnesium sulfate, filter and concentrate under reduced pressure. Purification by flash chromatography, eluting with ethyl acetate:hexanes (1:9) provides the title compound (1 g, 38%): Mass spectrum (M+1)=344.

EXAMPLE E-67

4-Cyano-5-$R^1$-3-(4-mercantophenyl)-thiophene-2-carboxylic acid ethyl ester

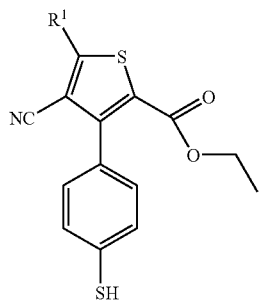

Place NaH (95% dispersed in oil, 0.222 g, 8.9 mmol) in a dry, 2-necked flask under nitrogen. Add dry THF (20 mL) under nitrogen and cool down the mixture to 0° C. Add triisopropyl-silanethiol (1.91 mL, 8.9 mmol) dropwise and stir at 0° C. for 15 min and then 5 min at 23° C. Add the reaction mixture to a warm solution of 4-cyano-5-$R^1$-3-(4-bromo-phenyl)-thiophene-2-carboxylic acid ethyl ester (2.5 g, 6.85 mmol) and tetrakis (triphenylphosphine)palladium(0) (0.79 g, 0.68 mmol) in dry toluene (30 ML) under nitrogen and stir the resulting mixture under reflux for 3 h and at 23° C. overnight. Cool down the mixture to 0° C. and add tetra n-butyl ammonium fluoride (1M solution in THF, 7 mL) and stir 45 min at 0-5° C. Then add glacial acetic acid (5 mL) and continue stirring 5-10 min. Add ethyl acetate and brine. Separate phases and wash organic phase with more brine. Back-extract combined aqueous layers with ethyl acetate. Dry combined organic layers (sodium sulfate) and concentrate in vacuo over Celite®. Purify by flash chromatography (silica gel) eluting with hexanes-ethyl acetate 10:1 to give 1.19 g of the title compound as a white solid: Mass spectrum ESI negative (m/z): 316 (M−1).

EXAMPLE E-68

4-Cyano-5-$R^1$-3-(4-mercapto-$R^4$, $R^5$-phenyl)-thiophene-2-carboxylic acid ethyl ester

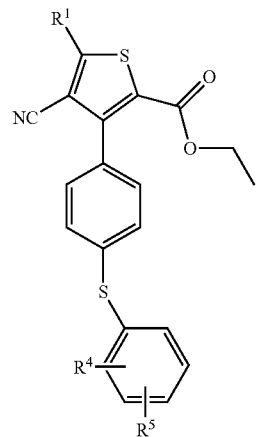

Add a solution of 4-Cyano-5-$R^1$-3-(4-mercaptophenyl)-thiophene-2-carboxylic acid ethyl ester (0.106 g, 0.33 mmol) in DMF (0.5 mL) to a suspension of the appropriate aryl halide (0.37 mmol) and potassium carbonate (0.67 mmol) in DMF (1.5 mL) under argon and warm to 100° C. in a sealed tube for 1.5 h. Cool down and add diethyl ether. Wash with 1M HCl (×3) and back-extract aqueous phase with diethyl ether. Wash combined organic layers with brine, dry (sodium sulfate-magnesium sulfate) and concentrate in vacuo over Celite®. Purify using SPE Strata® cartridges (silica gel) eluting with a gradient of hexanes-ethyl acetate (15:1 to 1:1).

By using method similar to the method described in example E-68, the following compounds are prepared:

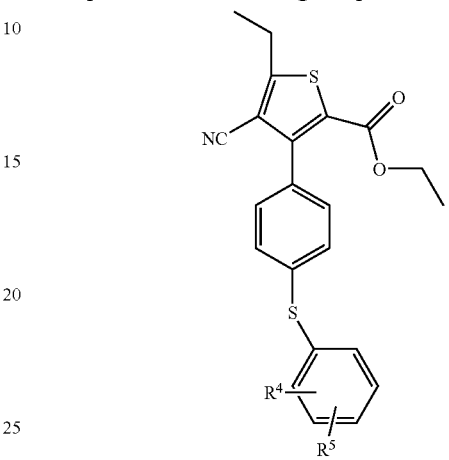

TABLE E-1

$R^5$ is hydrogen

| No. | $R^4$ | Data |
|---|---|---|
| E-68A | 2-cyano | Mass spectrum (m/z): 419(M + 1), 441(M + 23) |
| E-68B | 4-cyano | Mass spectrum (m/z): 419(M + 1), 441(M + 23) |
| E-68C | 2-cyano-5-fluoro | Mass spectrum (m/z): 454(M + 18), 459(M + 23) |
| E-68D | 2-cyano-4-fluoro | Mass spectrum (m/z): 454(M + 18), 459(M + 23) |

EXAMPLE E-69

4-Cyano-5-$R^1$-3-(4-mercapto-$R^4$, $R^5$-phenyl)-thiophene-2-carboxylic acid ethyl ester

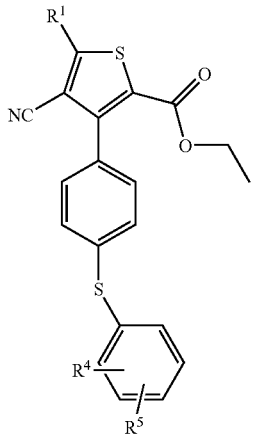

Using a Trident® Automated Synthesizer (Argonaut), add the appropriate thiol ($R^4$,$R^5$-phenylthioether) (1.02 mmol) in dioxane (1 mL) to a mixture of 3-(4-(Bromophenyl)4-cyano-5-$R^1$-thiophene-2-carboxylic acid ethyl ester (0.25 g, 0.68 mmol), tetrakis(triphenylphosphine)palladium(0) (0.158 g, 0.14 mmol) and cesium carbonate (0.031 g, 0.95 mmol) in dioxane (5 mL) under nitrogen in a Trident® reaction vessels using the Trident® work station. Warm the reaction to 110° C. and shake 16 h in a Trident® Automated Synthesizer. Collect automatically using ethyl acetate. Concentrate in vacuo over Celite® and purify using Triconex® flash tubes eluting with hexanes-ethyl acetate.

By using method similar to the method described in example E-69, the following compounds in Table E-2 are prepared:

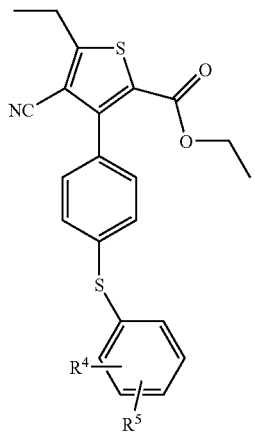

TABLE E-2

| | R⁵ is hydrogen | |
|---|---|---|
| No. | R⁴ | Data |
| E-70 | 2-methoxy | Mass spectrum (m/z): 424(M + 1), 446(M + 23) |
| E-71 | H | Mass spectrum (m/z): 394(M + 1), 416(M + 23) |
| E-72 | 2-chloro | Does not ionize * |
| E-73 | 3-chloro | Does not ionize * |
| E-74 | 4-chloro | Does not ionize * |
| E-75 | 3-methoxy | Mass spectrum (m/z): 424(M + 1), 446(M + 23) |
| E-78 | 4-methoxy | Mass spectrum (m/z): 424(M + 1), 446(M + 23) |

* Structure confirmed by subsequent transformation to the acid

By using method similar to the method described in example E-69, the following compounds in Table E-3 are prepared:

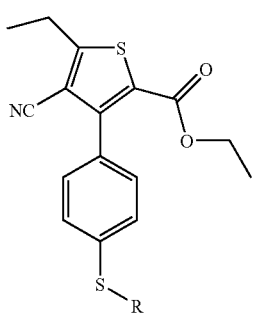

TABLE E-3

| No. | R | Data |
|---|---|---|
| E-79 | n-propyl | Mass spectrum (m/z): 360(M + 1), 382(M + 23) |
| E-80 | cyclopentyl | Mass spectrum (m/z): 386(M + 1), 408(M + 23 |
| E-80A | 2-(4-pyridyl)ethyl | Mass spectrum (m/z): 423(M + 1), 445(M + 23 |

EXAMPLE E-81

4-Cyano-3-[4-(3-dimethylamino-thiophen-2-yl)-phenyl]-5-ethyl-thiophene-2-carboxylic acid ethyl ester

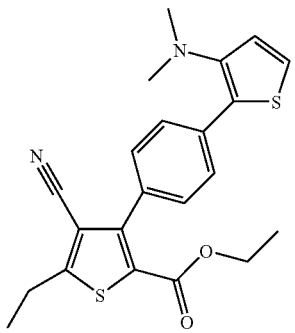

Prepare with procedure described in literature Sznaidman M. L.; Meade E. A.; Beauchamp, L. M.; Russell, R.; Tisdale, M., *Bioorg. Med. Chem. Lett.,* 1996, 6, 5, 565-568. Stir at room temperature under nitrogen a mixture of 3-[4-(3-amino-thiophen-2-yl)-phenyl]-4-cyano-5-ethyl-thiophene-2-carboxylic acid ethyl ester (0.05 g, 0.131 mmol), paraformaldehyde (0.041 g, 1.31 mmol), sodium cyanoborohydride (0.026 g, 0.393 mmol) and acetic acid (0.02 mL, 0.262 mmol) in dry acetonitrile (1 mL). After 3 h add water and extract with ethyl acetate. Combine the organic layers, dry over sodium sulfate, filter and concentrate under reduced pressure to give a residue. Purify the residue by flash chromatography (silica gel) eluting with ethyl acetate:hexane 1:2 to provide the title compound (0.033 g, 61%). Mass spectrum (m/e): 411 (M+1). $^1$H-NMR (CDCl$_3$) δ1.19 (t, 3H, J=7.2 Hz); 1.44 (t, 3H, J=7.5 Hz); 2.71 (s, 6H); 3.09 (c, 2H, J=7.5 Hz); 4.20 (c, 2H, J=7.2 Hz); 6.97 (d, 1H, J=5.4 Hz); 7.19 (d, 1H, J=5.6 Hz); 7.38-7.43 (m, 2H); 7.81-7.86 (m, 2H).

EXAMPLE E-82

4-Cyano-5-ethyl-{4-[3-(3-methyl-butylamino)-thiophen-2-yl)-2-carboxylic acid ethyl ester

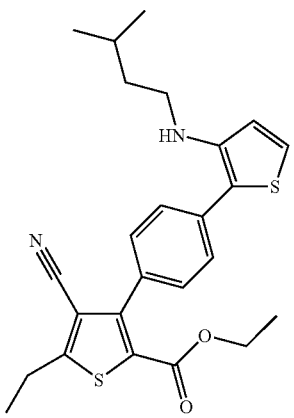

Add sodium triacetoxy borohydride (0.039 g, 0.183 mmol) to a mixture of 3-[4-(3-amino-thiophen-2-yl)-phenyl]-4-cyano-5-ethyl-thiophene-2-carboxylic acid ethyl ester (0.050 g, 0.131 mmol), 3-methyl butanal (0.016 mL, 0.144 mmol) and acetic acid (0.08 mL, 0.131 mmol) in dicloroethane (2 mL) and stir the mixture at room temperature under nitrogen for 3 h. Then, add a saturated solution of NaHCO$_3$ (10 mL) and extract with CH$_2$Cl$_2$. Combine the organic layers, dry over Na$_2$SO$_4$, filter and concentrate under reduced pressure to give a residue. Purify the residue by flash chromatography (silica gel) eluting with EtOAc/Hexane 1:7 to provide the title compound (0.026 g, 44%). Mass spectrum (m/e): 453 (M+1). $^1$H-NMR (CDCl$_3$) δ 0.93 (d, 6H, J=5.5 Hz); 1.22 (t, 3H, J=6.9 Hz); 1.42-1.53 (m, 5H); 1.62-1.73 (m, 1H); 3.06-3.21 (m, 4H); 4.22 (c, 2H, J=7.3 Hz); 6.80 (d, 1H, J=5.6 Hz); 7.20 (d, 1H, J=5.6 Hz); 7.26-7.44 (m, 2H); 7.47-7.59 (m, 2H).

EXAMPLE E-83

4-Cyano-5-ethyl-{4-[3-(3-methyl-butylamino)-thiophen-2-yl)-2-carboxylic acid ethyl ester

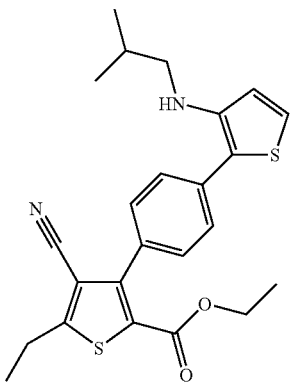

Prepare the title compound in a manner analogous to the procedure set forth in example E-82 using isobutyraldehyde. Purify the residue by flash chromatography (silica gel) eluting with EtOAc/Hexane 1:7 to provide the title compound. Mass spectrum (m/e): 439 (M+1). $^1$H-NMR (CDCl$_3$) δ 0.95 (d, 6H, J=6.5 Hz); 1.22 (t, 3H, J=6.7 Hz); 1.44 (t, 3H, J=7.6 Hz); 1.85 (sp, 1H, J=6.8 Hz); 2.99 (d, 2H, J=6.5 Hz); 3.10 (c, 2H, J=7.7 Hz); 4.22 (c, 2H, J=6.9 Hz); 6.77 (d, 1H, J=5.6 Hz); 7.20 (d, 1H, J=5.2 Hz); 7.45-7.48 (m, 2H); 7.57-7.61 (m, 2H).

EXAMPLE E-84

4-Cyano-5-methylsulfanyl-3-(4-morpholin-4-yl-phenyl)-thiophene-2-carboxylic acid ethyl ester

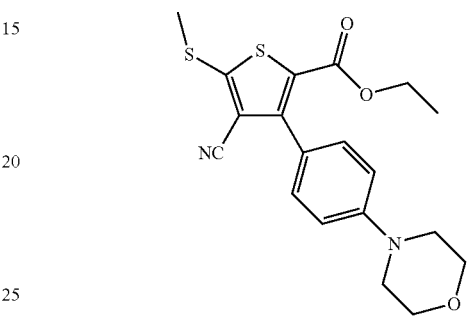

Combine 3-(4-Iodophenyl)-4-cyano-5-methylsulfanyl-thiophene-2-carboxylic acid ethyl ester (50 mg, 0.12 mmol), morpholine (20 μl, 0.23 mmol), Pd$_2$(dba)$_3$ (3.5 mg, 0.006 mmol), cessium carbonate (53 mg, 0.16 mmol) and (+)-BINAP (5.4 mg, 0.009 mmol) in anhydrous toluene (1 ml) and stir at 100° C. for 12 hours. Cool the reaction mixture to room temperature, filtered through celite and washed with ethyl acetate. Evaporate the solvent and purify the residue by column chromatography (silica gel) eluting with ethyl acetate: hexane 1:3 to provide the title compound (22 mg, 49%): $^1$H NMR (CDCl3, 200 MHz): δ 7.37 (d, 2H, J=8.9); 6.99 (d, 2H, J=8.9); 4.22 (q, 2H, J=7.2); 3.89 (m, 4H); 3.28 (m, 4H); 2.71 (s, 3H); 1.24 (t, 3H, J=7.2).

EXAMPLE E-85

3-(4-tert-Butyl-phenyl)-4-cyano-5-[(2-dimethylamino-ethyl)-methyl-amino]-thiophene-2-carboxylic acid ethyl ester

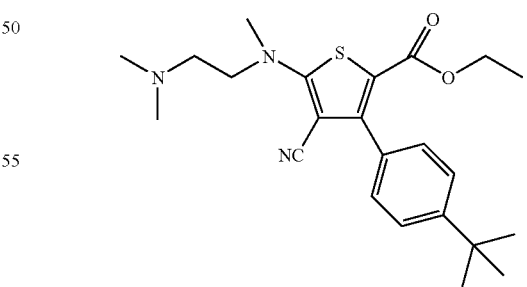

Add N,N,N'-Trimethyl-ethane-1,2-diamine (1.21 mmol) to a solution of 3-4-tert-Butyl-phenyl)-4-cyano-5-methanesulfanyl-thiophene-2-carboxylic acid ethyl ester (Example A-4) (0.061 mmol) in DMF (1 ml) and stir the mixture at room temperature for 16 hours. Dilute the reaction with ethyl acetate and wash with ice-water. Separate the organic layer,

EXAMPLE E-86

3-{-[2-(3-chloropropane-1-sulfonilamino)-ethyl]phenyl}-4-cyano-5-ethyl-thiophene-2-carboxylic acid ethyl ester

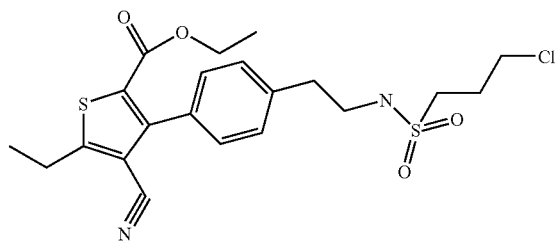

Prepare the title compound in a manner analogous to the procedure set forth in preparation of Example E-55 using boronate, 3-Chloropropane-1-sulfonic acid {2-[4-(4,4,5,5-tetramethyl-[1,3,2]dioxaborolan-2-yl)-phenyl]-ethyl}-amide, and stirring 2 h at 90° C. Purify by flash chromatography (silica gel) eluting with hexanes-ethyl acetate 2:1 to obtain 0.078 g of the title compound as pale yellow solid. Mass spectrum ESI positive (m/z): 469 (M+1), 486 (M+18), 461 (M+23).

EXAMPLE E-87

4-Cyano-3-{4-[2-(1,1-dioxo-1λ6-isothiaolidin-2-yl)-ethyl]phenyl}-5-ethyl-3-(4-[1,2,4]-thiadiazol-2-yl-phenyl)-thiophene-2-carboxylic acid ethyl ester

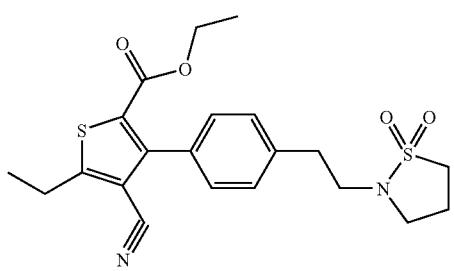

Obtain the title compound in the same reaction of Example E-86. Purify by flash chromatography (silica gel) eluting with hexanes-ethyl acetate 1:1 to obtain 0.148 g. Mass spectrum ESI positive (m/z): 433 (M+1), 450 (M+18), 455 (M+23).

dry over magnesium sulfate, and concentrate under reduced pressure to provide the title compound (90% yield). (EI+): m/z 414 (M$^+$+1).

EXAMPLE E-88

3-[4-(3-tert-Butoxycarbonaminol-thiophen-2-yl)phenyl]-4-cyano-5-ethyl-thiophene-2-carboxilyc acid ethyl ester

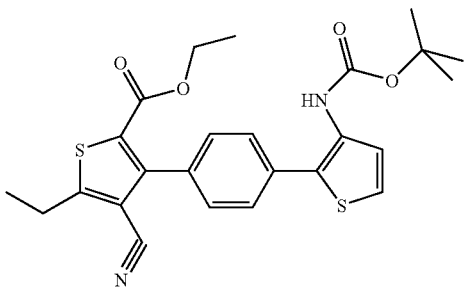

Prepare the title compound in a manner analogous to the procedure set forth in preparation of Example E-56 using material from Preparation 66 and stirring for 4 h. Purify by flash chromatography (silica gel) eluting with hexanes-ethyl acetate gradient (10:1 to 1:1) to give 0.3 g of the title compound as a white solid. Mass spectrum ESI positive (m/z): 505 (M+23).

EXAMPLE E-89

3-[4-(5-Carboxy-thiophen-2-yl-phenyl)-4-cyano-5-ethyl thiophene-2-carboxylic acid ethyl ester

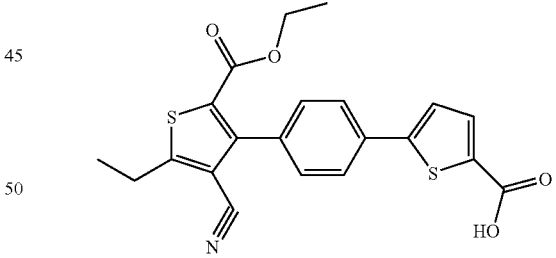

Mix 4-cyano-5-ethyl-3-(4-bromo-phenyl)-thiophene-2-carboxylic acid ethyl ester (0.2 g, 0.55 mmol), 5-(dihydroxyboryl)-2-thiophene carboxylic acid (0.104 g, 1.0 mmol) and tetrakis(triphenylphosphine) palladium(0) (0.063 g, 0.05 mmol). Add DME (3 mL), ethanol (1.5 mL), 2M aqueous solution of sodium carbonate (0.55 mL) and stir at 90° C. under nitrogen for 2 h. Add ethyl acetate and 1M NaOH solution and separate phases. Desired compound appears in both phases. Acidify organic and aqueous phases and concentrate them separately, to give 0.212 g of the title compound as beige solid. Mass spectrum ESI positive (m/z): 412 (M+1), 434 (M+23).

EXAMPLE E-90

3-(4-Bromo-phenyl)-4-cyano-5-ethyl-thiophene-2-carboxylic acid ethyl ester

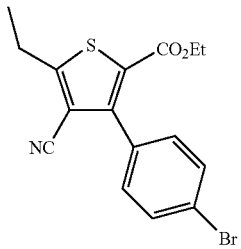

Add 4-cyano-5-ethyl-3-iodo-thiophene-2-carboxylic acid ethyl ester (268.1 g, 0.8 mol) and 4-bromophenyl boronic acid (173.5 g, 0.86 mol), to a solution of bis(tri-o-tolylphosphine)palladium (II) diacetate (7.00 g, 0.008 mole) in acetonitrile(1.9 L) within a 5000 mL, 3-neck round-bottom flask equipped with an overhead stirrer, internal temperature probe, heating mantle, and a glycol-cooled condenser fitted with a nitrogen inlet. Add a solution of sodium carbonate (169.6 g, 1.6 mol) in water (1.3 L) and stir the reactor contents at room temperature while sweeping the headspace with nitrogen for 10 min. the reaction apparatus was then set for a nitrogen by-pass and the reaction mixture was heated to 73° C. Observe that HPLC analysis indicates substantial (>98%) consumption of 4-bromophenyl boronic acid and 4-cyano-5-ethyl-3-iodo-thiophene-2-carboxylic acid ethyl ester (flow rate: 1.5 mL/min; detection: 210 nm; mobile phase: isocratic 65/35 (v/v) acetonitrile/0.1% trifluoroacetic acid in water; column: Zorbax® SB-Phenyl; 4.6 mm×25 cm; 5 microns at 35 C). Cool the mixture to 23° C. and separate the phases. Extract the aqueous phase twice with methyl t-butyl ether (300 mL). Combine the organic phases and concentrate under reduced pressure to an oil. Dissolve the oil in a mixture of heptane (500 mL) and methyl t-butyl ether (500 mL). This results in separation of an immiscible water phase which is separated, extracted with methyl t-butyl ether (100 mL) and discarded. The organic phases are combined and concentrated under reduced pressure to an oil. The oil is dissolved in a mixture of heptane (500 mL) and methyl t-butyl ether (300 mL) and the solution is transferred to a flask set for atmospheric distillation at 83° C. The distillation is continued until distillation at 83° C. and atmospheric pressure stops. The resulting solution is cooled to 30° C. and is seeded with 3-(4-Bromo-phenyl)-4-cyano-5-ethyl-thiophene-2-carboxylic acid ethyl ester, then the mixture is further cooled to 18° C. Filter the resulting suspension and wash the filter cake with heptane (3×100 mL). The resulting cake is air-dried and then transferred to a vacuum oven (40° C.) to afford the title compound (263 g, 90.4% yield). The title compound may be additionally purified as follows if desired.

Add 3-(4-Bromo-phenyl)-4-cyano-5-ethyl-thiophene-2-carboxylic acid ethyl ester (367 g, 1.007 mol) and heptane (700 mL) to a 5000 mL, 3-neck round-bottom flask equipped with an overhead stirrer, internal temperature probe, and a nitrogen inlet. Stir the reactor contents at room temperature for 30 min. Filter the resulting suspension and rinse the filter cake with heptane (100 mL). The resulting cake is vacuum-dried at 25° C., affording 346.9 g (94.5% recovery) of additionally purified 3-(4-Bromo-phenyl)-4-cyano-5-ethyl-thiophene-2-carboxylic acid ethyl ester (263 g, 90.4% yield).

$^1$H NMR (CDCl$_3$, 300 MHz): δ 7.58 (d, 2H, J=8.4); 7.29 (d, 2H, J=8.7); 4.21 (q, 2H, J=7.2); 3.09 (q, 2H, J=7.5); 1.43 (t, 3H, J=7.5); 1.22 (t, 3H, J=7.2).

EXAMPLE E-91

4-Cyano-5-ethyl-3-(2'-methylsulfanyl-biphenyl-4-yl)-thiophene-2-carboxylic acid ethyl ester

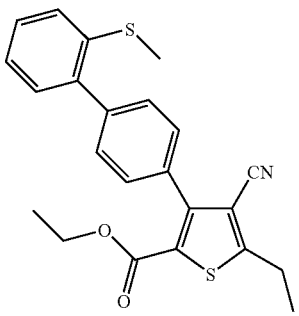

Combine potassium carbonate (54.4 g, 0.3937 moles, 2.1 eq) and water (1.32 L) in a 3 L 3-neck flask equipped with an overhead stirrer. Add 2-thiomethylphenyl boronic acid (34.65 g, 0.206 moles, 1.1 eq) to the resulting carbonate solution and stir about 15 minutes. Add Darco G-60 (7 g), and stir an additional 15 min at room temperature. Filter the suspension and add the filtrate to a 5 L 3-neck flask equipped with an overhead stirrer, heating mantle, thermocouple, condenser, and nitrogen inlet. Add palladium black 0.7 g (0.0658 mol) and ethyl acetate (250 ml) and sweep the headspace with nitrogen for about 10 minutes. Add 4-cyano-5-ethyl-3-(4-bromo-phenyl)-thiophene-2-carboxylic acid ethyl ester (68.3 g, 0.1875 moles, 1.0 eq.) and ethyl acetate (250 ml) and stir the mixture to dissolve the 4-cyano-5-ethyl-3-(4-bromo-phenyl)-thiophene-2-carboxylic acid ethyl ester. Set the flask for a nitrogen by-pass through a bubbler and heat to reflux at 70.5° C. until substantial depletion of 4-cyano-5-ethyl-3-(4-bromo-phenyl)-thiophene-2-carboxylic acid ethyl ester is observed HPLC. (mobile phase=27% 0.1% TFA in water, 73% ACN, 1.5 ml/min isocratic; Column=Zorbax SB-Phenyl 5 um 4.6 mm×25 cm at 35 C; UV detection at 210 nm). Cool the mixture to 60° C. and filter to remove palladium black. Separate the phases and extract the aqueous phase with 100 ml ethyl acetate. Combine the organic phases and strip to a solid. Dissolve the solid in hot (75° C.) ethanol (600 ml) and transfer the resulting solution to a 1 L flask equipped with an overhead stirrer, condenser, and thermocouple. Cool the solution to 65° C., seed with 4-Cyano-5-ethyl-3-(2'-methylsulfanyl-biphenyl-4-yl)-thiophene-2-carboxylic acid ethyl ester, and further cool to 18° C. Filter the resulting precipitate and rinse with cool (10° C.) ethanol. Vacuum dry the solids at 50° C., which affords the title compound (68.0 g, 89.0% yield). HPLC=98.1%. (mobile phase=27% 0.1% TFA in water, 73% ACN, 1.5 ml/min isocratic; Column=Zorbax SB-Phenyl 5 um 4.6 mm×25 cm at 35 C; UW detection at 210 nm).

EXAMPLE A-1

4-Cyano-3-(2'-methylsulfanyl-biphenyl-4-yl)-5-trifluoromethyl-thiophene-2-carboxylic acid

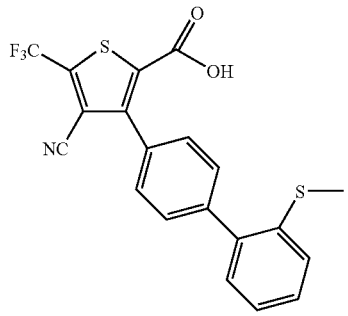

Using a method substantially in accordance with the method Example A-2, using 4-cyano-3-(2'-methylsulfanyl-biphenyl-4-yl)-5-trifluoromethyl-thiophene-2-carboxylic acid ethyl ester gives the title compound: $^1$H NMR (400 MHz, CDCl$_3$) δ 7.57-7.20 (m, 8H), 2.34 (s, 3H), $^{19}$F NMR (CDCl$_3$) δ-57.21 ppm (s), MS found (M−1) 418.

EXAMPLE A-2

3-(4-tert-Butyl-phenyl)-4-cyano-5-methylsulfanyl-thiophene-2-carboxylic acid

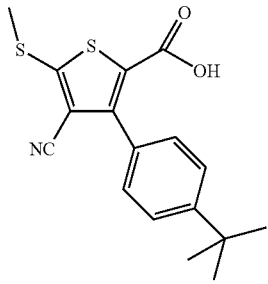

Add NaOH 1M (1 ml) to a suspension of 3-(4-tert-butyl-phenyl)-4-cyano-5-methylsulfanyl-thiophene-2-carboxylic acid ethyl ester (general preparation 28, general preparation 29, general example E-1) (0.128 mmol) in ethanol (1 ml) and stir 24 h. Add 6 N HCl until pH approx. 1 and white solid precipitates. Filter the solid to provide the title compound: MS (ES+, m/e): 332 (M+1).

EXAMPLE A-3

3-(4-tert-Butyl-phenyl)-4-cyano-5-methanesulfinyl-thiophene-2-carboxylic acid

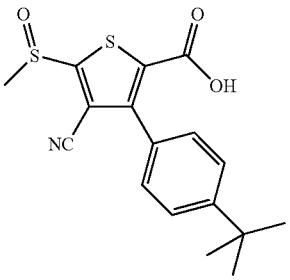

Step 1

Prepare the ester of the title compound in a manner analogous to the procedure set forth in the example E-6, 3-(4-iodophenyl)-4-cyano-5-methanesulfonyl-thiophene-2-carboxylic acid ethyl ester, using 3-(4-tert-butyl-phenyl)-4-cyano-5-methylsulfanyl-thiophene-2-carboxylic acid ethyl ester as starting material and 1.0 equivalents of MCPBA.

Step 2

Prepare the title compound in a manner analogous to the procedure set forth in the example A-2, 3-(4-tert-Butyl-phenyl)-4-cyano-5-methylsulfanyl-thiophene-2-carboxylic acid, to provide the title compound: Mass spectrum (m/e): 370.2 (M+23).

EXAMPLE A-4

3-(4-tert-Butyl-phenyl)-4-cyano-5-methanesulfonyl-thiophene-2-carboxylic acid

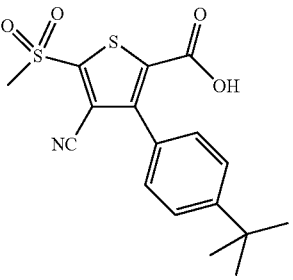

Step 1

Prepare the ester of the title compound in a manner analogous to the procedure set forth in example E-6, 3-(4-iodophenyl)-4-cyano-5-methanesulfonyl-thiophene-2-carboxylic acid ethyl ester, using the ethyl ester of 3-(4-tert-butyl-phenyl)-4-cyano-5-methanesulfinyl-thiophene-2-carboxylic acid as starting material and 1.5 equivalents of MCPBA Step 2

Prepare the title compound in a manner analogous to the procedure set forth in example A-2, 3-(4-tert-Butyl-phenyl)-4-cyano-5-methylsulfanyl-thiophene-2-carboxylic acid to provide the title compound: Mass spectrum (m/e): 386.2 (M+23).

EXAMPLE A-5

3-(4-tert-Butyl-phenyl)-4-cyano-5-methanesulfonyl-thiophene-2-carboxylic acid

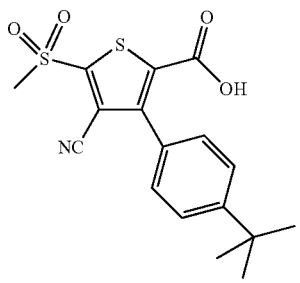

Step 1

Prepare the ester of the title compound in a manner analogous to the procedure set forth in example E-6, 3-(4-iodophenyl)-4-cyano-5-methanesulfonyl-thiophene-2-carboxylic acid ethyl ester, using 3-(4-tert-butyl-phenyl)-4-cyano-5-methylsulfanyl-thiophene-2-carboxylic acid ethyl ester as starting material and 3.0 equivalents of MCPBA.

Step 2

Prepare the title compound in a manner analogous to the procedure set forth in example A-2, 3-(4-tert-Butyl-phenyl)-4-cyano-5-methylsulfanyl-thiophene-2-carboxylic acid to provide the title compound: Mass spectrum (m/e): 386.2 (M+23).

GENERAL EXAMPLE A-6

3-(4-OR$^{16}$-phenyl)-4-cyano-5-R$^1$-thiophene-2-carboxylic acid

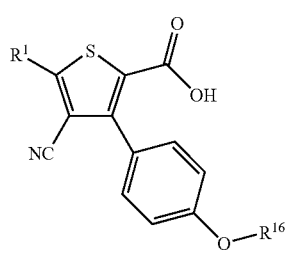

Prepare the title compound in a manner analogous to the hydrolysis procedure set forth in example A-2, 3-(4-tert-Butyl-phenyl)-4-cyano-5-methylsulfanyl-thiophene-2-carboxylic acid using the analogous 3-(4-OR$^{16}$-phenyl)-4-cyano-5-R$^1$-thiophene-2-carboxylic acid ethyl ester.

EXAMPLE A-7

4-Cyano-5-methylsulfanyl-3-{4-[2-(pronane-2-sulfonylamino)-ethoxy]-phenyl}-thiophene-2-carboxylic acid

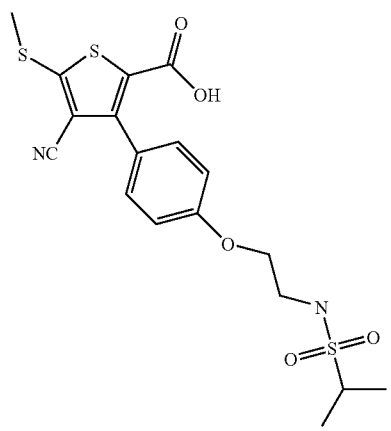

Prepare the title compound in a manner analogous to the hydrolysis procedure set forth in example A-2, 3-(4-tert-Butyl-phenyl)-4-cyano-5-methylsulfanyl-thiophene-2-carboxylic acid: Mass spectrum (EI+): m/z 441 (M$^+$+1); $^1$H NMR (DMSO, 300 MHz): δ 7.29 (d, 2H, J=8.5); 6.92 (d, 2H, J=8.5); 3.96 (m, 1H); 2.71 (s, 3H); 2.64 (m, 2H); 2.18 (m, 2H); 1.15 (d, 6H, J=6.9).

GENERAL EXAMPLE A-8

4-Cyano-3-(2'-R$^{10}$sulfonylamino-biphenyl-4-yl)-5-methylsulfanyl-thiophene-2-carboxylic acid

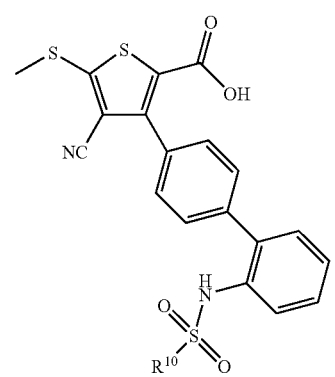

Step 1

Add DBU (4.0 mmol) to a solution of 3-(2'-amino-biphenyl-4-yl)-4-cyano-5-methylsulfanyl-thiophene-2-carboxylic acid ethyl ester in dichloromethane (5.0 mL) followed by the corresponding sulfonyl chloride (1.0-2.0 mmol) added drop wise and stir at room temperature for 24 h. Remove solvent under reduce pressure and purify the residue by silica and eluting with ethyl acetate:hexane to provide the title compound as ethyl ester. Obtain 3-(2'-amino-biphenyl-4-yl)-4-cyano-5-methylsulfanyl-thiophene-2-carboxylic acid ethyl ester) by using 2-nitrophenyl boronic acid and 3-(4-iodophenyl)-4-cyano-5-methylsulfanyl-thiophene-2-carboxylic acid ethyl ester (example E-3) following the procedure set forth Example A-9. Reduce the nitro group to the amino following the procedure set forth Scheme IV.

Step 2

Prepare the title compound compound in a manner analogous to the procedure set forth in example A-2, 3-(4-tert-butyl-phenyl)-4-cyano-5-methylsulfanyl-thiophene-2-carboxylic acid.

GENERAL EXAMPLE A-9

4-Cyano-3-(4-A-phenyl)-5-R¹-thiophene-2-carboxylic acid

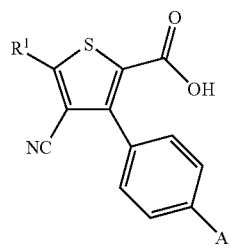

Step 1

Add 3-(4-X-phenyl)-4-Cyano-5-R¹-thiophene-2-carboxylic acid ethyl ester (X=Br, I, OTf)(1.0 mmol), the corresponding aryl boronic acid or the corresponding aryl tin or corresponding aryl zinc reagent (1.0-1.5 mmol), catalyst (0.05-0.10 mmol), and base (3-5 mmol) into solvent and heat to 60-100° C. After 1-18 hours cool to room temperature and add water. Extract with ethyl acetate. Combine the organics and wash with water and brine, dry over sodium sulfate, filer and concentrate under reduced pressure. Purify by flash chromatography eluting with ethyl acetate:hexanes to provide the ester of the title compound.

Step 2

Prepare the title compound in a manner analogous to the procedure set forth in Example A-2, 3-(4-tert-Butyl-phenyl)-4-cyano-5-methylsulfanyl-thiophene-2-carboxylic acid.

GENERAL EXAMPLE A-10

4-Cyano-3-(4-A-phenyl)-5-R¹-thiophene-2-carboxylic acid

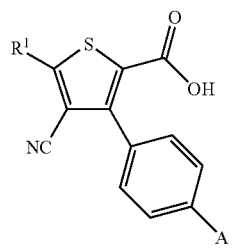

Step 1

Add the thiophene boronate (4-cyano-5-R¹-3-[4-(4,4,5,5-tetramethyl-[1,3,2]dioxaborolan-2-yl)-phenyl]-thiophene-2-carboxylic acid ethyl ester), the thiophene boronic acid (3-(4-boronic acid-phenyl)-4-cyano-5-R¹-thiophene-2-carboxylic acid ethyl ester), or the thiophene trimethylstannyl-5-R¹-3-(4-trimethylstannyl-phenyl)-thiophene-2-carboxylic acid ethyl ester) along with the corresponding aryl halide or corresponding aryl triflate as starting materials for the coupling as in example A-9 to provide the ester of the title compound.

Step 2

Prepare the title compound in a manner analogous to the procedure set forth in Example A-2, 3-(4-tert-Butyl-phenyl)-4-cyano-5-methylsulfanyl-thiophene-2-carboxylic acid.

EXAMPLE A-12

4-Cyano-3-(2'-cyano-biphenyl-4-yl)-5-trifluoromethyl-thiophene-2-carboxylic acid

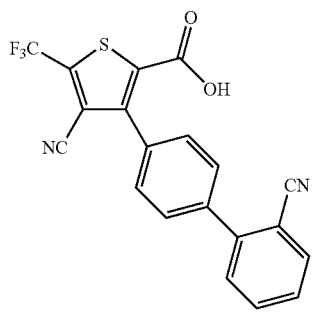

Using a method substantially in accordance with the method of example A-2, starting with the compound from example 4-cyano-3-(2'-cyano-biphenyl-4-yl)-5-trifluoromethyl-thiophene-2-carboxylic acid ethyl ester: $^1$H NMR (400 MHz, CDCl$_3$) δ 7.57-7.20 (m, 8H), $^{19}$F NMR (CDCl$_3$) δ-57.21 ppm (s), MS found (M−1) 397.0 and (M+1) +NH$_3$ 416.

GENERAL EXAMPLE A-13

4-Cyano-3-(4-A-phenyl)-5-R¹-thiophene-2-carboxylic acid

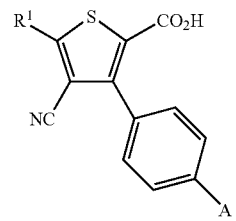

R¹ = SMe, Me, Et, iPr, CF$_3$

Step 1

Add 3-iodo4-Cyano-5-R¹-thiophene-2-carboxylic acid ethyl ester (1.0 mmol), the corresponding phenyl boronic acid or the corresponding phenyl tin or zinc reagent (1.0-1.5 mmol), catalyst (0.05-0.10 mmol), and base (3-5 mmol) into solvent and heat to 60-100° C. After 1-18 hours cool to room temperature and add water. Extract with ethyl acetate. Combine the organics and wash with water and brine, dry over sodium sulfate, filer and concentrate under reduced pressure. Purify by flash chromatography eluting with ethyl acetate:hexanes to provide the ester of the title compound.

Step 2

Prepare the title compound in a manner analogous to the procedure set forth in Example A-2, 3-(4-tert-Butyl-phenyl)-4-cyano-5-methylsulfanyl-thiophene-2-carboxylic acid.

EXAMPLE A-14

3-(4-tert-Butyl-phenyl)-4-cyano-5-ethylsulfanyl-thiophene-2-carboxylic acid

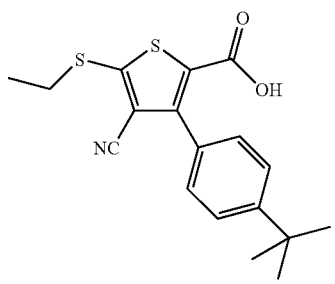

Prepare the title compound in a manner analogous to the procedure set forth in example A-2, 3-(4-tert-butyl-phenyl)-4-cyano-5-methylsulfanyl-thiophene-2-carboxylic acid, using 3-(4-tert-butyl-phenyl)-4-cyano-5-ethylsulfanyl-thiophene-2-carboxylic acid ethyl ester: Mass spectrum (m/e): 346 (M+1).

EXAMPLE A-15

3-(4-tert-Butyl-phenyl)-4-cyano-5-propylsulfanyl-thiophene-2-carboxylic acid

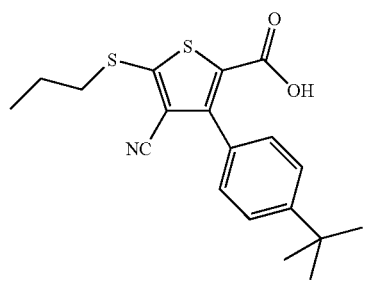

Prepare the title compound in a manner analogous to the procedure set forth in example A-2, 3-(4-tert-butyl-phenyl)-4-cyano-5-methylsulfanyl-thiophene-2-carboxylic acid using 3-(4-tert-butyl-phenyl)-4-cyano-5-propylsulfanyl-thiophene-2-carboxylic acid ethyl ester: Mass spectrum (m/e): 360 (M+1).

EXAMPLE A-15a 3-(4-tert-Butyl-phenyl)-4-cyano-5-isoproplsulfanyl-thiophene-2-carboxylic acid

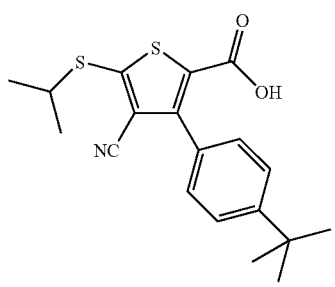

Prepare the title compound in a manner analogous to the procedure set forth in example A-2, 3-(4-tert-butyl-phenyl)-4-cyano-5-methylsulfanyl-thiophene-2-carboxylic acid using 3-(4-tert-butyl-phenyl)-4-cyano-5-methylsulfanyl-thiophene-2-carboxylic acid ethyl ester: Mass spectrum (m/e): 360(M+1).

Prepare the carboxylic acids in Table A-1 following the procedure indicated. Esters are hydrolyzed following Example A-2.

TABLE A-1

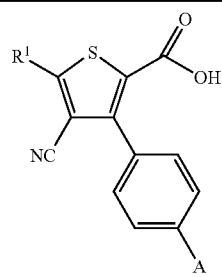

| No.: | Procedure | $R^1$ | A | Data |
|---|---|---|---|---|
| A-16 | general example A-13 or example E-27 and example A-2 | $F_3C$ | Tert-butyl | mass spectrum (m/e): 352.1 (M − 1). |

TABLE A-1-continued

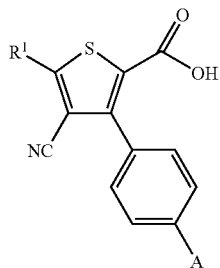

| No.: | Procedure | R¹ | A | Data |
|---|---|---|---|---|
| A-17 | general prep 29 and general example E-1 | MeS | 3,5-difluorophenyl | mass spectrum (m/e): 388.1 (M + 1). |
| A-18 | General Example A-9 | MeS | 2-fluorophenyl | mass spectrum (m/e): 370.1 (M + 1). |
| A-19 | General Example A-9 | MeS | 2-chlorophenyl | mass spectrum (m/e): 386.1 (M + 1). |
| A-20 | General Example A-9 | MeS | 2-methoxyphenyl | mass spectrum (m/e): 382.1 (M + 1). |
| A-21 | General Example A-9 | MeS | 3-methoxyphenyl | mass spectrum (m/e): 382.1 (M + 1). |
| A-22 | General Example A-9 | MeS | 4-fluorophenyl | mass spectrum (m/e): 370.1 (M + 1). |
| A-23 | General Example A-9 | MeS | 4-methoxyphenyl | mass spectrum (m/e): 382.1 (M + 1). |
| A-24 | General Example A-9 | MeS | 5-chloro-2-thienyl | mass spectrum (m/e): 392.1 (M + 1). |
| A-25 | General Example A-9 | MeS | 2,4-difluorophenyl | mass spectrum (m/e): 388.1 (M + 1). |
| A-26 | General Example A-9 | MeS | 2-trifluoro methylphenyl | mass spectrum (m/e): 420.1 (M + 1). |
| A-27 | General Example A-9 | MeS | 3,4-difluorophenyl | mass spectrum (m/e): 388.1 (M + 1). |
| A-28 | General Example A-9 | MeS | 3-fluorophenyl | mass spectrum (m/e): 370.1 (M + 1). |
| A-29 | General Example A-9 | MeS | 2,5-difluorophenyl | mass spectrum (m/e): 388.1 (M + 1). |
| A-30 | General Example A-9 | MeS | 3-benzothienyl | mass spectrum (m/e): 408.1 (M + 1). |
| A-31 | General Example A-9 | MeS | 2-thienyl | mass spectrum (m/e): 358.1 (M + 1). |
| A-32 | General Example A-9 | MeS | 3-thienyl | mass spectrum (m/e): 358.1 (M + 1). |
| A-33 | General Example A-9 | MeS | 2,3-difluorophenyl | mass spectrum (m/e): 388.1 (M + 1). |
| A-34 | General Example A-9 | MeS | 3-trifluoromethylphenyl | mass spectrum (m/e): 420.1 (M + 1). |
| A-35 | General Example A-9 using Boc protected 2H-pyrrole followed by deprotection | MeS | 2H-pyrrole | mass spectrum (m/e): 341.1 (M + 1). |
| A-36 | General Example A-9 | MeS | 2-ethoxyphenyl | mass spectrum (m/e): 396.1 (M + 1). |
| A-37 | General Example A-9 | MeS | 3-ethoxyphenyl | mass spectrum (m/e): 396.1 (M + 1). |
| A-38 | General Example A-9 | MeS | 4-ethoxyphenyl | mass spectrum (m/e): 396.1 (M + 1). |
| A-39 | General Example A-9 | MeS | 2-methoxy-5-fluorophenyl | mass spectrum (m/e): 400.1 (M + 1). |
| A-40 | A-35 and Example E-47 | MeS | N-methyl-2-pyrrole | mass spectrum (m/e): 355.1 (M + 1). |
| A-41 | A-61 | MeS | N-acetyl-2-pyrrole | mass spectrum (m/e): 383.1 (M + 1). |
| A-42 | General Example A-9 | MeS | 2-tolyl | mass spectrum (m/e): 366.1 (M + 1). |
| A-43 | General Example A-9 | MeS | 2-fluoro-6-methoxyphenyl | mass spectrum (m/e): 400.1 (M + 1). |
| A-44 | General Example A-9 | MeS | 2-nitrophenyl | mass spectrum (m/e): 397.1 (M + 1). |
| A-45 | General Example A-9 | Ethyl | 2-fluorophenyl | mass spectrum (m/e): 350.1 (M − 1). |

TABLE A-1-continued

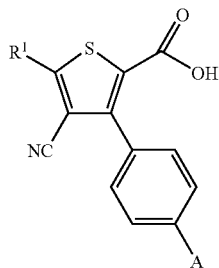

| No.: | Procedure | R¹ | A | Data |
|---|---|---|---|---|
| A-46 | General Preparation 30, 31, 32, 29 General Example E-1 | MeS | piperidin-1-yl | mass spectrum (m/e): 359 (M + 1). |
| A-47 | General Preparation 32, 29 and general example E-1 | MeS | pyrrolidin-1-yl | mass spectrum (m/e): 345 (M + 1). |
| A-48 | Example E-10 | Ethyl | pyrrolidin-2-yl | mass spectrum (m/e): 327 (M + 1). |
| A-49 | Example E-5 and Example E-62 | MeS | NH(SO$_2$)CH$_2$C$_6$H$_5$ | mass spectrum (m/e): 443 (M − 1). |
| A-50 | Example E-64 | MeS | dimethylamino | mass spectrum (m/e): 319 (M + 1). |
| A-51 | Example E-63 | MeS | cyclohexylamino | mass spectrum (m/e): 373 (M + 1). |
| A-52 | Example A-171 and Example A-173 | MeS | —CONH(CH$_2$)$_2$—NHSO$_2$iPr | mass spectrum (m/e): 466 (M − 1). |
| A-54 | General Prep 28, 29, 33 and general Example E-2 | Me$_2$N | tert-butyl | mass spectrum (m/e): 329 (M + 1). |
| A-55 | General Prep 29, 33 and general example E-2 | Me$_2$N | pyrrolidin-1-yl | mass spectrum (m/e): 342 (M + 1). |
| A-56 | general prep 28, 29 and general example E-1 | MeS | cyclopentyl | mass spectrum (m/e): 342 (M − 1). |
| A-57 | preparation 4 and general example A-13 | Ethyl | cyclopentyl | mass spectrum (m/e): 324 (M − 1). |
| A-58 | preparation 4, general example A-13, example E-37, E-38, E-39 | Me$_2$N | cyclopentyl | mass spectrum (m/e): 341 (M + 1). |
| A-59 | Preparation 6 and general example A-13 | Ethyl | 2-cyanoethyl | mass spectrum (m/e): 311 (M + 1). |
| A-60 | General Example A-9 | Ethyl | 2-methylthiophenyl | mass spectrum (m/e): 378 (M − 1). |
| A-61 | General Example A-9 Example E-45 | Ethyl | 2-methoxyphenyl | mass spectrum (m/e): 318 (M-COOH). |
| A-62 | General Example A-9 Example E-46 | Ethyl | 2-ethoxyphenyl | mass spectrum (m/e): 376 (M − 1). |
| A-63 | General Example A-9 Example E-47 | Ethyl | 2-(n-propoxy)phenyl | mass spectrum (m/e): 390 (M − 1). |
| A-64 | General Example A-9 Example E-48 | Ethyl | 2-isopropoxyphenyl | mass spectrum (m/e): 390 (M − 1). |
| A-65 | General Example A-9 Example E-45 | Ethyl | 2-hydroxyphenyl | mass spectrum (m/e): 348 (M − 1). |
| A-66 | Preparation 2 Example E-37 | MeS | 2-cyanophenyl | mass spectrum (m/e): 375 (M − 1). |
| A-67 | Preparation 2 Example E-42 | Ethyl | 2-cyanophenyl | mass spectrum (m/e): 313 (M-COOH). |
| A-68 | Preparation 2 Example E-39 | Me2N | 2-cyanophenyl | mass spectrum (m/e): 372 (M − 1). |

TABLE A-1-continued

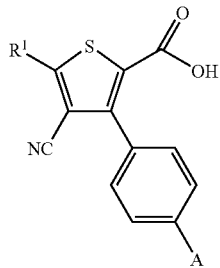

| No.: | Procedure | R$^1$ | A | Data |
|---|---|---|---|---|
| A-69 | Preparation 2 Example E-50 | H | 2-cyanophenyl | mass spectrum (m/e): 329 (M − 1). |
| A-70 | Example E-41 | Ethyl | tert-butyl | mass spectrum (m/e): 312 (M − 1). |
| A-71 | General Example A-9 | MeS | thiazol-2-yl | mass spectrum (m/e): 359 (M + 1). |
| A-72 | General Example A-9 | Ethyl | thiazol-2-yl | mass spectrum (m/e): 341 (M + 1). |
| A-73 | General Example A-9 | Me$_2$N | thiophen-2-yl | mass spectrum (m/e): 355 (M + 1). |
| A-74 | General Example A-9 | Ethyl | thiophen-2-yl | mass spectrum (m/e): 338 (M − 1). |
| A-75 | General Example A-9 | Ethyl | thiophen-3-yl | mass spectrum (m/e): 338 (M − 1). |
| A-76 | General Example A-9 | Ethyl | 3-cyanothiophen-2-yl | mass spectrum (m/e): 319 (M-COOH). |
| A-77 | General Example A-9 | Ethyl | 4-cyanothiophen-3-yl | mass spectrum (m/e): 319 (M-COOH). |
| A-78 | General Example A-9 | Ethyl | 2-cyanothiophen-3-yl | mass spectrum (m/e): 319 (M-COOH). |
| A-79 | General Example A-9 | Ethyl | 3-nitrothiophen-2-yl | mass spectrum (m/e): 339 (M-COOH). |
| A-80 | General Example A-9 and E-5 | Ethyl | 3-aminothiophen-2-yl | mass spectrum (m/e): 309 (M-COOH). |
| A-81 | General Example A-9 and E-81 | Ethyl | 3-dimethylamino-thiophen-2-yl | mass spectrum (m/e): 337 (M-COOH). |
| A-83 | general prep 28, 29 general example E-1 | MeS | 2-aminophenyl | mass spectrum (m/e): 367 (M + 1). |
| A-84 | Example A-8 | MeS | 2-(Methylsulfonylamino) phenyl | mass spectrum (m/e): 445 (M + 1). |
| A-85 | Example A-8 | MeS | 3-(propane-2-sulfonylamino)phen-2-yl | mass spectrum (m/e): 473 (M + 1). |
| A-86 | Prep 34, 35, 36, 7, 8, 9 10 and general example A-13 | Ethyl | 3-(propane-2-sulfonylamino)phen-2-yl | mass spectrum (m/e): 453 (M − 1). |
| A-87 | Example A-9 Example A-8 | Me$_2$N | 3-(propane-2-sulfonylamino)phen-2-yl | mass spectrum (m/e): 470 (M + 1). |
| A-88 | General Example E-17-A | MeS | benzyloxy | mass spectrum (EI+): 382 (M − 1). |
| A-89 | General Example E-17-A | Ethyl | benzyloxy | mass spectrum (EI+): 364 (M + 1). |
| A-90 | General Example E-17-A | MeS | Pyridin-2-yloxy | mass spectrum (EI+): 369 (M + 1). |
| A-91 | General Example E-17-C | MeS | 2-cyanophenoxy | mass spectrum (EI+): 393 (M + 1). |
| A-92 | General Example E-17-A | Ethyl | 2-cyanophenoxy | mass spectrum (EI+): 375 (M + 1). |
| A-93 | General Example E-17-A | Ethyl | 2-cyanophenylmethoxy | mass spectrum (EI+): 387 (M + 1). |
| A-94 | General Example E-17-A | Ethyl | 2-methoxyethoxy | mass spectrum (EI+): 332 (M + 1). |
| A-95 | General Example E-17-C | MeS | 4-fluorophenoxy | mass spectrum (EI+): 386 (M + 1). |
| A-97 | General Example E-17-B | MeS | cyclohexyloxy | mass spectrum (EI+): 374 (M + 1). |
| A-98 | General Example E-17-B | MeS | cyclopentyloxy | mass spectrum (EI+): 360 (M + 1). |

TABLE A-1-continued

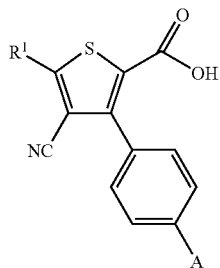

| No.: | Procedure | R¹ | A | Data |
|---|---|---|---|---|
| A-99 | General Example E-17-B | MeS | phenethyloxy | mass spectrum (EI+): 396 (M + 1). |
| A-99A | General Example E-17-B | Ethyl | pyridin-2-ylmethoxy | mass spectrum (EI+): 365 (M + 1). |
| A-99B | General Example E-17-B | Ethyl | 2-methylsulfanylethoxy | mass spectrum (EI+): 348 (M + 1). |
| A-100 | General Prep 27, 28, 29 General Example E1 | MeS | phenoxy | mass spectrum (EI+): 368 (M + 1). |
| A-101 | General prep 28, 29 General Example E1 | MeS | Phenyl | mass spectrum (m/e): 352.1 (M + 1). |
| A-102 | General prep 27, 28, 29 General Example E1 | MeS | isopropyl | mass spectrum (m/e): 318.1 (M + 1). |
| A-103 | General prep 27, 28, 29 General Example E1 | MeS | acetyl | mass spectrum (m/e): 318.1 (M + 1). |
| A-104 | General prep 27, 28, 29 General Example E1 | MeS | cyano | mass spectrum (m/c): 301.1 (M + 1). |
| A-105 | General prep 28, 29, General Example E1, Example A-171, and Example A-173 | MeS | CONH i-Pr | mass spectrum (m/e): 361.1 (M + 1). |
| A-106 | General prep 28, 29 General Example E1, E5 and Example E-61 | MeS | NHCOMe | mass spectrum (m/e): 333.1 (M + 1). |
| A-107 | General prep 28, 29 General Example E1, E5 and Example E-61 | MeS | NHCO i-Pr | mass spectrum (m/e): 361.1 (M + 1). |
| A-108 | General prep 28, 29 General Example E1, E5 and Example E-61 | MeS | NHCOphenyl | mass spectrum (m/e): 395.2 (M + 1). |
| A-109 | General prep 28, 29 General Example E1 | MeS | iodo | mass spectrum (m/e): 402.1 (M + 1). |
| A-110 | General prep 28, 29 General Example E1 and Example E-63 | MeS | Methylsulfonylamino | mass spectrum (m/e): 369.1 (M + 1). |
| A-111 | General prep 28, 29 General Example E1 | MeS | vinyl | mass spectrum (m/e): 302.1 (M + 1). |

TABLE A-1-continued

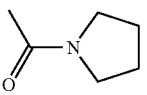

| No.: | Procedure | R¹ | A | Data |
|---|---|---|---|---|
| | and Example E-65 | | | |
| A-112 | General prep 28, 29 General Example E1, E5 and Example E-63 | MeS | Benzylamino | mass spectrum (m/e): 381.1 (M + 1). |
| A-113 | General prep 28, 29 General Example E1, E5 and Example E-64 | MeS | Methylamino | mass spectrum (m/e): 305.1 (M + 1). |
| A-114 | General prep 28, 29 General Example E1, A9 | MeS | 3-chlorophenyl | mass spectrum (m/e): 386.2 (M + 1). |
| A-115 | General prep 28, 29 General Example E1, A9 | MeS | 3-trifluoromethoxy phenyl | mass spectrum (m/e): 382.1 (M + 1). |
| A-116 | General prep 28, 29 General Example E1, A9 | MeS | 4-chlorophenyl | mass spectrum (m/e): 386.2 (M + 1). |
| A-117 | General prep 28, 29 General Example E1, A9 | MeS | 5-acetyl-2-thienyl | mass spectrum (m/e): 400.1 (M + 1). |
| A-118 | General prep 28, 29 General Example E1 | MeS | 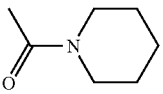 | mass spectrum (m/e): 373.1 (M + 1). |
| A-119 | General prep 28, 29 General Example E1 | MeS | 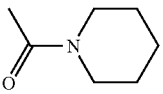 | mass spectrum (m/e) 387.1 (M + 1). |
| A-120 | General prep 28, 29 General Example E1, A9 | MeS | 4-trifluoro methylphenyl | mass spectrum (m/e): 420.1 (M + 1). |
| A-121 | A-35 and Example E-47 | MeS | N-ethyl-2-pyrrole | mass spectrum (m/e): 369.1 (M + 1). |
| A-122 | General Example A9 | Me₂N | 2-nitrophenyl | mass spectrum (m/e): 394.1 (M + 1). |
| A-123 | General prep 28, 29 General Example E1 | Ethyl | ethyl | mass spectrum (m/e): 286.1 (M + 1). |
| A-124 | Example E-16 | Ethyl | 4-Cyano-5-ethyl-thiophene-2-carboxylic acid-3-yl | mass spectrum (EI): 437 (M + 1). |
| A-125 | General Example A-10 | Ethyl | 3-methoxy-pyridin-2-yl | mass spectrum (EI+): 365 (M + 1). |
| A-126 | General Example A-10 | Ethyl | Pyrimidin-2-yl | mass spectrum (EI+): 336 (M + 1). |
| A-127 | General Example A-10 | Ethyl | 3-cyano-pyridin-2-yl | mass spectrum (EI+): 360 (M + 1). |

TABLE A-1-continued

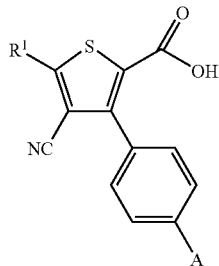

| No.: | Procedure | R¹ | A | Data |
|---|---|---|---|---|
| A-128 | General Example A-10 | Ethyl | Pyrimidin-5-yl | mass spectrum (EI+): 336 (M + 1). |
| A-130 | general example 13 | Methyl | 3-methylthio-thiophene-2-yl | mass spectrum (EI+): 372 (M + 1). |
| A-133 | General Example A-9 | Ethyl | Pyridin-5-yl | mass spectrum (EI+): 335 (M + 1). |
| A-134 | General Example A-10 | Ethyl | 3-(propane-2-sulfonylamino)-pyridine-2-yl | mass spectrum (EI+): 456 (M + 1). |
| A-135 | General Example A-10 | Ethyl | 6-(propane-2-sulfonylamino)-pyridine-2-yl | mass spectrum (EI+): 456 (M + 1). |
| A-136 | General Example A-9 | Ethyl | 3-thiomethylthiophen-2-yl | mass spectrum (m/e): 340 (M-COOH). |
| A-137 | General Example A-10 | Ethyl | 3-chlorothiophen-2-yl | mass spectrum (m/e): 328 (M-COOH). |
| A-138 | Example A-9 and Example E-82 | Ethyl | 3-(methyl-butyl amino)-thiophen-2-yl | mass spectrum (m/e): 425 (M + 1). |
| A-139 | Example A-9 and Example E-83 | Ethyl | 3-isobutyl amino-thiophen-2-yl | mass spectrum (m/e): 411 (M + 1). |
| A-140 | General Example A-9 | Ethyl | 4-(3-carbamoyl-thiophen-2-yl) | mass spectrum (m/e): 383 (M + 1). |

EXAMPLE A-141

4-Cyano-5-methylsulfanyl-3-(4-morpholin-4-yl-phenyl)-thiophene-2-carboxylic acid

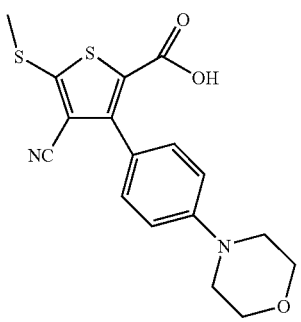

Prepare the title compound in a manner analogous to the procedure set forth in example A-2, 3-(4-tert-butyl-phenyl)-4-cyano-5-methylsulfanyl-thiophene-2-carboxylic acid using 4-Cyano-5-methylsulfanyl-3-(4-morpholin-4-yl-phenyl)-thiophene-2-carboxylic acid ethyl ester: Mass spectrum (m/e): 361(M+1).

EXAMPLE A-145

4-Cyano-5-ethyl-3-(4-[1,2,4]-thiadiazol-2-yl-phenyl)-thiophene-2-carboxylic acid di hydrochloride

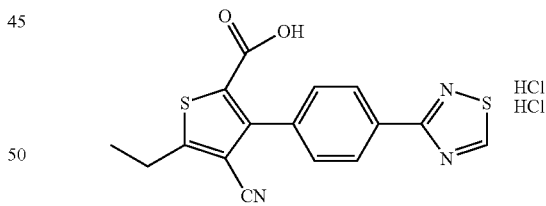

Dissolve 4-cyano-5-ethyl-3-(4-[1,2,4]-thiadiazol-2-yl-phenyl)-thiophene-2-carboxylic acid diethyl ester (0.030 g, 0.08 mmol) in THF (2 mL), add sodium hydroxide (1M aqueous solution, 2 mL) and stir the mixture overnight at 23° C. Next day add more THF (1 mL), sodium hydroxide (1 mL) and ethanol (2 mL) and stir 1.5 d at 23° C., until no 2262932 is left. Separate phases, wash aqueous layer with ethyl acetate and separate. Acidify aqueous phase with 3M HCl and allow to precipitate overnight. Filter to obtain 0.015 g (55%) of the title compound as a white solid. Mass spectrum ESI positive (m/z): 342 (M+1).

EXAMPLE A-146

Additional preparation of 4-Cyano-5-ethyl-3-(4-thiazol-2-yl-phenyl)-thiophene-2-carboxylic acid (see example A-72).

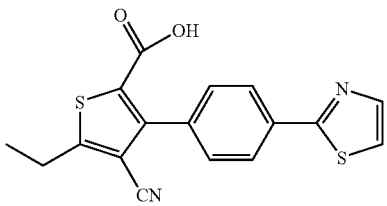

Add dioxane (1 vol) to 4-cyano-5-ethyl-3-(4-thiazol-2-yl-phenyl)-thiophene-2-carboxylic acid ethyl ester (1 equiv.) and then 2.5 M aqueous solution of LiOH (1 vol) and stir while heating at 60° C. for 15 min. Cool down, evaporate the dioxane under reduced pressure and add 3M HCl and filter. Purify by HLB (C18) cartridges to give 0.103 g of the title compound as a white solid.

EXAMPLE A-147

(R,S) 4-Cyano-3[4-(2-cyano-cyclopent-2-enyl)-phenyl]-5-ethyl-thiophene-2-carboxylic acid

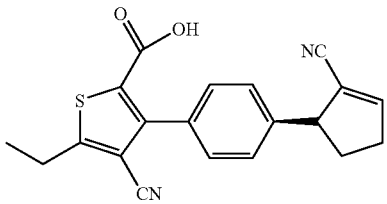

Starting with (R,S) 4-Cyano-3-[4-(2-cyano-cyclopent-2-enyl)-phenyl]-5-ethyl-thiophene-2-carboxylic acid ester, prepare the title compound in a manner analogous to the procedure set forth in preparation of Example A-145, using ethanol instead of tetrahydrofuran: mass spectrum ESI positive (m/z) 366 (M+18), 371 (M+23).

EXAMPLE A-148

4-Cyano-3-[4-(5-cyano-thiophen-2-yl-phenyl)-5-ethyl thiophene-2-carboxylic acid.

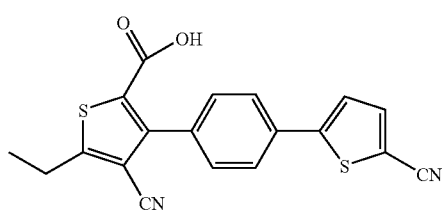

Add NaOH (1 mL) to a suspension of 4-cyano-3-[4-(5-cyano-thiophen-2-yl-phenyl)-5-ethyl thiophene-2-carboxylic acid ethyl ester in ethanol (1.5 mL) and stir at 60° C. for 10 min. Evaporate ethanol, add TFA (0.3 mL) and concentrate in vacuo. Suspend the residue in water, heat to 80° C. for 10 min and filter. Purify the solid using SPE Strata® silica gel cartridge eluting successively with ethyl acetate; ethyl acetate: MeOH 20:1; ethyl acetate: TFA 50:0.1. Suspend the solid in ethyl acetate and filter to obtain 0.12 g of the title compound as an off-white solid. 1H NMR (d6-acetone/d4-methanol (5.: 1), 300 MHZ) δ: 7.72 (d, J=8.1 Hz, 2H), 7.66 (d, J=4.0 Hz, 1H), 7.47 (d, J=4.0 Hz, 1H), 7.46 (d, J=8.1 Hz, 2H), 3.04 (q, J=7.4 Hz, 2H), 1.33 (t, J=7.5 Hz, 3H).

XAMPLE A-149

3-[4-5-Acetyl-thiophen-2-yl)-phenyl]-4-cyano-5-ethyl-thiophene-2-carboxylic acid

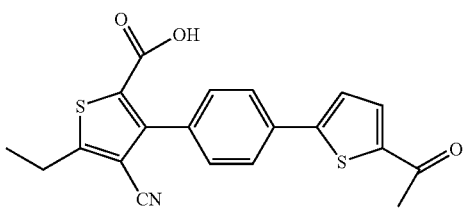

Prepare the title compound in a manner analogous to the procedure set forth in Example A-148, using 3-[4-5-acetyl-thiophen-2-yl)-phenyl]-4-cyano-5-ethyl-thiophene-2-carboxylic acid ethyl ester and 2.5 M aqueous solution of LiOH, stirring 15 min. Purify by reverse phase HPLC (using acetonitrile as organic solvent at pH about 2.5 (TFA 0.05%) to give 0.02 g of the title compound as beige solid. Mass spectrum ESI positive (m/z): 382 (M+1).

EXAMPLE A-150

3-(4-(Bromophenyl)-4-cyano-5-ethyl-thiophene-2-carboxylic acid

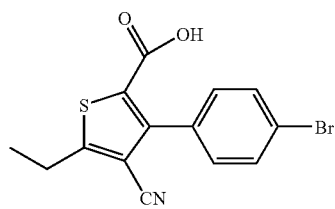

Add ethanol (50 ml) and 1M aqueous solution of NaOH to 3-(4-(bromophenyl)-4-cyano-5-ethyl-thiophene-2-carboxylic acid ethyl ester (5.0 g, 13.73 mmol) and stir at 60° C. for 1h. Cool down and acidify with 3M HCl until white solid precipitates. Filter and wash solid with water and hexanes successively. Dry overnight to give 4.34 g as a white solid. Mass spectrum ESI positive (m/z): 366 (M+1).

EXAMPLE A-151

3-[4-(5-(Chlorothiophen-2-yl)-phenyl]-4-cyano-5-ethyl-thiophene-2-carboxylic acid

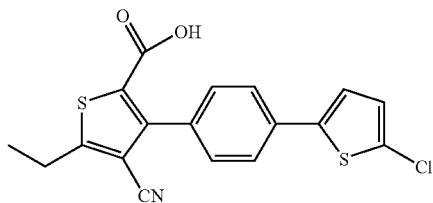

Mix 3-(4-(bromophenyl)-4-cyano-5-ethyl-thiophene-2-carboxylic acid (0.2 g, 0.59 mmol), 5-chloro-2-thiophene boronic acid (0.134 g, 0.82 mmol), tetrakis(triphenylphosphine)palladium(0) (0.063 g, 0.055 mmol) and 2M aqueous solution of sodium carbonate (0.55 mL) in DME (2 mL) and ethanol (1 mL). Bubble with nitrogen and stir at 90° C. in a sealed tube for 1.5 h. Add more 5-chloro-2-thiophen boronic acid (0.015 g) and tetrakis(triphenylphosphine)palladium(0) (0.025 g) and stir at 90° C. 3 h. Remove ethanol in vacuo, add TFA (0.3 mL) and filter through a silica gel cartridge. Concentrate the filtrate over Celite® and purify in SPE Strata® cartridges (silica gel) eluting with hexanes/TFA (0.05%)-isopropanol gradient (isopropanol from 2% to 30%). Final purification achieved by reverse phase HPLC (TFA 0.05% at pH 2.5, acetonitrile as organic solvent). Mass spectrum ESI positive (m/z): 374 (M+1), 396 (M+23).

EXAMPLE A-151 A

4-Cyano-3-(4'-cyanomethyl-biphenyl-4-yl)-5-ethyl-thiophene-2-carboxylic acid

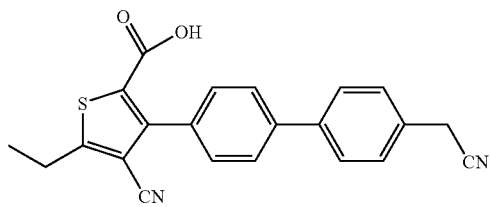

Prepare the title compound in a manner analogous to the procedure set forth in preparation of Example A-150 using 4-cyanomethylphenyl boronic acid. Purify following procedure on Example A-150 and recrystallize from acetone to give 0.052 g as a white powder. Mass spectrum ESI positive (m/z): 373 (M+1), 395 (M+23).

GENERAL EXAMPLE A-152

4-Cyano-5-$R^1$-3-(4-mercapto-$R^4$,$R^5$-phenyl)-thiophene-2-carboxylic acid

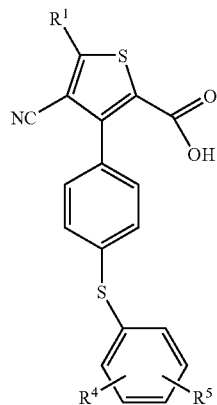

Add LiOH (2.5 M aqueous solution, 2 mL) to an ethanol (2 mL) solution of thioether and warm at 40° C. for 10 min. Cool down and acidify with 1.2 M HCl. Add ethyl acetate (2×3mL) and chloroform (3 mL) and separate phases. Filter through a short plug of silica gel, concentrate over Celite® and purify using SPE Strata® cartridges (silica gel). Recrystallize from acetone or ethyl acetate.

GENERAL EXAMPLE A-152A

4-Cyano-5-$R^1$-3-(4-mercapto-$R^4$,$R^5$-phenyl)-thiophene-2-carboxylic acid

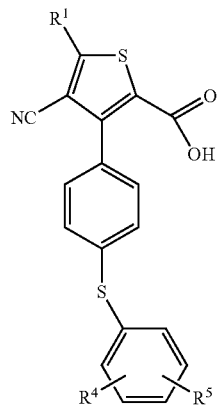

Add LiOH (2.5 M aqueous solution, 2 mL) to a THF (2 mL) solution of thioether (procedure E-68 and procedure E-69) and warm at 60° C. for 3 h. Cool down and acidify with 1.2 M HCl. Add ethyl acetate (2×3 mL) and chloroform (3 mL) and separate phases. Filter through a short plug of silica gel, concentrate over Celite® and purify using SPE Strata® cartridges (silica gel). Recrystallize from acetone or ethyl acetate.

By using a method similar to the general example A-152 and A-152A, the following compounds can be synthesized as set forth in Table A-2:

TABLE A-2

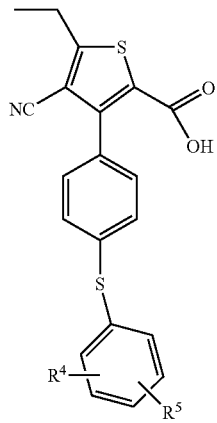

In the following examples R⁵ is hydrogen

| No. | R⁴ | Method | Data |
|---|---|---|---|
| A-153 | 2-methoxy | A-152A | Mass spectrum (m/z): 396 (M + 1), 418 (M + 23) |
| A-154 | H | A-152A | Mass spectrum (m/z): 366 (M + 1), 388 (M + 23) |
| A-155 | 2-chloro | A-152A | Mass spectrum (m/z): 398 (M − 1), 345 (M − 44) |
| A-156 | 3-chloro | A-152A | Mass spectrum (m/z): 398 (M − 1), 354 (M − 45) |
| A-157 | 4-chloro | A-152A | Mass spectrum (m/z): 398 (M − 1), 345 (M − 44) |
| A-158 | 3-methoxy | A-152A | Mass spectrum (m/z): 396 (M + 1), 418 (M + 23) |
| A-159 | 4-methoxy | A-152A | Mass spectrum (m/z): 396 (M + 1), 418 (M + 23) |
| A-160 | 2-cyano | A-152 | Mass spectrum (m/z): 391 (M + 1), 413 (M + 23) |
| A-161 | 4-cyano | A-152 | Mass spectrum (m/z): 391 (M + 1), 413 (M + 23) |

By using a method similar to the general example A-152, the following compounds can be synthesized as set forth in Table A-2:

TABLE A-3

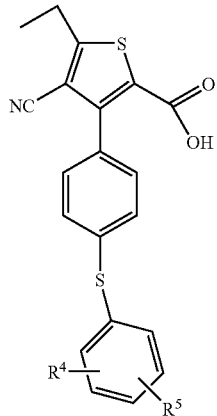

| No. | R⁴ | R⁵ | Data |
|---|---|---|---|
| A-162 | 3-F | 5-CN | Mass Spectrum (m/z) 431 (M + 23) |

TABLE A-3-continued

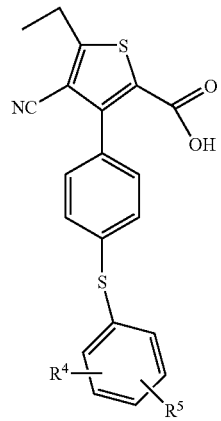

| No. | R⁴ | R⁵ | Data |
|---|---|---|---|
| A-163 | 4-F | 5-CN | Mass Spectrum (m/z) 431 (M + 23) |

By using a method similar to the general example A-152A, the following compounds can be synthesized as set forth in Table A-2:

TABLE A-4

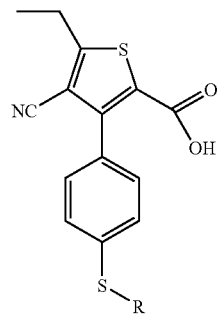

| No | R | Data |
|---|---|---|
| A-164 | n-propyl | Mass spectrum (m/z): 332 (M + 1), 354 (M + 23) |
| A-165 | cyclopentyl | Mass spectrum (m/z): 356 (M − 1), 312 (M − 45) |
| A-166 | 2-(4-pyridyl)ethyl | Mass spectrum (m/z): 395 (M + 1) |

EXAMPLE A-171

3-(4-Carboxy-phenyl)-4-cyano-5-methylsulfanyl-thiophene-2-carboxylic acid

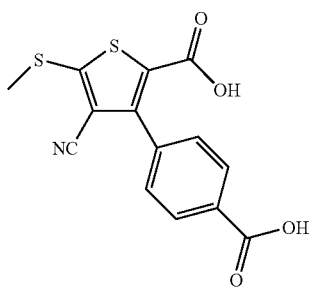

Prepare the title compound in a manner analogous to the procedure set forth in example A-2 using 4-cyano-3-(4-methoxycarbonyl-phenyl)-5-methylsulfanyl-thiophene-2-carboxylic acid ethyl ester as starting material: MS (ES+, m/e): 320 (M+1).

EXAMPLE A-172

4-Cyano-5-methylsulfanyl-3-(4-vinyl-phenyl)-thiophene-2-carboxylic acid

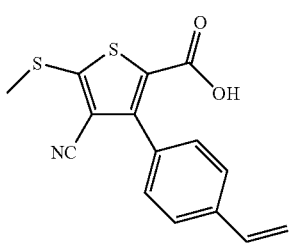

Prepare the title compound in a manner analogous to the procedure set forth in example A-2 using 4-Cyano-5-methylsulfanyl-3-(4-vinyl-phenyl)-thiophene-2-carboxylic acid ethyl ester as starting material: MS (ES+, m/e): 302 (M+1).

EXAMPLE A-173

4-Cyano-3-(4-isopropylcarbamoyl-phenyl)-5-methylsulfanyl-thiophene-2-carboxylic acid

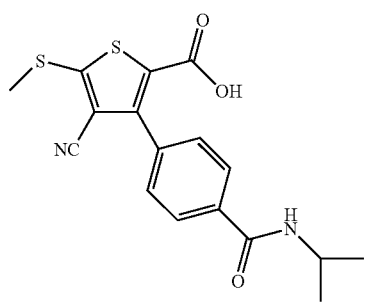

Combine 3-(4-Carboxy-phenyl)-4-cyano-5-methylsulfanyl-thiophene-2-carboxylic acid (0.1 g, 1.0 eq) in $CH_2Cl_2$ (5.0 mL) and stir. Add carbonyldiimidazole (2.0 eq). Stir the mixture overnight. Add isopropylamine (1.0 eq) and stir overnight at room temperature. Add 1N HCl water solution. Filter the precipitate to provide the title compound (0.03 g, Yield 27%). MS (ES+, m/e): 361 (M+1).

EXAMPLE A-174

3-(4-tert-Butyl-phenyl)-4-cyano-5-methylsulfanyl-furan-2-carboxylic acid

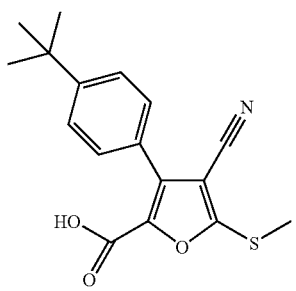

Dissolve 3-(4-tert-butyl-phenyl)-4-cyano-5-methylsulfanyl-furan-2-carboxylic acid ethyl ester (110 mg, 0.32 mmol) in a solution of THF: MeOH: H2O (3:2:1, 5 ml). Add lithium hydroxide (80 mg, 3.3 mmol) to the mixture and stir the reaction at 60° C. for 30 minutes. Add 6N HCl until pH approx. 1 to obtain the desired white solid of the titled compound (30 mg, 30%): Mass spectrum (M−1)=314. EA, Calculated: C; 61.91, H; 5.68, N; 4.25. Found: C; 61.75, H; 5.42, N; 3.91.

EXAMPLE A-175

3-(4-tert-Butyl-phenyl)-4-cyano-5-[(2-dimethylamino-ethyl)-methyl-amino]-thiophene-2-carboxylic acid

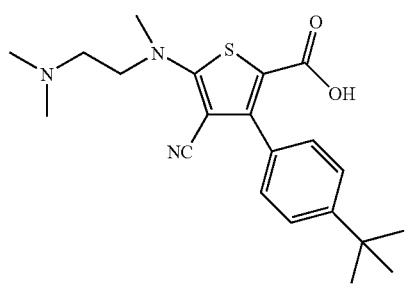

Prepare the title compound in a manner analogous to the procedure set forth in example A-2, 3-(4-tert-Butyl-phenyl)-4-cyano-5-[(2-dimethylamino-ethyl)-methyl-amino]-thiophene-2-carboxylic acid ethyl ester to provide the title compound: Mass spectrum (m/e): 386 (M+1). $^1$H NMR (DMSO, 200 MHz): δ 7.4 (d, 2H, J=8.2 Hz); 7.25 (d, 2H, J=8.2 Hz); 3.70 (m, 2H); 3.2 (s, 3H); 2.55 (m, 2H); 2.2 (s, 6H); 1.3 (s, 9H).

EXAMPLE A-176

3-{-[2-(3-chloropropane-1-sulfonilamino)-ethyl] phenyl}-4-cyano-5-ethyl-thiophene-2-carboxylic acid

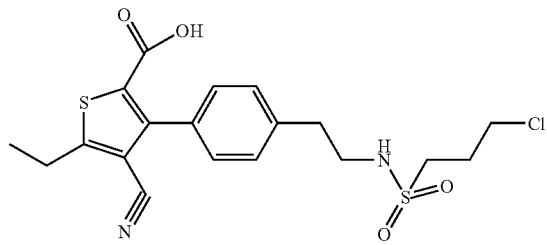

Add dioxane (1.0 mL) to compound from previous step (0.078 g, 0.16 mmol) and then 2.5 M aqueous solution of LiOH (1.0 mL) and stir at 15 min 40° C. Cool down, evaporate dioxane under reduce pressure and add 3M HCl and filter. Purify by reverse phase HPLC (0.05% TFA pH 2.5, using acetonitrile as organic solvent) to give 0.022 g of the title compound as a white semisolid. Mass spectrum ESI positive (m/z): 441 (M+1), 458 (M+18), 463 (M+23).

EXAMPLE A-177

4-Cyano-3-{4-[2-(1,1-dioxo-1λ,6-isothiaolidin-2-yl)-ethyl]phenyl}-5-ethyl-3-(4-[1,2,4]-thiadiazol-2-yl-phenyl)-thiophene-2-carboxylic acid

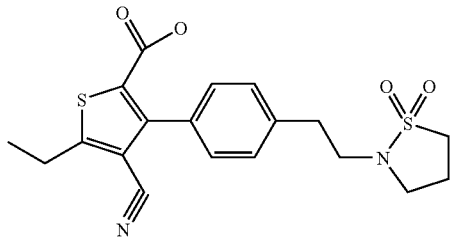

Prepare the title compound in a manner analogous to the procedure set forth in preparation of Example A-177, heating at 60° C. for 15 min. Purify by HLB (C18) cartridges to give 0.103 g of the title compound as a white solid. Mass spectrum ESI positive (m/z): 405 (M+1), 422 (M+18), 427 (M+23).

EXAMPLE A-178

3-[4-(3-tert-buthoxycarbonyl-thiophen-2-yl)phenyl]-4-cyano-5-ethyl-thiophene-2-carboxilyc acid

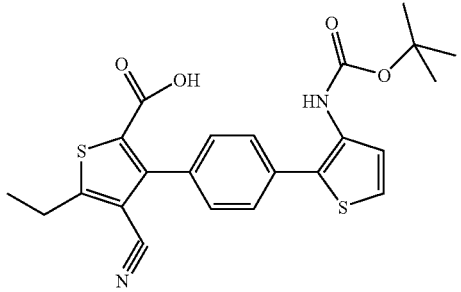

Stir 3-[4-(3-tert-butoxycarbonylamino-thiophen-2-yl)phenyl]-4-cyano-5-ethyl-thiophene-2-carboxilyc acid ethyl ester (0.17 g, 0.36 mmol) in a mixture of ethanol (4 mL) and 2.5 M LiOH aqueous solution (1 mL) at 60° C. for 1 h. Add ethyl acetate and separate phases. Acidify organic phase with acetic acid, dry (sodium sulfate) and concentrate in vacuo. Recrystallize the solid from ethyl acetate to give 0.042 g of the title compound as a white solid. Mass spectrum ESI positive (m/z): 477 (M+23).

EXAMPLE A-179

3-[4-(5-carboxy-thiophen-2-yl-phenyl)-4-cyano-5-ethyl thiophene-2-carboxylic acid

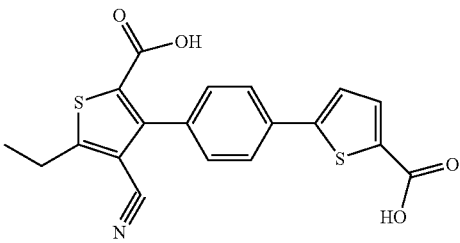

Add 2.5 M aqueous solution of LiOH (0.5 mL) to a suspension of material from 3-[4-(5-carboxy-thiophen-2-yl-phenyl)-4-cyano-5-ethyl thiophene-2-carboxylic acid ethyl ester (0.027 g, 0.06 mmol) in ethanol (1.5 mL) and stir at 60° C. for 20 min. Evaporate ethanol, add 1.2M HCl and filter. Purify the solid through a silica gel cartridge eluting with ethyl acetate first and then ethyl acetate-TFA(20:1) to give 0.02 g of the title compound. Mass spectrum ESI positive (m/z):384 (M+1), 401 (M+18).

EXAMPLE A-180

4-Cyano-5-ethyl-3-(2'-methalsulfanyl-biphenyl-4-yl)-thiothene-2-carboxylic acid ethyl ester

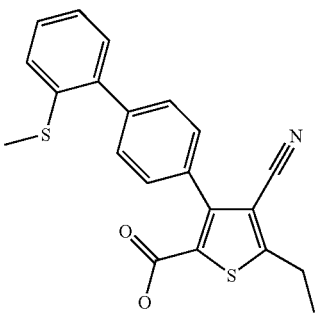

Add acetone, (1.87 L) and 4-Cyano-5-ethyl-3-(2'-methylsulfanyl-biphenyl-4-yl)-thiophene-2-carboxylic acid ethyl ester (144.1 g, 0.353 mol) to a 5 L reaction flask equipped with an overhead stirrer, condenser, nitrogen inlet, thermocouple, addition funnel, and heating mantle. Heat the mixture to 55° C. and add methanol (0.29 L). Add 2.0 N sodium hydroxide (221 mL, 0.442 mol) via an addition funnel. Observe substantial depletion of 4-Cyano-5-ethyl-3-(2'-methylsulfanyl-biphenyl-4-yl)-thiophene-2-carboxylic acid ethyl ester and 4-Cyano-5-ethyl-3-(2'-methylsulfanyl-biphenyl-4-yl)-thiophene-2-carboxylic acid methyl ester. Add deionized water (925 mL) and warm the resulting mixture to 67° C. Add 1.0 N hydrochloric acid (0.442 L, 1.25 eq) over 5 minutes and slowly cool the mixture to 23° C. over 4 hours. Collect the precipitate by filtration and rinse with aqueous acetone (1:1 acetone: water, three rinses of 60 ml each). This affords 219 g of wet cake. Add the wet cake, 115.6 g dry of 3-(4-tert-Butyl-phenyl)-4-cyano-5-methylsulfanyl-thiophene-2-carboxylic acid prepared in similar fashion, and acetone (1.5 L) to a 4 L beaker and stir at room temperature until a turbid solution is observed. Clarify the solution by filtration through Celite® and rinse with acetone (200 mL).

Transfer the filtrate to a 5 L reaction flask equipped with heating mantle, overhead stirrer, condenser, nitrogen inlet, thermocouple, and addition funnel. Warmed the solution to reflux. Add deionized water (1.45 L) while heating to 65° C. Stir and heat the resulting suspension at 65° C. for 1 hour, then cool the solution to 50° C. Stir at 50° C. for 9 hours. Slowly reduce the temperature from 50° C. to 24° C. over 6 hours and filter to collect the precipitate. Rinse the filter cake with aqueous acetone (1:1 acetone: water, two rinses of 150 ml each). Vacuum dry the solids at 50° C. to a constant weight. This affords the title compound (229 grams, 89.8% yield). HPLC=99.4% (mobile phase=27% 0.1% TFA in water, 73% ACN, 1.5 ml/min isocratic; Column=Zorbax SB-Phenyl 5 um 4.6 mm×25 cm at 35 C; UV detection at 210 nm).

EXAMPLE AM-1

4-Cyano-3-(2'-methysulfanyl-biphenyl-4-yl)-5-trifluoromethyl-thiophene-2-carboxylic acid amide

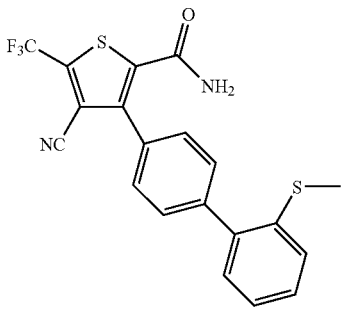

Prepare substantially in accordance with the method of general procedure 3-(4-tert-butyl-phenyl)-4-cyano-5-methylsulfanyl-thiophene-2-carboxylic acide amide starting with the title compound 4-cyano-3-(2'-methylsulfanyl-biphenyl-4-yl)-5-trifluoromethyl-thiophene-2-carboxylic acid: MS found (M−1) 417.

EXAMPLE AM-2

3-(4-tert-Butyl-phenyl)-4-cyano-5-methylsulfanyl-thiophene-2-carboxylic acide amide

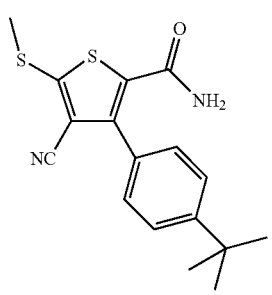

Combine 3-(4-tert-butyl-phenyl)-4-cyano-5-methylsulfanyl-thiophene-2-carboxylic acid (0.272 mmol) in 3 ml CH$_2$Cl$_2$ in a 25 ml round bottom. Add oxalyl chloride (0.33 mmol) followed by (0.06 mmol) of DMF. Stir mixture stir for 1 hr. at RT and concentrate on rotovap to dryness. Dissolve resultant residue in 3 ml CH$_2$Cl$_2$ and add (2.8 mmol) of conc. NH$_4$OH. A solid immediately precipitates. Concentrate reaction to dryness and chromatograph on 1000 micron (Si) radial chromatography plate eluting with 5% MeOH/CH$_2$Cl$_2$. Concentrate the desired fractions to provide the desired title compound: MS found (M+1) 331.4.

EXAMPLE AM-3

4-Cyano-3-(2'-cyano-biphenyl-4-yl)-5-methysulfanyl-thiophene-2-carboxylic acid amide

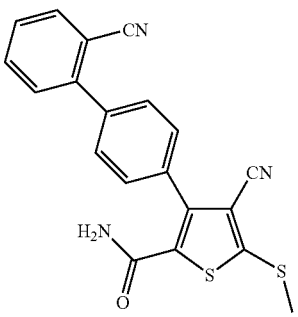

Prepare a solution of 4-cyano-3-(2'-cyano-biphenyl-4-yl)-5-methylsulfanyl-thiophene-2-carboxylic acid (250 mg, 0.66 mmol) in 5 mL of CH$_2$Cl$_2$ and stir under nitrogen. Add 2 drops of dry DMF and cool the mixture to 0° C. Next add oxalyl chloride (0.1 mL, 1.15 mmol) dropwise over five minutes. Remove the ice-bath and stir the reaction one hour. Add another 0.1 mL of oxalyl chloride and continue stirring for another hour. Concentrate the reaction mixture to a yellow solid. Dissolve the crude acid chloride in 5 mL of THF, cool to 0° C. and add 2 mL of concentrated NH$_4$OH. After stirring for 1 hour dilute the reaction with 20 mL of ice-water and filter off the solid, rinsing well with water. Vacuum-dry overnight to give the title compound, 175 mg (70%) as an off-white solid. MS (ES−, m/e)=374 (M$^+$−1); HPLC=97%.

EXAMPLE AM-4

4-Cyano-3-(2'-methylsulfanyl-biphenyl-4-yl)-5-trifluoromethy-thiophene-2-carboxylic acid amide

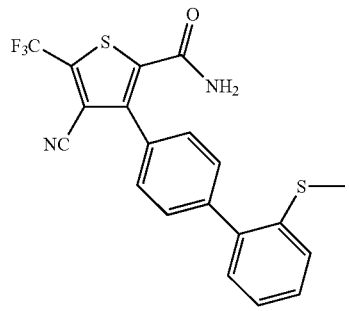

Prepare substantially in accordance with the procedure of 3-(4-tert-butyl-phenyl)-4-cyano-5-methylsulfanyl-thiophene-2-carboxylic acide amide starting with the title compound 4-cyano-3-(2'-methylsulfanyl-biphenyl-4-yl)-5-trifluoromethyl-thiophene-2-carboxylic acid: MS found (M−1) 417.

EXAMPLE AM-5

3-(4-tert-Butyl)-4-cyano-5-ethyl-thiophene-2-carboxylic acid amide

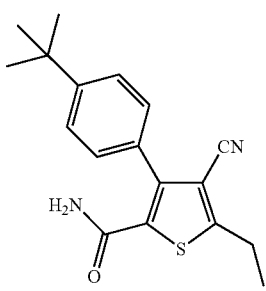

Prepare the title compound in a manner analogous to the procedure set forth in Example AM-3 using 3-(4-tert-Butyl-phenyl)-4-cyano-5-ethyl-thiophene-2-carboxylic acid (300 mg, 0.96 mmol) to give the title compound as a white solid. Yield=284 mg (95%). MS (ES+, m/e)=313 ($M^+$+1); HPLC=98%.

EXAMPLE AM-6

4-Cyano-3-(2'-cyano-biphenyl-4-yl)-5-ethyl-thiophene-2-carboxylic acid amide

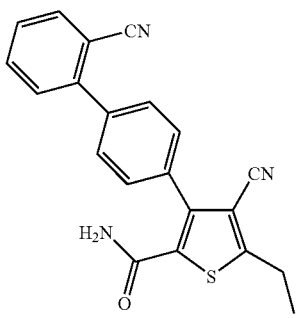

Prepare the title compound in a manner analogous to the procedure set forth in Example AM-3 using 4-cyano-3-(2'-cyano-biphenyl-4-yl)-5-ethyl-thiophene-2-carboxylic acid (300 mg, 0.84 mmol). Yield=241 mg (81%). MS(ES+, m/e)=358 ($M^+$+1); HPLC=94%.

EXAMPLE AM-7

4-Cyano-3-(4-cyclopentyl-phenyl)-5-ethyl-thiophene-2-carboxylic acid amide

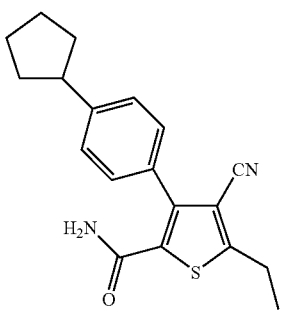

Prepare the title compound in a manner analogous to the procedure set forth in Example AM-3 using 4-cyano-3-(4-cyclopentyl-phenyl)-5-ethyl-thiophene-2-carboxylic acid (250 mg, 0.77 mmol). Yield=243 mg (97%). MS(ES+, m/e)=325 ($M^+$+1); HPLC=98%.

EXAMPLE AM-8

4-Cyano-5-ethyl-3-(2'-methylsulfanyl-biphenyl-4-yl)-thiophene-2-carboxylic acid amide

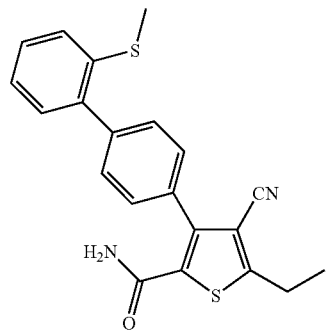

Prepare the title compound in a manner analogous to the procedure set forth in Example AM-3 using 4-cyano-5-ethyl-3-(2'-methylsulfanyl-biphenyl4-yl)-thiophene-2-carboxylic acid (174 mg, 0.46 mmol). Yield=139 mg (80%). MS(ES−, m/e)=377 ($M^+$−1); HPLC=95%.

Prepare the following amides as set forth in Table AM-1 in a manner analogous to the procedure set forth in Example AM-2:

TABLE AM-1

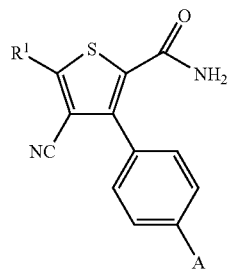

| No.: | $R^1$ | A | Data |
|---|---|---|---|
| AM-9 | MeS | 2-cyanophenyl | mass spectrum (m/e): 374 (M + 1). |
| AM-10 | Ethyl | Thiophen-2-yl | mass spectrum (m/e): 339 (M + 1). |
| AM-12 | Ethyl | 3-cyanopyridine-2-yl | mass spectrum (m/e): 359 (M + 1). |
| AM-14 | Ethyl | 3-methylthio-thiophen-2-yl | mass spectrum (m/e): 383 (M − 1). |
| AM-15 | Ethyl | 3-cyano-thiophen-2-yl | mass spectrum (m/e): 364 (M + 1). |

EXAMPLE AM-16

Preparation of 4-cyano-5-ethyl-3-(4-thiazol-2-yl-phenyl)-thiophene-2-carboxamide

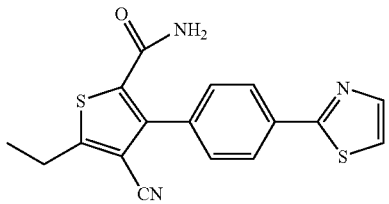

Add oxalyl chloride (0.050 mL, 0.57 mmol) to a suspension of 4-cyano-5-ethyl-3-(4-thiazol-2-yl-phenyl)-thiophene-2-carboxylic acid (0.15 g, 0.44 mmol) and DMF (0.1 mL) in dichloromethane at 0° C. Stir 1 h at 23° C. and add 1M solution of ammonia in dioxane (5 mL). Concentrate in vacuo, suspend the solid in ethyl acetate and filter to give 0.052 g of the title compound as a white solid. Mass spectrum ESI positive (m/z): 340 (M+1), 362 (M+23).

Prepare the following amides as set forth in Table AM-2 in a manner analogous to the procedure set forth in general preparation 3-(4-tert-butyl-phenyl)-4-cyano-5-methylsulfanyl-thiophene-2-carboxylic acide amide:

TABLE AM-2

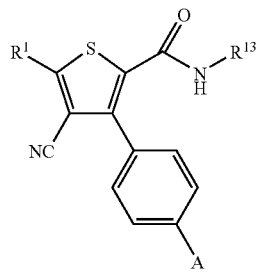

| No.: | R¹ | A | R¹³ | Data |
|---|---|---|---|---|
| AM-30 | Ethyl | Tert-butyl | 1H-Tetrazol-5-yl | mass spectrum (m/e): 381 (M + 1). |
| AM-31 | Ethyl | Tert-butyl | [1,3,4]Thiadiazol-2-yl | mass spectrum (m/e): 395 (M + 1). |
| AM-32 | Ethyl | Tert-butyl | [1,2,4]Triazol-3-yl | mass spectrum (m/e): 378 (M − 1). |
| AM-33 | Ethyl | 2-cyanophenyl | 1H-Tetrazol-5-yl | mass spectrum (m/e): 426 (M + 1). |
| AM-34 | Ethyl | Cyclopentyl | 1H-Tetrazol-5-yl | mass spectrum (m/e): 393 (M + 1). |

EXAMPLE AM-37

4-cyano-5-ethyl-3-(4-thiazol-2-yl-phenyl)-thiophene-2-carboxylic acid (2,2,2-trifluoroethyl) amide

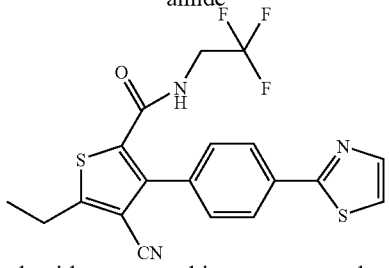

Prepare the title compound in a manner analogous to the procedure set forth in preparation of Example AM-16 using 2,2,2-(trifluoroethyl)amine (2 equiv). Wash the reaction mixture with water, 0.5M aqueous NaOH solution (×3), dry organic layer over sodium sulfate and evaporate. Wash the solid with diethyl ether-hexanes to give 0.015 g of the title compound as a white solid. Mass spectrum ESI positive (m/z): 422 (M+1), 444 (M+23).

EXAMPLE C-1

3-(4-tert-Butyl-phenyl)-5-methylsulfanyl-thiophene-2,4-dicarbonitrile

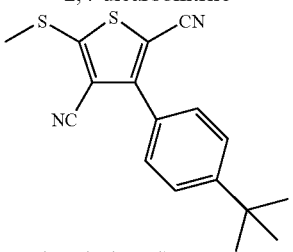

Add 3-(4-tert-butyl-phenyl)-4-cyano-5-methylsulfanyl-thiophene-2-carboxylic acid amide(0.121 mmol) to 0.5 ml of CH₃CN and add 18 mg paraformaldehyde and formic acid (1.59 mmol). Heat for 6 hrs. Concentrate and purify by radial chromatography eluting with ethyl acetate/hexanes to provide the title compound. $^1$H NMR (400 MHz, CDCl₃) δ 7.39 (q, 4H, J=12.0 Hz), 2.80 (s, 3H) and 1.42 (s, 9H).

EXAMPLE T-1

4-(4-tert-Butyl-phenyl)-2-ethyl-5-(2H-[1,2,4]triazol-3-yl)-thiophene-3-carbonitrile

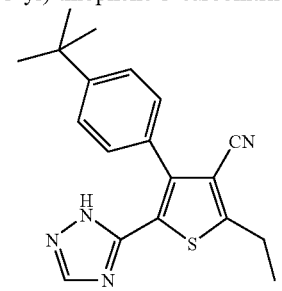

Dissolve 3-(4-tert-butyl-phenyl)-4-cyano-5-ethyl-thiophene-2-carboxylic acid dimethylaminomethyleneamide (261 mg, 0.71 mmol) in 2 mL of glacial acetic acid, add hydrazine monohydrate (50 µL, 1.03 mmol) and heat to 90° C. under nitrogen. After 90 minutes cool the reaction slightly, pour into 50 mL of ice-water and stir for twenty minutes. Filter off the resulting solid and rinse with 10 mL of water. Vacuum-dry overnight to give the title compound, 206 mg (86%). MS(ES+, m/e)=337 (M$^+$+1); HPLC=00%.

EXAMPLE T-2

4-(4-tert-Butyl-phenyl)-2-methylsulfanyl-5-(1H-tetrazol-5-yl)-thiophene-3-carbonitrile

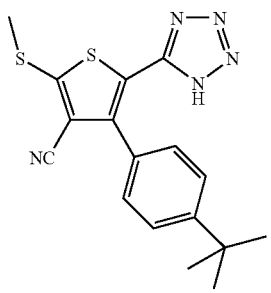

Combine 3-(4-tert-butyl-phenyl)-4-cyano-5-methylsulfanyl-thiophene-2-carboxylic acid amide (0.142 mmol) and 1.5 ml CH$_3$CN with NaN$_3$ (0.43 mmol) and SiCl$_4$ (0.142 mmol) in CH$_2$Cl$_2$ and reflux the mixture for 16 hrs. MS shows desired product and starting material. Conc. to dryness and purification by radial chromatography (Si) on a 1000 micron plate eluting with 5% MeOH/0.5% AcOH/CH$_2$Cl$_2$. Concentrate desired fractions to provide the desired title compound: $^1$H NMR (400 MHz, CDCl$_3$) δ 7.40 (q, 4H, J=22 Hz), 2.73 (s, 3H), and 1.35 (s, 9H), MS found (M+1) 356.2.

Prepare the following tetrazoles as set for Table T-1 in a manner analogous to the procedure set forth in Example 4-(4-tert-butyl-phenyl)-2-methylsulfanyl-5-(1-H-tetrazol-5-yl)-thiophene-3-carbonitrile.

TABLE T-1

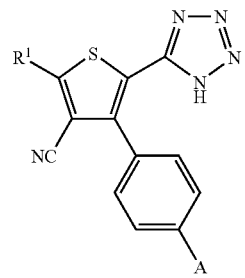

| No.: | R$^1$ | A | Data |
|---|---|---|---|
| T-3 | MeS | Tert-butyl | mass spectrum (m/e): 356 (M + 1). |
| T-4 | Ethyl | 2-fluorophenyl | mass spectrum (m/e): 376 (M + 1). |
| T-5 | MeS | 2-cyanophenyl | mass spectrum (m/e): 399 (M − 1). |
| T-6 | Ethyl | 2-cyanophenyl | mass spectrum (m/e): 383 (M + 1). |
| T-7 | Ethyl | 2-methylthiophenyl | mass spectrum (m/e): 404 (M + 1). |

TABLE T-1-continued

| No.: | R$^1$ | A | Data |
|---|---|---|---|
| T-8 | Ethyl | Tert-butyl | mass spectrum (m/e): 336 (M − 1). |
| T-9 | Ethyl | Cyclopentyl | mass spectrum (m/e): 350 (M + 1). |
| T-10 | Ethyl | Thiophen-2-yl | mass spectrum (m/e): 364 (M + 1). |
| T-11 | Ethyl | 3-cyanopyridine-2-yl | mass spectrum (m/e): 384 (M + 1). |
| T-12 | Ethyl | 3-chlorothiophen-2-yl | mass spectrum (m/e): 396 (M − 1). |

GENERAL EXAMPLE T-13

2-R$^1$-5-(1(2)H-tetrazol-5-yl)-4-(4-A-phenyl)-thiophene-3-carbonitrile

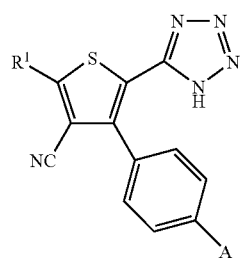

R = Me, Et

Combine 4-Iodo-2-R$^1$-5-(1H-tetrazol-5-yl)-thiophene-3-carbonitrile (preparation 53 and 56) (1.0 mmol), the corresponding phenyl boronate (1.0-1.1 mmol), tetrakis(triphenylphosphine)palladium (0) (0.05 mmol), and 2M sodium carbonate (4 mmol) solution in DME (10 ml) and heat to reflux. After 18-24 hours cool to room temperature and add water. Extract with ethyl acetate. Combine the organics and wash with water and brine, dry over sodium sulfate, filer and concentrate under reduced pressure. Purify by flash chromatography eluting with dichloromethane:MeOH to provide the title compound.

Prepare the following tetrazoles as set for Table T-2 in a manner analogous to the procedure set forth in General Example T-13, 2-R$^1$-5-(1(2)H-tetrazol-5-yl)-4-(4-A-phenyl)-thiophene-3-carbonitrile.

TABLE T-2

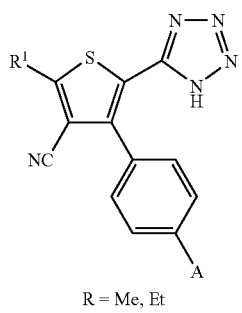

R = Me, Et

| Ex No. | R¹ | A | Data |
|---|---|---|---|
| T-14 | Methyl | 3-methylthio-thiophene-2-yl | mass spectrum (m/e): 396 (M + 1). |
| T-15 | Ethyl | 4-Cyano-5-ethyl-thiophene-2-(1H-tetrazol-5-yl)-3-yl | mass spectrum (m/e): 485 (M + 1). |
| T-16 | Ethyl | 3-thiomethylthiophen-2-yl | mass spectrum (m/e): 408 (M − 1). |
| T-18 | Ethyl | 3-cyanothiophen-2-yl | mass spectrum (m/e): 389 (M + 1). |

EXAMPLE T-19

2-Ethyl-5-(1(2)H-tetrazole-5-yl)-4-(4-thiazol-2-yl-phenyl)-thiophene-3-carbonitrile

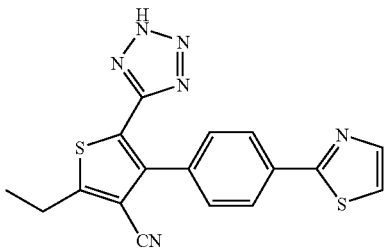

Add silicon tetrachloride (1M in dichloromethane, 0.59 mmol) to a suspension of sodium azide (0.116 g, 1.76 mmol) in dry acetonitrile (2 mL) and warm 5 min at 95° C. Add 4-cyano-5-ethyl-3-(4-thiazol-2-yl-phenyl)-thiophene-2-carboxamide (0.05 mg, 0.147 mmol, mixed with 1 equiv of silicon tetrachloride and 3 equiv of sodium azide) in acetonitrile and stir under reflux for 16 h. Add ethyl acetate and water and separate phases. Wash organic layer with water (×2) and back-extract aqueous layer with ethyl acetate (×2). Wash organic layers with brine, dry (sodium sulfate) and concentrate. Purify by reverse phase SPE cartridges to give 0.041 g of the title compound as a white solid. Mass spectrum ESI positive (m/z): 365 (M+1), 387 (M+23).

GENERAL EXAMPLE S-1

$R^{19}$-Sulfonic acid-[4-cyano-3-(4-A-phenyl)-5-$R^1$-thiophene-2-carbonyl]-amide

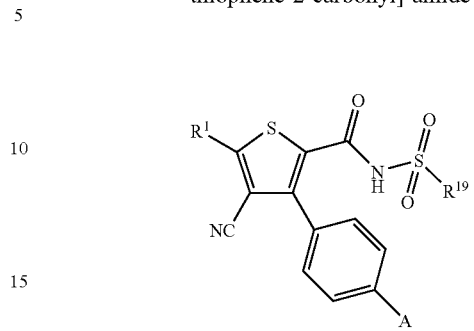

Dissolve the carboxylic acid (0.20 mmol) in 3 mL of $CH_2Cl_2$ and add Alkyl-sulfonamide (0.25 mmol), DMAP (0.23 mmol) and (3-dimethylamino-propyl)-ethyl-carbodiimide hydrochloride (0.25 mmol). Stir the resulting mixture under nitrogen at room temperature for 18 hours. Dilute with 20 mL of $CH_2Cl_2$ and wash with 1N HCl (1×5 mL), dry over $Na_2SO_4$, filter and evaporate. Chromatograph on silica gel in 1/9 $MeOH/CH_2Cl_2$ to give the title compound.

Prepare the following acyl sulfonamides as set forth in Table S-1 in a manner analogous to the procedure set forth in general example S-1:

TABLE S-1

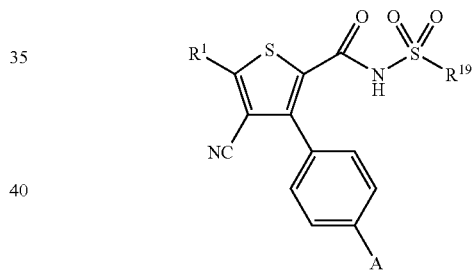

| No.: | R¹ | A | R¹⁹ | Data |
|---|---|---|---|---|
| S-2 | MeS | t-Butyl | Methyl | Mass spectrum (m/e): 407 (M − 1) |
| S-3 | MeS | t-Butyl | i-Propyl | Mass spectrum (m/e): 437 (M + 1) |
| S-4 | MeS | 1-pyrrolidine | i-Propyl | Mass spectrum (m/e): 450 (M + 1) |
| S-5 | MeS | 1-pyrrolidine | Methyl | Mass spectrum (m/e): 422 (M + 1) |
| S-6 | Ethyl | 2-fluorophenyl | Methyl | Mass spectrum (m/e): 429 (M + 1) |
| S-7 | Ethyl | 2-methylthiophenyl | Methyl | Mass spectrum (m/e): 429 (M + 1) |
| S-8 | Ethyl | 2-methylthiophenyl | Isopropyl | Mass spectrum (m/e): 429 (M + 1) |
| S-9 | MeS | 2-cyanophenyl | Methyl | Mass spectrum (m/e): 452 (M − 1) |
| S-10 | Me₂N | Thiophen-2-yl | Methyl | Mass spectrum (m/e): 432 (M + 1) |
| S-11 | Ethyl | Thiophen-2-yl | Methyl | Mass spectrum (m/e): 415 (M + 1) |

The ability of compounds of Formula I to potentiate glutamate receptor-mediated response can be determined by one of ordinary skill in the art. For example, see U.S. Pat. No. 6,303,816. In particular, the following test may be utilized:

HEK293 cells stably expressing human iGluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2-3 MΩ. Using the whole-cell voltage clamp technique (Hamill et al.(1981) Pflügers Arch., 391: 85-100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

In addition, certain behavioral despair animal models, which can be practiced by one of ordinary skill in the art to evaluate compounds of the present invention, are predictive of antidepressant activity in man, such as the Forced Swim Test and the Tail Suspension Test. For example, see "*Experimental Approaches to Anxiety and Depression*", Edited by J. M. Elliott, et al., (1992), John Wiley & Sons Ltd., Chapter 5, *Behavioural Models of Depression*, Porsolt and Lenegre, pages 73-85.

According to another aspect, the present invention provides a pharmaceutical composition, which comprises a compound of Formula I or a pharmaceutically acceptable salt thereof and a pharmaceutically acceptable carrier, diluent, or excipient. In addition, the present invention provides a pharmaceutical composition, which comprises a compound of Formula II or a pharmaceutically acceptable salt thereof and a pharmaceutically acceptable carrier, diluent, or excipient.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semisolid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 0.1 mg to about 300 mg, preferably about 0.1 mg to about 100 mg, and most preferably about 0.1 to about 50 mg of compound of Formula I or Formula II. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of Formula I or Formula II which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formula I or Formula II can be administered by a variety of routes including oral, rectal, transdermal, subcutaneous, intravenous, intramuscular, bucal or intranasal routes. Alternatively, the compounds of Formula I or Formula II may be administered by continuous infusion. A typical daily dose will contain from about 0.005 mg/kg to about 10 mg/kg of the compound of Formula I or Formula II. Preferably, daily doses will be about 0.005 mg/kg to about 5 mg/kg, more preferably from about 0.005 mg/kg to about 1 mg/kg.

The dosages of the drugs used in the combinations set forth herein, must also, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, are provide herein. Dosage guidelines for some of the drugs will first be given separately; in order to create a guideline for any desired combination, one would choose the guidelines for each of the component drugs.

Olanzapine: from about 0.25 to 50 mg, once/day; preferred, from 1 to 30 mg, once/day; and most preferably 1 to 25 mg once/day;

Clozapine: from about 12.5 to 900 mg daily; preferred, from about 150 to 450 mg daily;

Risperidone: from about 0.25 to 16 mg daily; preferred from about 2-8 mg daily;

Sertindole: from about 0.0001 to 1.0 mg/kg daily;

Quetiapine: from about 1.0 to 40 mg/kg given once daily or in divided doses;

Ziprasidone: from about 5 to 500 mg daily; preferred from about 50 to 100 mg daily;

Aripiprazole from about 1 to about 50 mg daily, preferred from about 5 to about 30 mg daily.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 20 to about 50 mg once/day; preferred, from about 20 to about 30 mg once/day.

Sertraline: from about 20 to about 500 mg once/day; preferred, from about 50 to about 200 mg once/day;

Donepizil: from about 1 mg to about 20 mg, once/day; with from about 5 mg to about 10 mg, once/day being preferred.

Rivastigmine: from about 1 mg to about 15 mg daily; with from about 5 to 12 mg daily being preferred;

Galantamine: from about 4 mg to 64 mg daily; with from about 4 mg to about 32 mg daily being preferred;

Memantine: from about 5 mg to about 30 mg/kg daily, with about 20 mg daily being preferred.

In more general terms, one would create a combination of the present invention by choosing a dosage of first and second component compounds according to the spirit of the above guideline.

The adjunctive therapy of the present invention is carried out by administering a first component together with the second component in any manner which provides effective levels of the compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the others may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

The adjunctive combination may be administered as a single pharmaceutical composition, and so pharmaceutical compositions incorporating both compounds are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of all compounds, or may contain a fraction of the daily doses, such as one-third of the doses. Alternatively, each dosage unit may contain the entire dose of one of the compounds, and a fraction of the dose of the other compounds. In such case, the patient would daily take one of the combination dosage units, and one or more units containing only the other compounds. The amounts of each drug to be contained in each dosage unit depends on the identity of the drugs chosen for the therapy, and other factors such as the indication for which the adjunctive therapy is being given.

The inert ingredients and manner of formulation of the adjunctive pharmaceutical compositions are conventional, except for the presence of the combination of the present invention. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations do not depend on the nature of the composition, so the compositions are chosen and formulated solely for convenience and economy. Any of the combinations may be formulated in any desired form of composition.

As with any group of structurally related compounds which possess a particular generic utility, certain groups and configurations are preferred for compounds of Formula I and Formula II as set forth below.

With respect to substituent $R^1$, compounds wherein $R^1$ is hydrogen, F, —$OCH_3$, —$SCH_3$, $CF_3$, —$C(=O)CH_3$, methyl, or ethyl are preferred, with hydrogen, —$SCH_3$, $CF_3$, methyl, or ethyl being especially preferred, and with ethyl being most especially preferred.

With respect to substituent $R^2$ in compounds of Formula I, compounds wherein is $R^2$ is —$CO_2H$, —$CONHSO_2$(1-4C) alkyl, or

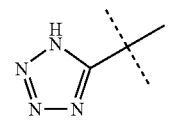

are preferred, with $CO_2H$ being especially preferred.

With respect to substituent A, compounds wherein A is; —$(CH_2)_m NHSO_2 R^{12}$, —$CH(CH_3)(CH_2)_p NHSO_2 R^{12}$, —$(CH_2)_p CH(CH_3) NHSO_2 R^{12}$, —$O(CH_2)_n NHSO_2$(1-4C)alkyl,

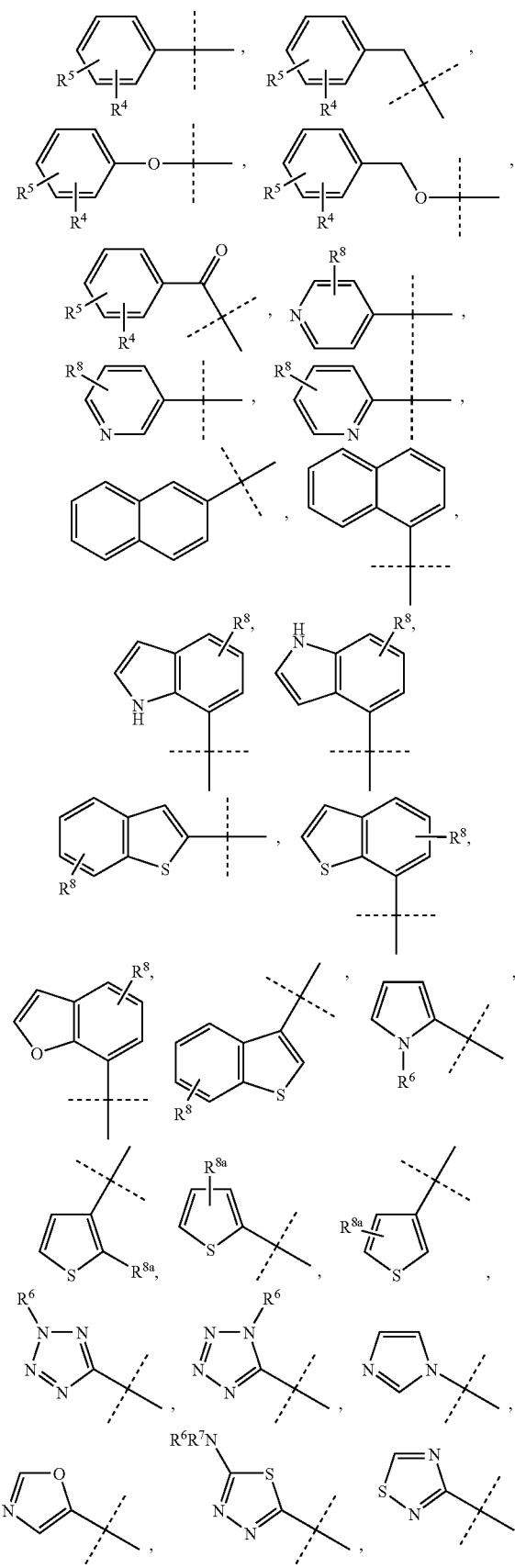
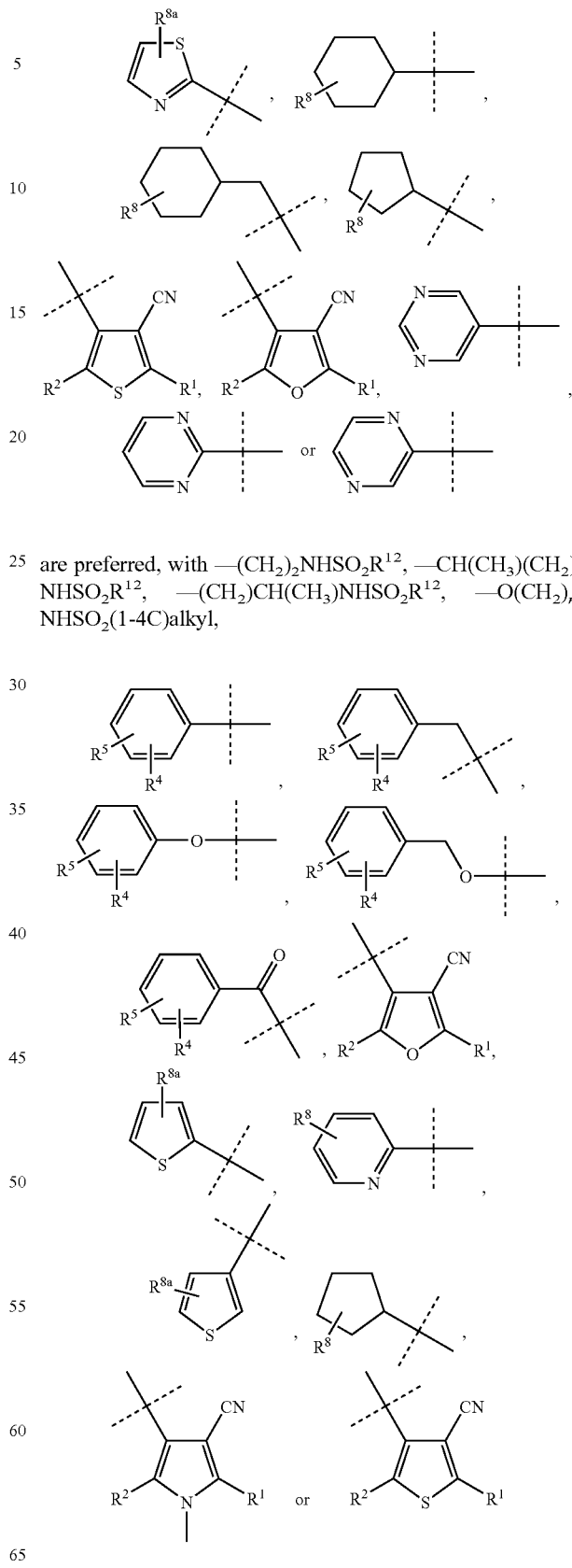
are preferred, with —(CH$_2$)$_2$NHSO$_2$R$^{12}$, —CH(CH$_3$)(CH$_2$)NHSO$_2$R$^{12}$, —(CH$_2$)CH(CH$_3$)NHSO$_2$R$^{12}$, —O(CH$_2$)$_n$NHSO$_2$(1-4C)alkyl,
being especially preferred, and;

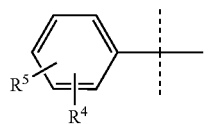

being most especially preferred.

With respect to substituent $R^4$, compounds wherein $R^4$ is hydrogen, F, -(1-4C)alkyl, -(1-4C)alkoxy, —C(=O)NH(1-4C)alkyl, —NHC(=O)(1-4C)alkyl, —NHSO$_2$R$^{10}$, —CN, —CO$_2$H, —C(=O)(1-4C)alkyl, or —S(1-4C)alkyl are preferred, and compounds wherein $R^4$ is hydrogen, -(1-4C)alkoxy, —CN, or —S(1-4C)alkyl are especially preferred, and compounds wherein $R^4$ is hydrogen, —CN, ethoxy, or —SCH$_3$ are most especially preferred.

With respect to substituent $R^5$, compounds wherein $R^5$ is hydrogen, F, Cl, and -(1-4C)alkyl are preferred, with hydrogen, F, and methyl being especially preferred, and hydrogen being most especially preferred.

With respect to substituent $R^6$, compounds wherein $R^6$ is hydrogen or methyl are preferred, with hydrogen being especially preferred.

With respect to substituent $R^7$, compounds wherein $R^7$ is hydrogen or methyl are preferred, with hydrogen being especially preferred.

With respect to substituent $R^8$, compounds wherein $R^8$ is hydrogen are preferred.

With respect to substituent $R^{10}$, compounds wherein $R^{10}$ is (1-4C)alkyl are preferred with methyl, ethyl, or 2-propyl being especially preferred, and with methyl being most especially preferred.

With respect to substituent $R^{11}$, compounds wherein $R^{11}$ is (1-4C)alkyl are preferred.

With respect to substituent $R^{12}$, compounds wherein $R^{12}$ is (1-4C)alkyl are preferred, with methyl, ethyl, and 2-propyl being especially preferred.

With respect to substituent $R^{13}$, compounds wherein $R^{13}$ is (1-4C)alkyl are preferred.

With respect to substituent $R^{14}$, compounds wherein $R^{14}$ is (1-4C)alkyl are preferred, with methyl, ethyl, or propyl being especially preferred.

With respect to m, compounds wherein m is 0, 1, or 2 are preferred, with 2 being especially preferred.

With respect to n, compounds wherein n is 1 or 2 are preferred.

With respect to p, compounds wherein p is 1 are preferred.

With respect to substituent Z, compounds wherein Z is —O(1-6C)alkyl are preferred, with methyl, ethyl, propyl, and isopropyl being preferred, with ethyl being especially preferred.

In particular, compounds of the following formulas and their pharmaceutically acceptable salts are especially preferred:

A
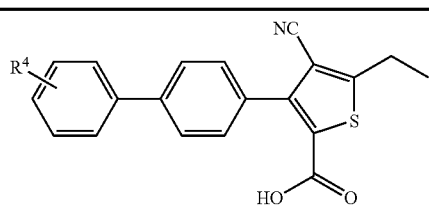

B
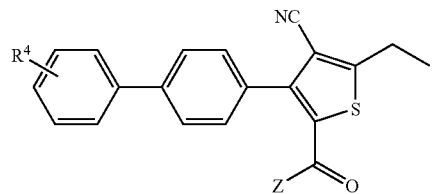

C
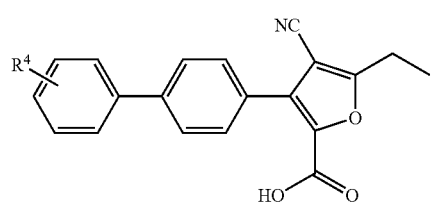

D
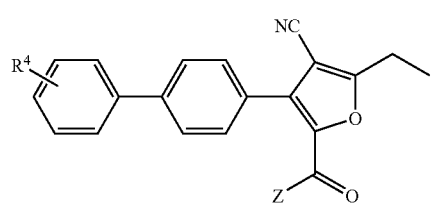

Compounds of the following formulas and their pharmaceutically acceptable salts are most especially preferred:

E
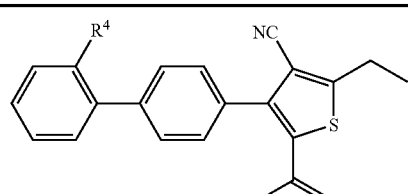

F
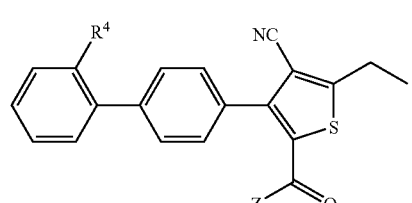

G
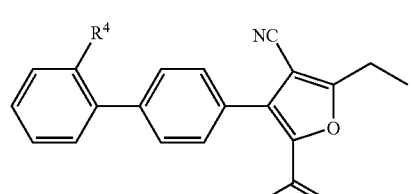

H
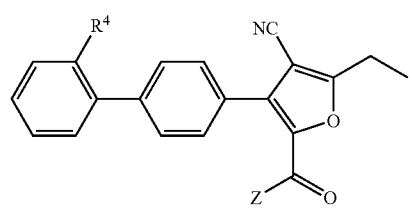

The following specific compounds and their pharmaceutically acceptable salts are particularly preferred:
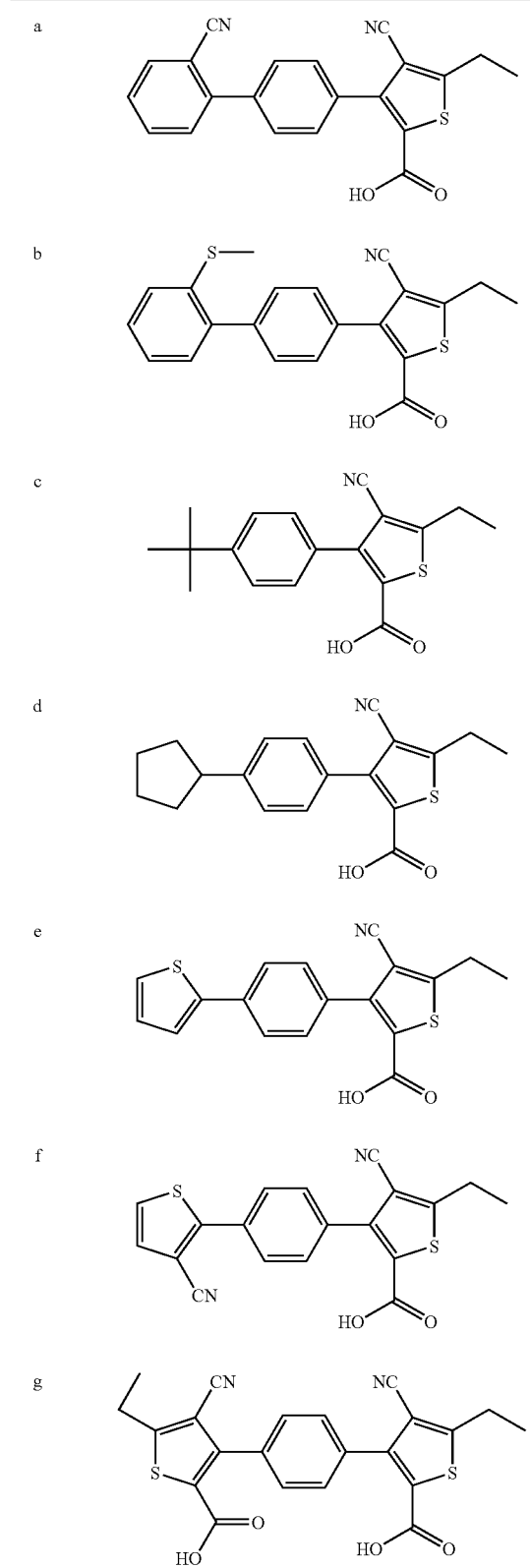
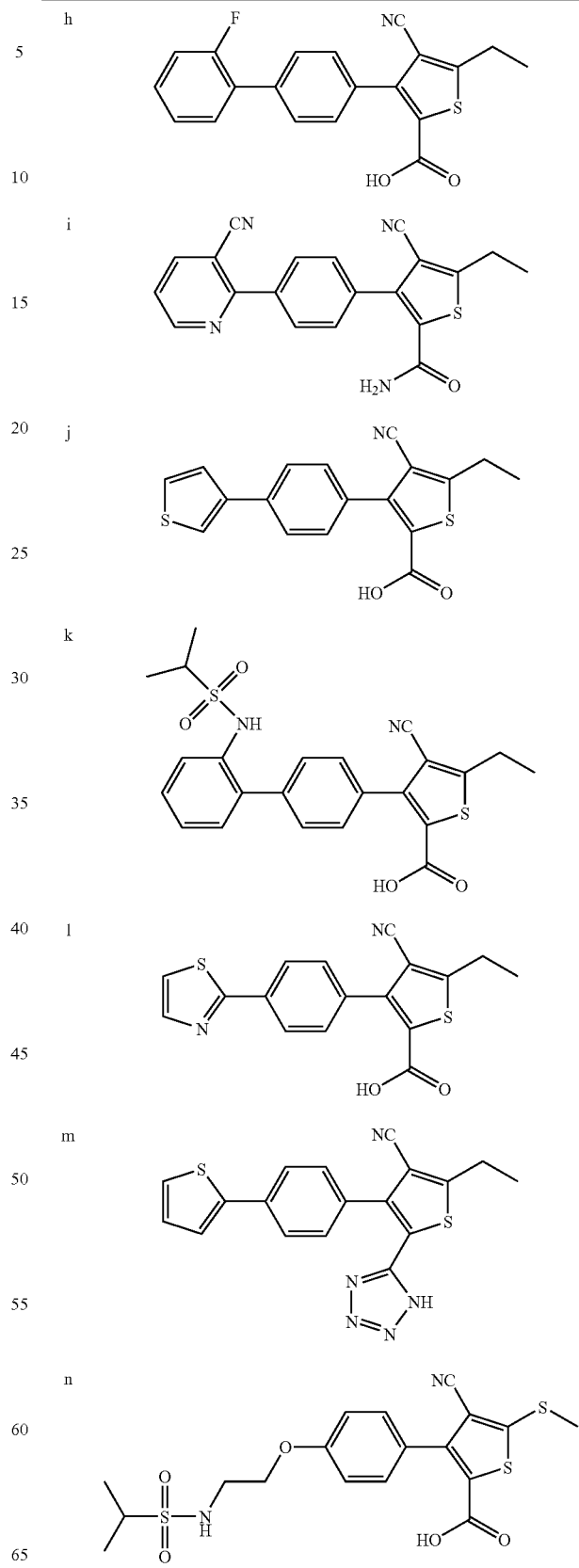

-continued o 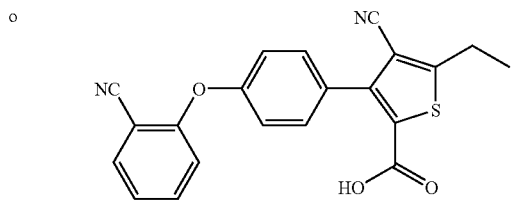

p 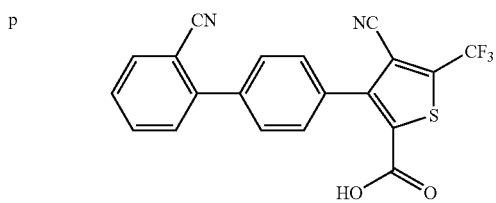

q 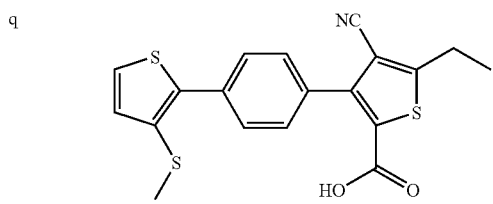

r 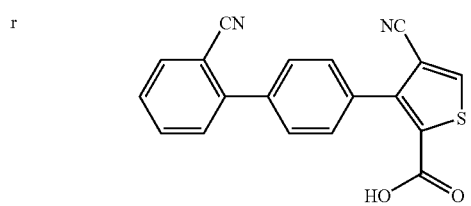

s 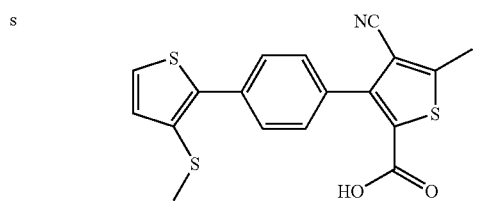

t 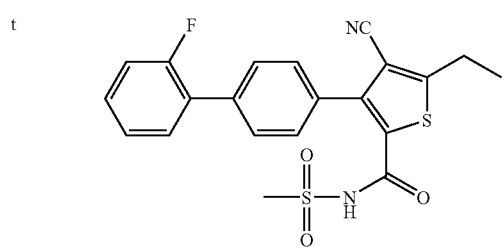

We claim:
1. A compound of Formula I:

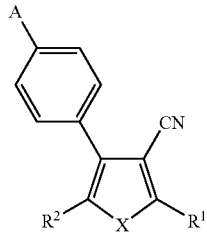

Formula I wherein
X represents S;
$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, —$SO_2$(1-4C)alkyl, —C(=O)(1-3C)alkyl, $NH_2$, —NH(1-4C)alkyl, —N[(1-4C)alkyl]$_2$, —NH(4-7C)cycloalkyl, or —N[(1-4C)alkyl]($CH_2$)$_r$N[(1-4C)alkyl]$_2$;
$R^2$ represents —$CO_2H$;
$R^4$ represents hydrogen, OH, —$CH_2OH$, —$CH_2CH_2OH$, —$CH_2O$(1-4C)alkyl, F, Cl, $CF_3$, $OCF_3$, —CN, $NO_2$, $NH_2$, —$CH_2NH_2$, -(1-4C)alkyl, -(1-4C)alkoxy, —C(=O)NH(1-4C)alkyl, —C(=O)$NH_2$, —$CH_2$C(=O)$NH_2$, —NHC(=O)(1-4C)alkyl, —($CH_2$)$_m$NHSO$_2R^{10}$, —($CH_2$)$_n$CN, —($CH_2$)$_m$CO$_2$H, —C(=NOH)$CH_3$, —($CH_2$)$_m$CO$_2$(1-6C)alkyl, —C(=O)H, —C(=O)(1-4C)alkyl, —NH(1-4C)alkyl, —N[(1-4C)alkyl]$_2$, —$SR^{10}$, —$SOR^{10}$, —$SO_2R^{10}$, SH, —$CH_2SO_2NH_2$, —$CH_2NHC$(=O)$CH_3$,

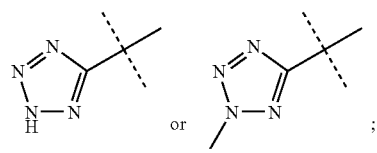

$R^5$ represents hydrogen, F, Cl, —CN, $NO_2$, $NH_2$, —($CH_2$)$_m$ $NHSO_2R^{10}$, -(1-4C)alkyl, or -(1-4C)alkoxy;
$R^6$ represents hydrogen, -(1-4C)alkyl, —$SO_2R^{11}$, or —C(=O)(1-4C)alkyl;
$R^7$ represents hydrogen or -(1-4C)alkyl;
$R_8$ represents hydrogen, F, Cl, Br, -(1-4C)alkyl, -(1-4C)alkoxy, $NO_2$, $NH_2$, —CN, —$NHSO_2R^{11}$, or —C(=O)(1-4C)alkyl;
$R^{8a}$ represents hydrogen, F, Cl, Br, -(1-4C)alkyl, $NO_2$, $NH_2$, NH(1-6C)alkyl, N[(1-6C)alkyl]$_2$, —C(=O)$NH_2$, —CN, —$CO_2H$, —S(1-4C)alkyl, —$NHCO_2$(1-4C)alkyl, —C(=O)NHCH$_2$CH$_2$CN, or —C(=O)(1-4C)alkyl;
$R_{10}$, $R_{11}$, and $R_{12}$ each independently represent -(1-4C)alkyl, —($CH_2$)$_3$Cl, $CF_3$, $NH_2$, NH(1-4C)alkyl, N[(1-4C)alkyl)]$_2$, thienyl, phenyl, —$CH_2$phenyl, or ($CH_2$)$_2$phenyl, wherein phenyl, as used in substituent $R^{10}$, $R^{11}$ or $R^{12}$, is unsubstituted or substituted with F, Cl, Br, $CF_3$, -(1-4C)alkyl, -(1-4)alkoxy, or acetyl;
$R_{13}$ represents hydrogen, -(1-4C)alkyl, —$CH_2CF_3$, triazole, or tetrazole;
$R^{14}$ represents -(1-4C)alkyl;
$R^{15}$ represents hydrogen or -(1-4C)alkyl;
$R^{19}$ represents (1-4C)alkyl or $CF_3$;

m represents 0, 1, 2, or 3;
n represents 1, 2, 3, or 4;
p represents 1 or 2;
r represents 1 or 2; and
A is selected from the group consisting of —(CH$_2$)$_2$NHSO$_2$R$^{12}$, —CH(CH$_3$)(CH$_2$)NHSO$_2$R$^{12}$, —(CH$_2$)CH(CH$_3$)NHSO$_2$R$^{12}$,
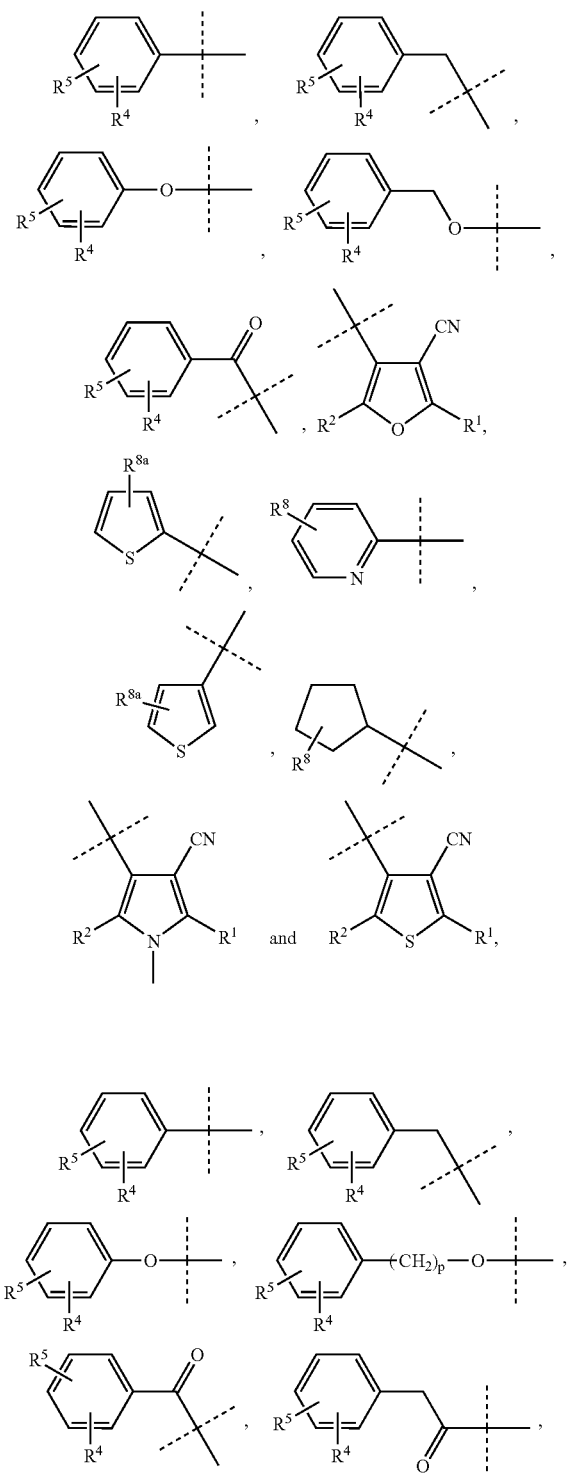
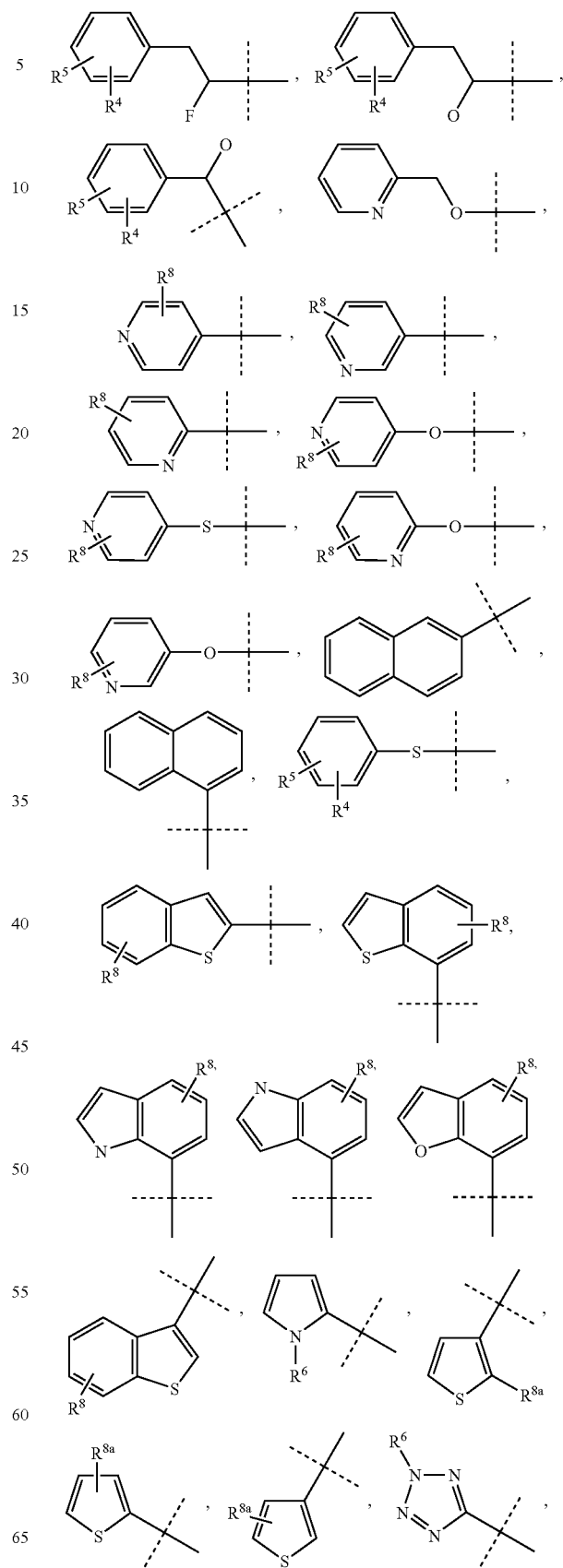

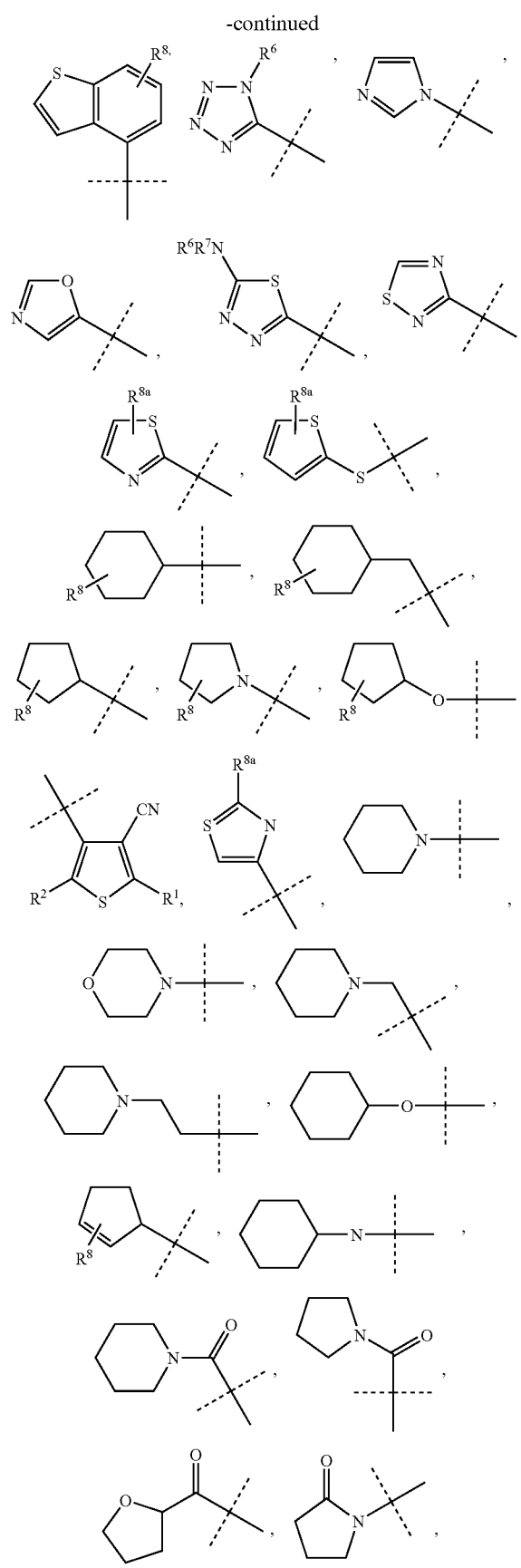
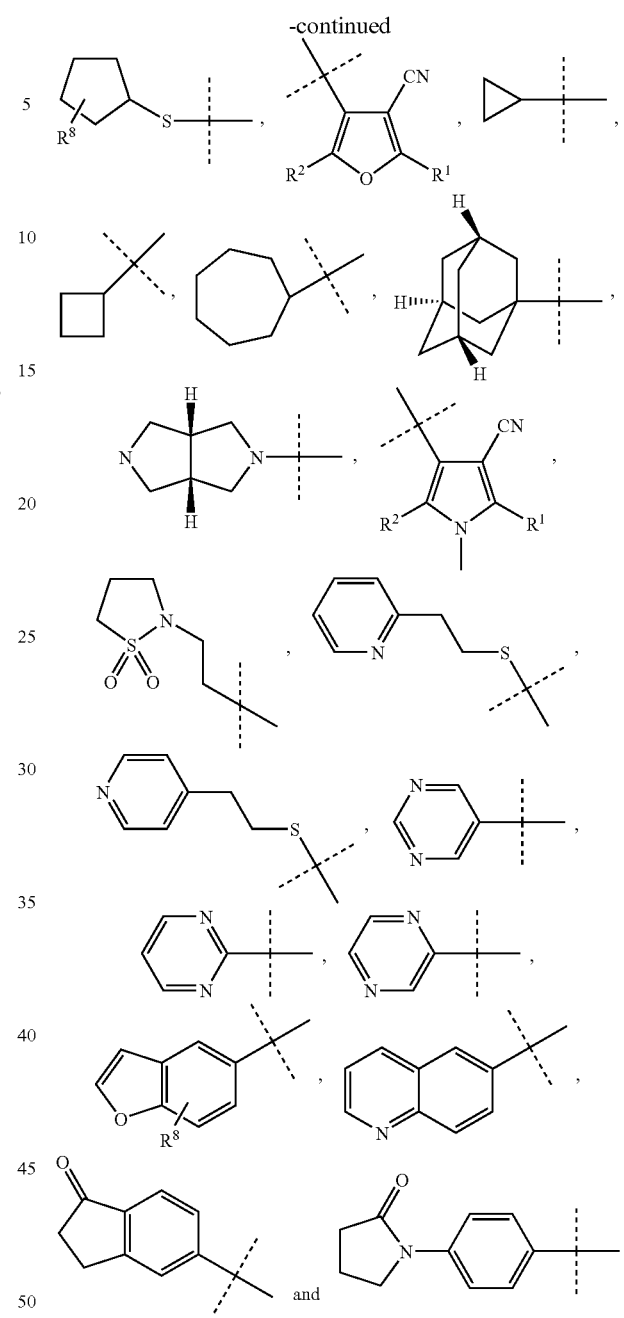
and the pharmaceutically acceptable salts thereof.
2. A compound according to claim 1 wherein A is
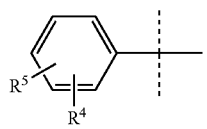
3. A compound according to claim 1 wherein $R^1$ represents hydrogen, —$SCH_3$, $CF_3$, methyl, or ethyl.
4. A compound according to claim 2 wherein $R^5$ represents hydrogen, F, Cl, or -(1-4C)alkyl.
5. A compound according to claim 4 wherein $R^4$ represents hydrogen, —CN, ethoxy, or —$SCH_3$.
* * * * *